United States Patent
Patten et al.

(10) Patent No.: US 11,015,206 B2
(45) Date of Patent: *May 25, 2021

(54) COMPOSITIONS AND METHODS COMPRISING SEQUENCES HAVING HYDROXYPHENYLPYRUVATE DIOXYGENASE (HPPD) ACTIVITY

(71) Applicant: PIONEER HI-BRED INTERNATIONAL, INC., Johnston, IA (US)

(72) Inventors: Phillip A Patten, Portola Valley, CA (US); Daniel Siehl, Menlo Park, CA (US); Yumin Tao, Fremont, CA (US); Henrik Albert, Alameda, CA (US); Ericka Bermudez, Aptos, CA (US); Linda A Castle, Mountain View, CA (US); Yuxia Dong, San Ramon, CA (US); Andrew Duncan Satterfield, Bear, DE (US)

(73) Assignee: PIONEER HI-BRED INTERNATIONAL, INC.

( * ) Notice: Subject to any disclaimer, the term of this patent is extended or adjusted under 35 U.S.C. 154(b) by 34 days.

This patent is subject to a terminal disclaimer.

(21) Appl. No.: 16/404,835

(22) Filed: May 7, 2019

(65) Prior Publication Data

US 2019/0271001 A1  Sep. 5, 2019

Related U.S. Application Data

(63) Continuation of application No. 15/305,457, filed as application No. PCT/US2015/028967 on May 2, 2015, now Pat. No. 10,316,326.

(60) Provisional application No. 61/987,965, filed on May 2, 2014.

(51) Int. Cl.
  *C12N 15/82* (2006.01)
  *C12N 9/02* (2006.01)
  *C12N 15/52* (2006.01)

(52) U.S. Cl.
  CPC ....... *C12N 15/8274* (2013.01); *C12N 9/0069* (2013.01); *C12N 15/52* (2013.01); *C12N 15/823* (2013.01); *C12N 15/8216* (2013.01); *C12N 15/8231* (2013.01); *C12N 15/8275* (2013.01); *C12N 15/8277* (2013.01); *C12N 15/8278* (2013.01); *C12Y 113/11027* (2013.01)

(58) Field of Classification Search
  CPC .............................................. C12N 15/8274
  See application file for complete search history.

(56) References Cited

U.S. PATENT DOCUMENTS

| | | | |
|---|---|---|---|
| 8,053,641 | B2 | 11/2011 | Andrews et al. |
| 8,993,837 | B2 | 3/2015 | Albert et al. |
| 9,139,842 | B2 | 9/2015 | Albert et al. |
| 9,187,762 | B2 | 11/2015 | Albert et al. |
| 2011/0039706 | A1 | 2/2011 | Busch et al. |
| 2012/0042413 | A1* | 2/2012 | Albert .................. C12N 15/82 800/278 |
| 2015/0275190 | A1 | 10/2015 | Albert et al. |
| 2016/0017351 | A1 | 1/2016 | Albert et al. |

FOREIGN PATENT DOCUMENTS

WO  2012021785 A1  2/2012

OTHER PUBLICATIONS

International Search Report and Written Opinion—PCT/US15/28967—dated Nov. 24, 2015.
Yang et al, Structural basis for herbicidal selectivity revealed by comparison of crystal structures of plant and mammalian 4-hydroxyphenylpyruvate dioxygenases, Biochemistry (2004) 43:10414-10423.
Lee et al., Functional Characterization of Sequence Motifs in the Transit Peptide of *Arabidopsis* Small Subunit of Rubisco, Plant Physiol. (2006) 140:466-483.
Kindle et al, Transit Peptide Mutations That Impair In vitro and in vivo Chloroplast Protein Import Do Not Affect Accumulation of the Gamma-Subunit of Chloroplast ATPase, Plant Physiol (1998) 116:1179-1190.
Chotewutmontri et al, Differential Transit Peptide Recognition During Preprotein Binding and Translocation into Flowering Plant Plastids, Plant Cell (2012) 24:3040-3059.
U.S. Appl. No. 13/208,966, filed Aug. 12, 2011, now U.S. Pat. No. 9,187,762, Granted Nov. 17, 2015.
U.S. Appl. No. 14/930,239, filed Nov. 2, 2015.
International Search Report and Written Opinion—PCT/US2011/047553, dated Jan. 19, 2012.
U.S. Appl. No. 13/209,017, filed Aug. 12, 2011, now U.S. Pat. No. 8,993,837, Granted Mar. 31, 2015.
U.S. Appl. No. 14/630,309, filed Feb. 24, 2015.
U.S. Appl. No. 13/208,960, filed Aug. 12, 2011, now U.S. Pat. No. 9,139,842, Granted Sep. 22, 2015.
U.S. Appl. No. 14/835,242, filed Aug. 25, 2015.
Skinner, M. M., & Terwilliger, T. C. (1996). Potential use of additivity of mutational effects in simplifying protein engineering. Proceedings of the National Academy of Sciences, 93(20), 10753-10757. (Year: 1996).

(Continued)

*Primary Examiner* — Weihua Fan

(57) ABSTRACT

Compositions and methods comprising polynucleotides and polypeptides having 4-hydroxyphenylpyruvate dioxygenase (HPPD) activity and having insensitivity to an HPPD inhibitor are provided. Further provided are nucleic acid constructs, plants, plant cells, explants, seeds and grain having the HPPD sequences. Various methods of employing the HPPD sequences are provided. Such methods include, for example, methods for producing an HPPD inhibitor tolerant plant, plant cell, explant or seed and methods of controlling weeds in a field containing a crop employing the plants and/or seeds disclosed herein. Methods are also provided to identify additional HPPD variants. Further provided are various methods and compositions that allow the various HPPD polypeptides and variant and fragments thereof to be expressed in a chloroplast or transported to a chloroplast.

20 Claims, 26 Drawing Sheets

Specification includes a Sequence Listing.

(56) References Cited

OTHER PUBLICATIONS

Kim, Moon-Sao, Jeremy D. Weaver, and Xin Gen Lei. "Assembly of mutations for improving thermostability of *Escherichia coli* AppA2 phytase." Applied microbiology and biotechnology 79.5 (2008): 751. (Year: 2008).

Desai, Priti N., Neeta Shrivastava, and Harish Padh. "Production of heterologous proteins in plants: strategies for optimal expression." Biotechnology advances 28.4 (2010): 427-435. (Year 2010).

Dufourmantel, Nathalie, et al. "Generation and characterization of soybean and marker-free tobacco plastid transformants over-expressing a bacterial 4-hydroxyphenylpyruvate dioxygenase which provides strong herbicide tolerance." Plant biotechnology journal 5.1 (2007): 118-133. (Year: 2007).

\* cited by examiner

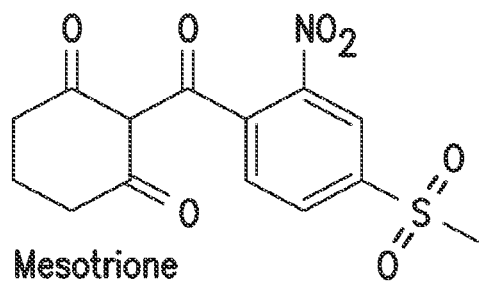
Mesotrione
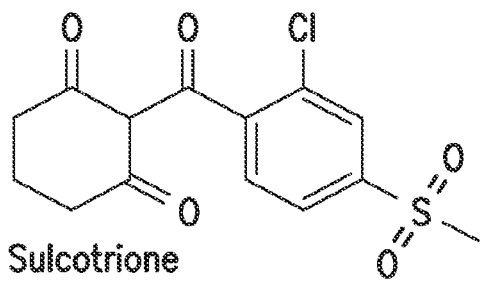
Sulcotrione
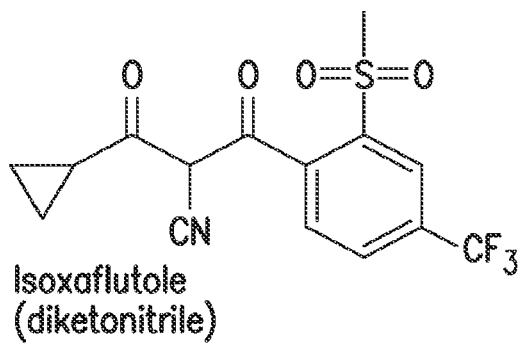
Isoxaflutole (diketonitrile)
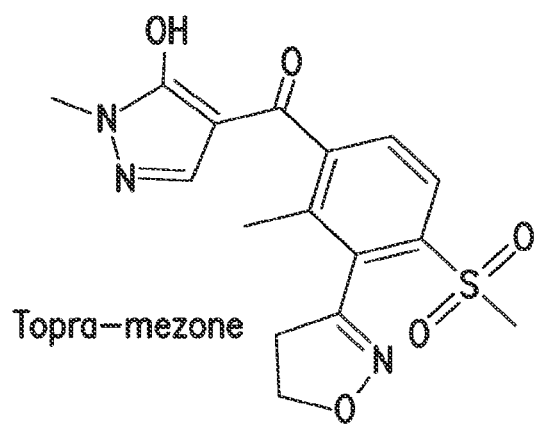
Topra-mezone
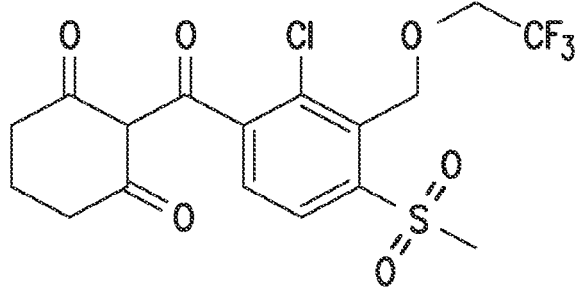
Tembotrione
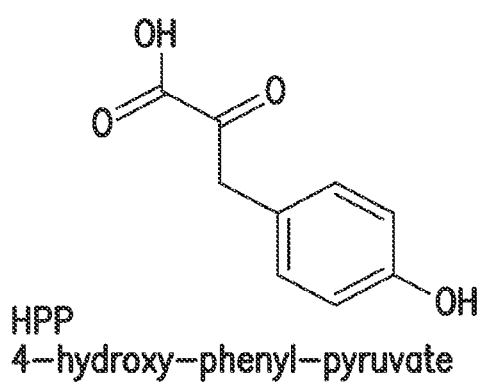
HPP
4-hydroxy-phenyl-pyruvate
FIG. 1

MGPTPTAAAAGAAVAAASAAEQAAFRLVGHRNFVRFNPRSDR
FHTLAFHHVELWCADAASAAGRFSFGLGAPLAARSDLSTGNS
AHASLLLRSGSLSFLFTAPYAHGADAATAALPSFSAAAARRF
AADHGLAVRAVALRVADAEDAFRASVAAGARPAFGPVDLGRG
FRLAEVELYGDVVLRYVSYPDGAAGEPFLPGFEGVASPGAAD
YGLSRFDHIVGNVPELAPAAAYFAGFTGFHEFAEFTTEDVGT
AESGLNSMVLANNSENVLLPLNEPVHGTKRRSQIQTFLDHHG
GPGVQHMALASDDVLRTLREMQARSAMGGFEFMAPPTSDYYD
GVRRRAGDVLTEAQIKECQELGVLVDRDDQGVLLQIFTKPVG
DRPTLFLEIIQRIGCMEKDEKGQEYQKGGCGGFGKGNFSQLF
KSIEDYEKSLEAKQAAAAAAQGS (SEQ ID NO: 1)

FIG. 3A

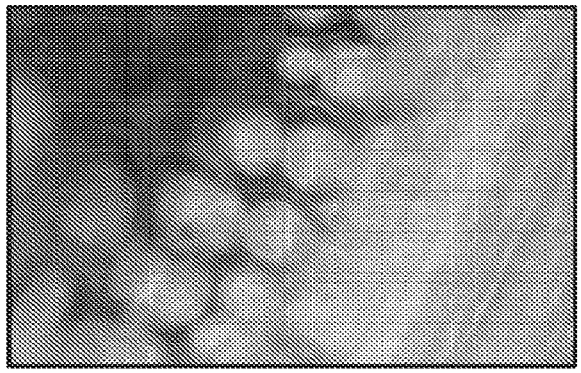

FIG. 3B

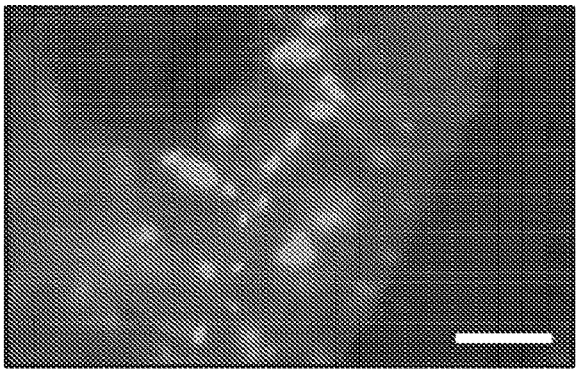

FIG. 3C

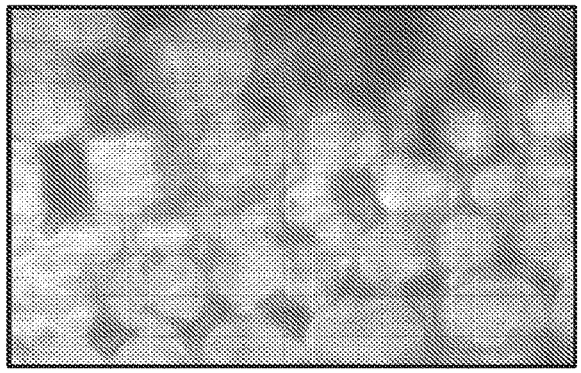

FIG. 3D

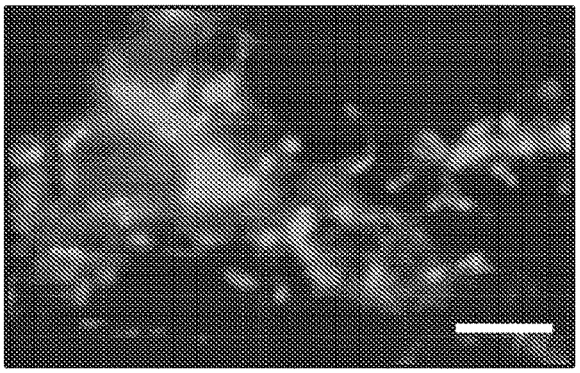

FIG. 3E

```
  1 MPMYTPSLSA PSSNHIQPSV TLPLYITTTK LNLKQQHHTT PMPIPMCNEI
 51 QAQAQAQAQP GFKLVGFKNF VRTNPKSDRF QVNRFHHIEF WCTDATNASR
101 RFSWGLGMPI VAKSDLSTGN QIHASYLLRS GDLSFLFSAP YSPSLSAGSS
151 AASSASIPSF DAATCLAFAA KHGFGVRAIA LEVADAEAAF SASVAKGAEP
201 ASPPVLVDDR TGFAEVRLYG DVVLRYVSYK DAAPQAPHAD PSRWFLPGFE
251 AAASSSSFPE LDYGIRRLDH AVGNVPELAP AVRYLKGFSG FHEFAEFTAE
301 DVGTSESGLN SVVLANNSET VLLPLNEPVY GTKRKSQIET YLEHNEGAGV
351 QHLALVTHDI FTTLREMRKR SFLGGFEFMP SPPPTYYANL HNRAADVLTV
401 DQIKQCEELG ILVDRDDQGT LLQIFTKPVG DRPTIFIEII QRIGCMVEDE
451 EGKVYQKGAC GGFGKGNFSE LFKSIEEYEK TLEAKRTA
```

FIG. 4A

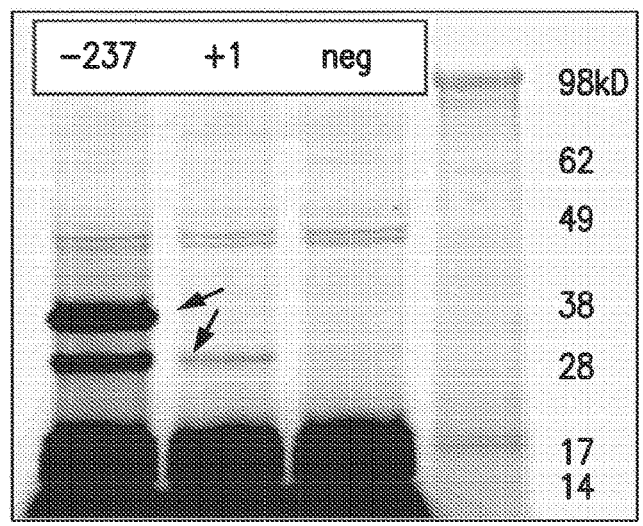

FIG. 4B

```
Gm MPMYTPSLSAPSSNHIQPSVTLPLYITTTKLNLKQQHHTTPMPIPMCNEIQAQAQAQAQP
Zm ------------------------------------MPPTPTAAAAGAAVAAASAAEQA
                                       *  *   *

Gm GFKLVGFKNFVRTNPKSDRFQVNRFHHIEFWCTDATNASRRFSWGLGMPIVAKSDLSTGN
Zm AFRLVGHRNFVRFNPRSDRFHTLAFHHVELWCADAASAAGRFSFGLGAPLAARSDLSTGN
    * ***  **** ** ****  :*** * ** **  *  *** ***  *  * *******

Gm QIHASYLLRSGDLSFLFSAPYSPSLSAGSSAASSASIPSFDAATCLAFAAKHGFGVRAIA
Zm SAHASLLLRSGSLSFLFTAPY-----AHGADAATAALPSFSAAAARRFAADHGLAVRAVA
    ***** ***** ***    *         *    *** **    *** **    *** *

Gm LEVADAEAAFSASVAKGAEPASPPVLVDDRTGFAEVRLYGDVVLRYVSYKDAAPQAPHAD
Zm LRVADAEDAFRASVAAGARPAFGPVDLGRGFRLAEVELYGDVVLRYVSYPDGAAGEP---
   * ***** ** **** **  **  **      *** ************ *    *

Gm PSRWFLPGFEAAASSSSFPELDYGIRRLDHAVGNVPELAPAVRYLKGFSGFHEFAEFTAE
Zm ----FLPGFEGVASPG---AADYGLSRFDHIVGNVPELAPAAAYFAGFTGFHEFAEFTTE
       ******   **      *** * ** ********** **  ** ********* *

Gm DVGTSESGLNSVVLANNSETVLLPLNEPVYGTKRKSQIETYLEHNEGAGVQHLALVTHDI
Zm DVGTAESGLNSMVLANNSENVLLPLNEPVHGTKRRSQIQTFLDHHGGPGVQHMALASDDV
   **** ****** ******* ******** **** ***  *  *    **** **     *

Gm FTTLREMRKRSFLGGFEFMPSPPPTYYANLHNRAADVLTVDQIKQCEELGILVDRDDQGT
Zm LRTLREMQARSAMGGFEFMAPPTSDYYDGVRRRAGDVLTEAQIKECQELGVLVDRDDQGV
    *****  ***  ****** **  ***    **   ****  **** ***** *******

Gm LLQIFTKPVGDRPTIFIEIIQRIGCMVEDEEGKVYQKGACGGFGKGNFSELFKSIEEYEK
   LLQIFTKPVGDRPTLFLEIIQRIGCMEKDEKGQEYQKGGCGGFGKGNFSQLFKSIEDYEK
   ************** * *********  *  *  **** ********* ****** ***

Gm TLEAKRTA--------
Zm SLEAKQAAAAAAQGS
     ****  *
```

FIG. 4F

TCAAGATGAGGATGATCCTCTTGTGTTAGTGTGTTTGATTGTTCTTTATAGTTTATACCTAATTT
TATCTATATAAGCTTATTAAATTAAATTATGTGCAATAGTGACCCCTGATCTTCTGTAATTAT
CATTCAATAGCTGTAGTCATTTGTTTCCAATTGTAACCGTAGCCAAGATGTACGGTGGCATAA
ACCTTGGAGATATTTTGTTCTCTCTTCCCTTCATAGAGGACAACCTTCATGTAATGGACATACT
AACGACAATTAAATTATTTATTCATTTAAAAGATTAAATATTTTCTTAAATTATTCCTGTGC
TTTAAATTCTTAACAGAAAATTTAAAATTAGACATTGTACCATTAGAGAAAACTGTGGGAC
TCATTGTTTATTAGATTATTTCAGCTAGCAACTGACTCTCTTGTACATTTCATTTTTACATTC
CTTTAATTATGCATCATTAACAGTAGTAGATTGCATCTCTTAAAAAAAATTAGATTGCAGTA
TTGCCTTGGAAATATGGAATTACAATGTCAAAATATTTTAACGAATAACGATGCGTAGCTTAAA
GTTCAAGACACAATTTTAACGTTATATAGTGCATGTTTGAAATTTTAGTGTATAAATAAC
GTATTTTGATAATATTTTCTTATCTTTTACACAATCCTCTAAATTTCTTATCTTATTCATTTAAC
CGTTCTCTTAAATTGTCTTAACTTTAGGAACCAAATATATAAATAATTTTTTTTTTTCATTAAC
TATTTGAGTTCTTAACTTTAGGAACCAAATGTGATAAGGCAAGAAGCGTGAACAAGAGAGACGAAT
ATAAATATAGAAGAGAAAAGGATGTGATAAGTGTGAATATAAGTAATAACGCTGAGCGTGAGGT
CTAGGTGGATTTGACGTACGTGAATGAATGTTGAATATAAGTAATAACGCTGAGCGTGAGGT
GTGGTAATAAAAAGAGAGAAGAGCCATCAACATCATCCAATATATGACGTTAAAGAGCG
TCGTAATCCATTTCCATTTCTCATCTATCTTCACTTCCTCGTCCTCATCCTCATCCACCTATTC
                                         M  P  M  Y  T  P  S  L  S  A  P  S  S  N  H  I
TCAACCCAGACGCAATGCCAATGCCCATGTACACTCCCATCTCCGCACTCCGATCCTCCAATCACATTCA

Q  P  S  V  T  L  P  L  Y  I  T  T  K  L  N  L  K  Q  Q  H  H
ACCAAGTGTCACACTCCCCCTTATATATCACAACCACCAAGCTCAATCTCAGCAGCATCAC

T  T  P  M  P  I  P  M  C  N  E  I  Q  A  Q  A  Q  A  Q
ACCACACCAATGCCAATACCCATGTGCAACGAAATTCAAGCCCAAGCCCAAGCCCAAGC

FIG. 8A

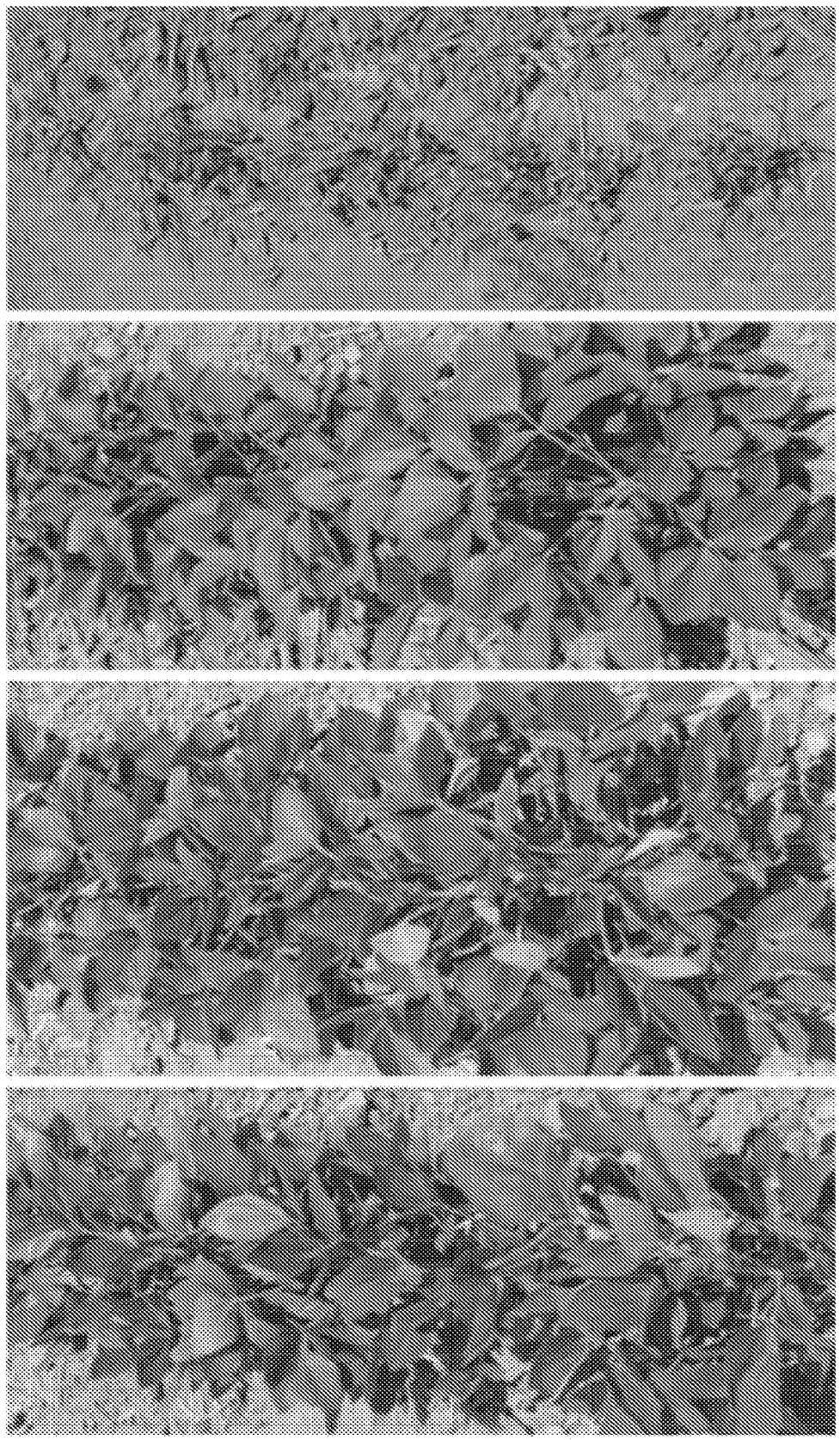

| MUT ID NO. | MUTA-TION | Kinetic parameters | | | Insensitivity parameter, ON x OFF | | | | |
|---|---|---|---|---|---|---|---|---|---|
| | | $k_{cat}$, min$^{-1}$ | $K_M$ (uM) | $k_{cat}/K_M$ | Tembo | Meso | Sulco | Isox(DKN) | Topra |
| 386 | 366E | 38.8 | 1.61 | 24.1 | 0.33 | 0.78 | 0.74 | 0.44 | 0.48 |
| 506 | 417Q | 33.5 | 1.56 | 21.5 | 0.33 | 0.73 | 0.74 | 0.39 | 0.39 |
| 549 | 432R | 56.7 | 1.97 | 28.8 | 0.23 | 0.53 | 0.59 | 0.27 | 0.31 |
| 505 | 432K | 67.5 | 2.08 | 32.4 | 0.21 | 0.52 | 0.59 | 0.26 | 0.29 |
| 421 | 417S | 26.7 | 1.41 | 18.9 | 0.33 | 0.67 | 0.77 | 0.41 | 0.41 |
| 230 | 214N | 84.6 | 3.62 | 23.4 | 0.25 | 0.48 | 0.59 | 0.33 | 0.32 |
| 547 | 385I | 46.1 | 2.29 | 20.1 | 0.28 | 0.56 | 0.70 | 0.41 | 0.38 |
| 270 | 158K | 47.1 | 2.49 | 18.9 | 0.29 | 0.54 | 0.63 | 0.38 | 0.37 |
| 420 | 385V | 30.3 | 1.91 | 15.9 | 0.34 | 0.65 | 0.78 | 0.33 | 0.49 |
| 61 | 191G | 71.7 | 2.46 | 29.1 | 0.19 | 0.40 | 0.51 | 0.25 | 0.24 |
| 375 | 211L | 77.6 | 3.2 | 24.2 | 0.22 | 0.37 | 0.47 | 0.25 | 0.27 |
| 374 | 340K | 73.5 | 2.41 | 30.5 | 0.16 | 0.44 | 0.54 | 0.23 | 0.22 |
| 345 | 206Q | 66.6 | 2.63 | 25.3 | 0.19 | 0.46 | 0.53 | 0.26 | 0.27 |
| 426 | 214T | 84.2 | 2.94 | 28.6 | 0.17 | 0.41 | 0.50 | 0.21 | 0.23 |
| 263 | 360L | 32.6 | 1.71 | 19.0 | 0.25 | 0.51 | 0.63 | 0.34 | 0.32 |
| 567 | 434H | 84.5 | 2.77 | 30.5 | 0.15 | 0.46 | 0.55 | 0.21 | 0.22 |

FIG. 15

| | | | | | | | | | |
|---|---|---|---|---|---|---|---|---|---|
| 231 | 387L | 74.3 | 2.46 | 30.2 | 0.15 | 0.46 | 0.56 | 0.26 | 0.21 |
| 564 | 356K | 65.8 | 2.6 | 25.3 | 0.18 | 0.48 | 0.55 | 0.25 | 0.23 |
| 170 | 356R | 79.0 | 2.89 | 27.3 | 0.16 | 0.44 | 0.53 | 0.21 | 0.24 |
| 166 | 182M | 56.1 | 2.88 | 19.5 | 0.23 | 0.44 | 0.60 | 0.30 | 0.29 |
| 135 | 434R | 80.9 | 2.74 | 29.5 | 0.15 | 039 | 0.47 | 0.18 | 0.22 |
| 434 | 206S | 67.9 | 3.36 | 20.2 | 0.20 | 0.46 | 0.53 | 0.29 | 0.29 |
| 353 | 191L | 32.9 | 2.74 | 12.0 | 0.33 | 0.45 | 0.56 | 0.38 | 0.37 |
| 273 | 227G | 45.3 | 2.61 | 17.4 | 0.22 | 0.52 | 0.63 | 0.26 | 0.28 |
| 541 | 390N | 50.2 | 2.86 | 17.5 | 0.20 | 0.45 | 0.58 | 0.29 | 0.27 |
| 147 | 342V | 54.2 | 2.59 | 20.9 | 0.17 | 0.42 | 0.51 | 0.22 | 0.23 |
| 292 | 431F | 30.8 | 1.77 | 17.4 | 0.19 | 0.53 | 0.59 | 0.26 | 0.27 |
| 379 | 189P | 41.8 | 3.35 | 12.5 | 0.25 | 0.51 | 0.62 | 0.32 | 0.31 |
| 224 | 205T | 34.4 | 2.72 | 12.6 | 0.22 | 0.47 | 0.60 | 0.30 | 0.29 |
| 407 | 376W | 36.1 | 5.51 | 6.5 | 0.31 | 0.39 | 0.16 | 0.37 | 0.32 |
| 2 | 9070 | 55.1 | 2.35 | 23.4 | 0.19 | 0.45 | 0.56 | 0.24 | 0.26 |
| 1 | Mz wt | 219 | 6.4 | 34.2 | 0.0051 | 0.0437 | 0.0872 | 0.0096 | 0.0154 |

FIG. 15 (continued)

| MUT ID | MUTA- | Trait fitness, ON x OFF x $k_{cat}/K_M$ | | | | Trait fitness, fold vs maize wt | | | | |
|---|---|---|---|---|---|---|---|---|---|---|
| NO. | TION | Tembo | Meso | Sulco | Isox(DKN) | Topra | Tembo | Meso | Sulco | ISOX (DKN) | Topra |
| 386 | 366E | 8.0 | 18.7 | 17.8 | 10.6 | 11.6 | 46.1 | 12.6 | 6.0 | 32.5 | 22.1 |
| 506 | 417Q | 7.0 | 15.8 | 15.8 | 8.4 | 8.4 | 40.2 | 10.6 | 5.3 | 25.7 | 16.0 |
| 549 | 432R | 6.7 | 15.2 | 17.0 | 7.8 | 8.8 | 38.6 | 10.2 | 5.7 | 23.7 | 16.8 |
| 505 | 432K | 6.7 | 17.0 | 19.2 | 8.5 | 9.4 | 38.5 | 11.4 | 6.4 | 25.8 | 17.9 |
| 421 | 417S | 6.2 | 12.6 | 14.5 | 7.7 | 7.8 | 35.6 | 8.5 | 4.9 | 23.4 | 14.9 |
| 230 | 214N | 5.8 | 11.2 | 13.8 | 7.6 | 7.5 | 33.2 | 7.5 | 4.6 | 23.2 | 14.2 |
| 547 | 385I | 5.6 | 11.4 | 14.2 | 8.2 | 7.6 | 32.3 | 7.6 | 4.8 | 24.9 | 14.5 |
| 270 | 158K | 5.5 | 10.3 | 12.0 | 7.1 | 7.1 | 31.3 | 6.9 | 4.0 | 21.7 | 13.5 |
| 420 | 385V | 5.4 | 10.3 | 12.4 | 5.2 | 7.8 | 31.1 | 6.9 | 4.2 | 15.9 | 14.8 |
| 61 | 191G | 5.4 | 11.7 | 14.9 | 7.2 | 6.9 | 31.0 | 7.9 | 5.0 | 22.0 | 13.1 |
| 375 | 211L | 5.4 | 9.1 | 11.5 | 6.1 | 6.5 | 30.9 | 6.1 | 3.8 | 18.6 | 12.4 |
| 374 | 340K | 5.0 | 13.3 | 16.4 | 7.0 | 6.7 | 28.5 | 8.9 | 5.5 | 21.3 | 12.7 |
| 345 | 206Q | 4.9 | 11.6 | 13.4 | 6.7 | 6.7 | 28.3 | 7.8 | 4.5 | 20.4 | 12.8 |
| 426 | 214T | 4.8 | 11.7 | 14.3 | 6.1 | 6.5 | 27.5 | 7.8 | 4.8 | 18.5 | 12.4 |

FIG. 15 (continued)

| | | | | | | | | | |
|---|---|---|---|---|---|---|---|---|---|
| 263 | 360L | 4.8 | 9.7 | 12.0 | 6.5 | 6.0 | 27.4 | 6.5 | 4.0 | 19.8 | 11.5 |
| 567 | 434H | 4.7 | 14.1 | 16.7 | 6.5 | 6.7 | 27.0 | 9.4 | 5.6 | 19.9 | 12.8 |
| 231 | 387L | 4.7 | 14.0 | 17.0 | 7.8 | 6.5 | 26.8 | 9.4 | 5.7 | 23.7 | 12.3 |
| 564 | 356K | 4.5 | 12.2 | 13.9 | 6.3 | 5.8 | 25.9 | 8.2 | 4.7 | 19.1 | 11.0 |
| 170 | 356R | 4.5 | 11.9 | 14.4 | 5.7 | 6.5 | 25.8 | 8.0 | 4.8 | 17.5 | 12.4 |
| 166 | 182M | 4.5 | 8.7 | 11.7 | 5.9 | 5.7 | 25.8 | 5.8 | 3.9 | 18.1 | 10.8 |
| 135 | 434R | 4.3 | 11.4 | 13.9 | 5.4 | 6.5 | 24.9 | 7.6 | 4.7 | 16.6 | 12.4 |
| 434 | 206S | 4.1 | 9.4 | 10.7 | 5.9 | 6.0 | 23.7 | 6.3 | 3.6 | 18.1 | 11.3 |
| 353 | 191L | 3.9 | 5.4 | 6.7 | 4.5 | 4.4 | 22.6 | 3.6 | 2.3 | 13.8 | 8.4 |
| 273 | 227G | 3.7 | 9.0 | 10.9 | 4.5 | 4.9 | 21.5 | 6.0 | 3.7 | 13.9 | 9.3 |
| 541 | 390N | 3.5 | 7.9 | 10.1 | 5.2 | 4.7 | 20.2 | 5.3 | 3.4 | 15.8 | 8.9 |
| 147 | 342V | 3.5 | 8.7 | 10.6 | 4.6 | 4.7 | 20.1 | 5.9 | 3.5 | 14.0 | 9.0 |
| 292 | 431F | 3.4 | 9.2 | 10.3 | 4.6 | 4.7 | 19.4 | 6.2 | 3.5 | 13.9 | 8.9 |
| 379 | 189P | 3.1 | 6.3 | 7.7 | 4.0 | 3.9 | 17.8 | 4.3 | 2.6 | 12.1 | 7.4 |
| 224 | 205T | 2.8 | 6.0 | 7.6 | 3.8 | 3.7 | 15.9 | 4.0 | 2.5 | 11.5 | 7.0 |
| 407 | 376W | 2.1 | 2.5 | 1.1 | 2.4 | 2.1 | 11.9 | 1.7 | 0.4 | 7.5 | 3.9 |
| 2 | 9070 | 4.4 | 10.5 | 13.0 | 5.6 | 6.2 | 25.5 | 7.0 | 4.4 | 17.2 | 11.7 |
| 1 | Mz wt | 0.174 | 1.494 | 2.981 | 0.328 | 0.525 | 1.0 | 1.0 | 1.0 | 1.0 | 1.0 |

FIG. 15 (continued)

SEQUENCE LISTING

<160> NUMBER OF SEQ ID NOS: 108

<210> SEQ ID NO 1

```
<211> LENGTH: 444
<212> TYPE: PRT
<213> ORGANISM: Zea mays

<400> SEQUENCE: 1

Met Gly Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
    290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Gln Gly Val
        355                 360                 365

Leu Leu Gln Ile Phe Thr Lys Pro Val Gly Asp Arg Pro Thr Leu Phe
    370                 375                 380

Leu Glu Ile Ile Gln Arg Ile Gly Cys Met Glu Lys Asp Glu Lys Gly
```

```
               385                 390                 395                 400
    Gln Glu Tyr Gln Lys Gly Gly Cys Gly Gly Phe Gly Lys Gly Asn Phe
                    405                 410                 415

Ser Gln Leu Phe Lys Ser Ile Glu Asp Tyr Glu Lys Ser Leu Glu Ala
                    420                 425                 430

Lys Gln Ala Ala Ala Ala Ala Ala Gln Gly Ser
                    435                 440

<210> SEQ ID NO 2
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 2

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
                    20                  25                  30

Phe Val Arg Phe Asn Pro Arg Ser Asp Arg Phe Gln Thr Leu Ala Phe
                35                  40                  45

His His Val Glu Leu Trp Cys Ala Asp Ala Ala Ser Ala Ala Gly Arg
            50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                    85                  90                  95

Ser Leu Leu Phe Thr Ala Pro Tyr Ala His Gly Ala Asp Ala Ala Thr
                    100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
                130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Val Ala Ser Pro Gly Ala
                195                 200                 205

Ala Asp Tyr Gly Leu Ser Arg Phe Asp His Ile Val Gly Asn Val Pro
            210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                    245                 250                 255

Leu Asn Ser Met Ala Leu Ala Asn Asn Ser Glu Asn Val Leu Leu Pro
                    260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
            290                 295                 300
```

```
Ser Asp Asp Val Leu Arg Thr Leu Arg Glu Met Ala Arg Ser Ala
305                 310                 315                 320

Met Gly Gly Phe Glu Phe Leu Pro Pro Leu Ser Asp Tyr Tyr Asp
            325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Gln Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 3
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 3

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
            85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
    115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Gly Ala Ala
            180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
    210                 215                 220
```

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Ala Thr Ala Gln Gly Ser
                435                 440

<210> SEQ ID NO 4
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 4

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala

```
            130                 135                 140
Glu Asp Ala Phe Arg Ala Ser Val Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
        210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
        290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
        370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Lys Gly Asn Phe
                405                 410                 415

Gly Gln Leu Phe Lys Ser Ile Glu Asp Tyr Gly Lys Ser Leu Glu Ala
            420                 425                 430

Lys Arg Ala Ala Ala Ala Thr Ala Gln Gly Ser
                435                 440

<210> SEQ ID NO 5
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 5

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45
```

His His Val Glu Leu Trp Cys Ala Asp Ala Ala Ser Ala Ala Gly Arg
 50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Arg Ser Gly Ser Leu
                 85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
                195                 200                 205

Ala Asp Tyr Gly Leu Ser Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Glu Gly Val
                355                 360                 365

Leu Leu Gln Ile Phe Thr Lys Pro Val Gly Asp Arg Pro Thr Phe Phe
370                 375                 380

Leu Glu Leu Ile Gln Arg Ile Gly Cys Met Glu Lys Asp Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Arg Ala Ala Ala Ala Thr Ala Gln Gly Ser
                435                 440

<210> SEQ ID NO 6
<211> LENGTH: 444
<212> TYPE: PRT

<213> ORGANISM: Artificial Sequence
<220> FEATURE:
<223> OTHER INFORMATION: Zea mays variant form created by artificial means.

<400> SEQUENCE: 6

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380
```

-continued

```
Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
        420                 425                 430

Lys Gln Ala Ala Ala Ala Thr Ala Gln Gly Ser
        435                 440

<210> SEQ ID NO 7
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 7

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Leu Gly Leu Asn Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300
```

```
Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
            325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Lys
            420                 425                 430

Lys Arg Ala Ala Ala Ala Ala Thr Ala Gln Gly Ser
            435                 440

<210> SEQ ID NO 8
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 8

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Leu Gly Leu Asn Arg Phe Asp His Ile Val Gly Asn Val Pro
```

```
                210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Glu Gly Val
                355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Arg Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Lys
                420                 425                 430

Lys Arg Ala Ala Ala Ala Thr Ala Gln Gly Ser
                435                 440

<210> SEQ ID NO 9
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 9

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
                35                  40                  45

His His Val Glu Leu Trp Cys Ala Asp Ala Ala Ser Ala Ala Gly Arg
                50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
                115                 120                 125
```

```
Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Val Ala Ser Ser Gly Ala
        195                 200                 205

Ala Asp Tyr Gly Leu Ser Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Lys Leu Gly Val Met Val Asp Arg Asp Glu Gly Val
        355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Arg Ser Leu Glu Ala
            420                 425                 430

Lys Gln Ala Ala Ala Val Ala Thr Ala Gln Gly Ser
        435                 440

<210> SEQ ID NO 10
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 10

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45
```

His His Val Glu Leu Trp Cys Ala Asp Ala Ala Ser Ala Ala Gly Arg
 50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Arg Ser Gly Ser Leu
                 85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
                180                 185                 190

Gly Glu Pro Phe Leu Pro Gly Phe Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Arg Ser Ile Glu Asp Tyr Glu Lys Ser Leu Glu Ala
            420                 425                 430

Lys Arg Ala Ala Ala Ala Thr Ala Gln Gly Ser
            435                 440

<210> SEQ ID NO 11
<211> LENGTH: 444

```
<212> TYPE: PRT
<213> ORGANISM: Artificial Sequence
<220> FEATURE:
<223> OTHER INFORMATION: Zea mays variant form created by artificial
      means.

<400> SEQUENCE: 11
```

| | | | | | | | | | | | | | | | |
|---|---|---|---|---|---|---|---|---|---|---|---|---|---|---|---|
| Met | Gly | Pro | Thr | Pro | Thr | Ala | Thr | Ala | Ala | Gly | Ala | Ala | Val | Ala | Ala |
| 1 | | | | 5 | | | | | 10 | | | | | 15 | |
| Ala | Ser | Ala | Ala | Glu | Gln | Ala | Ala | Phe | Arg | Leu | Val | Gly | His | Arg | Asn |
| | | | 20 | | | | | 25 | | | | | 30 | | |
| Phe | Val | Arg | Phe | Asn | Pro | Arg | Ser | Asp | Arg | Phe | Gln | Thr | Leu | Ala | Phe |
| | | 35 | | | | | 40 | | | | | 45 | | | |
| His | His | Val | Glu | Leu | Trp | Cys | Ala | Asp | Ala | Ala | Ser | Ala | Ala | Gly | Arg |
| | 50 | | | | | 55 | | | | | 60 | | | | |
| Phe | Ser | Phe | Ala | Leu | Gly | Val | Pro | Leu | Ala | Ala | Arg | Ser | Asp | Leu | Ser |
| 65 | | | | | 70 | | | | | 75 | | | | | 80 |
| Thr | Gly | Asn | Ser | Ala | His | Ala | Ser | Leu | Leu | Leu | Arg | Ser | Gly | Ser | Leu |
| | | | | 85 | | | | | 90 | | | | | 95 | |
| Ser | Leu | Leu | Phe | Thr | Ala | Pro | Tyr | Ala | His | Gly | Ala | Asp | Ala | Ala | Thr |
| | | | 100 | | | | | 105 | | | | | 110 | | |
| Ala | Ala | Leu | Pro | Ser | Phe | Ser | Ala | Ala | Ala | Arg | Arg | Phe | Ala | Ala |
| | | 115 | | | | | 120 | | | | | 125 | | | |
| Asp | His | Gly | Leu | Ala | Val | Arg | Ala | Val | Ala | Leu | Arg | Val | Ala | Asp | Ala |
| | 130 | | | | | 135 | | | | | 140 | | | | |
| Glu | Asp | Ala | Phe | Arg | Ala | Ser | Val | Ala | Ala | Gly | Ala | Arg | Pro | Ala | Phe |
| 145 | | | | | 150 | | | | | 155 | | | | | 160 |
| Gly | Pro | Val | Asp | Leu | Gly | Arg | Gly | Phe | Arg | Leu | Ala | Glu | Val | Glu | Leu |
| | | | | 165 | | | | | 170 | | | | | 175 | |
| Tyr | Gly | Asp | Val | Val | Leu | Arg | Tyr | Val | Ser | Tyr | Pro | Asp | Gly | Gly | Ala |
| | | | 180 | | | | | 185 | | | | | 190 | | |
| Gly | Glu | Pro | Phe | Leu | Pro | Gly | Phe | Glu | Gly | Val | Ala | Ser | Pro | Gly | Ala |
| | | 195 | | | | | 200 | | | | | 205 | | | |
| Ala | Asp | Tyr | Gly | Leu | Ser | Arg | Phe | Asp | His | Ile | Val | Gly | Asn | Val | Pro |
| | 210 | | | | | 215 | | | | | 220 | | | | |
| Glu | Leu | Ala | Pro | Ala | Ala | Ala | Tyr | Met | Ala | Gly | Phe | Thr | Gly | Phe | His |
| 225 | | | | | 230 | | | | | 235 | | | | | 240 |
| Glu | Phe | Ala | Glu | Phe | Thr | Thr | Glu | Asp | Val | Gly | Thr | Thr | Glu | Ser | Gly |
| | | | | 245 | | | | | 250 | | | | | 255 | |
| Leu | Asn | Ser | Met | Ala | Leu | Ala | Asn | Asn | Ser | Glu | Asn | Val | Leu | Leu | Pro |
| | | | 260 | | | | | 265 | | | | | 270 | | |
| Leu | Asn | Glu | Pro | Val | His | Gly | Thr | Lys | Arg | Arg | Ser | Gln | Ile | Gln | Thr |
| | | 275 | | | | | 280 | | | | | 285 | | | |
| Phe | Leu | Asp | His | His | Gly | Gly | Pro | Gly | Val | Gln | His | Ile | Ala | Leu | Ala |
| | 290 | | | | | 295 | | | | | 300 | | | | |
| Ser | Asp | Asp | Val | Leu | Arg | Thr | Leu | Arg | Glu | Met | Arg | Ala | Arg | Ser | Ala |
| 305 | | | | | 310 | | | | | 315 | | | | | 320 |
| Met | Gly | Gly | Phe | Glu | Phe | Leu | Pro | Pro | Leu | Ser | Asp | Tyr | Tyr | Asp |
| | | | | 325 | | | | | 330 | | | | | 335 | |
| Gly | Val | Arg | Lys | Cys | Ala | Gly | Asp | Val | Leu | Thr | Glu | Ala | Gln | Ile | Asn |
| | | | 340 | | | | | 345 | | | | | 350 | | |
| Glu | Cys | Gln | Glu | Leu | Gly | Val | Met | Val | Asp | Arg | Asp | Asp | Glu | Gly | Val |
| | | 355 | | | | | 360 | | | | | 365 | | | |
| Leu | Leu | Gln | Ile | Phe | Thr | Lys | Pro | Val | Gly | Asp | Arg | Pro | Thr | Phe | Phe |
| | 370 | | | | | 375 | | | | | 380 | | | | |

```
Leu Glu Ile Ile Gln Arg Ile Gly Cys Met Glu Lys Asp Glu Lys Gly
385                 390                 395                 400

Gln Glu Tyr Gln Lys Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
            420                 425                 430

Lys Arg Ala Ala Ala Ala Thr Ala Gln Gly Ser
        435                 440

<210> SEQ ID NO 12
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 12

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Leu Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
```

```
                290                 295                 300
Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Asp Glu Gly Val
                355                 360                 365

Leu Leu Gln Ile Phe Thr Lys Pro Val Gly Asp Arg Pro Thr Phe Phe
                370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440

<210> SEQ ID NO 13
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 13

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
                35                  40                  45

His His Val Glu Leu Trp Cys Ala Asp Ala Ala Ser Ala Ala Gly Arg
                50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
                130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
                195                 200                 205
```

```
Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Lys Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Arg Ala Ala Ala Ala Thr Ala Gln Gly Ser
        435                 440

<210> SEQ ID NO 14
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 14

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125
```

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Ser Gly Ala
                195                 200                 205

Ala Asp Tyr Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Glu Gly Val
                355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys His Ala Ala Ala Ala Ala Thr Ala Gln Gly Ser
                435                 440

<210> SEQ ID NO 15
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 15

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe

```
            35                  40                  45
His His Val Glu Leu Trp Cys Ala Asp Ala Ala Ser Ala Ala Gly Arg
 50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Leu Arg Ser Gly Ser Leu
                 85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Ser Gly Ala
            195                 200                 205

Ala Asp Leu Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
            370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 16
```

<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 16

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Ser Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe

```
                 370                 375                 380
Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440

<210> SEQ ID NO 17
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 17

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
        210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
            275                 280                 285
```

-continued

```
Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Arg Leu Gly Val Met Val Asp Arg Asp Glu Gly Val
            355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Cys Gly Gly Phe Gly Lys Gly Asn Phe
                405                 410                 415

Gly Gln Leu Phe Lys Ser Ile Glu Asp Tyr Gln Lys Ser Leu Glu Ala
                420                 425                 430

Lys Arg Ala Ala Ala Ala Ala Thr Ala Gln Gly Ser
            435                 440

<210> SEQ ID NO 18
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 18

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Pro Gly Ala
        195                 200                 205
```

Ala Asp Leu Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Arg
            420                 425                 430

Lys Arg Ala Ala Ala Ala Thr Ala Gln Gly Ser
        435                 440

<210> SEQ ID NO 19
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 19

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Ala Arg Arg Phe Ala Ala

```
                  115                 120                 125
Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Arg Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
        435                 440

<210> SEQ ID NO 20
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 20

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
                20                  25                  30
```

```
Phe Val Arg Phe Asn Pro Arg Ser Asp Arg Phe Gln Thr Leu Ala Phe
             35                  40                  45

His His Val Glu Leu Trp Cys Ala Asp Ala Ala Ser Ala Ala Gly Arg
 50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Leu Arg Ser Gly Ser Leu
                 85                  90                  95

Ser Leu Leu Phe Thr Ala Pro Tyr Ala His Gly Ala Asp Ala Ala Thr
             100                 105                 110

Ala Ala Leu Pro Ser Phe Ser Ala Ala Ala Arg Arg Phe Ala Ala
             115                 120                 125

Asp His Gly Leu Ala Val Arg Ala Val Ala Leu Arg Val Ala Asp Ala
         130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                 165                 170                 175

Tyr Gly Asp Val Val Met Arg Tyr Val Ser Tyr Pro Asp Gly Ala Ala
             180                 185                 190

Gly Glu Pro Phe Leu Pro Gly Phe Glu Gly Val Ala Ser Gln Gly Ala
         195                 200                 205

Ala Asp Tyr Gly Leu Ser Arg Phe Asp His Ile Val Gly Asn Val Pro
         210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
             245                 250                 255

Leu Asn Ser Met Ala Leu Ala Asn Asn Ser Glu Asn Val Leu Leu Pro
             260                 265                 270

Leu Asn Glu Pro Val Arg Gly Thr Lys Arg Arg Ser Gln Ile Gln Thr
         275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
             325                 330                 335

Gly Val Arg Lys Cys Ala Gly Asp Val Leu Thr Glu Ala Gln Ile Asn
             340                 345                 350

Glu Cys Gln Glu Leu Gly Val Met Val Asp Arg Asp Glu Gly Val
         355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
             405                 410                 415

Gly Gln Leu Phe Lys Ser Ile Glu Asp Tyr Glu Lys Ser Leu Glu Ala
             420                 425                 430

Lys Gln Ala Ala Ala Thr Ala Thr Ala Gln Gly Ser
             435                 440
```

<210> SEQ ID NO 21
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 21

```
Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Met Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Asn Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365
```

-continued

```
Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
        420                 425                 430

Lys Gln Ala Ala Ala Ala Thr Ala Gln Gly Ser
        435                 440

<210> SEQ ID NO 22
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 22

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285
```

```
Phe Leu Asp His His Gly Gly Pro Gly Val Gln His Ile Ala Leu Ala
        290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Asp Val Arg Arg Cys Ala Gly Asp Val Leu Thr Glu Ala Gln Ile Asn
                340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Val Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Arg Ala Ala Ala Ala Thr Ala Gln Gly Ser
        435                 440
```

<210> SEQ ID NO 23
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 23

```
Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Gln Gly Ala
```

```
                195                 200                 205
Ala Asp Leu Gly Leu Ser Arg Phe Asp His Ile Val Gly Asn Val Pro
    210                 215                 220
Glu Leu Ala Pro Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
                245                 250                 255
Leu Asn Ser Met Ala Leu Ala Asn Asn Ser Glu Asn Val Leu Leu Pro
            260                 265                 270
Leu Asn Glu Pro Val His Gly Thr Lys Arg Arg Ser Gln Ile Gln Thr
        275                 280                 285
Phe Leu Asp His His Gly Gly Pro Gly Val Gln His Ile Ala Leu Ala
    290                 295                 300
Ser Asp Asp Val Leu Arg Thr Leu Arg Glu Met Arg Ala Arg Ser Ala
305                 310                 315                 320
Met Gly Gly Phe Glu Phe Leu Pro Pro Pro Leu Ser Asp Tyr Tyr Asp
                325                 330                 335
Gly Val Arg Arg Cys Ala Gly Asp Val Leu Thr Glu Ala Gln Ile Asn
            340                 345                 350
Glu Cys Gln Lys Leu Gly Val Met Val Asp Arg Asp Glu Gly Val
        355                 360                 365
Leu Leu Gln Ile Phe Thr Lys Pro Val Gly Asp Arg Pro Thr Phe Phe
    370                 375                 380
Leu Glu Ile Ile Gln Arg Ile Gly Cys Met Glu Lys Asp Glu Lys Gly
385                 390                 395                 400
Gln Glu Tyr Gln Lys Gly Gly Cys Gly Gly Phe Gly Lys Gly Asn Phe
                405                 410                 415
Gly Gln Leu Phe Lys Ser Ile Glu Asp Tyr Glu Lys Ser Leu Glu Ala
            420                 425                 430
Lys Gln Ala Ala Ala Ala Ala Thr Ala Gln Gly Ser
        435                 440
```

<210> SEQ ID NO 24
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 24

```
Met Gly Pro Thr Pro Thr Ala Thr Ala Ala Gly Ala Ala Val Ala Ala
1               5                   10                  15
Ala Ser Ala Ala Glu Gln Ala Ala Phe Arg Leu Val Gly His Arg Asn
            20                  25                  30
Phe Val Arg Phe Asn Pro Arg Ser Asp Arg Phe Gln Thr Leu Ala Phe
        35                  40                  45
His His Val Glu Leu Trp Cys Ala Asp Ala Ala Ser Ala Ala Gly Arg
    50                  55                  60
Phe Ser Phe Ala Leu Gly Val Pro Leu Ala Ala Arg Ser Asp Leu Ser
65                  70                  75                  80
Thr Gly Asn Ser Ala His Ala Ser Leu Leu Leu Arg Ser Gly Ser Leu
                85                  90                  95
Ser Leu Leu Phe Thr Ala Pro Tyr Ala His Gly Ala Asp Ala Ala Thr
            100                 105                 110
```

```
Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Gly Lys Ser Leu Glu Ala
            420                 425                 430

Lys Gln Ala Ala Ala Ala Thr Ala Gln Gly Ser
        435                 440

<210> SEQ ID NO 25
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 25

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30
```

```
Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
 50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Arg Ser Gly Ser Leu
                 85                  90                  95

Ser Leu Leu Phe Thr Ala Pro Tyr Ala His Gly Ala Asp Ala Ala Thr
               100                 105                 110

Ala Ala Leu Pro Ser Phe Ser Ala Ala Ala Arg Arg Phe Ala Ala
             115                 120                 125

Asp His Gly Leu Ala Val Arg Ala Val Ala Leu Arg Val Ala Asp Ala
         130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
        210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
            290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Arg Leu Gly Val Met Val Asp Arg Asp Glu Gly Val
        355                 360                 365

Leu Leu Gln Ile Phe Thr Lys Pro Val Gly Asp Arg Pro Thr Phe Phe
370                 375                 380

Ile Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440
```

<210> SEQ ID NO 26
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 26

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Gln Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365
```

```
Leu Leu Gln Ile Phe Thr Lys Pro Val Gly Asp Arg Pro Thr Phe Phe
        370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
            435                 440

<210> SEQ ID NO 27
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 27

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Gln Gly Ala
        195                 200                 205

Ala Asp Leu Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
```

```
                  275                 280                 285
Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                    325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Glu Gly Val
                355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                    405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440
```

<210> SEQ ID NO 28
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 28

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
                    100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
                130                 135                 140

Glu Asp Ala Phe Arg Ala Ser Val Ala Ala Gly Ala Arg Lys Ala Phe
145                 150                 155                 160

Gly Pro Val Asp Leu Gly Arg Gly Phe Arg Leu Ala Glu Val Glu Leu
                    165                 170                 175

Tyr Gly Asp Val Val Leu Arg Tyr Val Ser Tyr Pro Asp Gly Ala Ala
                180                 185                 190
```

```
Gly Glu Pro Phe Leu Pro Gly Phe Glu Val Ala Ser Pro Gly Ala
            195                 200                 205

Ala Asp Leu Gly Leu Asn Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
            290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
            325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
            435                 440

<210> SEQ ID NO 29
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 29

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110
```

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Leu Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 30
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 30

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn

```
                20                  25                  30
Phe Val Arg Phe Asn Pro Arg Ser Asp Arg Phe Gln Thr Leu Ala Phe
            35                  40                  45
His His Val Glu Leu Trp Cys Ala Asp Ala Ala Ser Ala Ala Gly Arg
        50                  55                  60
Phe Ser Phe Ala Leu Gly Val Pro Leu Ala Ala Arg Ser Asp Leu Ser
 65                  70                  75                  80
Thr Gly Asn Ser Ala His Ala Ser Leu Leu Arg Ser Gly Ser Leu
                85                  90                  95
Ser Leu Leu Phe Thr Ala Pro Tyr Ala His Gly Ala Asp Ala Ala Thr
            100                 105                 110
Ala Ala Leu Pro Ser Phe Ser Ala Ala Ala Arg Arg Phe Ala Ala
            115                 120                 125
Asp His Gly Leu Ala Val Arg Ala Val Ala Leu Arg Val Ala Asp Ala
            130                 135                 140
Glu Asp Ala Phe Arg Ala Ser Val Ala Ala Gly Ala Arg Pro Ala Phe
145                 150                 155                 160
Gly Pro Val Asp Leu Gly Arg Gly Phe Arg Leu Ala Glu Val Glu Leu
            165                 170                 175
Tyr Gly Asp Val Val Met Arg Tyr Val Ser Tyr Pro Asp Gly Ala Ala
            180                 185                 190
Gly Glu Pro Phe Leu Pro Gly Phe Glu Gly Val Ala Ser Pro Gly Ala
            195                 200                 205
Ala Asp Tyr Gly Leu Ser Arg Phe Asp His Ile Val Gly Asn Val Pro
            210                 215                 220
Glu Leu Ala Pro Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
            245                 250                 255
Leu Asn Ser Met Ala Leu Ala Asn Asn Ser Glu Asn Val Leu Leu Pro
            260                 265                 270
Leu Asn Glu Pro Val His Gly Thr Lys Arg Arg Ser Gln Ile Gln Thr
            275                 280                 285
Phe Leu Asp His His Gly Gly Pro Gly Val Gln His Ile Ala Leu Ala
            290                 295                 300
Ser Asp Asp Val Leu Arg Thr Leu Arg Glu Met Arg Ala Arg Ser Ala
305                 310                 315                 320
Met Gly Gly Phe Glu Phe Leu Pro Pro Leu Ser Asp Tyr Tyr Asp
            325                 330                 335
Gly Val Arg Arg Cys Ala Gly Asp Val Leu Thr Glu Ala Gln Ile Asn
            340                 345                 350
Glu Cys Gln Glu Leu Gly Val Met Val Asp Arg Asp Glu Gly Val
            355                 360                 365
Leu Leu Gln Ile Phe Thr Lys Pro Val Gly Asp Arg Pro Thr Phe Phe
            370                 375                 380
Val Glu Ile Ile Gln Arg Ile Gly Cys Met Glu Lys Asp Glu Lys Gly
385                 390                 395                 400
Gln Glu Tyr Gln Lys Gly Gly Cys Gly Gly Phe Gly Lys Gly Asn Phe
            405                 410                 415
Gly Gln Leu Phe Lys Ser Ile Glu Asp Tyr Glu Lys Ser Leu Glu Ala
            420                 425                 430
Lys Gln Ala Ala Ala Ala Thr Ala Gln Gly Ser
            435                 440
```

<210> SEQ ID NO 31
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 31

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Asn Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Arg Leu Gly Val Met Val Asp Arg Asp Asp Glu Gly Val
```

-continued

```
                355                 360                 365
Leu Leu Gln Ile Phe Thr Lys Pro Val Gly Asp Arg Pro Thr Phe Phe
    370                 375                 380
Leu Glu Ile Ile Gln Arg Ile Gly Cys Met Glu Lys Asp Glu Lys Gly
385                 390                 395                 400
Gln Glu Tyr Gln Lys Gly Cys Gly Gly Phe Gly Lys Gly Asn Phe
                405                 410                 415
Gly Gln Leu Phe Lys Ser Ile Glu Asp Tyr Glu Lys Ser Leu Glu Ala
                420                 425                 430
Lys Gln Ala Ala Ala Ala Thr Ala Gln Gly Ser
                435                 440

<210> SEQ ID NO 32
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 32

Met Gly Pro Thr Pro Thr Ala Thr Ala Ala Gly Ala Ala Val Ala Ala
1               5                   10                  15
Ala Ser Ala Ala Glu Gln Ala Ala Phe Arg Leu Val Gly His Arg Asn
                20                  25                  30
Phe Val Arg Phe Asn Pro Arg Ser Asp Arg Phe Gln Thr Leu Ala Phe
                35                  40                  45
His His Val Glu Leu Trp Cys Ala Asp Ala Ala Ser Ala Ala Gly Arg
                50                  55                  60
Phe Ser Phe Ala Leu Gly Val Pro Leu Ala Ala Arg Ser Asp Leu Ser
65                  70                  75                  80
Thr Gly Asn Ser Ala His Ala Ser Leu Leu Arg Ser Gly Ser Leu
                85                  90                  95
Ser Leu Leu Phe Thr Ala Pro Tyr Ala His Gly Ala Asp Ala Ala Thr
                100                 105                 110
Ala Ala Leu Pro Ser Phe Ser Ala Ala Ala Arg Arg Phe Ala Ala
                115                 120                 125
Asp His Gly Leu Ala Val Arg Ala Val Ala Leu Arg Val Ala Asp Ala
                130                 135                 140
Glu Asp Ala Phe Arg Ala Ser Val Ala Gly Ala Arg Pro Ala Phe
145                 150                 155                 160
Gly Pro Val Asp Leu Gly Arg Gly Phe Arg Leu Ala Glu Val Glu Leu
                165                 170                 175
Tyr Gly Asp Val Val Met Arg Tyr Val Ser Tyr Pro Asp Gly Ala Ala
                180                 185                 190
Gly Glu Pro Phe Leu Pro Gly Phe Glu Gly Val Ala Ser Ser Gly Ala
                195                 200                 205
Ala Asp Tyr Gly Leu Asn Arg Phe Asp His Ile Val Gly Asn Val Pro
                210                 215                 220
Glu Leu Ala Pro Ala Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
                245                 250                 255
Leu Asn Ser Met Ala Leu Ala Asn Asn Ser Glu Asn Val Leu Leu Pro
                260                 265                 270
```

-continued

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
            370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 33
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 33

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Leu Asn Glu Pro Val His Gly Thr Arg Arg Ser Gln Ile Gln Thr
            275                 280                 285

Phe Leu Asp His His Gly Gly Pro Gly Val Gln His Ile Ala Leu Ala
            290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
            325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
370                 375                 380

Leu Glu Leu Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
            435                 440

<210> SEQ ID NO 34
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 34

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95

Ser Leu Leu Phe Thr Ala Pro Tyr Ala His Gly Ala Asp Ala Ala Thr

```
            100                 105                 110
Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
                195                 200                 205

Ala Asp Tyr Gly Leu Ser Arg Phe Asp His Ile Val Gly Asn Val Pro
                210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Lys Leu Gly Val Met Val Asp Arg Asp Asp Glu Gly Val
                355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440

<210> SEQ ID NO 35
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 35

Met Gly Pro Thr Pro Thr Ala Thr Ala Ala Gly Ala Ala Val Ala Ala
1               5                   10                  15
```

-continued

```
Ala Ser Ala Ala Glu Gln Ala Ala Phe Arg Leu Val Gly His Arg Asn
             20                  25                  30
Phe Val Arg Phe Asn Pro Arg Ser Asp Arg Phe Gln Thr Leu Ala Phe
         35                  40                  45
His His Val Glu Leu Trp Cys Ala Asp Ala Ala Ser Ala Ala Gly Arg
     50                  55                  60
Phe Ser Phe Ala Leu Gly Val Pro Leu Ala Ala Arg Ser Asp Leu Ser
 65                  70                  75                  80
Thr Gly Asn Ser Ala His Ala Ser Leu Leu Leu Arg Ser Gly Ser Leu
                 85                  90                  95
Ser Leu Leu Phe Thr Ala Pro Tyr Ala His Gly Ala Asp Ala Ala Thr
             100                 105                 110
Ala Ala Leu Pro Ser Phe Ser Ala Ala Ala Arg Arg Phe Ala Ala
         115                 120                 125
Asp His Gly Leu Ala Val Arg Ala Val Ala Leu Arg Val Ala Asp Ala
     130                 135                 140
Glu Asp Ala Phe Arg Ala Ser Val Ala Ala Gly Ala Arg Pro Ala Phe
145                 150                 155                 160
Gly Pro Val Asp Leu Gly Arg Gly Phe Arg Leu Ala Glu Val Glu Leu
                 165                 170                 175
Tyr Gly Asp Val Val Leu Arg Tyr Val Ser Tyr Pro Asp Gly Ala Ala
             180                 185                 190
Gly Glu Pro Phe Leu Pro Gly Phe Glu Gly Val Ala Ser Gln Gly Ala
         195                 200                 205
Ala Asp Tyr Gly Leu Ser Arg Phe Asp His Ile Val Gly Asn Val Pro
     210                 215                 220
Glu Leu Ala Pro Ala Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
                 245                 250                 255
Leu Asn Ser Met Ala Leu Ala Asn Asn Ser Glu Asn Val Leu Leu Pro
             260                 265                 270
Leu Asn Glu Pro Val His Gly Thr Lys Arg Arg Ser Gln Ile Gln Thr
         275                 280                 285
Phe Leu Asp His His Gly Gly Pro Gly Val Gln His Ile Ala Leu Ala
     290                 295                 300
Ser Asp Asp Val Leu Arg Thr Leu Arg Glu Met Arg Ala Arg Ser Ala
305                 310                 315                 320
Met Gly Gly Phe Glu Phe Leu Pro Pro Leu Ser Asp Tyr Tyr Asp
                 325                 330                 335
Gly Val Arg Arg Cys Ala Gly Asp Val Leu Thr Glu Ala Gln Ile Asn
             340                 345                 350
Glu Cys Gln Glu Leu Gly Val Met Val Asp Arg Asp Glu Gly Val
         355                 360                 365
Leu Leu Gln Ile Phe Thr Lys Pro Val Gly Asp Arg Pro Thr Phe Phe
     370                 375                 380
Ile Glu Leu Ile Gln Arg Ile Gly Cys Met Glu Lys Asp Glu Lys Gly
385                 390                 395                 400
Gln Glu Tyr Gln Lys Gly Gly Cys Gly Gly Phe Gly Lys Gly Asn Phe
                 405                 410                 415
Gly Gln Leu Phe Lys Ser Ile Glu Asp Tyr Glu Lys Ser Leu Glu Ala
             420                 425                 430
Lys Gln Ala Ala Ala Ala Ala Thr Ala Gln Gly Ser
```

<210> SEQ ID NO 36
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 36

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350
```

-continued

```
Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
435                 440
```

<210> SEQ ID NO 37
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 37

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Ser Asp Gly Ala Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270
```

```
Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
            290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
            370                 375                 380

Leu Glu Ile Ile Gln Arg Ile Gly Cys Met Glu Lys Asp Glu Lys Gly
385                 390                 395                 400

Gln Glu Tyr Gln Lys Gly Cys Gly Gly Phe Gly Lys Gly Asn Phe
                405                 410                 415

Gly Gln Leu Phe Lys Ser Ile Glu Asp Tyr Gly Lys Ser Leu Glu Ala
                420                 425                 430

Lys Gln Ala Ala Ala Ala Thr Ala Gln Gly Ser
            435                 440

<210> SEQ ID NO 38
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 38

Met Gly Pro Thr Pro Thr Ala Thr Ala Ala Gly Ala Ala Val Ala Ala
1               5                   10                  15

Ala Ser Ala Ala Glu Gln Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
```

```
                    180                 185                 190
Gly Glu Pro Phe Leu Pro Gly Phe Glu Gly Val Ala Ser Pro Gly Ala
            195                 200                 205

Ala Asp Leu Gly Leu Ser Arg Phe Asp His Ile Val Gly Asn Val Pro
        210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
    370                 375                 380

Leu Glu Leu Ile Gln Arg Ile Gly Cys Met Glu Lys Asp Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 39
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 39

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95
```

```
Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
                195                 200                 205

Ala Asp Leu Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Lys Leu Gly Val Met Val Asp Arg Asp Asp Glu Gly Val
                355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
            435                 440

<210> SEQ ID NO 40
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 40

Met Gly Pro Thr Pro Thr Ala Thr Ala Ala Gly Ala Ala Val Ala Ala
1               5                   10                  15
```

```
Ala Ser Ala Ala Glu Gln Ala Ala Phe Arg Leu Val Gly His Arg Asn
         20                  25                  30
Phe Val Arg Phe Asn Pro Arg Ser Asp Arg Phe Gln Thr Leu Ala Phe
         35                  40                  45
His His Val Glu Leu Trp Cys Ala Asp Ala Ala Ser Ala Ala Gly Arg
         50                  55                  60
Phe Ser Tyr Ala Leu Gly Val Pro Leu Ala Ala Arg Ser Asp Leu Ser
 65                  70                  75                  80
Thr Gly Asn Ser Ala His Ala Ser Leu Leu Leu Arg Ser Gly Ser Leu
                 85                  90                  95
Ser Leu Leu Phe Thr Ala Pro Tyr Ala His Gly Ala Asp Ala Ala Thr
             100                 105                 110
Ala Ala Leu Pro Ser Phe Ser Ala Ala Ala Arg Arg Phe Ala Ala
             115                 120                 125
Asp His Gly Leu Ala Val Arg Ala Val Ala Leu Arg Val Ala Asp Ala
         130                 135                 140
Glu Asp Ala Phe Arg Ala Ser Val Ala Ala Gly Ala Arg Pro Ala Phe
145                 150                 155                 160
Gly Pro Val Asp Leu Gly Arg Gly Phe Arg Leu Ala Glu Val Glu Leu
                 165                 170                 175
Tyr Gly Asp Val Val Leu Arg Tyr Val Ser Tyr Pro Asp Gly Ala Ala
             180                 185                 190
Gly Glu Pro Phe Leu Pro Gly Phe Glu Gly Val Ala Ser Pro Gly Ala
         195                 200                 205
Ala Asp Tyr Gly Leu Ser Arg Phe Asp His Ile Val Gly Asn Val Pro
210                 215                 220
Glu Leu Ala Pro Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
             245                 250                 255
Leu Asn Ser Met Ala Leu Ala Asn Asn Ser Glu Asn Val Leu Leu Pro
             260                 265                 270
Leu Asn Glu Pro Val His Gly Thr Lys Arg Arg Ser Gln Ile Gln Thr
             275                 280                 285
Phe Leu Asp His His Gly Gly Pro Gly Val Gln His Ile Ala Leu Ala
             290                 295                 300
Ser Asp Asp Val Leu Arg Thr Leu Arg Glu Met Arg Ala Arg Ser Ala
305                 310                 315                 320
Met Gly Gly Phe Glu Phe Leu Pro Pro Leu Ser Asp Tyr Tyr Asp
                 325                 330                 335
Gly Val Arg Lys Cys Ala Gly Asp Val Leu Thr Glu Ala Gln Ile Asn
             340                 345                 350
Glu Cys Gln Glu Leu Gly Val Met Val Asp Arg Asp Glu Gly Val
             355                 360                 365
Leu Leu Gln Ile Phe Thr Lys Pro Val Gly Asp Arg Pro Thr Phe Phe
             370                 375                 380
Ile Glu Leu Ile Gln Arg Ile Gly Cys Met Glu Lys Asp Glu Lys Gly
385                 390                 395                 400
Gln Glu Tyr Gln Lys Gly Cys Gly Gly Phe Gly Lys Gly Asn Phe
                 405                 410                 415
Gly Gln Leu Phe Lys Ser Ile Glu Asp Tyr Glu Lys Ser Leu Glu Ala
             420                 425                 430
```

```
Lys Gln Ala Ala Ala Ala Thr Ala Gln Gly Ser
        435                 440
```

```
<210> SEQ ID NO 41
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 41

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Asp Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Ser Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val Leu Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350
```

```
Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
            370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Ser Gln Leu Phe Lys Ser Ile Glu Asp Tyr Glu Lys Ser Leu Glu Ala
            420                 425                 430

Lys Arg Ala Ala Ala Ala Thr Ala Gln Gly Ser
            435                 440
```

<210> SEQ ID NO 42
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 42

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
            130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Ser Gly Ala
            195                 200                 205

Ala Asp Tyr Gly Leu Asn Arg Phe Asp His Ile Val Gly Asn Val Pro
            210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
```

```
                260                 265                 270
Leu Asn Glu Pro Val His Gly Thr Lys Arg Ser Gln Ile Gln Thr
            275                 280                 285

Phe Leu Asp His His Gly Gly Pro Gly Val Gln His Ile Ala Leu Ala
            290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Arg Leu Gly Val Met Val Asp Arg Asp Glu Gly Val
            355                 360                 365

Leu Leu Gln Ile Phe Thr Lys Pro Val Gly Asp Arg Pro Thr Phe Phe
            370                 375                 380

Val Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Ala Thr Ala Gln Gly Ser
                435                 440
```

<210> SEQ ID NO 43
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 43

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175
```

Tyr Gly Asp Val Val Met Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Cys Gly Gly Phe Gly Lys Asn Phe
                405                 410                 415

Gly Gln Leu Phe Lys Ser Ile Glu Asp Tyr Glu Lys Ser Leu Asp Ala
            420                 425                 430

Lys Gln Ala Ala Ala Ala Ala Thr Ala Gln Gly Ser
        435                 440

<210> SEQ ID NO 44
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 44

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Asn Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 45
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 45

Met Gly Pro Thr Pro Thr Ala Thr Ala Ala Gly Ala Ala Val Ala Ala

```
  1               5                   10                  15
Ala Ser Ala Ala Glu Gln Ala Ala Phe Arg Leu Val Gly His Arg Asn
         20                  25                  30
Phe Val Arg Phe Asn Pro Arg Ser Asp Arg Phe Gln Thr Leu Ala Phe
         35                  40                  45
His His Val Glu Leu Trp Cys Ala Asp Ala Ala Ser Ala Ala Gly Arg
         50                  55                  60
Phe Ser Phe Ala Leu Gly Val Pro Leu Ala Ala Arg Ser Asp Leu Ser
 65                  70                  75                  80
Thr Gly Asn Ser Ala His Ala Ser Leu Leu Arg Ser Gly Ser Leu
                 85                  90                  95
Ser Leu Leu Phe Thr Ala Pro Tyr Ala His Gly Ala Asp Ala Ala Thr
                100                 105                 110
Ala Ala Leu Pro Ser Phe Ser Ala Ala Thr Ala Arg Arg Phe Ala Ala
                115                 120                 125
Asp His Gly Leu Ala Val Arg Ala Val Ala Leu Arg Val Ala Asp Ala
                130                 135                 140
Glu Asp Ala Phe Arg Ala Ser Val Ala Ala Gly Ala Arg Pro Ala Phe
145                 150                 155                 160
Gly Pro Val Asp Leu Gly Arg Gly Phe Arg Leu Ala Glu Val Glu Leu
                165                 170                 175
Tyr Gly Asp Val Val Leu Arg Tyr Val Ser Tyr Pro Asp Gly Ala Ala
                180                 185                 190
Gly Glu Pro Phe Leu Pro Gly Phe Glu Gly Val Ala Ser Gln Gly Ala
                195                 200                 205
Ala Asp Tyr Gly Leu Ser Arg Phe Asp His Ile Val Gly Asn Val Pro
                210                 215                 220
Glu Leu Ala Pro Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
                245                 250                 255
Leu Asn Ser Met Ala Leu Ala Asn Asn Ser Glu Asn Val Leu Leu Pro
                260                 265                 270
Leu Asn Glu Pro Val His Gly Thr Lys Arg Arg Ser Gln Ile Gln Thr
                275                 280                 285
Phe Leu Asp His His Gly Gly Pro Gly Val Gln His Ile Ala Leu Ala
                290                 295                 300
Ser Asp Asp Val Leu Arg Thr Leu Arg Glu Met Arg Ala Arg Ser Ala
305                 310                 315                 320
Met Gly Gly Phe Glu Phe Leu Pro Pro Pro Leu Ser Asp Tyr Tyr Asp
                325                 330                 335
Gly Val Arg Arg Cys Ala Gly Asp Val Leu Thr Glu Ala Gln Ile Asn
                340                 345                 350
Glu Cys Gln Lys Leu Gly Val Met Val Asp Arg Asp Asp Glu Gly Val
                355                 360                 365
Leu Leu Gln Ile Phe Thr Lys Pro Val Gly Asp Arg Pro Thr Phe Phe
                370                 375                 380
Leu Glu Ile Ile Gln Arg Ile Gly Cys Met Glu Lys Asp Glu Lys Gly
385                 390                 395                 400
Gln Glu Tyr Gln Lys Gly Gly Cys Gly Gly Phe Gly Lys Gly Asn Phe
                405                 410                 415
Gly Gln Leu Phe Lys Ser Ile Glu Asp Tyr Glu Lys Ser Leu Glu Ala
                420                 425                 430
```

```
Lys Gln Ala Ala Ala Ala Ala Thr Ala Gln Gly Ser
        435                 440

<210> SEQ ID NO 46
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 46

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Gln Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asp Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Arg Cys Ala Gly Asp Val Leu Thr Glu Ala Gln Ile Asn
```

```
                    340                 345                 350
Glu Cys Gln Glu Leu Gly Val Met Val Asp Arg Asp Glu Gly Val
                355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440

<210> SEQ ID NO 47
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 47

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Thr Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255
```

-continued

```
Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
        420                 425                 430

Lys Gln Ala Ala Ala Ala Thr Ala Gln Gly Ser
            435                 440

<210> SEQ ID NO 48
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 48

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
            85                  90                  95

Ser Leu Leu Phe Thr Ala Pro Tyr Ala His Gly Ala Asp Ala Ala Thr
        100                 105                 110

Ala Ala Leu Pro Ser Phe Ser Ala Ala Ala Arg Arg Phe Ala Ala
    115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175
```

-continued

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
        435                 440

<210> SEQ ID NO 49
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 49

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu

```
            85                  90                  95
Ser Leu Leu Phe Thr Ala Pro Tyr Ala His Gly Ala Asp Ala Ala Thr
        100                 105                 110

Ala Ala Leu Pro Ser Phe Ser Ala Ala Ala Arg Arg Phe Ala Ala
    115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Met Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Leu Gly Leu Asn Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
        435                 440

<210> SEQ ID NO 50
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 50
```

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Ser Gly Ala
    195                 200                 205

Ala Asp Tyr Gly Leu Ser Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
    275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Arg Leu Gly Val Met Val Asp Arg Asp Glu Gly Val
    355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Ser Gln Leu Phe Lys Ser Ile Glu Asp Tyr Glu Lys Ser Leu Glu Ala
```

```
                    420             425             430
Lys Gln Ala Ala Ala Ala Thr Ala Gln Gly Ser
            435             440

<210> SEQ ID NO 51
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 51

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Met Arg Tyr Val Ser Tyr Pro Gly Ala Ala
            180                 185                 190

Gly Glu Pro Phe Leu Pro Gly Phe Glu Gly Val Ala Ser Gln Gly Ala
        195                 200                 205

Ala Asp Leu Gly Leu Asn Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335
```

```
Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
    370                 375                 380

Leu Glu Leu Ile Gln Arg Ile Gly Cys Met Glu Lys Asp Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
            435                 440

<210> SEQ ID NO 52
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 52

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Gln Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255
```

-continued

```
Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
    370                 375                 380

Ile Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
            435                 440
```

<210> SEQ ID NO 53
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 53

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
```

```
                165                 170                 175
Tyr Gly Asp Val Val Leu Arg Tyr Val Ser Tyr Pro Asp Gly Gly Ala
            180                 185                 190
Gly Glu Pro Phe Leu Pro Gly Phe Glu Gly Val Ala Ser Pro Gly Ala
            195                 200                 205
Ala Asp Tyr Gly Leu Ser Arg Phe Asp His Ile Val Gly Asn Val Pro
            210                 215                 220
Glu Leu Ala Pro Ala Ala Ala Tyr Met Ala Gly Phe Thr Gly Phe His
225                 230                 235                 240
Glu Phe Ala Glu Phe Thr Thr Glu Asp Val Gly Thr Thr Glu Ser Gly
            245                 250                 255
Leu Asn Ser Met Ala Leu Ala Asn Asn Ser Glu Asn Val Leu Leu Pro
            260                 265                 270
Leu Asn Glu Pro Val His Gly Thr Lys Arg Arg Ser Gln Ile Gln Thr
            275                 280                 285
Phe Leu Asp His His Gly Gly Pro Gly Val Gln His Ile Ala Leu Ala
            290                 295                 300
Ser Asp Asp Val Leu Arg Thr Leu Arg Glu Met Arg Ala Arg Ser Ala
305                 310                 315                 320
Met Gly Gly Phe Glu Phe Leu Pro Pro Leu Ser Asp Tyr Tyr Asp
            325                 330                 335
Gly Val Arg Arg Cys Ala Gly Asp Val Leu Thr Glu Ala Gln Ile Asn
            340                 345                 350
Glu Cys Gln Lys Leu Gly Val Met Val Asp Arg Asp Glu Gly Val
            355                 360                 365
Leu Leu Gln Ile Phe Thr Lys Pro Val Gly Asp Arg Pro Thr Phe Phe
370                 375                 380
Leu Glu Ile Ile Gln Arg Ile Gly Cys Met Glu Lys Asp Glu Lys Gly
385                 390                 395                 400
Gln Glu Tyr Gln Lys Gly Gly Cys Gly Gly Phe Gly Lys Gly Asn Phe
            405                 410                 415
Gly Gln Leu Phe Lys Ser Ile Glu Asp Tyr Glu Lys Ser Leu Glu Ala
            420                 425                 430
Lys Gln Ala Ala Ala Ala Thr Ala Gln Gly Ser
435                 440

<210> SEQ ID NO 54
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 54

Met Gly Pro Thr Pro Thr Ala Thr Ala Ala Gly Ala Ala Val Ala Ala
1               5                   10                  15
Ala Ser Ala Ala Glu Gln Ala Ala Phe Arg Leu Val Gly His Arg Asn
            20                  25                  30
Phe Val Arg Phe Asn Pro Arg Ser Asp Arg Phe Gln Thr Leu Ala Phe
            35                  40                  45
His His Val Glu Leu Trp Cys Ala Asp Ala Ala Ser Ala Ala Gly Arg
            50                  55                  60
Phe Ser Phe Ala Leu Gly Val Pro Leu Ala Ala Arg Ser Asp Leu Ser
65                  70                  75                  80
```

Thr Gly Asn Ser Ala His Ala Ser Leu Leu Leu Arg Ser Gly Ser Leu
                 85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Met Arg Tyr Val Ser Tyr Pro Asp Gly Ala Ala
            180                 185                 190

Gly Glu Pro Phe Leu Pro Gly Phe Glu Gly Val Ala Ser Gln Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 55
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 55

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Ser Gly Ala
        195                 200                 205

Ala Asp Tyr Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
        290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
            325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
        370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415
```

-continued

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
            435                 440

<210> SEQ ID NO 56
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 56

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Ala Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

```
Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Ser Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
            435                 440

<210> SEQ ID NO 57
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 57

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Gly Gly Ala
            180                 185                 190

Gly Glu Pro Phe Leu Pro Gly Phe Glu Gly Val Ala Ser Ser Gly Ala
            195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
```

-continued

```
            245                 250                 255
Leu Asn Ser Met Ala Leu Ala Asn Asn Ser Glu Asn Val Leu Leu Pro
        260                 265                 270

Leu Asn Glu Pro Val His Gly Thr Lys Arg Arg Ser Gln Ile Gln Thr
    275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
        370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gln Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440
```

<210> SEQ ID NO 58
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 58

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
            85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160
```

Gly Pro Val Asp Leu Gly Arg Gly Phe Arg Leu Ala Glu Val Glu Leu
                165                 170                 175

Tyr Gly Asp Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
        210                 215                 220

Glu Leu Ala Pro Ala Ala Tyr Met Ala Gly Phe Thr Gly Phe His
225                 230                 235                 240

Glu Phe Ala Lys Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Lys Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Ala Thr Ala Gln Gly Ser
        435                 440

<210> SEQ ID NO 59
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 59

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Leu Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gln Gln Leu Phe Lys Ser Ile Glu Asp Tyr Glu Lys Ser Leu Glu Ala
            420                 425                 430

Lys Arg Ala Ala Ala Ala Thr Ala Gln Gly Ser
            435                 440

<210> SEQ ID NO 60
<211> LENGTH: 444
<212> TYPE: PRT
<213> ORGANISM: Artificial Sequence
<220> FEATURE:
<223> OTHER INFORMATION: Zea mays variant form created by artificial
      means.

```
<400> SEQUENCE: 60

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
            210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
            325                 330                 335

Gly Val Arg Arg Cys Ala Gly Asp Val Leu Thr Glu Ala Gln Ile Asn
        340                 345                 350

Glu Cys Gln Arg Leu Gly Val Met Val Asp Arg Asp Glu Gly Val
    355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415
```

-continued

```
Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 61
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 61

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Gln Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
```

-continued

```
               325                 330                 335
Gly Val Arg Lys Cys Ala Gly Asp Val Leu Thr Glu Ala Gln Ile Asn
               340                 345                 350

Glu Cys Gln Glu Leu Gly Val Met Val Asp Arg Asp Glu Gly Val
               355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
               405                 410                 415

Gly Gln Leu Phe Lys Ser Ile Glu Asp Tyr Glu Lys Ser Leu Glu Ala
               420                 425                 430

Lys Gln Ala Ala Ala Ala Thr Ala Gln Gly Ser
               435                 440
```

<210> SEQ ID NO 62
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 62

```
Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
               20                  25                  30

Phe Val Arg Phe Asn Pro Arg Ser Asp Arg Phe Gln Thr Leu Ala Phe
               35                  40                  45

His His Val Glu Leu Trp Cys Ala Asp Ala Ala Ser Ala Ala Gly Arg
               50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
               85                  90                  95

Ser Leu Leu Phe Thr Ala Pro Tyr Ala His Gly Ala Asp Ala Ala Thr
               100                 105                 110

Ala Ala Leu Pro Ser Phe Ser Ala Ala Ala Arg Arg Phe Ala Ala
               115                 120                 125

Asp His Gly Leu Ala Val Arg Ala Val Ala Leu Arg Val Ala Asp Ala
               130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
               165                 170                 175

Tyr Gly Asp Val Val Leu Arg Tyr Val Ser Tyr Pro Asp Gly Gly Ala
               180                 185                 190

Gly Glu Pro Phe Leu Pro Gly Phe Glu Gly Val Ala Ser Pro Gly Ala
               195                 200                 205

Ala Asp Tyr Gly Leu Asn Arg Phe Asp His Ile Val Gly Asn Val Pro
               210                 215                 220

Glu Leu Ala Pro Ala Ala Ala Tyr Met Ala Gly Phe Thr Gly Phe His
225                 230                 235                 240
```

```
Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 63
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 63

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160
```

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asp Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Lys Ser Leu Glu Ala
        420                 425                 430

Lys Gln Ala Ala Ala Ala Ala Thr Ala Gln Gly Ser
    435                 440

<210> SEQ ID NO 64
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 64

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser

```
                65                  70                  75                  80
        Thr Gly Asn Ser Ala His Ala Ser Leu Leu Arg Ser Gly Ser Leu
                            85                  90                  95

Ser Leu Leu Phe Thr Ala Pro Tyr Ala His Gly Ala Asp Ala Ala Thr
                        100                 105                 110

Ala Ala Leu Pro Ser Phe Ser Ala Ala Ala Arg Arg Phe Ala Ala
                    115                 120                 125

Asp His Gly Leu Ala Val Arg Ala Val Ala Leu Arg Val Ala Asp Ala
                130                 135                 140

Glu Asp Ala Phe Arg Ala Ser Val Ala Ala Gly Ala Arg Pro Ala Phe
        145                 150                 155                 160

Gly Pro Val Asp Leu Gly Arg Gly Phe Arg Leu Ala Glu Val Glu Leu
                        165                 170                 175

Tyr Gly Asp Val Val Leu Arg Tyr Val Ser Tyr Pro Asp Gly Gly Ala
                        180                 185                 190

Gly Glu Pro Phe Leu Pro Gly Phe Glu Gly Val Ala Ser Pro Gly Ala
                    195                 200                 205

Ala Asp Tyr Gly Leu Ser Arg Phe Asp His Ile Val Gly Asn Val Pro
                210                 215                 220

Glu Leu Ala Pro Ala Ala Ala Tyr Met Ala Gly Phe Thr Gly Phe His
        225                 230                 235                 240

Glu Phe Ala Glu Phe Thr Thr Glu Asp Val Gly Thr Thr Glu Ser Gly
                        245                 250                 255

Leu Asn Ser Met Ala Leu Ala Asn Asn Ser Glu Asn Val Leu Leu Pro
                        260                 265                 270

Leu Asn Glu Pro Val His Gly Thr Lys Arg Arg Ser Gln Ile Gln Thr
                    275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Arg Ala Arg Ser Ala
        305                 310                 315                 320

Met Gly Gly Phe Glu Phe Leu Pro Pro Leu Ser Asp Tyr Tyr Asp
                        325                 330                 335

Gly Val Arg Arg Cys Ala Gly Asp Val Leu Thr Glu Ala Gln Ile Asn
                        340                 345                 350

Glu Cys Gln Glu Leu Gly Val Met Val Asp Arg Asp Glu Gly Val
                    355                 360                 365

Leu Leu Gln Ile Phe Thr Lys Pro Val Gly Asp Arg Pro Thr Phe Phe
                370                 375                 380

Ile Glu Ile Ile Gln Arg Ile Gly Cys Thr Glu Lys Asp Glu Lys Gly
        385                 390                 395                 400

Gln Glu Tyr Gln Lys Gly Gly Cys Gly Gly Phe Gly Lys Gly Asn Phe
                        405                 410                 415

Ser Gln Leu Phe Lys Ser Ile Glu Asp Tyr Glu Lys Ser Leu Glu Ala
                        420                 425                 430

Lys Gln Ala Ala Ala Ala Ala Thr Ala Gln Gly Ser
                    435                 440

<210> SEQ ID NO 65
<211> LENGTH: 444
<212> TYPE: PRT
<213> ORGANISM: Artificial Sequence
<220> FEATURE:
<223> OTHER INFORMATION: Zea mays variant form created by artificial
      means.
```

<400> SEQUENCE: 65

```
Met Gly Pro Thr Pro Thr Ala Thr Ala Ala Gly Ala Ala Val Ala Ala
 1               5                  10                  15

Ala Ser Ala Ala Glu Gln Ala Ala Phe Arg Leu Val Gly His Arg Asn
             20                  25                  30

Phe Val Arg Phe Asn Pro Arg Ser Asp Arg Phe Gln Thr Leu Ala Phe
         35                  40                  45

His His Val Glu Leu Trp Cys Ala Asp Ala Ala Ser Ala Ala Gly Arg
     50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Arg Ser Gly Ser Leu
             85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Leu Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
```

```
                       405                 410                 415
Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 66
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 66

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Ser Gly Ala
        195                 200                 205

Ala Asp Leu Gly Leu Asn Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320
```

```
Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Lys Leu Gly Val Met Val Asp Arg Asp Glu Gly Val
        355                 360                 365

Leu Leu Gln Ile Phe Thr Lys Pro Val Gly Asp Arg Pro Thr Phe Phe
370                 375                 380

Leu Glu Leu Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Ala Thr Ala Gln Gly Ser
                435                 440

<210> SEQ ID NO 67
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 67

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240
```

```
Glu Phe Ala Glu Phe Thr Thr Glu Asp Val Gly Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys His Ala Ala Ala Ala Thr Ala Gln Gly Ser
        435                 440

<210> SEQ ID NO 68
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 68

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Lys Ala Phe
```

```
                145                 150                 155                 160
Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Val Ala Ser Pro Gly Ala
                195                 200                 205

Ala Asp Leu Gly Leu Ser Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Glu Leu Gly Val Met Val Asp Arg Asp Glu Gly Val
                355                 360                 365

Leu Leu Gln Ile Phe Thr Lys Pro Val Gly Asp Arg Pro Thr Phe Phe
                370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440

<210> SEQ ID NO 69
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 69

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
                35                  40                  45

His His Val Glu Leu Trp Cys Ala Asp Ala Ala Ser Ala Ala Gly Arg
                50                  55                  60
```

```
Phe Ser Phe Ala Leu Gly Val Pro Leu Ala Ala Arg Ser Asp Leu Ser
 65                  70                  75                  80

Thr Gly Asn Ser Ala His Ala Ser Leu Leu Arg Ser Gly Ser Leu
             85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
            130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Gln Gly Ala
            195                 200                 205

Ala Asp Tyr Gly Leu Ser Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Arg Pro Thr Phe Phe
370                 375                 380

Leu Glu Leu Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Gly Lys Ser Leu Glu Ala
            420                 425                 430

Lys Gln Ala Ala Ala Ala Ala Thr Ala Gln Gly Ser
            435                 440
```

<210> SEQ ID NO 70
<211> LENGTH: 444
<212> TYPE: PRT
<213> ORGANISM: Artificial Sequence
<220> FEATURE:
<223> OTHER INFORMATION: Zea mays variant form created by artificial means.

<400> SEQUENCE: 70

```
Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Lys Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
    210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
    275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Pro Pro Pro Leu Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400
```

```
Gln Glu Tyr Gln Lys Gly Gly Cys Gly Gly Phe Gly Lys Gly Asn Phe
            405                 410                 415

Gln Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 71
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 71

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Ala Tyr Val Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320
```

Met Gly Gly Phe Glu Phe Leu Pro Pro Leu Ser Asp Tyr Tyr Asp
            325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Lys Gly
385                 390                 395                 400

Gln Glu Tyr Gln Lys Gly Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 72
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 72

Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
        130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Leu Gly Leu Ser Arg Phe Asp His Ile Val Gly Asn Val Pro
        210                 215                 220

Glu Leu Ala Pro Ala Ala Ala Tyr Met Ala Gly Phe Thr Gly Phe His

```
            225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
    370                 375                 380

Ile Glu Leu Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 73
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 73

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140
```

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Gly Ala
            180                 185                 190

Gly Glu Pro Phe Leu Pro Gly Phe Glu Gly Val Ala Ser Gln Gly Ala
            195                 200                 205

Ala Asp Leu Gly Leu Asn Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
            325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Asp Glu Gly Val
            355                 360                 365

Leu Leu Gln Ile Phe Thr Lys Pro Val Gly Asp Arg Pro Thr Phe Phe
370                 375                 380

Ile Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
            405                 410                 415

Gln Gln Leu Phe Lys Ser Ile Glu Asp Tyr Glu Lys Ser Leu Glu Ala
            420                 425                 430

Lys Arg Ala Ala Ala Ala Thr Ala Gln Gly Ser
            435                 440

<210> SEQ ID NO 74
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 74

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Met Arg Tyr Val Ser Tyr Pro Asp Gly Ala Ala
                180                 185                 190

Gly Glu Pro Phe Leu Pro Gly Phe Glu Gly Val Ala Ser Gln Gly Ala
            195                 200                 205

Ala Asp Tyr Gly Leu Asn Arg Phe Asp His Ile Val Gly Asn Val Pro
210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Leu Ile Gln Arg Ile Gly Cys Met Glu Lys Asp Glu Lys Gly
385                 390                 395                 400

Gln Glu Tyr Gln Lys Gly Gly Cys Gly Phe Gly Lys Gly Asn Phe
            405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
435                 440

<210> SEQ ID NO 75
<211> LENGTH: 444
<212> TYPE: PRT
<213> ORGANISM: Artificial Sequence
<220> FEATURE:

-continued

<223> OTHER INFORMATION: Zea mays variant form created by artificial
      means.

<400> SEQUENCE: 75

```
Met Gly Pro Thr Pro Thr Ala Thr Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Gln Gly Ala
            195                 200                 205

Ala Asp Tyr Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
            340                 345                 350

Glu Cys Gln Arg Leu Gly Val Met Val Asp Arg Asp Glu Gly Val
        355                 360                 365

Leu Leu Gln Ile Phe Thr Lys Pro Val Gly Asp Arg Pro Thr Phe Phe
    370                 375                 380

Leu Glu Ile Ile Gln Arg Ile Gly Cys Met Glu Lys Asp Glu Lys Gly
385                 390                 395                 400
```

```
Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
        435                 440

<210> SEQ ID NO 76
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 76

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95

Ser Leu Leu Phe Thr Ala Pro Tyr Ala His Gly Ala Asp Ala Ala Thr
        100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Leu Gly Leu Ser Arg Phe Asp His Ile Val Gly Asn Val Pro
    210                 215                 220

Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
```

```
305                 310                 315                 320
Met Gly Gly Phe Glu Phe Leu Pro Pro Leu Ser Asp Tyr Tyr Asp
                325                 330                 335

Gly Val Arg Lys Cys Ala Gly Asp Val Leu Thr Glu Ala Gln Ile Asn
                340                 345                 350

Glu Cys Gln Lys Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Cys Gly Gly Phe Gly Lys Gly Asn Phe
            405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
            435                 440

<210> SEQ ID NO 77
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 77

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
                20                  25                  30

Phe Val Arg Phe Asn Pro Arg Ser Asp Arg Phe Gln Thr Leu Ala Phe
            35                  40                  45

His His Val Glu Leu Trp Cys Ala Asp Ala Ala Ser Ala Ala Gly Arg
        50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Lys Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
210                 215                 220
```

```
Glu Leu Ala Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Ile Ala Leu Ala
    290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Glu Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Val Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 78
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 78

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Ala Leu Gly Ala Pro Leu Ala Ala Arg Ser Asp Leu Ser
65                  70                  75                  80

Thr Gly Asn Ser Ala His Ala Ser Leu Leu Leu Arg Ser Gly Ser Leu
            85                  90                  95

Ser Phe Leu Phe Thr Ala Pro Tyr Ala His Gly Ala Asp Ala Ala Thr
        100                 105                 110

Ala Ala Leu Pro Ser Phe Ser Ala Ala Ala Arg Arg Phe Ala Ala
            115                 120                 125

Asp His Gly Leu Ala Val Arg Ala Val Ala Leu Arg Val Ala Asp Ala
    130                 135                 140
```

```
Glu Asp Ala Phe Arg Ala Ser Val Ala Gly Ala Arg Pro Ala Phe
145                 150                 155                 160

Gly Pro Val Asp Leu Gly Arg Gly Phe Arg Leu Ala Glu Val Glu Leu
            165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
            195                 200                 205

Ala Asp Tyr Gly Leu Ser Arg Phe Asp His Ile Val Gly Asn Val Pro
210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Ala Leu Ala Asn Asn Ser Glu Asn Val Leu Leu Pro
            260                 265                 270

Leu Asn Glu Pro Val His Gly Thr Lys Arg Arg Ser Gln Ile Gln Thr
            275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Gln Ala Arg Ser Ala
305                 310                 315                 320

Met Gly Gly Phe Glu Phe Leu Pro Pro Pro Ser Asp Tyr Tyr Asp
                325                 330                 335

Gly Val Arg Arg Cys Ala Gly Asp Val Leu Thr Glu Ala Gln Ile Asn
            340                 345                 350

Glu Cys Gln Glu Leu Gly Val Met Val Asp Arg Asp Gln Gly Val
            355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
            420                 425                 430

Lys Gln Ala Ala Ala Ala Thr Ala Gln Gly Ser
            435                 440

<210> SEQ ID NO 79
<211> LENGTH: 444
<212> TYPE: PRT
<213> ORGANISM: Artificial Sequence
<220> FEATURE:
<223> OTHER INFORMATION: Zea mays variant form created by artificial
      means.

<400> SEQUENCE: 79

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Leu Trp Cys Ala Asp Ala Ala Ser Ala Ala Gly Arg
```

```
            50                  55                  60
Phe Ser Phe Ala Leu Gly Val Pro Leu Ala Ala Arg Ser Asp Leu Ser
 65                  70                  75                  80

Thr Gly Asn Ser Ala His Ala Ser Leu Leu Leu Arg Ser Gly Ser Leu
                 85                  90                  95

Ser Leu Leu Phe Thr Ala Pro Tyr Ala His Gly Ala Asp Ala Ala Thr
                100                 105                 110

Ala Ala Leu Pro Ser Phe Ser Ala Ala Ala Arg Arg Phe Ala Ala
                115                 120                 125

Asp His Gly Leu Ala Val Arg Ala Val Ala Leu Arg Val Ala Asp Ala
                130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
                180                 185                 190

Gly Glu Pro Phe Leu Pro Gly Phe Glu Gly Val Ala Ser Pro Gly Ala
                195                 200                 205

Ala Asp Tyr Gly Leu Ser Arg Phe Asp His Ile Val Gly Asn Val Pro
210                 215                 220

Glu Leu Ala Pro Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                245                 250                 255

Leu Asn Ser Met Ala Leu Ala Asn Asn Ser Glu Asn Val Leu Leu Pro
                260                 265                 270

Leu Asn Glu Pro Val His Gly Thr Lys Arg Arg Ser Gln Ile Gln Thr
                275                 280                 285

Phe Leu Asp His His Gly Gly Pro Gly Val Gln His Ile Ala Leu Ala
                290                 295                 300

Ser Asp Asp Val Leu Arg Thr Leu Arg Glu Met Gln Ala Arg Ser Ala
305                 310                 315                 320

Met Gly Gly Phe Glu Phe Leu Pro Pro Leu Ser Asp Tyr Tyr Asp
                325                 330                 335

Gly Val Arg Arg Cys Ala Gly Asp Val Leu Thr Glu Ala Gln Ile Asn
                340                 345                 350

Glu Cys Gln Glu Leu Gly Val Met Val Asp Arg Asp Gln Gly Val
                355                 360                 365

Leu Leu Gln Ile Phe Thr Lys Pro Val Gly Asp Arg Pro Thr Phe Phe
370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Gly Gln Leu Phe Lys Ser Ile Glu Asp Tyr Glu Lys Ser Leu Glu Ala
                420                 425                 430

Lys Gln Ala Ala Ala Ala Thr Ala Gln Gly Ser
                435                 440

<210> SEQ ID NO 80
<211> LENGTH: 444
<212> TYPE: PRT
<213> ORGANISM: Artificial Sequence
```

-continued

```
<220> FEATURE:
<223> OTHER INFORMATION: Zea mays variant form created by artificial
      means.
<220> FEATURE:
<221> NAME/KEY: MISC_FEATURE
<222> LOCATION: (52)..(52)
<223> OTHER INFORMATION: Glu, Asp, Gly, His, Arg, Ser or Thr
<220> FEATURE:
<221> NAME/KEY: MISC_FEATURE
<222> LOCATION: (53)..(53)
<223> OTHER INFORMATION: Leu, Phe, Ile or Met
<220> FEATURE:
<221> NAME/KEY: MISC_FEATURE
<222> LOCATION: (54)..(54)
<223> OTHER INFORMATION: Trp, Cys, Leu or Gln
<220> FEATURE:
<221> NAME/KEY: MISC_FEATURE
<222> LOCATION: (55)..(55)
<223> OTHER INFORMATION: Cys, Ala, Gly, Thr or Val
<220> FEATURE:
<221> NAME/KEY: MISC_FEATURE
<222> LOCATION: (56)..(56)
<223> OTHER INFORMATION: Ala, His, Leu, Asn, Gln, Ser or Thr
<220> FEATURE:
<221> NAME/KEY: MISC_FEATURE
<222> LOCATION: (58)..(58)
<223> OTHER INFORMATION: Ala, Gly or Thr
<220> FEATURE:
<221> NAME/KEY: MISC_FEATURE
<222> LOCATION: (125)..(125)
<223> OTHER INFORMATION: Arg or Leu
<220> FEATURE:
<221> NAME/KEY: MISC_FEATURE
<222> LOCATION: (147)..(147)
<223> OTHER INFORMATION: Ala or Ser
<220> FEATURE:
<221> NAME/KEY: MISC_FEATURE
<222> LOCATION: (148)..(148)
<223> OTHER INFORMATION: Phe, Trp or Tyr
<220> FEATURE:
<221> NAME/KEY: MISC_FEATURE
<222> LOCATION: (149)..(149)
<223> OTHER INFORMATION: Arg, Ala, Ile, Lys, Met, Pro, Ser, Thr, Val or
      Trp
<220> FEATURE:
<221> NAME/KEY: MISC_FEATURE
<222> LOCATION: (152)..(152)
<223> OTHER INFORMATION: Val or Glu
<220> FEATURE:
<221> NAME/KEY: MISC_FEATURE
<222> LOCATION: (153)..(153)
<223> OTHER INFORMATION: Ala, Phe, Ile, Lys, Leu, Gln, Arg, Thr or Val
<220> FEATURE:
<221> NAME/KEY: MISC_FEATURE
<222> LOCATION: (154)..(154)
<223> OTHER INFORMATION: Ala, Cys, Gly, Asn, Arg or Thr
<220> FEATURE:
<221> NAME/KEY: MISC_FEATURE
<222> LOCATION: (157)..(157)
<223> OTHER INFORMATION: Arg, His, Asn, Thr or Val
<220> FEATURE:
<221> NAME/KEY: MISC_FEATURE
<222> LOCATION: (158)..(158)
<223> OTHER INFORMATION: Pro, Ala, Glu, Gly or Lys
<220> FEATURE:
<221> NAME/KEY: MISC_FEATURE
<222> LOCATION: (159)..(159)
<223> OTHER INFORMATION: Ala, Cys, Met, Ser, Thr or Val
<220> FEATURE:
<221> NAME/KEY: MISC_FEATURE
<222> LOCATION: (160)..(160)
<223> OTHER INFORMATION: Phe, Leu, Met or Tyr
<220> FEATURE:
<221> NAME/KEY: MISC_FEATURE
<222> LOCATION: (161)..(161)
<223> OTHER INFORMATION: Gly, Ala, Glu, Leu, Met, Asn, Pro, Gln, Arg,
      Ser, Thr, Trp or Tyr
<220> FEATURE:
<221> NAME/KEY: MISC_FEATURE
```

-continued

```
<222> LOCATION: (162)..(162)
<223> OTHER INFORMATION: Pro or Thr
<220> FEATURE:
<221> NAME/KEY: MISC_FEATURE
<222> LOCATION: (163)..(163)
<223> OTHER INFORMATION: Val, Ala, Cys, Met or Thr
<220> FEATURE:
<221> NAME/KEY: MISC_FEATURE
<222> LOCATION: (164)..(164)
<223> OTHER INFORMATION: Asp, Ala, Glu, His, Ser or Thr
<220> FEATURE:
<221> NAME/KEY: MISC_FEATURE
<222> LOCATION: (165)..(165)
<223> OTHER INFORMATION: Leu, Cys, Met or Val
<220> FEATURE:
<221> NAME/KEY: MISC_FEATURE
<222> LOCATION: (166)..(166)
<223> OTHER INFORMATION: Gly, Ala or Pro
<220> FEATURE:
<221> NAME/KEY: MISC_FEATURE
<222> LOCATION: (167)..(167)
<223> OTHER INFORMATION: Arg or Val
<220> FEATURE:
<221> NAME/KEY: MISC_FEATURE
<222> LOCATION: (169)..(169)
<223> OTHER INFORMATION: Phe, Ala, His, Trp or Tyr
<220> FEATURE:
<221> NAME/KEY: MISC_FEATURE
<222> LOCATION: (170)..(170)
<223> OTHER INFORMATION: Arg, Cys, Gly, Ile, Lys, Leu, Met, Pro, Gln,
      Ser, Thr, Val or Trp
<220> FEATURE:
<221> NAME/KEY: MISC_FEATURE
<222> LOCATION: (171)..(171)
<223> OTHER INFORMATION: Leu, Phe, Ile, Met or Val
<220> FEATURE:
<221> NAME/KEY: MISC_FEATURE
<222> LOCATION: (172)..(172)
<223> OTHER INFORMATION: Ala, Pro, Arg or Ser
<220> FEATURE:
<221> NAME/KEY: MISC_FEATURE
<222> LOCATION: (173)..(173)
<223> OTHER INFORMATION: Glu or Pro
<220> FEATURE:
<221> NAME/KEY: MISC_FEATURE
<222> LOCATION: (174)..(174)
<223> OTHER INFORMATION: Val, Cys or Ile
<220> FEATURE:
<221> NAME/KEY: MISC_FEATURE
<222> LOCATION: (175)..(175)
<223> OTHER INFORMATION: Glu, Asp, Val or Trp
<220> FEATURE:
<221> NAME/KEY: MISC_FEATURE
<222> LOCATION: (176)..(176)
<223> OTHER INFORMATION: Leu, Ala or Met
<220> FEATURE:
<221> NAME/KEY: MISC_FEATURE
<222> LOCATION: (181)..(181)
<223> OTHER INFORMATION: Val, Phe, Ile, Met or Asn
<220> FEATURE:
<221> NAME/KEY: MISC_FEATURE
<222> LOCATION: (182)..(182)
<223> OTHER INFORMATION: Leu or Met
<220> FEATURE:
<221> NAME/KEY: MISC_FEATURE
<222> LOCATION: (187)..(187)
<223> OTHER INFORMATION: Tyr, Cys, Glu, Gly, His, Met or Val
<220> FEATURE:
<221> NAME/KEY: MISC_FEATURE
<222> LOCATION: (188)..(188)
<223> OTHER INFORMATION: Pro, Asp, Gly or Gln
<220> FEATURE:
<221> NAME/KEY: MISC_FEATURE
<222> LOCATION: (189)..(189)
<223> OTHER INFORMATION: Asp, Glu, Pro, Ser or Thr
<220> FEATURE:
<221> NAME/KEY: MISC_FEATURE
<222> LOCATION: (190)..(190)
<223> OTHER INFORMATION: Gly, Ala, Cys, Asp, Glu, Leu, Met, Asn, Pro,
```

```
              Gln, Arg, Ser, Thr, Val or Trp
<220> FEATURE:
<221> NAME/KEY: MISC_FEATURE
<222> LOCATION: (191)..(191)
<223> OTHER INFORMATION: Ala, Glu, Phe, Gly, His, Ile, Lys, Leu, Met,
      Asn, Arg, Ser, Thr or Val
<220> FEATURE:
<221> NAME/KEY: MISC_FEATURE
<222> LOCATION: (192)..(192)
<223> OTHER INFORMATION: Ala or Val
<220> FEATURE:
<221> NAME/KEY: MISC_FEATURE
<222> LOCATION: (193)..(193)
<223> OTHER INFORMATION: Gly, Ala, His, Ile, Leu, Pro, Gln, Arg, Ser,
      Thr or Val
<220> FEATURE:
<221> NAME/KEY: MISC_FEATURE
<222> LOCATION: (194)..(194)
<223> OTHER INFORMATION: Glu, Asp or Leu
<220> FEATURE:
<221> NAME/KEY: MISC_FEATURE
<222> LOCATION: (195)..(195)
<223> OTHER INFORMATION: Pro, Ala, Cys, Asp, Glu, Gln, Ser, Thr or Val
<220> FEATURE:
<221> NAME/KEY: MISC_FEATURE
<222> LOCATION: (196)..(196)
<223> OTHER INFORMATION: Phe or Trp
<220> FEATURE:
<221> NAME/KEY: MISC_FEATURE
<222> LOCATION: (200)..(200)
<223> OTHER INFORMATION: Phe or Cys
<220> FEATURE:
<221> NAME/KEY: MISC_FEATURE
<222> LOCATION: (202)..(202)
<223> OTHER INFORMATION: Gly, Ala, Glu, Lys, Leu, Thr, Val or Tyr
<220> FEATURE:
<221> NAME/KEY: MISC_FEATURE
<222> LOCATION: (204)..(204)
<223> OTHER INFORMATION: Ala, Cys, Asp, Glu, Gly, His, Lys, Leu, Met,
      Asn, Gln, Thr or Val
<220> FEATURE:
<221> NAME/KEY: MISC_FEATURE
<222> LOCATION: (205)..(205)
<223> OTHER INFORMATION: Ser, Asp, Gly, Leu, Gln, Thr or Val
<220> FEATURE:
<221> NAME/KEY: MISC_FEATURE
<222> LOCATION: (206)..(206)
<223> OTHER INFORMATION: Pro, Cys, Asp, Lys, Leu, Gln, Ser or Thr
<220> FEATURE:
<221> NAME/KEY: MISC_FEATURE
<222> LOCATION: (207)..(207)
<223> OTHER INFORMATION: Gly, Gln, Ser or Val
<220> FEATURE:
<221> NAME/KEY: MISC_FEATURE
<222> LOCATION: (208)..(208)
<223> OTHER INFORMATION: Ala, Gly, His, Gln, Arg or Trp
<220> FEATURE:
<221> NAME/KEY: MISC_FEATURE
<222> LOCATION: (209)..(209)
<223> OTHER INFORMATION: Ala, Cys, Asp, Glu, Gly, Ile, Lys, Leu, Met,
      Pro, Gln, Ser, Thr or Trp
<220> FEATURE:
<221> NAME/KEY: MISC_FEATURE
<222> LOCATION: (210)..(210)
<223> OTHER INFORMATION: Asp, Glu, Gly, Ser or Thr
<220> FEATURE:
<221> NAME/KEY: MISC_FEATURE
<222> LOCATION: (211)..(211)
<223> OTHER INFORMATION: Tyr, Cys, Phe, Leu, Ser or Trp
<220> FEATURE:
<221> NAME/KEY: MISC_FEATURE
<222> LOCATION: (212)..(212)
<223> OTHER INFORMATION: Gly or Lys
<220> FEATURE:
<221> NAME/KEY: MISC_FEATURE
<222> LOCATION: (213)..(213)
<223> OTHER INFORMATION: Leu or Trp
<220> FEATURE:
<221> NAME/KEY: MISC_FEATURE
```

-continued

```
<222> LOCATION: (214)..(214)
<223> OTHER INFORMATION: Ser, Lys, Met, Asn, Gln, Arg or Thr
<220> FEATURE:
<221> NAME/KEY: MISC_FEATURE
<222> LOCATION: (215)..(215)
<223> OTHER INFORMATION: Arg, Ala or Gly
<220> FEATURE:
<221> NAME/KEY: MISC_FEATURE
<222> LOCATION: (217)..(217)
<223> OTHER INFORMATION: Asp, Gln or Tyr
<220> FEATURE:
<221> NAME/KEY: MISC_FEATURE
<222> LOCATION: (220)..(220)
<223> OTHER INFORMATION: Val or Thr
<220> FEATURE:
<221> NAME/KEY: MISC_FEATURE
<222> LOCATION: (221)..(221)
<223> OTHER INFORMATION: Gly, Ala, Phe, His, Ile, Leu, Met, Thr or Val
<220> FEATURE:
<221> NAME/KEY: MISC_FEATURE
<222> LOCATION: (222)..(222)
<223> OTHER INFORMATION: Asn, Gly or Val
<220> FEATURE:
<221> NAME/KEY: MISC_FEATURE
<222> LOCATION: (227)..(227)
<223> OTHER INFORMATION: Ala, Asp, Glu, Gly, Ile, Lys, Leu, Met, Asn,
      Gln, Arg, Ser, Thr or Val
<220> FEATURE:
<221> NAME/KEY: MISC_FEATURE
<222> LOCATION: (229)..(229)
<223> OTHER INFORMATION: Ala or Thr
<220> FEATURE:
<221> NAME/KEY: MISC_FEATURE
<222> LOCATION: (230)..(230)
<223> OTHER INFORMATION: Ala, Arg or Val
<220> FEATURE:
<221> NAME/KEY: MISC_FEATURE
<222> LOCATION: (231)..(231)
<223> OTHER INFORMATION: Ala, Cys, His, Leu, Ser or Thr
<220> FEATURE:
<221> NAME/KEY: MISC_FEATURE
<222> LOCATION: (233)..(233)
<223> OTHER INFORMATION: Met or Val
<220> FEATURE:
<221> NAME/KEY: MISC_FEATURE
<222> LOCATION: (234)..(234)
<223> OTHER INFORMATION: Ala, Cys, Glu, Gly, Lys, Leu, Met, Gln, Ser or
      Val
<220> FEATURE:
<221> NAME/KEY: MISC_FEATURE
<222> LOCATION: (238)..(238)
<223> OTHER INFORMATION: Gly or Ser
<220> FEATURE:
<221> NAME/KEY: MISC_FEATURE
<222> LOCATION: (240)..(240)
<223> OTHER INFORMATION: His or Arg
<220> FEATURE:
<221> NAME/KEY: MISC_FEATURE
<222> LOCATION: (241)..(241)
<223> OTHER INFORMATION: Glu, Ala, Asp, Gly, Asn, Pro, Arg, Ser or Thr
<220> FEATURE:
<221> NAME/KEY: MISC_FEATURE
<222> LOCATION: (242)..(242)
<223> OTHER INFORMATION: Phe, Ala, Asp or Ser
<220> FEATURE:
<221> NAME/KEY: MISC_FEATURE
<222> LOCATION: (273)..(273)
<223> OTHER INFORMATION: Leu or Val
<220> FEATURE:
<221> NAME/KEY: MISC_FEATURE
<222> LOCATION: (292)..(292)
<223> OTHER INFORMATION: His or Asn
<220> FEATURE:
<221> NAME/KEY: MISC_FEATURE
<222> LOCATION: (331)..(331)
<223> OTHER INFORMATION: Leu, Asp, Gly, Asn or Arg
<220> FEATURE:
<221> NAME/KEY: MISC_FEATURE
<222> LOCATION: (332)..(332)
```

```
-continued

<223> OTHER INFORMATION: Ser or Ala
<220> FEATURE:
<221> NAME/KEY: MISC_FEATURE
<222> LOCATION: (339)..(339)
<223> OTHER INFORMATION: Arg or Lys
<220> FEATURE:
<221> NAME/KEY: MISC_FEATURE
<222> LOCATION: (340)..(340)
<223> OTHER INFORMATION: Arg, Glu, Lys or Asn
<220> FEATURE:
<221> NAME/KEY: MISC_FEATURE
<222> LOCATION: (342)..(342)
<223> OTHER INFORMATION: Ala, Cys, Leu, Met, Asn, Arg or Val
<220> FEATURE:
<221> NAME/KEY: MISC_FEATURE
<222> LOCATION: (343)..(343)
<223> OTHER INFORMATION: Gly or Arg
<220> FEATURE:
<221> NAME/KEY: MISC_FEATURE
<222> LOCATION: (345)..(345)
<223> OTHER INFORMATION: Val or Ile
<220> FEATURE:
<221> NAME/KEY: MISC_FEATURE
<222> LOCATION: (347)..(347)
<223> OTHER INFORMATION: Thr or Ser
<220> FEATURE:
<221> NAME/KEY: MISC_FEATURE
<222> LOCATION: (348)..(348)
<223> OTHER INFORMATION: Glu or Tyr
<220> FEATURE:
<221> NAME/KEY: MISC_FEATURE
<222> LOCATION: (349)..(349)
<223> OTHER INFORMATION: Ala, Glu, Gln, Arg or Ser
<220> FEATURE:
<221> NAME/KEY: MISC_FEATURE
<222> LOCATION: (351)..(351)
<223> OTHER INFORMATION: Ile, Cys or Val
<220> FEATURE:
<221> NAME/KEY: MISC_FEATURE
<222> LOCATION: (352)..(352)
<223> OTHER INFORMATION: Asn, Glu, Lys, Leu, Gln or Arg
<220> FEATURE:
<221> NAME/KEY: MISC_FEATURE
<222> LOCATION: (353)..(353)
<223> OTHER INFORMATION: Glu, Leu, Met, Ser or Thr
<220> FEATURE:
<221> NAME/KEY: MISC_FEATURE
<222> LOCATION: (356)..(356)
<223> OTHER INFORMATION: Glu, Lys or Arg
<220> FEATURE:
<221> NAME/KEY: MISC_FEATURE
<222> LOCATION: (357)..(357)
<223> OTHER INFORMATION: Leu or Tyr
<220> FEATURE:
<221> NAME/KEY: MISC_FEATURE
<222> LOCATION: (358)..(358)
<223> OTHER INFORMATION: Gly, Glu or Arg
<220> FEATURE:
<221> NAME/KEY: MISC_FEATURE
<222> LOCATION: (360)..(360)
<223> OTHER INFORMATION: Met, Leu or Thr
<220> FEATURE:
<221> NAME/KEY: MISC_FEATURE
<222> LOCATION: (364)..(364)
<223> OTHER INFORMATION: Asp, Gly, Ser or Val
<220> FEATURE:
<221> NAME/KEY: MISC_FEATURE
<222> LOCATION: (365)..(365)
<223> OTHER INFORMATION: Asp or Ala
<220> FEATURE:
<221> NAME/KEY: MISC_FEATURE
<222> LOCATION: (366)..(366)
<223> OTHER INFORMATION: Gln or Glu
<220> FEATURE:
<221> NAME/KEY: MISC_FEATURE
<222> LOCATION: (368)..(368)
<223> OTHER INFORMATION: Val or Leu
<220> FEATURE:
<221> NAME/KEY: MISC_FEATURE
```

```
<222> LOCATION: (369)..(369)
<223> OTHER INFORMATION: Leu, Met or Val
<220> FEATURE:
<221> NAME/KEY: MISC_FEATURE
<222> LOCATION: (372)..(372)
<223> OTHER INFORMATION: Ile, Ala, Lys, Gln, Ser or Thr
<220> FEATURE:
<221> NAME/KEY: MISC_FEATURE
<222> LOCATION: (373)..(373)
<223> OTHER INFORMATION: Phe, Gly, Leu, Arg or Val
<220> FEATURE:
<221> NAME/KEY: MISC_FEATURE
<222> LOCATION: (375)..(375)
<223> OTHER INFORMATION: Lys, Leu or Arg
<220> FEATURE:
<221> NAME/KEY: MISC_FEATURE
<222> LOCATION: (376)..(376)
<223> OTHER INFORMATION: Pro, Cys, Gly, Ser, Val or Trp
<220> FEATURE:
<221> NAME/KEY: MISC_FEATURE
<222> LOCATION: (377)..(377)
<223> OTHER INFORMATION: Val, Glu, Gly or Leu
<220> FEATURE:
<221> NAME/KEY: MISC_FEATURE
<222> LOCATION: (379)..(379)
<223> OTHER INFORMATION: Asp or Lys
<220> FEATURE:
<221> NAME/KEY: MISC_FEATURE
<222> LOCATION: (381)..(381)
<223> OTHER INFORMATION: Pro or Asn
<220> FEATURE:
<221> NAME/KEY: MISC_FEATURE
<222> LOCATION: (382)..(382)
<223> OTHER INFORMATION: Thr, Ala, Phe or Ser
<220> FEATURE:
<221> NAME/KEY: MISC_FEATURE
<222> LOCATION: (383)..(383)
<223> OTHER INFORMATION: Phe, Leu or Met
<220> FEATURE:
<221> NAME/KEY: MISC_FEATURE
<222> LOCATION: (384)..(384)
<223> OTHER INFORMATION: Phe, Trp or Tyr
<220> FEATURE:
<221> NAME/KEY: MISC_FEATURE
<222> LOCATION: (385)..(385)
<223> OTHER INFORMATION: Leu, Ile or Val
<220> FEATURE:
<221> NAME/KEY: MISC_FEATURE
<222> LOCATION: (386)..(386)
<223> OTHER INFORMATION: Glu, Cys, Ile or Val
<220> FEATURE:
<221> NAME/KEY: MISC_FEATURE
<222> LOCATION: (387)..(387)
<223> OTHER INFORMATION: Ile, Gly or Leu
<220> FEATURE:
<221> NAME/KEY: MISC_FEATURE
<222> LOCATION: (388)..(388)
<223> OTHER INFORMATION: Ile, Leu, Ser or Val
<220> FEATURE:
<221> NAME/KEY: MISC_FEATURE
<222> LOCATION: (389)..(389)
<223> OTHER INFORMATION: Gln, Gly, Lys or Thr
<220> FEATURE:
<221> NAME/KEY: MISC_FEATURE
<222> LOCATION: (390)..(390)
<223> OTHER INFORMATION: Arg or Asn
<220> FEATURE:
<221> NAME/KEY: MISC_FEATURE
<222> LOCATION: (391)..(391)
<223> OTHER INFORMATION: Ile, Leu or Val
<220> FEATURE:
<221> NAME/KEY: MISC_FEATURE
<222> LOCATION: (392)..(392)
<223> OTHER INFORMATION: Gly, Arg or Val
<220> FEATURE:
<221> NAME/KEY: MISC_FEATURE
<222> LOCATION: (394)..(394)
<223> OTHER INFORMATION: Met, Ile, Lys, Leu, Gln, Val or Tyr
<220> FEATURE:
```

```
<221> NAME/KEY: MISC_FEATURE
<222> LOCATION: (395)..(395)
<223> OTHER INFORMATION: Glu, Lys, Gln, Ser or Val
<220> FEATURE:
<221> NAME/KEY: MISC_FEATURE
<222> LOCATION: (396)..(396)
<223> OTHER INFORMATION: Lys, Ala, Leu, Met, Gln, Arg, Thr or Val
<220> FEATURE:
<221> NAME/KEY: MISC_FEATURE
<222> LOCATION: (397)..(397)
<223> OTHER INFORMATION: Asp, Gly or Ser
<220> FEATURE:
<221> NAME/KEY: MISC_FEATURE
<222> LOCATION: (398)..(398)
<223> OTHER INFORMATION: Glu, Ala, Asp, Gly, Pro or Ser
<220> FEATURE:
<221> NAME/KEY: MISC_FEATURE
<222> LOCATION: (399)..(399)
<223> OTHER INFORMATION: Lys, Ala, Asp, Gly, His, Ile, Met, Asn, Gln,
      Arg, Ser, Thr, Val or Tyr
<220> FEATURE:
<221> NAME/KEY: MISC_FEATURE
<222> LOCATION: (400)..(400)
<223> OTHER INFORMATION: Gly, Glu, Lys or Ser
<220> FEATURE:
<221> NAME/KEY: MISC_FEATURE
<222> LOCATION: (401)..(401)
<223> OTHER INFORMATION: Gln, Ala, Glu, Ser or Val
<220> FEATURE:
<221> NAME/KEY: MISC_FEATURE
<222> LOCATION: (406)..(406)
<223> OTHER INFORMATION: Gly or Cys
<220> FEATURE:
<221> NAME/KEY: MISC_FEATURE
<222> LOCATION: (407)..(407)
<223> OTHER INFORMATION: Gly, Ala, Lys, Leu, Arg, Ser or Thr
<220> FEATURE:
<221> NAME/KEY: MISC_FEATURE
<222> LOCATION: (408)..(408)
<223> OTHER INFORMATION: Cys, Gly, Arg, Thr, Val or Trp
<220> FEATURE:
<221> NAME/KEY: MISC_FEATURE
<222> LOCATION: (411)..(411)
<223> OTHER INFORMATION: Phe, Ala or Leu
<220> FEATURE:
<221> NAME/KEY: MISC_FEATURE
<222> LOCATION: (413)..(413)
<223> OTHER INFORMATION: Lys, Ala, Pro, Arg or Ser
<220> FEATURE:
<221> NAME/KEY: MISC_FEATURE
<222> LOCATION: (415)..(415)
<223> OTHER INFORMATION: Asn or Ala
<220> FEATURE:
<221> NAME/KEY: MISC_FEATURE
<222> LOCATION: (416)..(416)
<223> OTHER INFORMATION: Phe, Arg or Val
<220> FEATURE:
<221> NAME/KEY: MISC_FEATURE
<222> LOCATION: (417)..(417)
<223> OTHER INFORMATION: Gly, Gln or Ser
<220> FEATURE:
<221> NAME/KEY: MISC_FEATURE
<222> LOCATION: (418)..(418)
<223> OTHER INFORMATION: Gln, Ala, Cys, Glu, Gly, Leu or Thr
<220> FEATURE:
<221> NAME/KEY: MISC_FEATURE
<222> LOCATION: (422)..(422)
<223> OTHER INFORMATION: Ser or Met
<220> FEATURE:
<221> NAME/KEY: MISC_FEATURE
<222> LOCATION: (423)..(423)
<223> OTHER INFORMATION: Ile, Val or Trp
<220> FEATURE:
<221> NAME/KEY: MISC_FEATURE
<222> LOCATION: (424)..(424)
<223> OTHER INFORMATION: Glu or Gln
<220> FEATURE:
<221> NAME/KEY: MISC_FEATURE
<222> LOCATION: (425)..(425)
```

```
<223> OTHER INFORMATION: Asp, Ala, Glu, Gly, Met, Ser or Thr
<220> FEATURE:
<221> NAME/KEY: MISC_FEATURE
<222> LOCATION: (426)..(426)
<223> OTHER INFORMATION: Tyr, Leu or Trp
<220> FEATURE:
<221> NAME/KEY: MISC_FEATURE
<222> LOCATION: (427)..(427)
<223> OTHER INFORMATION: Glu, Ala, Leu or Met
<220> FEATURE:
<221> NAME/KEY: MISC_FEATURE
<222> LOCATION: (428)..(428)
<223> OTHER INFORMATION: Lys, Arg or Val
<220> FEATURE:
<221> NAME/KEY: MISC_FEATURE
<222> LOCATION: (429)..(429)
<223> OTHER INFORMATION: Ser, Cys, Asp, Gly or Thr
<220> FEATURE:
<221> NAME/KEY: MISC_FEATURE
<222> LOCATION: (430)..(430)
<223> OTHER INFORMATION: Leu, Met or Val
<220> FEATURE:
<221> NAME/KEY: MISC_FEATURE
<222> LOCATION: (431)..(431)
<223> OTHER INFORMATION: Glu, Ala, Phe, Gly, Leu or Asn
<220> FEATURE:
<221> NAME/KEY: MISC_FEATURE
<222> LOCATION: (432)..(432)
<223> OTHER INFORMATION: Ala, Asp, Gly, Lys, Leu, Arg, Ser or Val
<220> FEATURE:
<221> NAME/KEY: MISC_FEATURE
<222> LOCATION: (433)..(433)
<223> OTHER INFORMATION: Lys, Glu, His, Leu, Pro, Arg, Ser or Val
<220> FEATURE:
<221> NAME/KEY: MISC_FEATURE
<222> LOCATION: (434)..(434)
<223> OTHER INFORMATION: Gln, Ala, Cys, Asp, Phe, Gly, His, Lys, Leu or
      Arg
<220> FEATURE:
<221> NAME/KEY: MISC_FEATURE
<222> LOCATION: (437)..(437)
<223> OTHER INFORMATION: Ala, Phe, Lys or Val
<220> FEATURE:
<221> NAME/KEY: MISC_FEATURE
<222> LOCATION: (438)..(438)
<223> OTHER INFORMATION: Ala, Gly or Arg
<220> FEATURE:
<221> NAME/KEY: MISC_FEATURE
<222> LOCATION: (439)..(439)
<223> OTHER INFORMATION: Ala or Arg

<400> SEQUENCE: 80

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Xaa Xaa Xaa Xaa Asp Xaa Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Xaa Phe Ala Ala
        115                 120                 125

Asp His Gly Leu Ala Val Arg Ala Val Ala Leu Arg Val Ala Asp Ala
    130                 135                 140
```

Glu Asp Xaa Xaa Xaa Ala Ser Xaa Xaa Xaa Gly Ala Xaa Xaa Xaa Xaa
145                 150                 155                 160

Xaa Xaa Xaa Xaa Xaa Xaa Xaa Gly Xaa Xaa Xaa Xaa Xaa Xaa Xaa Xaa
                165                 170                 175

Tyr Gly Asp Val Xaa Xaa Arg Tyr Val Ser Xaa Xaa Xaa Xaa Xaa
            180                 185                 190

Xaa Xaa Xaa Xaa Leu Pro Gly Xaa Glu Xaa Val Xaa Xaa Xaa Xaa
            195                 200                 205

Xaa Xaa Xaa Xaa Xaa Xaa Phe Xaa His Ile Xaa Xaa Xaa Val Pro
            210                 215                 220

Glu Leu Xaa Pro Xaa Xaa Xaa Tyr Xaa Xaa Gly Phe Thr Xaa Phe Xaa
225                 230                 235                 240

Xaa Xaa Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
            260                 265                 270

Xaa Asn Glu Pro Val His Gly Thr Lys Arg Arg Ser Gln Ile Gln Thr
            275                 280                 285

Phe Leu Asp Xaa His Gly Gly Pro Gly Val Gln His Ile Ala Leu Ala
            290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Xaa Xaa Asp Tyr Tyr Asp
            325                 330                 335

Gly Val Xaa Xaa Cys Xaa Xaa Asp Leu Xaa Xaa Xaa Gln Xaa Xaa
            340                 345                 350

Xaa Cys Gln Xaa Xaa Xaa Val Xaa Val Asp Arg Xaa Xaa Xaa Gly Xaa
            355                 360                 365

Xaa Leu Gln Xaa Xaa Thr Xaa Xaa Xaa Gly Xaa Arg Xaa Xaa Xaa Xaa
            370                 375                 380

Xaa Xaa Xaa Xaa Xaa Xaa Xaa Cys Xaa Xaa Xaa Xaa Xaa Xaa Xaa Xaa
385                 390                 395                 400

Xaa Glu Tyr Gln Lys Xaa Xaa Xaa Gly Gly Xaa Gly Xaa Gly Xaa Xaa
            405                 410                 415

Xaa Xaa Leu Phe Lys Xaa Xaa Xaa Xaa Xaa Xaa Xaa Xaa Xaa Xaa
            420                 425                 430

Xaa Xaa Ala Ala Xaa Xaa Xaa Thr Ala Gln Gly Ser
            435                 440

```
<210> SEQ ID NO 81
<211> LENGTH: 444
<212> TYPE: PRT
<213> ORGANISM: Artificial Sequence
<220> FEATURE:
<223> OTHER INFORMATION: Zea mays variant form created by artificial
      means.
<220> FEATURE:
<221> NAME/KEY: MISC_FEATURE
<222> LOCATION: (53)..(53)
<223> OTHER INFORMATION: Leu or Phe
<220> FEATURE:
<221> NAME/KEY: MISC_FEATURE
<222> LOCATION: (56)..(56)
<223> OTHER INFORMATION: Ala or Ser
<220> FEATURE:
<221> NAME/KEY: MISC_FEATURE
<222> LOCATION: (125)..(125)
<223> OTHER INFORMATION: Arg or Leu
<220> FEATURE:
```

```
<221> NAME/KEY: MISC_FEATURE
<222> LOCATION: (158)..(158)
<223> OTHER INFORMATION: Pro or Lys
<220> FEATURE:
<221> NAME/KEY: MISC_FEATURE
<222> LOCATION: (159)..(159)
<223> OTHER INFORMATION: Ala or Cys
<220> FEATURE:
<221> NAME/KEY: MISC_FEATURE
<222> LOCATION: (161)..(161)
<223> OTHER INFORMATION: Gly, Glu, Gln, Ser, Tyr, Asn or Leu
<220> FEATURE:
<221> NAME/KEY: MISC_FEATURE
<222> LOCATION: (166)..(166)
<223> OTHER INFORMATION: Gly, Pro or Ala
<220> FEATURE:
<221> NAME/KEY: MISC_FEATURE
<222> LOCATION: (169)..(169)
<223> OTHER INFORMATION: Phe or His
<220> FEATURE:
<221> NAME/KEY: MISC_FEATURE
<222> LOCATION: (171)..(171)
<223> OTHER INFORMATION: Leu or Phe
<220> FEATURE:
<221> NAME/KEY: MISC_FEATURE
<222> LOCATION: (182)..(182)
<223> OTHER INFORMATION: Leu or Met
<220> FEATURE:
<221> NAME/KEY: MISC_FEATURE
<222> LOCATION: (189)..(189)
<223> OTHER INFORMATION: Asp or Pro
<220> FEATURE:
<221> NAME/KEY: MISC_FEATURE
<222> LOCATION: (190)..(190)
<223> OTHER INFORMATION: Gly or Thr
<220> FEATURE:
<221> NAME/KEY: MISC_FEATURE
<222> LOCATION: (191)..(191)
<223> OTHER INFORMATION: Ala, Ser, Leu or Gly
<220> FEATURE:
<221> NAME/KEY: MISC_FEATURE
<222> LOCATION: (193)..(193)
<223> OTHER INFORMATION: Gly or Gln
<220> FEATURE:
<221> NAME/KEY: MISC_FEATURE
<222> LOCATION: (206)..(206)
<223> OTHER INFORMATION: Pro, Gln, Ser, Lys or Leu
<220> FEATURE:
<221> NAME/KEY: MISC_FEATURE
<222> LOCATION: (211)..(211)
<223> OTHER INFORMATION: Tyr, Leu or Ser
<220> FEATURE:
<221> NAME/KEY: MISC_FEATURE
<222> LOCATION: (214)..(214)
<223> OTHER INFORMATION: Ser, Asn, Thr, Arg or Met
<220> FEATURE:
<221> NAME/KEY: MISC_FEATURE
<222> LOCATION: (215)..(215)
<223> OTHER INFORMATION: Arg or Gly
<220> FEATURE:
<221> NAME/KEY: MISC_FEATURE
<222> LOCATION: (217)..(217)
<223> OTHER INFORMATION: Asp or Tyr
<220> FEATURE:
<221> NAME/KEY: MISC_FEATURE
<222> LOCATION: (221)..(221)
<223> OTHER INFORMATION: Gly, Val or Ala
<220> FEATURE:
<221> NAME/KEY: MISC_FEATURE
<222> LOCATION: (227)..(227)
<223> OTHER INFORMATION: Ala or Gly
<220> FEATURE:
<221> NAME/KEY: MISC_FEATURE
<222> LOCATION: (331)..(331)
<223> OTHER INFORMATION: Leu, Asn, Arg, Gly or Asp
<220> FEATURE:
<221> NAME/KEY: MISC_FEATURE
<222> LOCATION: (332)..(332)
<223> OTHER INFORMATION: Ser or Ala
```

```
<220> FEATURE:
<221> NAME/KEY: MISC_FEATURE
<222> LOCATION: (340)..(340)
<223> OTHER INFORMATION: Arg or Lys
<220> FEATURE:
<221> NAME/KEY: MISC_FEATURE
<222> LOCATION: (342)..(342)
<223> OTHER INFORMATION: Ala, Val, Met or Cys
<220> FEATURE:
<221> NAME/KEY: MISC_FEATURE
<222> LOCATION: (349)..(349)
<223> OTHER INFORMATION: Ala, Gln or Glu
<220> FEATURE:
<221> NAME/KEY: MISC_FEATURE
<222> LOCATION: (352)..(352)
<223> OTHER INFORMATION: Asn or Arg
<220> FEATURE:
<221> NAME/KEY: MISC_FEATURE
<222> LOCATION: (356)..(356)
<223> OTHER INFORMATION: Glu, Lys or Arg
<220> FEATURE:
<221> NAME/KEY: MISC_FEATURE
<222> LOCATION: (358)..(358)
<223> OTHER INFORMATION: Gly or Glu
<220> FEATURE:
<221> NAME/KEY: MISC_FEATURE
<222> LOCATION: (360)..(360)
<223> OTHER INFORMATION: Met or Leu
<220> FEATURE:
<221> NAME/KEY: MISC_FEATURE
<222> LOCATION: (366)..(366)
<223> OTHER INFORMATION: Gln or Glu
<220> FEATURE:
<221> NAME/KEY: MISC_FEATURE
<222> LOCATION: (373)..(373)
<223> OTHER INFORMATION: Phe or Val
<220> FEATURE:
<221> NAME/KEY: MISC_FEATURE
<222> LOCATION: (375)..(375)
<223> OTHER INFORMATION: Lys, Leu or Arg
<220> FEATURE:
<221> NAME/KEY: MISC_FEATURE
<222> LOCATION: (376)..(376)
<223> OTHER INFORMATION: Pro or Trp
<220> FEATURE:
<221> NAME/KEY: MISC_FEATURE
<222> LOCATION: (381)..(381)
<223> OTHER INFORMATION: Pro or Asn
<220> FEATURE:
<221> NAME/KEY: MISC_FEATURE
<222> LOCATION: (382)..(382)
<223> OTHER INFORMATION: Thr or Ser
<220> FEATURE:
<221> NAME/KEY: MISC_FEATURE
<222> LOCATION: (383)..(383)
<223> OTHER INFORMATION: Phe, Met or Leu
<220> FEATURE:
<221> NAME/KEY: MISC_FEATURE
<222> LOCATION: (385)..(385)
<223> OTHER INFORMATION: Leu, Val or Ile
<220> FEATURE:
<221> NAME/KEY: MISC_FEATURE
<222> LOCATION: (387)..(387)
<223> OTHER INFORMATION: Ile or Leu
<220> FEATURE:
<221> NAME/KEY: MISC_FEATURE
<222> LOCATION: (390)..(390)
<223> OTHER INFORMATION: Arg or Asn
<220> FEATURE:
<221> NAME/KEY: MISC_FEATURE
<222> LOCATION: (396)..(396)
<223> OTHER INFORMATION: Lys, Thr, Met or Leu
<220> FEATURE:
<221> NAME/KEY: MISC_FEATURE
<222> LOCATION: (398)..(398)
<223> OTHER INFORMATION: Glu, Asp or Ala
<220> FEATURE:
<221> NAME/KEY: MISC_FEATURE
<222> LOCATION: (399)..(399)
```

```
<223> OTHER INFORMATION: Lys, Asn, Arg, Gln or Ser
<220> FEATURE:
<221> NAME/KEY: MISC_FEATURE
<222> LOCATION: (413)..(413)
<223> OTHER INFORMATION: Lys or Ala
<220> FEATURE:
<221> NAME/KEY: MISC_FEATURE
<222> LOCATION: (417)..(417)
<223> OTHER INFORMATION: Gly, Ser or Gln
<220> FEATURE:
<221> NAME/KEY: MISC_FEATURE
<222> LOCATION: (418)..(418)
<223> OTHER INFORMATION: Gln or Glu
<220> FEATURE:
<221> NAME/KEY: MISC_FEATURE
<222> LOCATION: (423)..(423)
<223> OTHER INFORMATION: Ile or Trp
<220> FEATURE:
<221> NAME/KEY: MISC_FEATURE
<222> LOCATION: (429)..(429)
<223> OTHER INFORMATION: Ser, Gly or Thr
<220> FEATURE:
<221> NAME/KEY: MISC_FEATURE
<222> LOCATION: (431)..(431)
<223> OTHER INFORMATION: Glu or Phe
<220> FEATURE:
<221> NAME/KEY: MISC_FEATURE
<222> LOCATION: (432)..(432)
<223> OTHER INFORMATION: Ala, Arg, Lys or Ser
<220> FEATURE:
<221> NAME/KEY: MISC_FEATURE
<222> LOCATION: (434)..(434)
<223> OTHER INFORMATION: Gln, Arg, His, Leu or Lys
<220> FEATURE:
<221> NAME/KEY: MISC_FEATURE
<222> LOCATION: (437)..(437)
<223> OTHER INFORMATION: Ala, Lys or Phe
<220> FEATURE:
<221> NAME/KEY: MISC_FEATURE
<222> LOCATION: (438)..(438)
<223> OTHER INFORMATION: Ala, Gly or Arg
<220> FEATURE:
<221> NAME/KEY: MISC_FEATURE
<222> LOCATION: (439)..(439)
<223> OTHER INFORMATION: Ala or Arg

<400> SEQUENCE: 81

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe Gln Thr Leu Ala Phe
        35                  40                  45

His His Val Glu Xaa Trp Cys Xaa Asp Ala Ala Ser Ala Ala Gly Arg
    50                  55                  60

Phe Ser Phe Ala Leu Gly Val Pro Leu Ala Ala Arg Ser Asp Leu Ser
65                  70                  75                  80

Thr Gly Asn Ser Ala His Ala Ser Leu Leu Leu Arg Ser Gly Ser Leu
                85                  90                  95

Ser Leu Leu Phe Thr Ala Pro Tyr Ala His Gly Ala Asp Ala Ala Thr
            100                 105                 110

Ala Ala Leu Pro Ser Phe Ser Ala Ala Ala Arg Xaa Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Xaa Xaa Phe
145                 150                 155                 160

Xaa Pro Val Asp Leu Xaa Arg Gly Xaa Arg Xaa Ala Glu Val Glu Leu
```

```
                    165                 170                 175
Tyr Gly Asp Val Val Xaa Arg Tyr Val Ser Tyr Pro Xaa Xaa Xaa Ala
            180                 185                 190

Xaa Glu Pro Phe Leu Pro Gly Phe Glu Gly Val Ala Ser Xaa Gly Ala
        195                 200                 205

Ala Asp Xaa Gly Leu Xaa Xaa Phe Xaa His Ile Val Xaa Asn Val Pro
    210                 215                 220

Glu Leu Xaa Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
            245                 250                 255

Leu Asn Ser Met Ala Leu Ala Asn Asn Ser Glu Asn Val Leu Leu Pro
        260                 265                 270

Leu Asn Glu Pro Val His Gly Thr Lys Arg Arg Ser Gln Ile Gln Thr
    275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Pro Xaa Xaa Asp Tyr Tyr Asp
            325                 330                 335

Gly Val Arg Xaa Cys Xaa Gly Asp Val Leu Thr Glu Xaa Gln Ile Xaa
        340                 345                 350

Glu Cys Gln Xaa Leu Xaa Val Xaa Val Asp Arg Asp Xaa Gly Val
    355                 360                 365

Leu Leu Gln Ile Xaa Thr Xaa Xaa Val Gly Asp Arg Xaa Xaa Xaa Phe
370                 375                 380

Xaa Glu Xaa Ile Gln Xaa Ile Gly Cys Met Glu Xaa Asp Xaa Xaa Gly
385                 390                 395                 400

Gln Glu Tyr Gln Lys Gly Gly Cys Gly Gly Phe Gly Xaa Gly Asn Phe
            405                 410                 415

Xaa Xaa Leu Phe Lys Ser Xaa Glu Asp Tyr Glu Lys Xaa Leu Xaa Xaa
        420                 425                 430

Lys Xaa Ala Ala Xaa Xaa Xaa Thr Ala Gln Gly Ser
    435                 440
```

<210> SEQ ID NO 82
<211> LENGTH: 444
<212> TYPE: PRT
<213> ORGANISM: Artificial Sequence
<220> FEATURE:
<223> OTHER INFORMATION: Zea mays variant form created by artificial
      means.
<220> FEATURE:
<221> NAME/KEY: MISC_FEATURE
<222> LOCATION: (158)..(158)
<223> OTHER INFORMATION: Pro or Lys
<220> FEATURE:
<221> NAME/KEY: MISC_FEATURE
<222> LOCATION: (182)..(182)
<223> OTHER INFORMATION: Leu or Met
<220> FEATURE:
<221> NAME/KEY: MISC_FEATURE
<222> LOCATION: (189)..(189)
<223> OTHER INFORMATION: Asp or Pro
<220> FEATURE:
<221> NAME/KEY: MISC_FEATURE
<222> LOCATION: (191)..(191)
<223> OTHER INFORMATION: Ala, Gly or Leu
<220> FEATURE:
<221> NAME/KEY: MISC_FEATURE

```
<222> LOCATION: (205)..(205)
<223> OTHER INFORMATION: Ser or Thr
<220> FEATURE:
<221> NAME/KEY: MISC_FEATURE
<222> LOCATION: (206)..(206)
<223> OTHER INFORMATION: Pro, Gln or Ser
<220> FEATURE:
<221> NAME/KEY: MISC_FEATURE
<222> LOCATION: (211)..(211)
<223> OTHER INFORMATION: Tyr or Leu
<220> FEATURE:
<221> NAME/KEY: MISC_FEATURE
<222> LOCATION: (214)..(214)
<223> OTHER INFORMATION: Ser, Asn or Thr
<220> FEATURE:
<221> NAME/KEY: MISC_FEATURE
<222> LOCATION: (227)..(227)
<223> OTHER INFORMATION: Ala or Gly
<220> FEATURE:
<221> NAME/KEY: MISC_FEATURE
<222> LOCATION: (340)..(340)
<223> OTHER INFORMATION: Arg or Lys
<220> FEATURE:
<221> NAME/KEY: MISC_FEATURE
<222> LOCATION: (342)..(342)
<223> OTHER INFORMATION: Ala or Val
<220> FEATURE:
<221> NAME/KEY: MISC_FEATURE
<222> LOCATION: (356)..(356)
<223> OTHER INFORMATION: Glu, Lys or Arg
<220> FEATURE:
<221> NAME/KEY: MISC_FEATURE
<222> LOCATION: (360)..(360)
<223> OTHER INFORMATION: Met or Leu
<220> FEATURE:
<221> NAME/KEY: MISC_FEATURE
<222> LOCATION: (366)..(366)
<223> OTHER INFORMATION: Gln or Glu
<220> FEATURE:
<221> NAME/KEY: MISC_FEATURE
<222> LOCATION: (376)..(376)
<223> OTHER INFORMATION: Pro or Trp
<220> FEATURE:
<221> NAME/KEY: MISC_FEATURE
<222> LOCATION: (385)..(385)
<223> OTHER INFORMATION: Leu, Ile or Val
<220> FEATURE:
<221> NAME/KEY: MISC_FEATURE
<222> LOCATION: (387)..(387)
<223> OTHER INFORMATION: Ile or Leu
<220> FEATURE:
<221> NAME/KEY: MISC_FEATURE
<222> LOCATION: (390)..(390)
<223> OTHER INFORMATION: Arg or Asn
<220> FEATURE:
<221> NAME/KEY: MISC_FEATURE
<222> LOCATION: (417)..(417)
<223> OTHER INFORMATION: Gly, Gln or Ser
<220> FEATURE:
<221> NAME/KEY: MISC_FEATURE
<222> LOCATION: (431)..(431)
<223> OTHER INFORMATION: Glu or Phe
<220> FEATURE:
<221> NAME/KEY: MISC_FEATURE
<222> LOCATION: (432)..(432)
<223> OTHER INFORMATION: Ala, Arg or Lys
<220> FEATURE:
<221> NAME/KEY: MISC_FEATURE
<222> LOCATION: (434)..(434)
<223> OTHER INFORMATION: Gln, His or Arg

<400> SEQUENCE: 82

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30
```

```
Phe Val Arg Phe Asn Pro Arg Ser Asp Arg Phe Gln Thr Leu Ala Phe
         35                  40                  45

His His Val Glu Leu Trp Cys Ala Asp Ala Ala Ser Ala Ala Gly Arg
 50                  55                  60

Phe Ser Phe Ala Leu Gly Val Pro Leu Ala Ala Arg Ser Asp Leu Ser
 65                  70                  75                  80

Thr Gly Asn Ser Ala His Ala Ser Leu Leu Leu Arg Ser Gly Ser Leu
                 85                  90                  95

Ser Leu Leu Phe Thr Ala Pro Tyr Ala His Gly Ala Asp Ala Ala Thr
             100                 105                 110

Ala Ala Leu Pro Ser Phe Ser Ala Ala Ala Arg Arg Phe Ala Ala
             115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Xaa Ala Phe
145                 150                 155                 160

Gly Pro Val Asp Leu Gly Arg Gly Phe Arg Leu Ala Glu Val Glu Leu
                 165                 170                 175

Tyr Gly Asp Val Val Xaa Arg Tyr Val Ser Tyr Pro Xaa Gly Xaa Ala
             180                 185                 190

Gly Glu Pro Phe Leu Pro Gly Phe Glu Gly Val Ala Xaa Xaa Gly Ala
             195                 200                 205

Ala Asp Xaa Gly Leu Xaa Arg Phe Asp His Ile Val Gly Asn Val Pro
         210                 215                 220

Glu Leu Xaa Pro Ala Ala Ala Tyr Met Ala Gly Phe Thr Gly Phe His
225                 230                 235                 240

Glu Phe Ala Glu Phe Thr Thr Glu Asp Val Gly Thr Thr Glu Ser Gly
                 245                 250                 255

Leu Asn Ser Met Ala Leu Ala Asn Asn Ser Glu Asn Val Leu Leu Pro
             260                 265                 270

Leu Asn Glu Pro Val His Gly Thr Lys Arg Arg Ser Gln Ile Gln Thr
             275                 280                 285

Phe Leu Asp His His Gly Gly Pro Gly Val Gln His Ile Ala Leu Ala
290                 295                 300

Ser Asp Asp Val Leu Arg Thr Leu Arg Glu Met Arg Ala Arg Ser Ala
305                 310                 315                 320

Met Gly Gly Phe Glu Phe Leu Pro Pro Leu Ser Asp Tyr Tyr Asp
                 325                 330                 335

Gly Val Arg Xaa Cys Xaa Gly Asp Val Leu Thr Glu Ala Gln Ile Asn
             340                 345                 350

Glu Cys Gln Xaa Leu Gly Val Xaa Val Asp Arg Asp Xaa Gly Val
             355                 360                 365

Leu Leu Gln Ile Phe Thr Lys Xaa Val Gly Asp Arg Pro Thr Phe Phe
370                 375                 380

Xaa Glu Xaa Ile Gln Xaa Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                 405                 410                 415

Xaa Gln Leu Phe Lys Ser Ile Glu Asp Tyr Glu Lys Ser Leu Xaa Xaa
             420                 425                 430

Lys Xaa Ala Ala Ala Ala Thr Ala Gln Gly Ser
             435                 440
```

```
<210> SEQ ID NO 83
<211> LENGTH: 444
<212> TYPE: PRT
<213> ORGANISM: Artificial Sequence
<220> FEATURE:
<223> OTHER INFORMATION: Zea mays variant form created by artificial
      means.
<220> FEATURE:
<221> NAME/KEY: MISC_FEATURE
<222> LOCATION: (158)..(158)
<223> OTHER INFORMATION: Pro or Lys
<220> FEATURE:
<221> NAME/KEY: MISC_FEATURE
<222> LOCATION: (182)..(182)
<223> OTHER INFORMATION: Leu or Met
<220> FEATURE:
<221> NAME/KEY: MISC_FEATURE
<222> LOCATION: (191)..(191)
<223> OTHER INFORMATION: Ala or Gly
<220> FEATURE:
<221> NAME/KEY: MISC_FEATURE
<222> LOCATION: (206)..(206)
<223> OTHER INFORMATION: Pro, Ser or Gln
<220> FEATURE:
<221> NAME/KEY: MISC_FEATURE
<222> LOCATION: (211)..(211)
<223> OTHER INFORMATION: Tyr or Leu
<220> FEATURE:
<221> NAME/KEY: MISC_FEATURE
<222> LOCATION: (214)..(214)
<223> OTHER INFORMATION: Ser or Asn
<220> FEATURE:
<221> NAME/KEY: MISC_FEATURE
<222> LOCATION: (233)..(233)
<223> OTHER INFORMATION: Met or Val
<220> FEATURE:
<221> NAME/KEY: MISC_FEATURE
<222> LOCATION: (340)..(340)
<223> OTHER INFORMATION: Arg or Lys
<220> FEATURE:
<221> NAME/KEY: MISC_FEATURE
<222> LOCATION: (356)..(356)
<223> OTHER INFORMATION: Glu, Lys or Arg
<220> FEATURE:
<221> NAME/KEY: MISC_FEATURE
<222> LOCATION: (366)..(366)
<223> OTHER INFORMATION: Gln or Glu
<220> FEATURE:
<221> NAME/KEY: MISC_FEATURE
<222> LOCATION: (385)..(385)
<223> OTHER INFORMATION: Leu, Ile or Val
<220> FEATURE:
<221> NAME/KEY: MISC_FEATURE
<222> LOCATION: (387)..(387)
<223> OTHER INFORMATION: Ile or Leu
<220> FEATURE:
<221> NAME/KEY: MISC_FEATURE
<222> LOCATION: (394)..(394)
<223> OTHER INFORMATION: Met, Val or Lys
<220> FEATURE:
<221> NAME/KEY: MISC_FEATURE
<222> LOCATION: (417)..(417)
<223> OTHER INFORMATION: Gly, Ser or Gln
<220> FEATURE:
<221> NAME/KEY: MISC_FEATURE
<222> LOCATION: (428)..(428)
<223> OTHER INFORMATION: Lys or Arg
<220> FEATURE:
<221> NAME/KEY: MISC_FEATURE
<222> LOCATION: (432)..(432)
<223> OTHER INFORMATION: Ala, Lys or Arg
<220> FEATURE:
<221> NAME/KEY: MISC_FEATURE
<222> LOCATION: (434)..(434)
<223> OTHER INFORMATION: Gln, Arg or His

<400> SEQUENCE: 83

Met Gly Pro Thr Pro Thr Ala Thr Ala Ala Gly Ala Ala Val Ala Ala
```

```
            1               5                   10                  15
            Ala Ser Ala Ala Glu Gln Ala Ala Phe Arg Leu Val Gly His Arg Asn
                            20                  25                  30
            Phe Val Arg Phe Asn Pro Arg Ser Asp Arg Phe Gln Thr Leu Ala Phe
                            35                  40                  45
            His His Val Glu Leu Trp Cys Ala Asp Ala Ala Ser Ala Ala Gly Arg
                            50                  55                  60
            Phe Ser Phe Ala Leu Gly Val Pro Leu Ala Ala Arg Ser Asp Leu Ser
            65                              70                  75                  80
            Thr Gly Asn Ser Ala His Ala Ser Leu Leu Arg Ser Gly Ser Leu
                                    85                  90                  95
            Ser Leu Leu Phe Thr Ala Pro Tyr Ala His Gly Ala Asp Ala Ala Thr
                                100                 105                 110
            Ala Ala Leu Pro Ser Phe Ser Ala Ala Ala Arg Arg Phe Ala Ala
                                115                 120                 125
            Asp His Gly Leu Ala Val Arg Ala Val Ala Leu Arg Val Ala Asp Ala
                            130                 135                 140
            Glu Asp Ala Phe Arg Ala Ser Val Ala Ala Gly Ala Arg Xaa Ala Phe
            145                 150                 155                 160
            Gly Pro Val Asp Leu Gly Arg Gly Phe Arg Leu Ala Glu Val Glu Leu
                                165                 170                 175
            Tyr Gly Asp Val Val Xaa Arg Tyr Val Ser Tyr Pro Asp Gly Xaa Ala
                                180                 185                 190
            Gly Glu Pro Phe Leu Pro Gly Phe Glu Gly Val Ala Ser Xaa Gly Ala
                                195                 200                 205
            Ala Asp Xaa Gly Leu Xaa Arg Phe Asp His Ile Val Gly Asn Val Pro
                    210                 215                 220
            Glu Leu Ala Pro Ala Ala Ala Tyr Xaa Ala Gly Phe Thr Gly Phe His
            225                 230                 235                 240
            Glu Phe Ala Glu Phe Thr Thr Glu Asp Val Gly Thr Thr Glu Ser Gly
                                245                 250                 255
            Leu Asn Ser Met Ala Leu Ala Asn Asn Ser Glu Asn Val Leu Leu Pro
                                260                 265                 270
            Leu Asn Glu Pro Val His Gly Thr Lys Arg Arg Ser Gln Ile Gln Thr
                    275                 280                 285
            Phe Leu Asp His His Gly Gly Pro Gly Val Gln His Ile Ala Leu Ala
                            290                 295                 300
            Ser Asp Asp Val Leu Arg Thr Leu Arg Glu Met Arg Ala Arg Ser Ala
            305                 310                 315                 320
            Met Gly Gly Phe Glu Phe Leu Pro Pro Leu Ser Asp Tyr Tyr Asp
                                325                 330                 335
            Gly Val Arg Xaa Cys Ala Gly Asp Val Leu Thr Glu Ala Gln Ile Asn
                            340                 345                 350
            Glu Cys Gln Xaa Leu Gly Val Met Val Asp Arg Asp Asp Xaa Gly Val
                            355                 360                 365
            Leu Leu Gln Ile Phe Thr Lys Pro Val Gly Asp Arg Pro Thr Phe Phe
                    370                 375                 380
            Xaa Glu Xaa Ile Gln Arg Ile Gly Cys Xaa Glu Lys Asp Glu Lys Gly
            385                 390                 395                 400
            Gln Glu Tyr Gln Lys Gly Gly Cys Gly Gly Phe Gly Lys Gly Asn Phe
                                405                 410                 415
            Xaa Gln Leu Phe Lys Ser Ile Glu Asp Tyr Glu Xaa Ser Leu Glu Xaa
                                420                 425                 430
```

Lys Xaa Ala Ala Ala Ala Ala Thr Ala Gln Gly Ser
        435                 440

<210> SEQ ID NO 84
<211> LENGTH: 22
<212> TYPE: DNA
<213> ORGANISM: Artificial Sequence
<220> FEATURE:
<223> OTHER INFORMATION: PCR primer directed to Glycine max genomic
      target.

<400> SEQUENCE: 84
gcaagtattt caatacaata gc                                          22

<210> SEQ ID NO 85
<211> LENGTH: 20
<212> TYPE: DNA
<213> ORGANISM: Artificial Sequence
<220> FEATURE:
<223> OTHER INFORMATION: PCR primer directed to Glycine max genomic
      target.

<400> SEQUENCE: 85
gttatctgat atgatgttgc                                             20

<210> SEQ ID NO 86
<211> LENGTH: 21
<212> TYPE: DNA
<213> ORGANISM: Artificial Sequence
<220> FEATURE:
<223> OTHER INFORMATION: PCR primer directed to Glycine max genomic
      target.

<400> SEQUENCE: 86
gttttccgcg ggtgttgatc c                                           21

<210> SEQ ID NO 87
<211> LENGTH: 29
<212> TYPE: DNA
<213> ORGANISM: Artificial Sequence
<220> FEATURE:
<223> OTHER INFORMATION: PCR primer directed to Glycine max genomic
      target.

<400> SEQUENCE: 87
tcattggtac ctggtgtggt gtgatgctg                                   29

<210> SEQ ID NO 88
<211> LENGTH: 27
<212> TYPE: DNA
<213> ORGANISM: Artificial Sequence
<220> FEATURE:
<223> OTHER INFORMATION: PCR primer directed to Glycine max genomic
      target.

<400> SEQUENCE: 88
agcatggtac cttgcgtctg ggttgag                                     27

<210> SEQ ID NO 89
<211> LENGTH: 25
<212> TYPE: DNA
<213> ORGANISM: Artificial Sequence
<220> FEATURE:
<223> OTHER INFORMATION: PCR primer directed to Glycine max genomic
      target.

<400> SEQUENCE: 89

```
atctggtacc tgatgttgat gcggc                                          25
```

<210> SEQ ID NO 90
<211> LENGTH: 25
<212> TYPE: DNA
<213> ORGANISM: Artificial Sequence
<220> FEATURE:
<223> OTHER INFORMATION: PCR primer directed to Glycine max genomic
      target.

<400> SEQUENCE: 90

```
aggaggtacc gtcaaatcca cctag                                          25
```

<210> SEQ ID NO 91
<211> LENGTH: 33
<212> TYPE: DNA
<213> ORGANISM: Artificial Sequence
<220> FEATURE:
<223> OTHER INFORMATION: PCR primer directed to Glycine max genomic
      target.

<400> SEQUENCE: 91

```
agcctggtac cttgtgtgta aaaagataa gac                                  33
```

<210> SEQ ID NO 92
<211> LENGTH: 28
<212> TYPE: DNA
<213> ORGANISM: Artificial Sequence
<220> FEATURE:
<223> OTHER INFORMATION: PCR primer directed to Glycine max genomic
      target.

<400> SEQUENCE: 92

```
tccttggtac ctgatgcact atataacg                                       28
```

<210> SEQ ID NO 93
<211> LENGTH: 45
<212> TYPE: DNA
<213> ORGANISM: Artificial Sequence
<220> FEATURE:
<223> OTHER INFORMATION: PCR primer directed to Glycine max genomic
      target.

<400> SEQUENCE: 93

```
acaaccacca agctcaatct caagcagcag catcacacca cacca                    45
```

<210> SEQ ID NO 94
<211> LENGTH: 53
<212> TYPE: PRT
<213> ORGANISM: Artificial Sequence
<220> FEATURE:
<223> OTHER INFORMATION: Consensus sequence

<400> SEQUENCE: 94

Met Pro Pro Thr Pro Thr Thr Ala Ala Ala Thr Gly Ala Gly Ala Ala
1               5                   10                  15

Ala Ala Val Thr Pro Glu His Ala Ala Phe Arg Leu Val Gly His Arg
            20                  25                  30

Arg Phe Val Arg Phe Asn Pro Arg Ser Asp Arg Phe His Thr Leu Ala
        35                  40                  45

Phe His His Val Glu
    50

<210> SEQ ID NO 95

-continued

<210> SEQ ID NO 95
<211> LENGTH: 10
<212> TYPE: DNA
<213> ORGANISM: Artificial Sequence
<220> FEATURE:
<223> OTHER INFORMATION: Glycine max tata box

<400> SEQUENCE: 95
gtataaataa                                                          10

<210> SEQ ID NO 96
<211> LENGTH: 10
<212> TYPE: DNA
<213> ORGANISM: Artificial Sequence
<220> FEATURE:
<223> OTHER INFORMATION: Glycine max tata box

<400> SEQUENCE: 96
ccaatatatg                                                          10

<210> SEQ ID NO 97
<211> LENGTH: 11
<212> TYPE: DNA
<213> ORGANISM: Artificial Sequence
<220> FEATURE:
<223> OTHER INFORMATION: Glycine max tata box

<400> SEQUENCE: 97
ccttatatat c                                                        11

<210> SEQ ID NO 98
<211> LENGTH: 10
<212> TYPE: DNA
<213> ORGANISM: Artificial Sequence
<220> FEATURE:
<223> OTHER INFORMATION: Glycine max tata box

<400> SEQUENCE: 98
tatataataa                                                          10

<210> SEQ ID NO 99
<211> LENGTH: 9
<212> TYPE: DNA
<213> ORGANISM: Artificial Sequence
<220> FEATURE:
<223> OTHER INFORMATION: Glycine max tata box

<400> SEQUENCE: 99 gaatataag                                                            9

<210> SEQ ID NO 100
<211> LENGTH: 488
<212> TYPE: PRT
<213> ORGANISM: Glycine max

<400> SEQUENCE: 100

Met Pro Met Tyr Thr Pro Ser Leu Ser Ala Pro Ser Ser Asn His Ile
1               5                   10                  15

Gln Pro Ser Val Thr Leu Pro Leu Tyr Ile Thr Thr Lys Leu Asn
            20                  25                  30

Leu Lys Gln Gln His His Thr Thr Pro Met Pro Ile Pro Met Cys Asn
        35                  40                  45

Glu Ile Gln Ala Gln Ala Gln Ala Gln Ala Gln Pro Gly Phe Lys Leu
    50                  55                  60

Val Gly Phe Lys Asn Phe Val Arg Thr Asn Pro Lys Ser Asp Arg Phe

```
                65                  70                  75                  80
           Gln Val Asn Arg Phe His His Ile Glu Phe Trp Cys Thr Asp Ala Thr
                               85                  90                  95

Asn Ala Ser Arg Arg Phe Ser Trp Gly Leu Gly Met Pro Ile Val Ala
                              100                 105                 110

Lys Ser Asp Leu Ser Thr Gly Asn Gln Ile His Ala Ser Tyr Leu Leu
                              115                 120                 125

Arg Ser Gly Asp Leu Ser Phe Leu Phe Ser Ala Pro Tyr Ser Pro Ser
                              130                 135                 140

Leu Ser Ala Gly Ser Ser Ala Ala Ser Ser Ala Ser Ile Pro Ser Phe
           145                 150                 155                 160

Asp Ala Ala Thr Cys Leu Ala Phe Ala Ala Lys His Gly Phe Gly Val
                              165                 170                 175

Arg Ala Ile Ala Leu Glu Val Ala Asp Ala Glu Ala Ala Phe Ser Ala
                              180                 185                 190

Ser Val Ala Lys Gly Ala Glu Pro Ala Ser Pro Pro Val Leu Val Asp
                              195                 200                 205

Asp Arg Thr Gly Phe Ala Glu Val Arg Leu Tyr Gly Asp Val Val Leu
                              210                 215                 220

Arg Tyr Val Ser Tyr Lys Asp Ala Ala Pro Gln Ala Pro His Ala Asp
           225                 230                 235                 240

Pro Ser Arg Trp Phe Leu Pro Gly Phe Glu Ala Ala Ser Ser Ser
                              245                 250                 255

Ser Phe Pro Glu Leu Asp Tyr Gly Ile Arg Arg Leu Asp His Ala Val
                              260                 265                 270

Gly Asn Val Pro Glu Leu Ala Pro Ala Val Arg Tyr Leu Lys Gly Phe
                              275                 280                 285

Ser Gly Phe His Glu Phe Ala Glu Phe Thr Ala Glu Asp Val Gly Thr
                              290                 295                 300

Ser Glu Ser Gly Leu Asn Ser Val Val Leu Ala Asn Asn Ser Glu Thr
           305                 310                 315                 320

Val Leu Leu Pro Leu Asn Glu Pro Val Tyr Gly Thr Lys Arg Lys Ser
                              325                 330                 335

Gln Ile Glu Thr Tyr Leu Glu His Asn Glu Gly Ala Gly Val Gln His
                              340                 345                 350

Leu Ala Leu Val Thr His Asp Ile Phe Thr Thr Leu Arg Glu Met Arg
                              355                 360                 365

Lys Arg Ser Phe Leu Gly Gly Phe Glu Phe Met Pro Ser Pro Pro Pro
                              370                 375                 380

Thr Tyr Tyr Ala Asn Leu His Asn Arg Ala Ala Asp Val Leu Thr Val
           385                 390                 395                 400

Asp Gln Ile Lys Gln Cys Glu Glu Leu Gly Ile Leu Val Asp Arg Asp
                              405                 410                 415

Asp Gln Gly Thr Leu Leu Gln Ile Phe Thr Lys Pro Val Gly Asp Arg
                              420                 425                 430

Pro Thr Ile Phe Ile Glu Ile Ile Gln Arg Ile Gly Cys Met Val Glu
                              435                 440                 445

Asp Glu Glu Gly Lys Val Tyr Gln Lys Gly Ala Cys Gly Gly Phe Gly
                              450                 455                 460

Lys Gly Asn Phe Ser Glu Leu Phe Lys Ser Ile Glu Glu Tyr Glu Lys
           465                 470                 475                 480

Thr Leu Glu Ala Lys Arg Thr Ala
                              485
```

-continued

```
<210> SEQ ID NO 101
<211> LENGTH: 444
<212> TYPE: PRT
<213> ORGANISM: Artificial sequence
<220> FEATURE:
<223> OTHER INFORMATION: Zea mays variant form created by artificial
      means.

<400> SEQUENCE: 101

Met Gly Pro Thr Pro Thr Ala Thr Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
    290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Asp Gln Gly Val
```

```
                     355                 360                 365
Leu Leu Gln Ile Phe Thr Lys Pro Val Gly Asp Arg Pro Thr Leu Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
                420                 425                 430

Lys Gln Ala Ala Ala Ala Ala Ala Gln Gly Ser
            435                 440

<210> SEQ ID NO 102
<211> LENGTH: 47
<212> TYPE: PRT
<213> ORGANISM: Avena sativa

<400> SEQUENCE: 102

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu
        35                  40                  45

<210> SEQ ID NO 103
<211> LENGTH: 46
<212> TYPE: PRT
<213> ORGANISM: Hordeum vulgare

<400> SEQUENCE: 103

Met Pro Pro Thr Pro Thr Thr Pro Ala Ala Thr Gly Ala Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu
        35                  40                  45

<210> SEQ ID NO 104
<211> LENGTH: 48
<212> TYPE: PRT
<213> ORGANISM: Triticum aestivum

<400> SEQUENCE: 104

Met Pro Pro Thr Pro Thr Thr Pro Ala Ala Thr Gly Ala Gly Ala Ala
1               5                   10                  15

Ala Ala Val Thr Pro Glu His Ala Arg Pro Arg Arg Met Val Arg Phe
            20                  25                  30

Asn Pro Arg Ser Asp Arg Phe His Thr Leu Ser Phe His His Val Glu
        35                  40                  45

<210> SEQ ID NO 105
<211> LENGTH: 53
<212> TYPE: PRT
<213> ORGANISM: Oryza sativa

<400> SEQUENCE: 105

Met Pro Pro Thr Pro Thr Pro Thr Ala Thr Thr Gly Ala Val Ser Ala
1               5                   10                  15
```

```
Ala Ala Ala Ala Gly Glu Asn Ala Gly Phe Arg Leu Val Gly His Arg
            20                  25                  30

Arg Phe Val Arg Ala Asn Pro Arg Ser Asp Arg Phe Gln Ala Leu Ala
            35                  40                  45

Phe His His Val Glu
    50

<210> SEQ ID NO 106
<211> LENGTH: 52
<212> TYPE: PRT
<213> ORGANISM: Sorghum bicolor

<400> SEQUENCE: 106

Met Pro Pro Thr Pro Thr Thr Ala Ala Ala Thr Gly Ala Ala Val Ala
1               5                   10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
            35                  40                  45

His His Val Glu
    50

<210> SEQ ID NO 107
<211> LENGTH: 52
<212> TYPE: PRT
<213> ORGANISM: Zea mays

<400> SEQUENCE: 107

Met Pro Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
            35                  40                  45

His His Val Glu
    50

<210> SEQ ID NO 108
<211> LENGTH: 1275
<212> TYPE: DNA
<213> ORGANISM: Glycine max

<400> SEQUENCE: 108
tcaagatgag gatgatcctc ttgttagtgt gttttgattg ttctttatag tttataccta      60
attttatcta tataagctta ttaaattaaa tttatgtgca atagtgaccc ctgatcttct     120
gtaattatca ttcaatagct gtagtcattt tgtttccaat tgtaaccgta gccaagatgt     180
acggtggcat aaaccttgga gatattttgt tctctcttcc cttcatagag acaaccttc      240 atgtaatgga catactaacg acaattaaat tatttatcat tttaaagat taaatatttt      300 ttcttaaatt attcctgtgc tttaaaattc ttaacagaaa atttaaaatt agacatttgt     360
accattagag aaaaactgtg ggactcattt gttattaga ttatttcagc tagcaactga      420
ctctcttgta catttcattt ttacattcct ttaattatgc atcattaaca gtagtagatt     480
gcatctctta aaaaaaaat tagattgcag tattgccttg gaaatatgga attacaatgt     540
caaaatattt taacgaataa cgatgcgtag cttaaagttc aagacacaat tttaacgtta     600
tatagtgcat caatgtttga aatttagtg tataaataac gtattttga taatattttt      660
```

-continued

```
tacacaacaa tcctcttaaa ttttcttatc ttatttcatt taaccgttct cttaaattgt    720
cttatctttt ttacacacaa atgaatccca ataaacatgg ttgggattta tttgagttct    780
taactttagg aaccaaatat ataataattt ttttttttta aaaaaaaaga agataaatat    840
agaagaaaag gatgtgataa aggcaagaga agcgtgtgaa caagagagag acgaatctag    900
gtggatttga cgtacgttga atgaatgttg aatataagta ataacgctga ggctgtaggt    960
gtgggtaata aaaaaagaga gaagccgcat caacatcatc caatatatgg acgttaaaag   1020
agcgtcgtaa tccatttcca tttctcatct atcttcactt cctcgtcctc atcctcatcc   1080
acctattctc aacccagacg caatgcccat gtacactcca tcactctccg caccctcctc   1140
caatcacatt caaccaagtg tcacactccc cttatatatc acaaccacca agctcaatct   1200
caagcagcag catcacacca caccaatgcc aatacccatg tgcaacgaaa ttcaagccca   1260
agcccaagcc caagc                                                   1275
```

COMPOSITIONS AND METHODS COMPRISING SEQUENCES HAVING HYDROXYPHENYLPYRUVATE DIOXYGENASE (HPPD) ACTIVITY

CROSS-REFERENCE TO RELATED APPLICATIONS

This application is a continuation of U.S. patent application Ser. No. 15/305,457 filed Oct. 20, 2016, which is a 371 (National Stage) of PCT/US2015/028967, filed May 2, 2015, and which claims the benefit of U.S. Provisional Application No. 61/987,965, filed on May 2, 2014, each of which are incorporated herein by reference in their entirety.

REFERENCE TO A SEQUENCE LISTING SUBMITTED ELECTRONICALLY

The official copy of the sequence listing is submitted electronically via EFS-Web as an ASCII formatted sequence listing with a file named BB2336_SequenceListing_ST25.txt, created on Jun. 27, 2018, and having a size of 361,624 bytes and is filed concurrently with the specification. The sequence listing contained in this ASCII formatted document is part of the specification and is herein incorporated by reference in its entirety.

BACKGROUND OF THE INVENTION

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system would involve the use of crop plants which are tolerant to a herbicide so that when the herbicide was sprayed on a field of herbicide-tolerant crop plants, the crop plants would continue to thrive while non-herbicide-tolerant weeds were killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

Crop tolerance to specific herbicides can be conferred by engineering genes into crops which encode appropriate herbicide metabolizing enzymes and/or insensitive herbicide targets. In some cases these enzymes, and the nucleic acids that encode them, originate in a plant. In other cases, they are derived from other organisms, such as microbes. See, e.g., Padgette et al. (1996) "New weed control opportunities: Development of soybeans with a Roundup Ready® gene" and Vasil (1996) "Phosphinothricin-resistant crops," both in *Herbicide-Resistant Crops*, ed. Duke (CRC Press, Boca Raton, Fla.) pp. 54-84 and pp. 85-91. Indeed, transgenic plants have been engineered to express a variety of herbicide tolerance genes from a variety of organisms.

For nearly two decades, corn, soybean, and cotton farmers have relied on glyphosate and glyphosate resistant crops for weed control. While favored for its efficacy, economy and convenience, the onset of glyphosate-resistant weeds, now numbering 26 species (Heap, 2014), signals a need for new herbicide and trait systems that meet similar criteria (Green and Castle, 2010; Duke, 2012). The silver bullet solution would be another herbicide and trait combination as effective as glyphosate. Unfortunately, prospects for novel herbicide chemistries are not encouraging (Duke, 2012).

Inhibitors of 4-hydroxyphenylpyruvate dioxygenase (HPPD) disrupt production of tocopherols (antioxidants) and plastoquinone (essential for photosynthetic electron transfer) by blocking conversion of tyrosine, through 4-hydroxyphenyl pyruvate (HPP), to homogentisate (Moran, 2014). The result is that the plant cannot protect itself from the radicals generated by light activation of chlorophyll, causing bleaching, necrosis, and death. Registered HPPD inhibitors include mesotrione, tembotrione, sulcotrione, isoxaflutole, and topramezone. HPPD inhibitors are most effective on broad-leaf weeds but control some grasses as well. Currently, HPPD herbicides are selective for use in corn, while soybeans and other dicot crop species are sensitive. A broad spectrum HPPD tolerance trait in soybeans, used in combination with glyphosate tolerance and other traits or selective herbicides, will prolong the positive impact of the glyphosate systems and slow appearance of resistant weeds. Two such products, one for tolerance to isoxaflutole (APHIS, 2009) and the other to mesotrione and isoxaflutole (APHIS, 2012) are in the USDA regulatory approval process. The former uses a *Pseudomonas fluorescens* HPPD with a single amino acid change (Matringe et al., 2005), while the latter uses HPPD from oat, with a single amino acid change (Hawkes et al., 2010). There are presently no reports of tembotrione or broad spectrum tolerance.

To develop a robust and stable HPPD tolerance trait in soybean, expression patterns of the native gene and localization of native and transgenic protein were studied, and the efficacy of low to moderate expression of a desensitized protein were evaluated. Data regarding the subcellular location of HPPD are ambiguous, perhaps resulting from species diversity. Early work with organelle fractions attributed most HPPD activity to the chloroplast in spinach (Fiedler et al., 1982) or *Lemna gibba* (Loeffelhardt and Kindl, 1979). Organelle targeting can be conjectured from the observation that the N-terminal sequence of mature HPPD isolated from maize leaf begins at either ala-17 (Fritze et al., 2004) or ala-23 (Yang et al., 2004) with respect to the translated full-length gene. Two HPPD genes identified from EST libraries prepared from cotton tissue were 98.6 percent identical, each with a 23-amino acid sequence deemed likely to function in chloroplast targeting by analysis with the ChloroP prediction program (Moshiri et al., 2007). In the same publication, tomato, but not *Brassica* HPPD was predicted to have a CTP. Subcellular fractionation supported a cytosolic location of the carrot cell enzyme (Garcia et al., 1997). Although the N-terminal sequence of the purified enzyme was truncated with respect to the translated cDNA, this was attributed to proteolysis during purification. Later, the same authors determined that after PSORT analysis failed to identify a targeting signal within the *Arabidopsis* HPPD amino acid sequence, native *Arabidopsis* HPPD heterologously expressed in tobacco was located exclusively in the cytosol (Garcia et al., 1999).

While a number of HPPD crop plants are presently commercially available, improvements in every aspect of crop production, weed control options, extension of residual weed control, and improvement in crop yield are continuously in demand. Particularly, due to local and regional variation in dominant weed species as well as preferred crop species, a continuing need exists for customized systems of crop protection and weed management which can be adapted to the needs of a particular region, geography, and/or locality. A continuing need therefore exists for compositions and methods of crop protection and weed management.

BRIEF SUMMARY OF THE INVENTION

Compositions and methods comprising polynucleotides and polypeptides having 4-hydroxyphenylpyruvate dioxygenase (HPPD) activity and having an insensitivity to at least one HPPD inhibitor are provided. Further provided are nucleic acid constructs, plants, plant cells, explants, seeds and grain having the HPPD sequences.

Various methods of employing the HPPD sequences are provided. Such methods include methods for producing an HPPD inhibitor tolerant plant, plant cell, explant or seed and methods of controlling weeds in a field containing a crop employing the plants and/or seeds disclosed herein.

Methods are also provided to identify additional HPPD variants.

Further provided are methods and compositions that allow the various HPPD polypeptides and variants and fragments thereof to be expressed in a chloroplast or transported to a chloroplast. Such methods and compositions find use in producing plant cells, plants and explants having tolerance to various HPPD inhibitors.

BRIEF DESCRIPTION OF THE DRAWINGS

FIG. 1. Structures of herbicidal HPPD inhibitors and a HPPD substrate, 4-hydroxyphenylpyruvate.

FIG. 2A: HPPD reaction and essential downstream products in plants. FIG. 2B: Bleaching symptoms of HPPD-inhibiting herbicides in soybean.

FIGS. 3A-3M. Z. mays HPPD protein characterization. FIG. 3A: Z. mays HPPD amino acid sequence. FIG. 3C: Fluorescence observed in chloroplasts of maize leaf expressing rubisco activase CTP-Ds-Red2, with the same sample photographed under white light shown in FIG. 3B. FIG. 3E: Fluorescence observed in chloroplasts of maize leaf expressing N-terminal 50 amino acids of maize HPPD-Ds-Red2, with the same sample photographed under white light shown in FIG. 3D. FIG. 3G: Fluorescence observed in cytosol of maize leaf expressing untargeted Ds-Red2, with the same sample photographed under white light shown in FIG. 3F. FIGS. 3H-3J: Maize cells transiently expressing DsRed fused to 30, 40 and 50 amino acid N-terminal region of HPPD protein sequence (FIGS. 3H, 3I, and 3J, respectively). FIG. 3K: Expression in both chloroplasts and cytoplasm of soybean leaf epidermal cell transiently expressing AcGFP fused to amino acids 1-50 of maize HPPD. FIG. 3L: Expression in chloroplasts of guard cells in soybean stably expressing AcGFP linked to amino acids 1-50 of maize HPPD. FIG. 3M: alignment of monocot HPPD N-terminal region sequences (Avena sativa HPPD WO0246387 (SEQ ID NO: 102), Hordeum vulgare HPPD 048604.1 (SEQ ID NO: 103), Triticum aestivum HPPD AAZ67144.1 (SEQ ID NO: 104), Oryza sativa HPPD BAD26248.1 (SEQ ID NO: 105), Sorghum bicolor HPPD XP_002453359 (SEQ ID NO: 106), and Zea mays_WO1997049816Seq #11 (SEQ ID NO: 107)) and consensus monocot functional CTP (SEQ ID NO: 94). Sources of sequences are indicated. Gray shading shows identities in sequences.

FIGS. 4A-4F. Genomic analysis of soybean HPPD. FIG. 4A: G. max HPPD protein sequence (SEQ ID NO: 100) with in-frame N-terminal extension (underlined). FIG. 4B: Protein gel of in vitro transcription-translation products of the two (3' truncated) HPPD transcripts. Predicted protein mass from −237 mRNA: 30.6 kD; +1 mRNA: 26.0 kD. FIG. 4C: Transient expression of N-terminal fragment 1-44 with DsRed2 in soybean. FIG. 4D: Transient expression of N-terminal fragment 42-86 with AcGFP1 in soybean. FIG. 4E: Transient expression of N-terminal fragment 1-86 with AcGFP1 in soybean. FIG. 4F, Alignment of Z. mays (SEQ ID NO: 1) and G. max (SEQ ID NO: 100) HPPD proteins. An asterisk indicates identity; a colon shows the fusion point of soybean to maize insensitive HPPD proteins.

FIGS. 8A and 8B. FIG. 8A: Upstream 1225 bp G. max promoter sequence and N-terminal regions of the long and short HPPD proteins (nucleotide sequence set forth as SEQ ID NO: 108; amino acid sequence shown in FIG. 8A corresponds to the first fifty-seven amino acids of SEQ ID NO: 100). Underlined bold denotes predicted TATA sequences; bold denotes methionine initiation sites for long and short proteins; grey background denotes actual transcription start sites at positions −237 and +1; Grey box denotes the upORF in the long transcript. FIG. 8B: Schematic of G. max HPPD promoter and coding region.

FIGS. 9A-9D. Field trial with transgenic soybean events treated with 2× maize field rate of tembotrione, 14 days after treatment. FIG. 9A: Promoter HSP206 and full length maize HPPD variant 6-1. FIG. 9B: 35S enhanced promoter SHP110 with fused Gm:Zm HPPD variant 6-1. FIG. 9C: Non-transgenic unsprayed control. FIG. 9D: Non-transgenic sprayed control. Treatment was as described in Table 6.

FIG. 10A: Immuno-localization of native HPPD in maize leaf shows label only in chloroplasts. Serum containing anti-maize or anti-soybean HPPD antibodies was raised in rabbits inoculated with recombinant wild-type 6×-his-HPPD produced in E coli and purified by nickel chelate affinity chromatography. The serum was passed through Protein A Ceramin Hyper DF to adsorb the IgG fraction. After washing, IgG was eluted with citrate buffer, pH 2.55, with a yield of 50 mg of IgG per gram of serum protein. Ten mg of IgG protein were subjected to the manufacturer's linkage protocol for Affi-Gel Hz (Bio-Rad, Hercules, Calif.), which, in the case of the maize enzyme, resulted in the capture of 2 mg of IgG, 20% of which was anti-maize HPPD. Anti-HPPD antibodies were further purified by passage through a column of immobilized Rubisco, to remove a small fraction of antibodies that reacted with both HPPD and Rubisco. Leaf punches from mature line A63 maize plants or native or stably transformed soybean plants expressing a gene encoding the maize HPPD protein driven by an SCP1 synthetic promoter (Cahoon and Coughlan, 2007) were fixed in 2% paraformaldehyde, 0.25% glutaraldehyde in 100 mM Na phosphate buffer, pH 7.0, for 3 hours at room temperature, dehydrated by passage through progressively higher concentrations of ethanol, embedded in LR White resin and cured at 55° C. for 48 hours. Immuno-localizations were performed with the primary antibody being the double-purified anti-maize HPPD (1:200) and the secondary antibody goat anti-rabbit F(ab') conjugated with µltrasmall gold particles (Aurion, The Netherlands). Gold labeling was followed by silver enhancement (Aurion). Sections were counterstained with 4% uranyl acetate (aqueous) followed by Reynold's lead citrate and examined with a Hitachi S4800 scanning electron microscope. Gold labeling was observed mainly in bundle sheath chloroplasts (range; 5-28 particles per chloroplast, 50 chloroplasts observed. The highest frequency of observations was 6 chloroplasts that contained 8 particles. Particles were also found in mesophyll chloroplasts, 31 of which had 1 to 5 particles and 19, of which had no particles. A small number of particles were also observed randomly in other locations including cytosol and voids, and were considered to be artifacts. FIG. 10B: shows the inner indicated rectangle at higher digital magnification.

FIGS. 11A-11D, Co-expression of untargeted C3GFP and HPPD N-terminal 50AA::DsRed2. FIGS. 11E-11G, Co-expression of untargeted C3GFP and Rubisco activase CTP::DsRed. FIGS. 11H-11J, untargeted C3GFP. The red channel (FIGS. 11B, 11F and 11I) shows the pattern of DsRed fluorescence, the green channel (FIGS. 11D, 11G, and 11J) shows untargeted C3GFP fluorescence and the blue channel (FIG. 11C), chlorophyll autofluorescence. Overlays of the red and green channels are shown in FIGS. 11A, 11E and 11H. Plastid targeting by the N-terminal 50 amino acids of maize HPPD is evident from the co-localization of the DsRed with chlorophyll autofluorescence (FIGS. 11B and 11C) and the lack of overlap with the untargeted C3CFP (FIGS. 11B and 11D). Note that exclusion of the C3GFP signal marks the location of the guard cell plastids. Similarly, the positive control vector for chloroplast localization showed a lack of overlap between the cytosolic C3GFP signal and the DsRed signal (FIGS. F and G). Untargeted DsRed shows spatial overlap of the DsRed and C3GFP signals and an absence of DsRed in the regions of C3GFP exclusion that mark the position of the plastids. Maize seedlings were generated in the absence of soil by embedding kernels between two sheets of blotting paper hydrated in tap water amended with 0.1 mg/ml sucrose. Leaf segments were detached from seedlings at 15 days post-planting immediately before biolistic transformation. The lower epidermis of the leaf segments was bombarded and the segments were placed in sterile moist chambers. The tissue was co-bombarded with DNA from DsRed-containing test plasmids and a plasmid encoding untargeted Cycle 3 Green Fluorescence Protein (C3GFP, Life Technologies) using the PDS-1000 He biolistic particle delivery system (Bio-Rad, Hercules Calif.). Gold particles (0.6 µm in diameter; Bio-Rad) were coated with plasmid DNA as follows. Fifty µl of freshly prepared gold particles in water (20 mg/ml), and 20 µl of DNA mixture (containing 10 µg of equimolar quantities of the DsRed-containing test plasmid and the untargeted C3GFP plasmid) were combined. While gently vortexing, 50 µl of a 2.5 M CaCl2 solution and 20 µl of freshly prepared 0.1 M spermidine (Sigma-Aldrich, St Louis Mo.) were slowly added. The mixture was incubated at room temperature for 5 min and pelleted at 13,000 g in a micro-centrifuge for 5 sec. The supernatant was carefully removed and the pellet was resuspended in 85 µl of 100% ethanol. While gently vortexing, a 5 µl aliquot of suspension was drawn and dispensed onto the center of a macrocarrier membrane. The membrane was allowed to dry completely for 2-5 min and used immediately. Leaf segments were bombarded at a distance of 9 cm from an 1100-psi rupture disk. Three replicate shots were performed from each coating preparation. Initial examination was conducted at approximately 24 h post-bombardment with a Lumar fluorescence stereomicroscope (Carl Zeiss Inc., Thornwood N.Y.) equipped with both a UV-exciting (Zeiss Set 01) and red-emitting (Zeiss Set 43 HE) filter set to image the C3GFP and the DsRed2, respectively. The leaf segments containing DsRed2-positive cells identified in the stereomicroscope were placed in a 0.01% Tween 20 solution and a vacuum was applied for about 10 min to remove internal air and to wet the leaf surface. The leaves were placed into coverglass chambers in the same solution, sealed with an additional coverglass and examined in the LSM510 (Carl Zeiss). C3GFP fluorescence was captured using a 488 nm argon laser for excitation and a 500-550 nm band pass emission filter. DsRed fluorescence was imaged using a 561 nm diode laser for excitation and a 575-615 nm band pass emission filter. Chlorophyll fluorescence was captured by combining 561 nm excitation and a 650-710 nm band pass emission filter.

FIGS. 13A and 13B: Time course, reaction with wt maize HPPD or a shuffled variant; 100 µM HPP+4 µM mesotrione. For wild type maize HPPD, rapidly slowing reaction indicates a relatively high $k_{ON}$. For the shuffled variant, resistance to inactivation indicates a lower value for $k_{ON}$. The smaller the actual $k_{ON}$, the more slowly the HPPD reaction decelerates and the higher the value is for the ON rate ratio. FIGS. 13C and 13D: OFF rate ratio. A quantitative indicator of $k_{OFF}$ was obtained by observing the time course of an HPPD reaction as inhibitor is released from a pre-formed enzyme-inhibitor complex. The ratio of the maximum rate attained in mixtures containing inhibitor to the initial velocity of mixtures lacking inhibitor is termed the "OFF rate ratio". The plateau of absorbance is due to exhaustion of the substrate. With improved variants, not only was the steady state attained in a shorter time span, the velocity attained was higher than with wild type, though the enzymes were present at the same concentration (240 nM). This is because a larger fraction of the variant enzyme was free of inhibitor compared to the wild-type enzyme, which can due to a higher KD.

FIG. 15. Kinetic parameters, insensitivity parameters, trait fitness parameters, and trait fitness (fold vs. wild-type) for the indicated mutants is given. The various data were determined using the methods described herein below. In the figure, the following abbreviations are used: "Tembo" indicates tembotrione; "Meso" indicates mesotrione; "Sulco" indicates sulcotrione; "Isox(DKN)" indicates isoxaflutole (diketonitrile); and "Topra" indicates topramezone.

DETAILED DESCRIPTION OF THE INVENTION

The present disclosure now will be described more fully hereinafter with reference to the accompanying drawings, in which some, but not all embodiments or aspects are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

I. Compositions

A. Hydroxyphenylpyruvate Dioxygenase (HPPD) Polynucleotides and Polypeptides

Hydroxyphenylpyruvate dioxygenase (HPPD) converts hydroxyphenylpyruvate, derived from the aromatic amino acid biosynthesis pathway, to homogentisate. Homogentisate is a precursor of tocopherols and plastoquinones, an electron carrier essential in the biosynthesis of carotenoids. Consequently, when HPPD is inhibited by herbicide inhibitors, the plant can not protect itself from the radicals generated by light activation of chlorophyll. More specifically, inhibition of HPPD polypeptide leads to the depletion of protective pigments in the plant tissue resulting in bleaching of tissues which leaves the plants vulnerable to damage by light. HPPD inhibitors are an important class of herbicides, and transgenes that confer crop tolerance to HPPD inhibitors would be of significant value, especially for managing weed resistance to glyphosate.

Figure 2A:
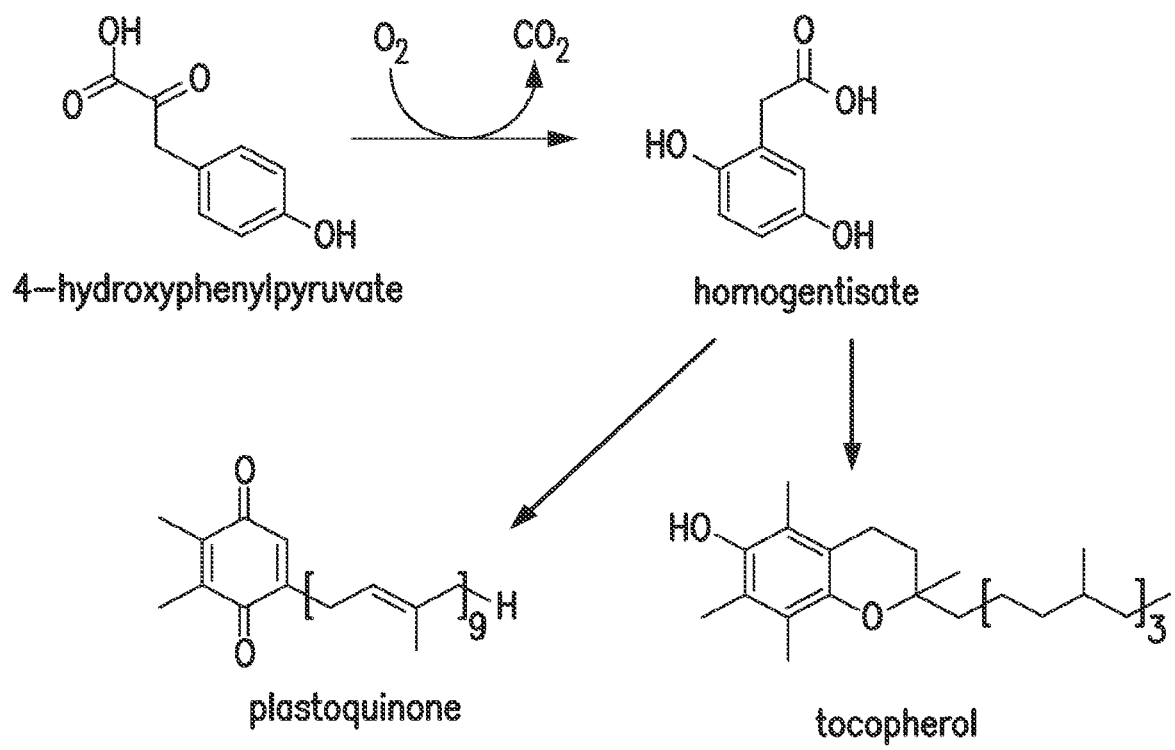
FIGS. 2A and 2B. HPPD inhibitor herbicide site of action and symptoms.
Figure 2B:
Figure 17:
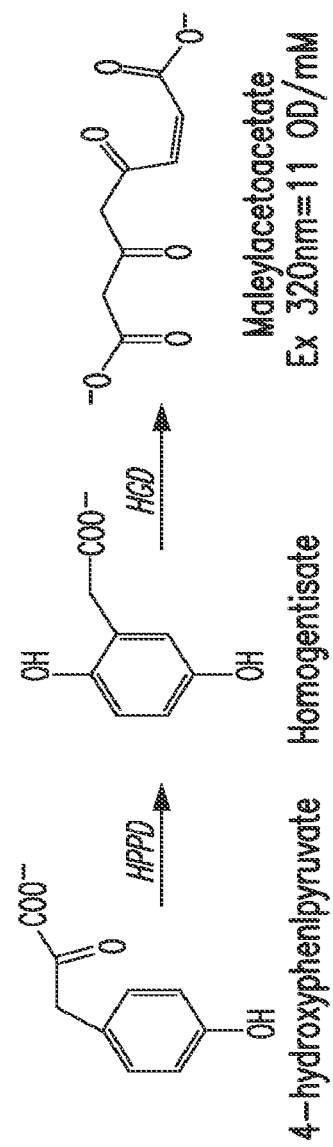
FIG. 17. The figure shows the enzymatic conversion of 4-hydroxyphenylpyruvate by HPPD to homogentisate, and the subsequent enzymatic conversion of homogentisate to maleylacetoacetate by HGD. The detection parameters for maleylacetoacetate are shown in the figure.

As used herein, "hydroxyphenylpyruvate dioxygenase," "HPPD," "4-hydroxy phenyl pyruvate (or pyruvic acid) dioxygenase (4-HPPD)," and "p-hydroxy phenyl pyruvate (or pyruvic acid) dioxygenase (p-OHPP)" are synonymous and refer to a non-heme iron-dependent oxygenase that catalyzes the conversion of 4-hydroxyphenylpyruvate to homogentisate (see FIG. 17). In organisms that degrade tyrosine, the reaction catalyzed by HPPD is the second step in the pathway. In plants, formation of homogentisate is necessary for the synthesis of plastoquinone, an essential redox cofactor, and tocopherol (see FIG. 2A). The structures of various HPPD polypeptides are known.

Various methods and compositions are provided which employ polypeptides having HPPD activity and having an increased insensitivity to at least one HPPD inhibitor when compared to an appropriate control, and the polynucleotides encoding these polypeptides. In an aspect, HPPD polypeptides having HPPD activity and having an increased insensitivity to at least one HPPD inhibitor when compared to an appropriate control include those set forth in any one of SEQ ID NO:2-83, and biologically active variants and fragments thereof. In various aspects, HPPD polypeptides having HPPD activity and having an increased insensitivity to at least one HPPD inhibitor when compared to an appropriate control include those set forth in any one of SEQ ID NO:4, 7, 8, 18, and 22, and biologically active variants and fragments thereof. Further provided are the polynucleotides encoding these various polypeptides and active variants and fragments thereof.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. In various aspects, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. In an aspect, a disclosed polypeptide, or biologically active portion thereof, is recombinantly produced, culture medium represents less than about 30%, 20%, 10%, 5%, or 1% (by dry weight) of chemical precursors or non-protein-of-interest chemicals.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

A "control" or "control plant" or "control plant cell" provides a reference point for measuring changes in phenotype of the subject plant or plant cell, and may be any suitable plant or plant cell. A control plant or plant cell may comprise, for example: (a) a wild-type or native plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; or (e) the subject plant or plant cell itself, under conditions in which the gene of interest is not expressed.

i. Hydroxyphenylpyruvate Dioxygenase Activity

As used herein, "hydroxyphenylpyruvate dioxygenase activity" or "HPPD activity" refers to the conversion of 4-hydroxyphenylpyruvate to homogentisate. As used herein, a polypeptide having "HPPD activity" comprises an HPPD polypeptide or an active variant or fragment thereof that retains sufficient HPPD activity such that (i) when expressed at sufficient levels in a cell that requires HPPD activity for viability, the HPPD polypeptide or active variant or fragment exhibits sufficient HPPD activity to maintain viability of the cell in which it is expressed; or (ii) when expressed in a cell that requires HPPD activity for viability, the HPPD polypeptide, or active variant or fragment thereof, when expressed in combination with one or more additional HPPD polypeptides results in the viability of the cell. In one embodiment, the HPPD activity of an HPPD polypeptide, or an active variant or fragment thereof, is such that in the absence of an HPPD inhibitor said polypeptide or active variant or fragment thereof displays at least about 5%, 15%, 20%, 25%, 30%, 35%, 40%, 45%, 50%, 55%, 60%, 65%, 70%, 75%, 80%, 85%, 90%, or 95% or greater of the HPPD activity displayed in any one of SEQ ID NO:2-83. Methods to determine such kinetic parameters (i.e., $K_m$, $k_{cat}$, $k_{cat}/K_m$) are known and discussed elsewhere herein.

In still further embodiments, the HPPD polypeptide or active variant or fragment thereof has an activity that is at least equivalent to a native HPPD polypeptide or has an activity that is increased when compared to a native HPPD polypeptide. An "equivalent" HPPD activity refers to an activity level that is not statistically significantly different from the control as determined through any enzymatic kinetic parameter, including for example, via $K_m$, $k_{cat}$, or $k_{cat}/K_m$. An increased HPPD activity comprises any statistically significant increase in HPPD activity as determined through any enzymatic kinetic parameter, such as, for example, $K_m$, $k_{cat}$, or $k_{cat}/K_m$. In specific embodiments, an increase in HPPD activity comprises at least a 1.1, 1.2, 1.3, 1.4, 1.5, 1.6, 1.7, 1.8, 2, 3, 4, 5, 6, 7, 8, 9, or 10 fold or greater improvement in a given kinetic parameter when compared to the maize wild-type HPPD sequence as set forth in SEQ ID NO:1 or when compared to a native HPPD polypeptide. Methods to determine such kinetic parameters are known.

Briefly, HPPD catalyzes the conversion of 4-hydroxyphenylpyruvate (HPP) to homogentisate. Substrate and product do not differ in absorbance of light at any useful wavelength. However, homogentisate dioxygenase (HGD) catalyzes the conversion of homogentisate into maleylacetoacetate which absorbs strongly at 320 nm. Thus, by combining 4-hydroxyphenylpyruvate with both HPPD and HGD under the appropriate reaction conditions HPPD activity can be assayed.

As used herein, a "native" HPPD polypeptide comprises any wild-type HPPD sequence. Such sequences are known in the art, and representative native/wild-type HPPD sequences from various monocot and dicot plants are set forth in FIG. 4 and SEQ ID NO:1. In specific embodiments, the biologically active fragments and variants of the HPPD sequences is compared to the maize wild-type HPPD polypeptide (SEQ ID NO:1) or to a native HPPD polypeptide.

As used herein, a "corresponding native" HPPD polypeptide comprises the native or wild type sequence from which the biologically active variant is derived. For example, for a biologically active variant or fragment of a soy HPPD polypeptide, the corresponding native HPPD polypeptide would be the native soy sequence as set forth in SEQ ID NO:100.

ii. Insensitivity to HPPD Inhibitors

In order to provide plants with tolerance to commercially useful application rates of at least one desired HPPD inhibitor, it is advantageous to use polynucleotides which encode HPPD polypeptides having sufficient HPPD activity and having an insensitivity to inhibition by at least one or more HPPD inhibitor. Thus, in specific embodiments, the HPPD polynucleotides and polypeptides and active variants and fragments thereof provided herein display an increased insensitivity to an HPPD inhibitor when compared to a corresponding native HPPD polypeptide and/or an increased insensitivity when compared to the maize native HPPD polypeptide (SEQ ID NO:1).

As used herein, an "HPPD inhibitor" comprises any compound or combinations of compounds which decrease the ability of HPPD to catalyze the conversion of 4-hydroxyphenylpyruvate to homogentisate. In specific embodiments, the HPPD inhibitor comprises a herbicidal inhibitor of HPPD. Non-limiting examples of HPPD inhibitors include, triketones (such as, mesotrione, sulcotrione, topramezone, and tembotrione); isoxazoles (such as, pyrasulfotole and isoxaflutole); pyrazoles (such as, benzofenap, pyrazoxyfen, and pyrazolynate); and benzobicyclon. Agriculturally acceptable salts of the various inhibitors include salts, the cations or anions of which are known and accepted in the art for the formation of salts for agricultural or horticultural use. See, for example, International Publication No. WO 2005/053407 herein incorporated by reference.

An "increased" or an "improved" insensitivity are used interchangeably herein. An "increased" or an "improved" insensitivity to an HPPD inhibitor comprises any significant increase in the insensitivity of the HPPD polypeptide to the inhibitor as determined through any enzymatic kinetic parameter, such as, for example, the dissociation constant ($K_D$) of the enzyme-inhibitor complex, the rates of association ($k_{ON}$), or dissociation ($k_{OFF}$) of inhibitor with or from enzyme, or the ratio of $k_{OFF}/k_{ON}$. This disclosure additionally defines parameters, "ON rate ratio", "OFF rate ratio", and "insensitivity parameter" that are not direct measurements of on and off rates but are measurements of the effect of the on and off rates inherent to a particular HPPD enzyme on its catalytic function when the enzyme is exposed to the inhibitor. An improvement in insensitivity need not show an improvement in all kinetic parameters. The improvement of a single kinetic parameter or any combination thereof is sufficient to classify the change as an improvement in insensitivity. In specific embodiments, the increased insensitivity to the HPPD inhibitor is determined by measuring these novel insensitivity parameters of the enzyme. Thus, in specific embodiments, the increased insensitivity to an HPPD inhibitor comprises at least a 0.2, 0.3, 0.5, 0.7, 0.9, 1, 2, 3, 4, 5, 6, 7, 8, 9, 10, 11, 12, 13, 14, 15, 16, 17, 18, 19, 20, 30, 40, 50, 60, 70 fold or greater improvement in a given kinetic parameter when compared to a native HPPD polypeptide and/or when compared to the maize wild-type HPPD sequence as set forth in SEQ ID NO:1.

In specific embodiments, an improved insensitivity to an HPPD inhibitor comprises (a) a slower rate of association of enzyme and inhibitor as quantified, for example, by a higher ON rate ratio than native HPPD; (b) a faster rate of dissociation of inhibitor from enzyme as quantified, for example, by a higher OFF rate ratio than native HPPD; and/or (c) both a slower rate of association of inhibitor with enzyme and a faster rate of dissociation of inhibitor from enzyme as quantified, for example, by a higher product of ON rate ratio and OFF rate ratio than native HPPD.

Methods to determine kinetic parameters for measuring the insensitivity of HPPD to an inhibitor are known. See also, Examples 1 and 4. Briefly, herbicidal inhibitors of HPPD form a tight complex with the enzyme by the dual mechanisms of coordination to the active site iron atom through a pair of keto oxygens and a Pi stack of the aromatic ring of the inhibitor between a pair of active site phenylalanines. As a result, conventional $I_{50}$ determinations are not able to distinguish differences in binding affinity among various forms of HPPD and the inhibitor. All values will be the same, namely, 50% of the enzyme concentration. To devise a parameter for detecting changes in inhibitor binding affinity, $K_D$, one can utilize the relationship between $K_D$ and the rates of binding and release of inhibitor (I) to and from the enzyme (E).

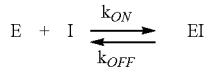

At equilibrium, rates of binding and release are equal. Thus, $$k_{ON}[E][I]=k_{OFF}[EI]$$

Written as a dissociation (products over reactants), the equation can be re-arranged to:

$$\frac{[E][I]}{[EI]} = \frac{k_{OFF}}{k_{ON}} = K_D$$

Higher $K_D$ (reduced affinity or increased insensitivity) can be attained with a numerically smaller ON rate, a larger OFF rate or both. To detect changes in ON and OFF rates, one can observe the time course of an HPPD reaction as inhibitor binds to and inactivates the enzyme (ON rate), or is released from a pre-formed enzyme-inhibitor complex (OFF rate). See, for example, Example 1.

A quantitative indicator of ON rate can be obtained by monitoring the time courses of HPPD reactions in the presence and absence of inhibitor (e.g. mesotrione). The ratio of the reaction rate with inhibitor to that without inhibitor during the 70 to 90 second interval of the reaction is the "ON rate ratio".

A quantitative indicator of OFF rate can be obtained by observing the time course of an HPPD reaction as the HPPD inhibitor (such as mesotrione) is released from a pre-formed enzyme-inhibitor complex. Reaction velocity accelerates as inhibitor is released from the enzyme until a steady state is reached, during which the reaction velocity is constant. The ratio of the steady state rate in mixtures containing mesotrione (or other herbicidal inhibitor) to the initial velocity of mixtures lacking inhibitor is termed the "OFF rate ratio". Another parameter to record is the time span required for the reactions with inhibitor to reach the steady state. In still further embodiments, to be sure that improvement in ON rates is being taken into account, the ON and OFF rate ratios are multiplied together and the product is termed the "insensitivity parameter."

The increased insensitivity of an HPPD inhibitor can also be determined by assaying the increased insensitivity of a cell, a plant, a plant cell expressing said HPPD polypeptide or active fragment or variant thereof. In such instances, the cell, plant, or plant cell expressing an HPPD sequence having an increased insensitivity to an HPPD inhibitor will display an increased tolerance to the HPPD inhibitor or to a combination of HPPD inhibitors when compared to a control cell, plant or plant cell not expressing the HPPD sequence. "Increased tolerance" to a herbicide is demonstrated when plants which display the increased tolerance to a herbicide are subjected to the HPPD inhibitor and a dose/response curve is shifted to the right when compared with that provided by an appropriate control plant. Such dose/response curves have "dose" plotted on the x-axis and "percentage injury", "herbicidal effect" etc. plotted on the y-axis. Plants which are substantially "resistant" or "tolerant" to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field.

For example, a plant expressing an HPPD polypeptide which displays an increased insensitivity to an HPPD inhibitor will tolerate statistically significantly higher levels of the HPPD inhibitor than a control plant not expressing the HPPD polypeptide. In specific embodiments, a plant transfected and expressing one or more HPPD polypeptide sequence disclosed herein, and the active variants and fragments thereof, allow for an increased insensitivity to an HPPD inhibitor comprising, for example, at least a 2, 3, 4, 5, 6, 7, 8, 9, 10, 11, 12, 13, 14, 15, 16, 17, 18, 19, 20, 100 fold or greater increase in a given performance parameter when compared to untransformed plants. See, also, Examples 1 for exemplary assays.

Different HPPD polypeptides can provide different levels of tolerance to different HPPD-inhibitor herbicides. While a given HPPD polypeptide may provide a useful level of tolerance to some HPPD-inhibitor herbicides it may be quite inadequate to provide commercial levels of tolerance to a different HPPD-inhibitor herbicide which, for example, may control a different spectrum of weeds, be cheaper to make or offer environmental benefits. Thus, the various HPPD polypeptides disclosed herein can be used in combination in a single plant, plant explant or plant cell to expand and/or improve the tolerance to a desired HPPD herbicide or combination of HPPD herbicides.

B. Active Fragments and Variants of HPPD Sequences

Methods and compositions are provided which employ polynucleotides and polypeptides having HPPD activity and having an insensitivity to at least one HPPD inhibitor.

i. Polynucleotide and Polypeptide Fragments

Fragments and variants of HPPD polynucleotides and polypeptides are also encompassed by the present disclosure. By "fragment" is intended a portion of the polynucleotide or a portion of the amino acid sequence and hence protein encoded thereby. Fragments of a polynucleotide may encode protein fragments that retain HPPD activity and HPPD inhibitor insensitivity. Alternatively, fragments of a polynucleotide that is useful as hybridization probes generally do not encode fragment proteins retaining biological activity. Thus, fragments of a nucleotide sequence may range from at least about 20 nucleotides, about 50 nucleotides, about 100 nucleotides, about 150 nucleotides, and up to the full-length polynucleotide encoding the HPPD polypeptides.

A fragment of an HPPD polynucleotide that encodes a biologically active portion of an HPPD protein of the disclosure will encode at least 20, 50, 75, 100, 150, 175, 200, 225, 250, 275, 300, 325, 350, 375, 400, 410, 415, 420, 425, 430, 435, or 440 contiguous amino acids, or up to the total number of amino acids present in a full-length HPPD polypeptide. Fragments of an HPPD polynucleotide that are useful as hybridization probes or PCR primers generally need not encode a biologically active portion of an HPPD protein.

Thus, a fragment of an HPPD polynucleotide may encode a biologically active portion of an HPPD polypeptide, or it may be a fragment that can be used as a hybridization probe or PCR primer using methods disclosed below. A biologically active portion of an HPPD polypeptide can be prepared by isolating a portion of one of the HPPD polynucleotides, expressing the encoded portion of the HPPD polypeptides (e.g., by recombinant expression in vitro), and assessing the activity of the HPPD portion of the HPPD protein. Polynucleotides that are fragments of an HPPD nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length HPPD polynucleotide disclosed herein.

In one embodiment, the HPPD polynucleotides and/or polypeptides comprise or encode an N-terminal truncation of the HPPD polypeptide. Such active HPPD fragments comprise an N-terminal deletion of at least the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids of the HPPD polypeptide of any one of SEQ ID NO:2-83. In specific embodiments, N-terminal deletions are designed to comprise a methionine residue on the N-terminus. In specific embodiments, a fragment of the HPPD polypeptide or polynucleotide comprising or encoding an N-terminal truncated HPPD polypeptide comprises or encodes a polypeptide having a deletion of amino acids 2-23 of any one of SEQ ID NO:2-83.

ii. Polynucleotide and Polypeptide Variants

"Variant" protein is intended to mean a protein derived from a native protein by deletion (i.e., truncation at the 5' and/or 3' end) and/or a deletion, or addition, of one or more amino acids at one or more internal sites in the native protein and/or substitution of one or more amino acids at one or more sites in the native protein. Variant proteins encompassed are biologically active, that is they continue to possess the desired biological activity of the native protein, that is, have HPPD activity and/or display insensitivity to a HPPD inhibitor as described herein. Such variants may result from, for example, genetic polymorphism or from human manipulation.

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the HPPD polypeptides of the disclosure. Naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis or gene synthesis but which still encode an HPPD polypeptide.

Biologically active variants of an HPPD polypeptide (and the polynucleotide encoding the same) will have at least about 90%, 91%, 92%, 93%, 94%, 95%, 95.5%, 95.7%, 95.9%, 96%, 96.3%, 96.5%, 96.9%, 97%, 97.3%, 97.5%, 97.9%, 98%, 98.3%, 98.5%, 98.9%, 99%, 99.3%, 99.5%, 99.6% or more sequence identity to the polypeptide of any one of SEQ ID NO:2-83.

In an aspect, biologically active variants of an HPPD polypeptide (and the polynucleotide encoding the same) will have at least about 90%, 91%, 92%, 93%, 94%, 95%, 95.5%, 95.7%, 95.9%, 96%, 96.3%, 96.5%, 96.9%, 97%, 97.3%, 97.5%, 97.9%, 98%, 98.3%, 98.5%, 98.9%, 99%, 99.3%, 99.5%, 99.6% or more sequence identity to the polypeptide of any one of SEQ ID NO:4, 7, 8, 18, and 18.

In other embodiments, variants of a HPPD polypeptides (and polynucleotide encoding the same) will have at least about 90%, 91%, 92%, 93%, 94%, 95%, 95.5%, 95.7%, 95.9%, 96%, 96.3%, 96.5%, 96.9%, 97%, 97.3%, 97.5%, 97.9%, 98%, 98.3%, 98.5%, 98.9%, 99%, 99.3%, 99.5% or more sequence identity to an HPPD polypeptide having an N-terminal deletion. For example, such polypeptides comprise an N-terminal truncation of any one of SEQ ID NO:2-83, comprising an N-terminal deletion of at least the first 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 amino acids wherein said active variant of the HPPD polypeptide comprises at least 90%, 91%, 92%, 93%, 94%, 95%, 95.5%, 95.7%, 95.9%, 96%, 96.3%, 96.5%, 96.9%, 97%, 97.3%, 97.5%, 97.9%, 98%, 98.3%, 98.5%, 98.9%, 99%, 99.3%, 99.5% or more sequence identity to an N-terminal deletion of the HPPD polypeptide. In further embodiments, the N-terminal truncates further comprise a methionine amino acid residue on the N-terminus. In specific embodiments, fragments of the HPPD polypeptide have a deletion of amino acids 2-23 of any one of SEQ ID NO:2-83. Thus, further provided are HPPD polypeptides comprising at least 90%, 91%, 92%, 93%, 94%, 95%, 95.5%, 95.7%, 95.9%, 96%, 96.3%, 96.5%, 96.9%, 97%, 97.3%, 97.5%, 97.9%, 98%, 98.3%, 98.5%, 98.9%, 99%, 99.3%, 99.5% or more sequence identity to the amino acid sequence set forth in any one of SEQ ID NO:2-83.

In other embodiments, variants of a particular polypeptide (and polynucleotide encoding the same) will have a bit score of at least 700, 710, 720, 721, 722, 723, 724, 725, 726, 728, 729, 730, 731, 732, 733, 734, 735, 736, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 828, 829, 830, 831, 832, 833, 834, 835, 836, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890 or greater as determined by parameters described elsewhere herein to a polypeptide of any one of SEQ ID NO:2-83.

The HPPD polypeptide and the active variants and fragments thereof may be altered in various ways including amino acid substitutions, deletions, truncations, and insertions. Methods for such manipulations are generally known in the art. For example, amino acid sequence variants and fragments of the HPPD proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different HPPD coding sequences can be manipulated to create a new HPPD possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the HPPD sequences disclosed herein and other known HPPD genes to obtain a new gene coding for a protein with an improved property of interest, such as a decreased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

In still further embodiments, the HPPD polypeptide or active variants and fragments thereof have been modified to remove one or more sequences that are present in other proteins which are allergens. As used herein, a "matching sequence" comprises a region of 8 contiguous identical amino acids present in a known protein allergen. See, for example, Ladics (2008) *Food and Chemical Toxicology* 46: S20-S23, herein incorporated by reference. Such identified 8-amino acid sequences, however, do not necessarily have any allergenic potential or confer allergenicity. Nonetheless, to comply with established criteria governing the potential for allergenic cross-reactivity (FAO/WHO 2001, Codex 2003), the matching sequences can be altered so the resulting polypeptide no longer contains the 8 residue contiguous match. Identification of such matching sequences is done by comparing the predicted amino acid sequence of the transgene product with that of a database of known or putative protein allergens and subsequently altering the identified amino acid sequence to remove the allergenic match. The database utilized for this analysis was the AllergenOnline database of known protein allergens housed at the University of Nebraska (www.allergenonline.org). It is recognized that in specific embodiments, removal of the matching sequence via substitution, deletion and/or addition of amino acids will not impact the HPPD activity or the HPPD inhibitor insensitivity of the protein when compared to an appropriate control. TAAAAGAA (amino acids 6-13 in maize wild-type HPPD SEQ ID NO:1) was changed to TATAAGAA (SEQ ID NO:101) to eliminate the 8 amino acid match to an allergen sequence in the database. Such a change does not alter the activity or insensitivity to herbicides of HPPD enzymes. See, for example, Codex Alimentarius Commission, Alinorm 03/34: Joint FAO/WHO Food Standard Programme, Codex Alimentarius Commission, Twenty-Fifth Session, Rome, Italy, Jun. 30-Jul. 5, 2003. Appendix III, Guideline for the conduct of food safety assessment of foods derived from recombinant-DNA plants, and Appendix IV, Annex of the assessment of possible allergenicity, 47-60 and FAO/WHO, 2001. Evaluation of allergenicity of genetically modified foods. Report of a Joint FAO/WHO Expert Consultation on Allergenicity of Foods Derived from Biotechnology. Jan. 22-25, 2001. Rome, Italy.

C. Chloroplast Transit Peptides

Further provided are various methods and compositions which comprise HPPD polypeptides and active variants and fragments thereof, and polynucleotides encoding the same, wherein the HPPD sequence comprises a chloroplast transit peptide. As used herein, the term "chloroplast transit peptide" will be abbreviated "CTP" and refers to the N-terminal portion of a chloroplast precursor protein that directs the latter into chloroplasts and is subsequently cleaved off by the chloroplast processing protease. When a CTP is operably linked to the N-terminus of a polypeptide, the polypeptide is translocated into the chloroplast. Removal of the CTP from a native protein reduces or abolishes the ability of the native protein from being transported into the chloroplast. An operably linked chloroplast transit peptide is found at the N-terminus of the protein to be targeted to the chloroplast and is located upstream and immediately adjacent to the transit peptide cleavage site that separates the transit peptide from the mature protein to be targeted to the chloroplast.

The term "chloroplast transit peptide cleavage site" refers to a site between two amino acids in a chloroplast-targeting sequence at which the chloroplast processing protease acts.

Chloroplast transit peptides target the desired protein to the chloroplast and can facilitate the proteins translocation into the organelle. This is accompanied by the cleavage of the transit peptide from the mature polypeptide or protein at the appropriate transit peptide cleavage site by a chloroplast processing protease, native to the chloroplast. Accordingly, a chloroplast transit peptide further comprises a suitable cleavage site for the correct processing of the pre-protein to the mature polypeptide contained within the chloroplast.

Thus, any one of the polypeptides, or the polynucleotide encoding the same, or active variants and fragments thereof set forth in any one of SEQ ID NO:2-83, and biologically active variants and fragments thereof, can comprise a heterologous CTP sequence. Additional CTPs from HPPD polypeptides can be employed (see for example, PCT Publication No. WO 2012/021797, entitled "Methods and Compositions for Targeting Sequences of Interest to a Chloroplast.").

In still further embodiments, an HPPD polypeptide, and a polynucleotide encoding the same, is provided, wherein the HPPD polypeptide comprises a heterologous chloroplast transit peptide that is not from the wild-type maize HPPD polypeptide or an active variant or fragment thereof. Such heterologous chloroplast transit peptides are known, including but not limited to those derived from *Pisum* (JP 1986224990; E00977), carrot (Luo et al. (1997) *Plant Mol. Biol.*, 33 (4), 709-722 (Z33383), *Nicotiana* (Bowler et al., EP 0359617; A09029), *Oryza* (de Pater et al. (1990) *Plant Mol. Biol.*, 15 (3), 399-406 (X51911), as well as synthetic sequences such as those provided in EP 0189707; U.S. Pat. Nos. 5,728,925; 5,717,084 (A10396 and A10398). In one embodiment, the heterologous chloroplast transit peptide is from the ribulose-1,5-bisphosphate carboxylase (Rubisco) small subunit precursor protein isolated from any plant. The Rubisco small subunit is well characterized from a variety of plants and the transit peptide from any of them are suitable for use in the compositions and methods of the present disclosure. See for example, *Physcomitrella* (Quatrano et al., AW599738); Lotus (Poulsen et al., AW428760); *Citrullus* (J. S. Shin, AI563240); *Nicotiana* (Appleby et al. (1997) *Heredity* 79(6), 557-563); alfalfa (Khoudi et al. (1997) *Gene*, 197(1/2), 343-351); potato and tomato (Fritz et al. (1993) *Gene*, 137(2), 271-4); wheat (Galili et al. (1991) *Theor. Appl. Genet.* 81(1), 98-104); and rice (Xie et al. (1987) *Sci. Sin.*, Ser. B (Engl. Ed.), 30(7), 706-19). For example, transit peptides may be derived from the Rubisco small subunit isolated from plants including but not limited to, soybean, rapeseed, sunflower, cotton, corn, tobacco, alfalfa, wheat, barley, oats, sorghum, rice, *Arabidopsis*, sugar beet, sugar cane, canola, millet, beans, peas, rye, flax, and forage grasses. In an aspect, methods and compositions of the present disclosure can utilize the Rubisco small subunit precursor protein from, for example, *Arabidopsis* or tobacco.

In other embodiments, the HPPD polypeptides and active variants and fragments thereof, and polynucleotide encoding the same, do not comprise a CTP. In such instances, the HPPD polypeptide and active variants and fragments thereof, or polynucleotides encoding the same, do not comprise a chloroplast transit peptide. Such polypeptides can be expressed in the cytoplasm of a plant, plant cell or explant and still confer insensitivity of the cell, plant or plant cell to an HPPD inhibitor. In still other embodiments, the HPPD polynucleotides lacking the chloroplast transit peptide are introduced directly into the chloroplast via chloroplast transformation. Such methods of chloroplast transformation are discussed in detail elsewhere herein.

Thus, further provided herein are HPPD polynucleotides and polypeptides and variants and fragments thereof that have HPPD activity and display insensitivity to an HPPD inhibitor and lack a chloroplast transit peptide. Various N-terminal truncations are described elsewhere herein.

In other embodiments, the HPPD polypeptide or polynucleotide encoding the same, lacks the first 10, 11, 12, 13, 14, 15, 16, 17, 18, 19, 20, 21, 22, 23, 24, 25, 26, 27, 28, 29, 30, 31, 32, 33, 34, 35, 36, 0.37, 38, 39, 40, 41, 42, 43, 44, 45, 46, 47, 48, 49, or 50 or more amino acids of any one of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 74, 65, 66, 67, 68, 69, 70, 71, 72, 73, 74, 75, 76, 77, 78, 79, 80, 81, 82, 83, 84, 85, 86, 87, 88, 89, 90, 61, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 212, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 383, 384, 385, 386, 387, 388, 389, 404, 405, 406, 407, 408, 409, 410, 411, 412, 413, 414, 415, 416, 417, 418, 419, 420, 421, 422, 423, 424, 425, 426, 427, 428, 429, 430, 458, or 459 or biologically active variant or fragment thereof. In specific embodiments, the sequence set forth in any one of SEQ ID NO:2-83, and biologically active variants and fragments thereof, or the polynucleotide encoding the same, lack the first the 2-23 amino acid of the corresponding SEQ ID NO.

D. Sequence Comparisons

The following terms are used to describe the sequence relationships between two or more polynucleotides or polypeptides: (a) "reference sequence", (b) "comparison window", (c) "sequence identity", and, (d) "percent sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

(b) As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acid in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the present disclosure. BLAST protein searches can be performed with the BLASTX program, score=50, wordlength=3, to obtain amino acid sequences homologous to a protein or polypeptide of the present disclosure. BLASTP protein searches can be performed using default parameters. For example, see blast.ncbi.nlm.nih.gov/Blast.cgi.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTP for proteins) can be used. See www.ncbi.nlm.nih.gov. Alignment may also be performed manually by inspection.

In one embodiment, sequence identity/similarity values provided herein refer to the value obtained using GAP Version 10 using the following parameters: % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

(e) Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acids substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al, (1997) Nucleic Acids Res. 25:3389-3402, and made available to the public at the National Center for Biotechnology Information Website (http://www.ncbi.nlm.nih.gov). Optimal alignments, including multiple alignments, can be prepared using, e.g., PSI-BLAST, available through http://www.ncbi.nlm.nih.gov and described by Altschul et al, (1997) Nucleic Acids Res. 25:3389-3402.

As used herein, similarity score and bit score is determined employing the BLAST alignment used the BLOSUM62 substitution matrix, a gap existence penalty of 11, and a gap extension penalty of 1. For the same pair of sequences, if there is a numerical difference between the scores obtained when using one or the other sequence as query sequences, a greater value of similarity score is selected.

E. Plants

Plants, plant cells, plant parts, explants, seeds, and grain having the HPPD sequences disclosed herein are provided. In specific embodiments, the plants and/or plant parts have stably incorporated at least one heterologous HPPD polypeptide disclosed herein or an active variant or fragment thereof. Thus, plants, plant cells, plant parts and seed are provided which comprise at least one heterologous HPPD sequence of any one of SEQ ID NO:2-83, and biologically active variants and fragments thereof, or any one of other variants disclosed herein, or a biologically active fragment and/or variant of the HPPD sequence. In specific embodiments, the HPPD sequences are characterized as having HPPD activity and having an insensitivity to an HPPD inhibitor.

Further provided are plants, plant cells, plant parts, explants, seeds, and grain having the HPPD sequences having a heterologous CTP as discussed elsewhere herein. In light of employing HPPDs with and without CTP sequences, the term "stably incorporated" in a plant, plant cell, plant part, explant, seed, or grain refers to the integration of the polynucleotide into the genomic DNA or to the integration of the polynucleotide into the genome of a plastid (i.e., the chloroplast, amyloplasts, chromoplasts, statoliths, leucoplasts, elaioplasts, and proteinoplasts).

In specific embodiments, the heterologous polynucleotide in the plant or plant part is operably linked to a constitutive, tissue-preferred, or other promoter for expression in plants.

As used herein, the term "plant" includes immature or mature whole plant, including a plant from which seed, grain, or anthers have been removed, as well as plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

As used herein, "grain" is intended to mean the mature seed produced by commercial growers for purposes other than growing or reproducing the species. Progeny, variants, and mutants of the regenerated plants are also included within the scope of the disclosure, provided that these parts comprise introduced polynucleotides encoding a disclosed HPPD polypeptide.

As used herein, the term "plant part" or "plant parts" refers to any plant part whether part of an intact living or growing plant or whether isolated or separated from an intact living plant. Plant part includes, but is not limited to, protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

As used herein, "explant" refers to plant tissue that is directly excised from an intact plant, such as a leaf, petal, sepal, stamen, filament anther, root, or stem.

The HPPD sequences and active variants and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), *Citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing methods of the present disclosure include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and *Eucalyptus*. In specific embodiments, plants of the present disclosure are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

F. Polynucleotide Constructs

The use of the term "polynucleotide" is not intended to limit the present disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the disclosure also encompass all forms of sequences including, but not limited to, single-stranded forms, double-stranded forms, hairpins, stem-and-loop structures, and the like.

The HPPD polynucleotides disclosed herein can be provided in expression cassettes for expression in the plant of interest. The cassette can include 5' and 3' regulatory sequences operably linked to an HPPD polynucleotide or active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the HPPD polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), an HPPD polynucleotide or active variant or fragment thereof, and a transcriptional and translational termination region (i.e., termination region) functional in plants. The regulatory regions (i.e., promoters, transcriptional regulatory regions, and translational termination regions) and/or the HPPD polynucleotide or active variant or fragment thereof may be native/analogous to the host cell or to each other. Alternatively, the regulatory regions and/or the HPPD polynucleotide of or active variant or fragment thereof may be heterologous to the host cell or to each other. As discussed in further detail elsewhere herein, the expression cassette can comprises a chimeric polynucleotide comprising a heterologous CTP operably linked to an HPPD polynucleotide.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

While it may be optimal to express the sequences using heterologous promoters, the native promoter sequences may be used. Such constructs can change expression levels of the HPPD polynucleotide in the plant or plant cell. Thus, the phenotype of the plant or plant cell can be altered.

The termination region may be native with the transcriptional initiation region, may be native with the operably linked HPPD polynucleotide or active variant or fragment thereof, may be native with the plant host, or may be derived from another source (i.e., foreign or heterologous) to the promoter, the HPPD polynucleotide or active fragment or variant thereof, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989)

*Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various HPPD sequence disclosed herein, including the native promoter of the polynucleotide sequence of interest. The promoters can be selected based on the desired outcome. Such promoters include, for example, constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced HPPD expression within a particular plant tissue. Tissue-preferred promoters include those described in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

As discussed in more detail elsewhere herein, promoters that direct expression in a plastid, such as a chloroplast, can also be used to express the HPPD sequences or biologically active variants and fragments thereof.

Synthetic promoters can be used to express HPPD sequences or biologically active variants and fragments thereof. In one non-limiting embodiment, the HPPD sequences are expressed with a synthetic constitutive promoter (see for example U.S. Pat. Nos. 6,072,050 and 6,555,673) or with a promoter disclosed in International Publication No. WO 2012/021794 and U.S. Pat. No. 8,993,837, entitled "Chimeric Promoters and Methods of Use."), In still further embodiments, the HPPD variants operably linked to such synthetic promoters further comprise an *Arabidopsis* ubiquitin3 gene terminator (Callis et al. (1995) *Genetics* 139 (2), 921-939; Genbank L05363).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present disclosure, including, for example, DsRed as described in Example 1.

G. Stacking Other Traits of Interest

In some embodiments, the HPPD polynucleotides or active variants and fragments thereof disclosed herein are engineered into a molecular stack. Thus, the various plants, plant cells, plant parts, explants, seeds, and grain disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant (i.e., both traits are incorporated into the nuclear genome, one trait is incorporated into the nuclear genome and one trait is incorporated into the genome of a plastid, or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. In one embodiment, the molecular stack comprises at least one additional polynucleotide that also confers tolerance to at least one HPPD inhibitor and/or at least one additional polynucleotide that confers tolerance to a second herbicide.

Thus, in one embodiment, the plants, plant cells, plant parts, explants, seeds, and grain having the HPPD polynucleotide or active variants or fragments thereof disclosed herein is stacked with at least one other HPPD sequence, include the HPPD sequence, and variants and fragment thereof disclosed herein, as well as other HPPD sequence, which include but are not limited to the HPPD sequences set forth in U.S. Pat. Nos. 6,245,968 B1; 6,268,549; and 6,069,115; and international publication WO 99/23886, each of which is herein incorporated by reference.

In still other embodiments, plants, plant cells, plant parts, explants, seeds, and grain comprise expression cassettes comprising the HPPD sequences or active variant and fragment thereof are stacked with a sequence that confers tolerance to HPPD inhibitors through a different mechanism than the HPPD polypeptide. For example, a P450 sequence could be employed which provides tolerance to HPPD-inhibitors by metabolism of the herbicide. Such sequences including, but are not limited to, the NSF1 gene. See, US 2007/0214515 and US 2008/0052797 both of which are herein incorporated by reference in their entirety.

In some embodiments, plants, plant cells, plant parts, explants, seeds, and grain having the HPPD polynucleotides or active variants or fragment thereof may be stacked with other herbicide-tolerance traits to create a transgenic plant of the disclosure with further improved properties. Other herbicide-tolerance polynucleotides that could be used in such embodiments include those conferring tolerance to glyphosate such as, for example, glyphosate N-acetyltransferase. See, for example, WO02/36782, US Publication 2004/0082770 and WO 2005/012515, U.S. Pat. Nos. 7,462,481, 7,405,074, each of which is herein incorporated by reference.

Additional glyphosate-tolerance traits include a sequence that encodes a glyphosate oxido-reductase enzyme as described more fully in U.S. Pat. Nos. 5,776,760 and 5,463,175. Other traits that could be combined with the HPPD sequence disclosed herein include those derived from polynucleotides that confer on the plant the capacity to produce a higher level or glyphosate insensitive 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 00/66746; WO 01/66704; and WO 00/66747. Other traits that could be combined with the HPPD sequences disclosed herein include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

Additional known genes that confer tolerance to herbicides and can be employed in the methods and compositions disclosed herein include, for example e.g., auxin, HPPD, glyphosate, dicamba, glufosinate, sulfonylurea, bromoxynil and norflurazon herbicides can be stacked either as a molecular stack or a breeding stack with plants expressing the traits disclosed herein. Polynucleotide molecules encoding proteins involved in herbicide tolerance include, but are not limited to, a polynucleotide molecule encoding 5-enolpyruvyl shikimate-3-phosphate synthase (EPSPS) disclosed in U.S. Pat. Nos. 39,247; 6,566,587 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Pat. Nos. 7,622,641; 7,462,481; 7,531,339; 7,527,955; 7,709,709; 7,714,188 and 7,666,643 also for providing glyphosate tolerance; dicamba monooxygenase disclosed in U.S. Pat. No. 7,022,896 and WO2007146706A2 for providing dicamba tolerance; a polynucleotide molecule encoding AAD12 disclosed in U.S. Pat. App. Pub. No. 2005731044 or WO2007053482A2 or encoding AAD1 disclosed in US20110124503A1 or U.S. Pat. No. 7,838,733 for providing tolerance to auxin herbicides (2,4-D); a polynucleotide molecule encoding hydroxyphenylpyruvate dioxygenase (HPPD) for providing tolerance to HPPD inhibitors (e.g., hydroxyphenylpyruvate dioxygenase) disclosed in e.g., U.S. Pat. No. 7,935,869; US20090055976A1; and US20110023180A1; each publication is herein incorporated by reference in its entirety.

In other embodiments, plants, plant cells, plant parts, explants, seeds, and grain having the HPPD sequence or an active variant or fragment thereof is stacked with, for example, a sequence which confers tolerance to an acetolactate synthase ("ALS") inhibitor. As used herein, an "ALS inhibitor-tolerant polypeptide" comprises any polypeptide which when expressed in a plant confers tolerance to at least one ALS inhibitor. A variety of ALS inhibitors are known and include, for example, sulfonylurea, imidazolinone, triazolopyrimidines, pryimidinyoxy(thio)benzoates, and/or sulfonylaminocarbonyltriazolinone herbicides. Additional ALS inhibitors are known and are disclosed elsewhere herein. It is known in the art that ALS mutations fall into different classes with regard to tolerance to sulfonylureas, imidazolinones, triazolopyrimidines, and pyrimidinyl(thio) benzoates, including mutations having the following characteristics: (1) broad tolerance to all four of these groups; (2) tolerance to imidazolinones and pyrimidinyl(thio)benzoates; (3) tolerance to sulfonylureas and triazolopyrimidines; and (4) tolerance to sulfonylureas and imidazolinones.

Various ALS inhibitor-tolerant polypeptides can be employed. In some embodiments, the ALS inhibitor-tolerant polynucleotides contain at least one nucleotide mutation resulting in one amino acid change in the ALS polypeptide. In specific embodiments, the change occurs in one of seven substantially conserved regions of acetolactate synthase. See, for example, Hattori et al. (1995) *Molecular Genetics and Genomes* 246:419-425; Lee et al. (1998) *EMBO Journal* 7:1241-1248; Mazur et al. (1989) *Ann. Rev. Plant Phys.* 40:441-470; and U.S. Pat. No. 5,605,011, each of which is incorporated by reference in their entirety. The ALS inhibitor-tolerant polypeptide can be encoded by, for example, the SuRA or SuRB locus of ALS. In specific embodiments, the ALS inhibitor-tolerant polypeptide comprises the C3 ALS mutant, the HRA ALS mutant, the S4 mutant or the S4/HRA mutant or any combination thereof. Different mutations in ALS are known to confer tolerance to different herbicides and groups (and/or subgroups) of herbicides; see, e.g., Tranel and Wright (2002) *Weed Science* 50:700-712. See also, U.S. Pat. Nos. 5,605,011, 5,378,824, 5,141,870, and 5,013,659, each of which is herein incorporated by reference in their entirety. The soybean, maize, and *Arabidopsis* HRA sequences are disclosed, for example, in WO2007/024782, herein incorporated by reference.

In some embodiments, the ALS inhibitor-tolerant polypeptide confers tolerance to sulfonylurea and imidazolinone herbicides. The production of sulfonylurea-tolerant plants and imidazolinone-tolerant plants is described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes. In specific embodiments, the ALS inhibitor-tolerant polypeptide comprises a sulfonamide-tolerant acetolactate synthase (otherwise known as a sulfonamide-tolerant acetohydroxy acid synthase) or an imidazolinone-tolerant acetolactate synthase (otherwise known as an imidazolinone-tolerant acetohydroxy acid synthase).

In further embodiments, plants, plant cells, plant parts, explants, seeds, and grain having the HPPD sequence or an active variant or fragment thereof is stacked with, or example, a sequence which confers tolerance to an ALS inhibitor and glyphosate tolerance. In one embodiment, the HPPD sequence or active variant or fragment thereof is stacked with HRA and a glyphosate N-acetyltransferase. See, WO2007/024782, 2008/0051288 and WO 2008/112019, each of which is herein incorporated by reference.

In still other embodiments, plants, plant cells, plant parts, explants, seeds, and grain having the HPPD sequence or an active variant or fragment thereof may be stacked with, for example, aryloxyalkanoate dioxygenase polynucleotides (which confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) *J. Biol. Chem.* 280: 24759-24767, auxin polypeptides and an acetyl coenzyme A carboxylase (ACCase) polypeptides.

Other examples of herbicide-tolerance traits that could be combined with the plant or plant cell or plant part having the HPPD sequence or an active variant or fragment thereof include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the plants or plant cell or plant part having the HPPD sequence or an active variant or fragment thereof include those conferred by polynucleotides conferring altered protoporphyrinogen oxidase (protox) activity, as described in U.S. Pat. Nos. 6,288,306 B1; 6,282,837 B1; and 5,767,373; and international publication WO 01/12825. Plants containing such polynucleotides can exhibit improved tolerance to any of a variety of herbicides which target the protox enzyme (also referred to as "protox inhibitors").

Other examples of herbicide-tolerance traits that could be combined with the plants or plant cell or plant part having the HPPD sequence or an active variant or fragment thereof include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) *Weed Technology* 12: 474-477; Green and Ulrich (1993) *Weed Science* 41: 508-516. The trait(s) responsible for these tolerances can be combined by breeding or via other methods with the plants or plant cell or plant part having the HPPD sequence or an active variant or fragment thereof to provide a plant of the disclosure as well as methods of use thereof.

In still further embodiments, the HPPD sequences can be stacked with at least one polynucleotide encoding a homogentisate solanesyltransferase (HST). See, for example, WO2010023911 herein incorporated by reference in its entirety. In such embodiments, classes of herbicidal compounds—which act wholly or in part by inhibiting HST can be applied over the plants having the HTS polypeptide.

Plants, plant cells, plant parts, explants, seeds, and grain having the HPPD sequence or an active variant or fragment thereof can also be combined with at least one other trait to produce plants that further comprise a variety of desired trait combinations including, but not limited to, traits desirable for animal feed such as high oil content (e.g., U.S. Pat. No. 6,232,529); balanced amino acid content (e.g., hordothionins (U.S. Pat. Nos. 5,990,389; 5,885,801; 5,885,802; and 5,703,409; 5,850,016); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) *Appl. Microbiol. Biotechnol.* 59: 224-230) and OLCH (high oleic acid content; see, e.g., Fernandez-Moya et al. (2005) *J. Agric. Food Chem.* 53: 5326-5330).

Plants, plant cells, plant parts, explants, seeds, and grain having the HPPD sequence or an active variant or fragment thereof can also be combined with other desirable traits such as, for example, fumonisim detoxification genes (U.S. Pat. No. 5,792,931), avirulence and disease resistance genes (Jones et al. (1994) *Science* 266: 789; Martin et al. (1993) *Science* 262: 1432; Mindrinos et al. (1994) *Cell* 78: 1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In other embodiments, plants, plant cells, plant parts, explants, seeds, and grain having the HPPD sequence or an active variant or fragment thereof may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) *Gene* 48: 109; Lee et al. (2003) *Appl. Environ. Microbiol.* 69: 4648-4657 (Vip3A); Galitzky et al. (2001) *Acta Crystallogr. D. Biol. Crystallogr.* 57: 1101-1109 (Cry3Bb1); and Herman et al. (2004) *J. Agric. Food Chem.* 52: 2726-2734 (Cry1F)), lectins (Van Damme et al. (1994) *Plant Mol. Biol.* 24: 825, pentin (described in U.S. Pat. No. 5,981,722), and the like. The combinations generated can also include multiple copies of any one of the polynucleotides of interest.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

H. Method of Introducing

Various methods can be used to introduce a sequence of interest into a plant or plant part. "Introducing" is intended to mean presenting to the plant, plant cell or plant part the polynucleotide or polypeptide in such a manner that the sequence gains access to the interior of a cell of the plant. The methods of the disclosure do not depend on a particular method for introducing a sequence into a plant or plant part, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology*

14:745-750 (maize via *Agrobacterium tumefaciens*); all of which are herein incorporated by reference.

In specific embodiments, the HPPD sequences or active variant or fragments thereof can be provided to a plant, plant cell, plant part, or host cell using a variety of transient transformation methods. Such transient transformation methods include, but are not limited to, the introduction of the HPPD protein or active variants and fragments thereof directly into the plant, plant part, or plant cell. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107: 775-784, all of which are herein incorporated by reference.

In other embodiments, polynucleotides encoding the peptides of the disclosure can be introduced into plants, plant parts, or plant cells by contacting plants, plant parts, or plant cells with a virus or viral nucleic acids. Generally, such methods involve incorporating a nucleotide construct of the disclosure within a DNA or RNA molecule. It is recognized that the an HPPD sequence may be initially synthesized as part of a viral polyprotein, which later may be processed by proteolysis in vivo or in vitro to produce the desired recombinant protein. Further, it is recognized that promoters of the disclosure also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, polynucleotides encoding polypeptides of the disclosure can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

The plant cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seeds (also referred to as "transgenic seed") having a polynucleotide encoding polypeptides of the disclosure, for example, an expression cassette of the disclosure, stably incorporated into their genome.

I. Chloroplast Transformation

In specific embodiments, the HPPD polypeptides and active variants and fragments thereof, and polynucleotide encoding the same, do not comprise or encode a CTP. Such polynucleotides can be expressed from the nuclear genome of plants, plant cells, plant parts, explants, seeds, and grain and the polypeptides acting from the cytoplasm still confer insensitivity of the cell, plant or plant cell to an HPPD inhibitor. In still other embodiments, the HPPD polynucleotides lacking the chloroplast transit peptide are introduced directly into the chloroplast via chloroplast transformation. Such methods of chloroplast transformation are discussed in detail elsewhere herein. Thus, chloroplasts having stably incorporated in their genome a polynucleotide encoding an HPPD polypeptide or an active variant or fragment thereof lacking a CTP as described herein are provided.

In other embodiments, only the HPPD polypeptides or active variants and fragments thereof are in the chloroplast of a plant or plant cell. In such instances, the HPPD polypeptide can comprise a chloroplast transit peptide and can be expressed from a polynucleotide incorporated into the nuclear genome. In such an instance, the HPPD polypeptide is transported into the chloroplast, the CTP is removed, and the mature form of the HPPD polypeptide is then found within the chloroplast.

In other embodiments, the polynucleotide encoding the HPPD polypeptide or active variant or fragment thereof is incorporated directly into the genome of the chloroplast. In such instances, the HPPD polypeptide need not comprise a CTP.

The sequences to be targeted to the chloroplast may be optimized for expression in the chloroplast to account for differences in codon usage between the plant nucleus and this organelle. In this manner, the polynucleotide of interest may be synthesized using chloroplast-preferred codons. See, for example, U.S. Pat. No. 5,380,831, herein incorporated by reference.

As used herein, a "plastid" refers to an organelle present in plant cells that stores and manufactures chemical compounds used by the cell, such as starch, fatty acids, terpenes, and that has been derived from a proplastid. Thus, plastids of plants typically have the same genetic content. Plastids include chloroplasts, which are responsible for photosynthesis, amyloplasts, chromoplasts, statoliths, leucoplasts, elaioplasts, and proteinoplasts.

The plastid genome is circular and varies in size among plant species from about 120 to about 217 kilobase pairs (kb). The genome typically includes a large inverted repeat, which can contain up to about 76 kilobase pairs, but which is more typically in the range of about 20 to about 30 kilobase pairs. The inverted repeat present in the plastid genome of various organisms has been described (Palmer (1990) *Trends Genet* 6:115-120).

Methods are known in the art for introducing genes into the plastid genome. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606; and U.S. Pat. Nos. 5,451,513 and 5,545,818; each of which is herein incorporated by reference in its entirety.

One method involves the integration of a polynucleotide of interest into the plastid genome through homologous recombination. Such methods involve the introduction of a polynucleotide of interest flanked by regions of homology with regions of the plastid genome into a plant cell. Delivery of the polynucleotide of interest into the plant cell can be via any method of transformation known in the art, including those described elsewhere herein. These include, but are not limited to, particle gun delivery (Svab, Z. et al. (1990) *Proc Natl Acad Sci USA* 87:8526-8530; Svab and Maliga (1993) *Proc Natl Acad Sci USA* 90:913-917; and Staub and Maliga (1993) *EMBO J* 12:601-606; and U.S. Pat. Nos. 5,451,513 and 5,545,818; each of which is herein incorporated by reference in its entirety). In some species, protoplasts can also be used for chloroplast transformation (O'Neill et al. (1993) *Plant J* 3:729-38; and Spoerlein et al. (1991) *Theor Appl Gen* 82:717-722; each of which is herein incorporated by reference in its entirety). Once the polynucleotide of interest flanked by the homologous regions enters the cell, the polynucleotide of interest will be integrated within the plastid genome.

The homologous regions flanking the polynucleotide of interest, and in some embodiments, its operably linked promoter, and in particular embodiments, the selectable marker gene as well may vary in length. In some embodiments, the region of homology with the plastid genome is about 50, 75, 100, 200, 300, 400, 500, 600, 700, 800, 900, 1000 base pairs or greater in length. In most instances, the frequency of recombination and thus the frequency of obtaining plants having transformed plastids decreases with the decreasing size of the homologous regions. In those embodiments wherein the regions of homology are present in the inverted repeat regions of the plastid genome, two copies of the polynucleotide of interest are expected per transformed plastid.

In some embodiments, the polynucleotide of interest can be co-delivered with a selectable marker gene that is active in the plastid. The selectable marker gene and the polynucleotide of interest can be present on a single DNA construct or on separate constructs. A number of markers have been developed for use with plant cells, such as resistance to chloramphenicol, the aminoglycoside G418, hygromycin, or the like. Genes conferring resistance to kanamycin (NPTII or AphA6) have been used as a selectable marker for plastid transformation (Carrer et al. (1993) *Mol Gen Genetics* 241:49-56; and Huang et al. (2002) *Mol Gen Genomics* 268:19-27; each of which is herein incorporated by reference in its entirety). Other genes which encode a product involved in chloroplast metabolism may also be used as selectable markers.

Another example of a selectable marker gene for plastid transformation is a selectable marker gene that confers resistance to a substance which inhibits protein synthesis by the plastids, such that cells which have acquired the phenotype are selected for by contacting the cells with a substance which inhibits protein synthesis by the plastids. The plastid DNA encoding the nonlethal selectable phenotype may comprise 16S ribosomal DNA mutated to confer resistance to the effects of streptomycin, or to spectinomycin, or to both antibiotics simultaneously. Expression of heterologous genes that modify non-lethal antibiotics such as streptomycin or spectinomycin by phosphorylation, adenylation or acetylation also are suitable for the selection of plastid transformation events. Another non-limiting example of a gene that confers resistance to streptomycin and spectinomycin is the bacterial aadA gene that codes for streptomycin/spectinomycin adenyltransferase (Svab et al. (1993) *Proc Natl Acad Sci USA* 90:913-917). The aadA gene product allows for continued growth and greening of cells in the presence of streptomycin or spectinomycin whose chloroplasts comprise the selectable marker gene product. Cells which do not contain the selectable marker gene product are bleached. Selection for the aadA gene marker is thus based on identification of plant cells which are not bleached by the presence of streptomycin or spectinomycin, in the plant growth medium.

Other examples of selectable marker genes are those that confer resistance to an herbicide, including a photosystem II herbicide, such as a triazine herbicide, specifically the triazine herbicide atrazine. This phenotype not only provides nonlethal selection, but also provides herbicide resistance. Genes that provide resistance to plant herbicides such as glyphosate, bromoxynil, or imidazolinone may find use as a selectable marker gene. Such genes have been reported (Stalker et al. (1985) *J Biol Chem* 260:4724-4728 (glyphosate resistant EPSP); Stalker et al. (1985) *J Biol Chem* 263:6310-6314 (bromoxynil resistant nitrilase gene); and Sathasivan et al. (1990) *Nucl Acids Res* 18:2188 (AHAS imidazolinone resistance gene); each of which is herein incorporated by reference in its entirety).

The selectable marker gene and/or the polynucleotide of interest can be placed under the regulatory control of a chloroplast 5' promoter and 3' transcription termination regions, such as the tobacco 16S rRNA promoter rrn region and rps16 3' termination region. Numerous additional promoter regions may also be used to drive expression of the selectable marker gene and/or the polynucleotide of interest, including various plastid promoters and bacterial promoters which have been shown to function in plant plastids. Further, if nuclear expression of the selectable marker gene and/or the polynucleotide of interest is not desired, plastid introns can be incorporated into the selectable marker gene and/or the polynucleotide of interest. Certain classes of plastid introns cannot be correctly spliced out in the nucleus, thereby preventing expression of the selectable marker gene and/or the polynucleotide of interest within the nucleus. The polynucleotide of interest and/or the heterologous polynucleotide encoding the cell proliferation factor may be optimized for expression in the chloroplast to account for differences in codon usage between the plant nucleus and this organelle. In this manner, the polynucleotide may be synthesized using chloroplast-preferred codons. See, for example, U.S. Pat. No. 5,380,831, herein incorporated by reference.

An additional method of plastid transformation occurs through the transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91: 7301-7305, which is herein incorporated by reference in its entirety. In these methods, the heterologous polynucleotide encoding the cell proliferation factor is introduced into the cell and expressed prior to, during, or immediately after the expression of the plastid-directed RNA polymerase.

In order to select those cells having transformed plastids, following introduction of the chloroplast transformation vectors, the treated tissue is placed on tissue culture medium containing the appropriate selection agent. After a suitable period of incubation on selection medium, transformed cells can be identified and grown to a stage that allows regeneration of the whole plants. The regeneration processes are basically identical to those used for standard nuclear transformation events. Special care must be taken to ensure that selection and regeneration conditions promote the elimination of most wild-type chloroplast genomes. The status of the proportion of wild-type to transformed chloroplast genomes can be monitored by standard molecular techniques including Southern and PCR analysis.

For tobacco and a number of other species, leaves are a preferred target for plastid transformation. Chloroplast transformation has been described for tobacco (Svab, Zora; Hajdukiewicz et al. (1990) *Proceedings of the National Academy of Sciences of the United States of America* 87(21): 8526-30), *Arabidopsis* (Sikdar, S. R.; Serino, G.; Chaudhuri, S.; Maliga, P (1998) *Plant Cell Reports* 18(1-2):20-24), tomato (Ruf et al. (2001) *Nature Biotechnology:*19(9):870-875), potato (Sidorov et al. (1999) *Plant Journal* 19(2): 209-216). For soybean, embryogenic suspension cultures can be targeted for transformation (Dufourmantel et al. (2004) *Plant Molecular Biology:*55(4), 479-489; US20070039075 A1).

II. Methods of Use

A. Methods for Increasing Concentration of at Least One HPPD Sequence or an Active Variant or Fragment Therefore in a Plant or Plant Part A method for increasing the concentration of an HPPD polypeptide disclosed herein or an active variant or fragment thereof in plants, plant cells, plant parts, explants, seeds, grain or a chloroplast is provided. HPPD activity and insensitivity to HPPD inhibitors are discussed in detail elsewhere herein. In further embodiments, the concentration/level of the HPPD polypeptide is increased in a plant or plant part by at least 10%, 20%, 30%, 40%, 50%, 60%, 70%, 80%, 90%, 100%, 200%, 500%, 1000%, 5000%, or 10,000% relative to an appropriate control plant, plant part, or cell which did not have the HPPD sequence. In still other embodiments, the level of the HPPD polypeptide in the plant or plant part is increased by 10, 20, 30, 40, 50, 60, 70, 80, 90, 100 fold or more compared to the level of the native HPPD sequence. Such an increase in the level of the HPPD polypeptide can be achieved in a variety of ways including, for example, by the expression of multiple copies of one or more HPPD polypeptide and/or by employing a promoter to drive higher levels of expression of the sequence.

In specific embodiments, the polypeptide or the HPPD polynucleotide or active variant or fragment thereof is introduced into plants, plant cells, plant parts, explants, seeds, and grain. Subsequently, a plant cell having the introduced sequence of the disclosure is selected using methods known to those of skill in the art such as, but not limited to, Southern blot analysis, DNA sequencing, PCR analysis, or phenotypic analysis. A plant cell altered or modified by the foregoing embodiments is grown under plant forming conditions for a time sufficient to modulate the concentration and/or activity of polypeptides of the present disclosure in the plant. Plant forming conditions are well known in the art and discussed briefly elsewhere herein.

In one embodiment, a method of producing an HPPD herbicide tolerant plant cell is provided and comprises transforming a plant cell with a polynucleotide encoding an HPPD polypeptide or active variant or fragment thereof. In specific embodiments, the method further comprises selecting a plant cell which is resistant or tolerant to an HPPD herbicide by growing the plant cells in a sufficient concentration of an HPPD herbicide, such that the herbicide bleaches the plant cells which do not comprise the HPPD polypeptide of interest.

It is recognized that the incubation of the cells with the HPPD herbicide can occur before or after transformation with the HPPD polynucleotide of interest. For example, in one embodiment, a method comprises culturing a plant cell in the presence of a sufficient concentration of an HPPD herbicide such that said plant cell displays bleaching and then transforming into the bleached plant cells a polynucleotide encoding an HPPD polypeptide as disclosed herein. The plant cells are then grown, wherein the transformed plants cells no longer display bleaching. See, for example, U.S. Pat. No. 6,791,014, herein incorporated by reference it its entirety.

It is also recognized that the level and/or activity of the native HPPD sequence in a plant may be altered by employing a polynucleotide that is not capable of directing, in a transformed plant, the expression of a protein or an RNA. For example, the HPPD polynucleotide or active variant or fragment thereof disclosed herein may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

It is therefore recognized that methods of the present disclosure do not depend on the incorporation of the entire polynucleotide into the genome, only that the plant or cell thereof is altered as a result of the introduction of the polynucleotide into a cell. In one embodiment of the disclosure, the genome may be altered following the introduction of the polynucleotide into a cell. Alterations to the genome of the present disclosure include, but are not limited to, additions, deletions, and substitutions of nucleotides into the genome. While the methods of the present disclosure do not depend on additions, deletions, and substitutions of any particular number of nucleotides, it is recognized that such additions, deletions, or substitutions comprises at least one nucleotide.

B. Method of Producing Crops and Controlling Weeds

Methods for controlling weeds in an area of cultivation, preventing the development or the appearance of herbicide resistant weeds in an area of cultivation, producing a crop, and increasing crop safety are provided. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

Methods provided comprise planting the an area of cultivation with a transgenic seed derived there from a plant having an HPPD sequence or active variant or fragment thereof disclosed herein or, and in specific embodiments, applying to the crop, seed, weed or area of cultivation thereof an effective amount of a herbicide of interest. It is recognized that the herbicide can be applied before or after the crop is planted in the area of cultivation (e.g., seeds are planted). Herbicide applications can include an application of an HPPD inhibitor including, but not limited to, triketones (such as, mesotrione, sulcotrione, topremezone, and tembotrione) including agriculturally suitable salts (e.g., sodium salts) thereof; isoxazoles (such as, pyrasulfotole and isoxaflutole) including agriculturally suitable salts (e.g., sodium salts) thereof; pyrazoles (such as, benzofenap, pyrazoxyfen, and pyrazolynate) including agriculturally suitable salts (e.g., sodium salts) thereof; and benzobicyclon, including agriculturally suitable salts (e.g., sodium salts) thereof. See, WO2005/053407. In specific embodiments, a combination of two or more HPPD inhibitors is applied. Generally, the effective amount of herbicide applied to the field is sufficient to selectively control the weeds without significantly affecting the crop.

"Weed" as used herein refers to a plant which is not desirable in a particular area. Conversely, a "crop plant" as used herein refers to a plant which is desired in a particular area, such as, for example, a maize or soy plant. Thus, in some embodiments, a weed is a non-crop plant or a non-crop species, while in some embodiments, a weed is a crop species which is sought to be eliminated from a particular area, such as, for example, an inferior and/or non-transgenic soy plant in a field planted with a plant having the HPPD sequence disclosed herein or an active variant or fragment thereof.

Further provided is a method for producing a crop by growing a crop plant that is tolerant to an HPPD herbicide as a result of being transformed with an HPPD polynucleotide or active variant or fragment thereof disclosed herein, under conditions such that the crop plant produces a crop, and harvesting the crop. Preferably, an HPPD inhibitor is applied to the plant, or in the vicinity of the plant, at a concentration effective to control weeds without preventing the transgenic crop plant from growing and producing the crop. The application of the HPPD inhibitor can be before planting, or at any time after planting up to and including the time of harvest. The HPPD inhibitor can be applied once or multiple times. The timing of the HPPD inhibitor application, amount applied, mode of application, and other parameters will vary based upon the specific nature of the crop plant and the growing environment, and can be readily determined by one of skill in the art. The disclosure further provides the crop produced by this method.

Further provided are methods for the propagation of a plant containing a HPPD polypeptide or active variant or fragment thereof. The plant can be, for example, a monocot or a dicot. In one aspect, propagation entails crossing a plant containing a HPPD polynucleotide transgene with a second plant, such that at least some progeny of the cross display HPPD inhibitor tolerance.

The methods of the disclosure further allow for the development of herbicide applications to be used with the plants having the HPPD sequence or active variants or fragments thereof. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, seed of the crop or area of cultivation.

Any herbicide or combination of herbicides can be applied to the plant having the HPPD sequence or active variant or fragment thereof disclosed herein or transgenic seed derived there from, crop part, or the area of cultivation containing the crop plant. By "treated with a combination of" or "applying a combination of" herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. The application of each herbicide and/or chemical may be simultaneous or the applications may be at different times (sequential), so long as the desired effect is achieved. Furthermore, the application can occur prior to the planting of the crop.

Classifications of herbicides (i.e., the grouping of herbicides into classes and subclasses) are well-known in the art and include classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 1.

Herbicides can be classified by their mode of action and/or site of action and can also be classified by the time at which they are applied (e.g., preemergent or postemergent), by the method of application (e.g., foliar application or soil application), or by how they are taken up by or affect the plant or by their structure. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 1 which shows an abbreviated version of HRAC Herbicide Classification).

Often, a herbicide-tolerance gene that confers tolerance to a particular herbicide or other chemical on a plant expressing it will also confer tolerance to other herbicides or chemicals in the same class or subclass, for example, a class or subclass set forth in Table 1. Thus, in some embodiments, a transgenic plant is tolerant to more than one herbicide or chemical in the same class or subclass, such as, for example, an HPPD inhibitor, glyphosate, an ALS chemistry, an inhibitor of PPO, a sulfonylurea, and/or a synthetic auxin.

Typically, the plants of the present disclosure can tolerate treatment with different types of herbicides (i.e., herbicides having different modes of action and/or different sites of action) thereby permitting improved weed management strategies that are recommended in order to reduce the incidence and prevalence of herbicide-tolerant weeds.

TABLE 1

I. ALS Inhibitors (WSSA Group 2)
    A. Sulfonylureas
        1. Azimsulfuron
        2. Chlorimuron-ethyl
        3. Metsulfuron-methyl TABLE 1-continued 4. Nicosulfuron
   5. Rimsulfuron
   6. Sulfometuron-methyl
   7. Thifensulfuron-methyl
   8. Tribenuron-methyl
   9. Amidosulfuron
  10. Bensulfuron-methyl
  11. Chlorsulfuron
  12. Cinosulfuron
  13. Cyclosulfamuron
  14. Ethametsulfuron-methyl
  15. Ethoxysulfuron
  16. Flazasulfuron
  17. Flupyrsulfuron-methyl
  18. Foramsulfuron
  19. Imazosulfuron
  20. Iodosulfuron-methyl
  21. Mesosulfuron-methyl
  22. Oxasulfuron
  23. Primisulfuron-methyl
  24. Prosulfuron
  25. Pyrazosulfuron-ethyl
  26. Sulfosulfuron
  27. Triasulfuron
  28. Trifloxysulfuron
  29. Triflusulfuron-methyl
  30. Tritosulfuron
  31. Halosulfuron-methyl
  32. Flucetosulfuron
 B. Sulfonylaminocarbonyltriazolinones
   1. Flucarbazone
   2. Procarbazone
 C. Triazolopyrimidines
   1. Cloransulam-methyl
   2. Flumetsulam
   3. Diclosulam
   4. Florasulam
   5. Metosulam
   6. Penoxsulam
   7. Pyroxsulam
 D. Pyrimidinyloxy(thio)benzoates
   1. Bispyribac
   2. Pyriftalid
   3. Pyribenzoxim
   4. Pyrithiobac
   5. Pyriminobac-methyl
 E. Imidazolinones
   1. Imazapyr
   2. Imazethapyr
   3. Imazaquin
   4. Imazapic
   5. Imazamethabenz-methyl
   6. Imazamox
II. Other Herbicides--Active Ingredients/
Additional Modes of Action
 A. Inhibitors of Acetyl CoA carboxylase
    (ACCase) (WSSA Group 1)
   1. Aryloxyphenoxypropionates ('FOPs')
      a. Quizalofop-P-ethyl
      b. Diclofop-methyl
      c. Clodinafop-propargyl
      d. Fenoxaprop-P-ethyl
      e. Fluazifop-P-butyl
      f. Propaquizafop
      g. Haloxyfop-P-methyl
      h. Cyhalofop-butyl
      i. Quizalofop-P-ethyl
   2. Cyclohexanediones ('DIMs')
      a. Alloxydim
      b. Butroxydim
      c. Clethodim
      d. Cycloxydim
      e. Sethoxydim
      f. Tepraloxydim
      g. Tralkoxydim
 B. Inhibitors of Photosystem II-HRAC
    Group C1/WSSA Group 5
   1. Triazines
      a. Ametryne
      b. Atrazine
      c. Cyanazine
      d. Desmetryne
      e. Dimethametryne
      f. Prometon
      g. Prometryne
      h. Propazine
      i. Simazine
      j. Simetryne
      k. Terbumeton
      l. Terbuthylazine
      m. Terbutryne
      n. Trietazine
   2. Triazinones
      a. Hexazinone
      b. Metribuzin
      c. Metamitron
   3. Triazolinone
      a. Amicarbazone
   4. Uracils
      a. Bromacil
      b. Lenacil
      c. Terbacil
   5. Pyridazinones
      a. Pyrazon
   6. Phenyl carbamates
      a. Desmedipham
      b. Phenmedipham
 C. Inhibitors of Photosystem II--HRAC
    Group C2/WSSA Group 7
   1. Ureas
      a. Fluometuron
      b. Linuron
      c. Chlorobromuron
      d. Chlorotoluron
      e. Chloroxuron
      f. Dimefuron
      g. Diuron
      h. Ethidimuron
      i. Fenuron
      j. Isoproturon
      k. Isouron
      l. Methabenzthiazuron
      m. Metobromuron
      n. Metoxuron
      o. Monolinuron
      p. Neburon
      q. Siduron
      r. Tebuthiuron
   2. Amides
      a. Propanil
      b. Pentanochlor
 D. Inhibitors of Photosystem II--HRAC
    Group C3/WSSA Group 6
   1. Nitriles
      a. Bromofenoxim
      b. Bromoxynil
      c. Ioxynil
   2. Benzothiadiazinone (Bentazon)
      a. Bentazon
   3. Phenylpyridazines
      a. Pyridate
      b. Pyridafol
 E. Photosystem-I-electron diversion
    (Bipyridyliums) (WSSA Group 22)
   1. Diquat
   2. Paraquat
 F. Inhibitors of PPO (protoporphyrinogen
    oxidase) (WSSA Group 14)
   1. Diphenylethers
      a. Acifluorfen-Na
      b. Bifenox
      c. Chlomethoxyfen
      d. Fluoroglycofen-ethyl
      e. Fomesafen
      f. Halosafen
      g. Lactofen
      h. Oxyfluorfen
   2. Phenylpyrazoles
      a. Fluazolate
      b. Pyraflufen-ethyl TABLE 1-continued 3. N-phenylphthalimides
   a. Cinidon-ethyl
   b. Flumioxazin
   c. Flumiclorac-pentyl
4. Thiadiazoles
   a. Fluthiacet-methyl
   b. Thidiazimin
5. Oxadiazoles
   a. Oxadiazon
   b. Oxadiargyl
6. Triazolinones
   a. Carfentrazone-ethyl
   b. Sulfentrazone
7. Oxazolidinediones
   a. Pentoxazone
8. Pyrimidindiones
   a. Benzfendizone
   b. Butafenicil
9. Others
   a. Pyrazogyl
   b. Profluazol
G. Bleaching: Inhibition of carotenoid biosynthesis at the phytoene desaturase step (PDS) (WSSA Group 12)
   1. Pyridazinones
      a. Norflurazon
   2. Pyridinecarboxamides
      a. Diflufenican
      b. Picolinafen
   3. Others
      a. Beflubutamid
      b. Fluridone
      c. Flurochloridone
      d. Flurtamone
H. Bleaching: Inhibition of 4-hydroxyphenyl-pyruvate-dioxygenase (4-HPPD) (WSSA Group 28)
   1. Triketones
      a. Mesotrione
      b. Sulcotrione
      c. topramezone
      d. tembotrione
   2. Isoxazoles
      a. Pyrasulfotole
      b. Isoxaflutole
   3. Pyrazoles
      a. Benzofenap
      b. Pyrazoxyfen
      c. Pyrazolynate
   4. Others
      a. Benzobicyclon
I. Bleaching: Inhibition of carotenoid biosynthesis (unknown target) (WSSA Group 11 and 13)
   1. Triazoles (WSSA Group 11)
      a. Amitrole
   2. Isoxazolidinones (WSSA Group 13)
      a. Clomazone
   3. Ureas
      a. Fluometuron
   3. Diphenylether
      a. Aclonifen
J. Inhibition of EPSP Synthase
   1. Glycines (WSSA Group 9)
      a. Glyphosate
      b. Sulfosate
K. Inhibition of glutamine synthetase
   1. Phosphinic Acids
      a. Glufosinate-ammonium
      b. Bialaphos
L. Inhibition of DHP (dihydropteroate) synthase (WSSA Group 18)
   1 Carbamates
      a. Asulam
M. Microtubule Assembly Inhibition (WSSA Group 3)
   1. Dinitroanilines
      a. Benfluralin
      b. Butralin
      c. Dinitramine
      d. Ethalfluralin
      e. Oryzalin
      f. Pendimethalin
      g. Trifluralin
   2. Phosphoroamidates
      a. Amiprophos-methyl
      b. Butamiphos
   3. Pyridines
      a. Dithiopyr
      b. Thiazopyr
   4. Benzamides
      a. Pronamide
      b. Tebutam
   5. Benzenedicarboxylic acids
      a. Chlorthal-dimethyl
N. Inhibition of mitosis/microtubule organization WSSA Group 23)
   1. Carbamates
      a. Chlorpropham
      b. Propham
      c. Carbetamide
O. Inhibition of cell division (Inhibition of very long chain fatty acids as proposed mechanism; WSSA Group 15)
   1. Chloroacetamides
      a. Acetochlor
      b. Alachlor
      c. Butachlor
      d. Dimethachlor
      e. Dimethanamid
      f. Metazachlor
      g. Metolachlor
      h. Pethoxamid
      i. Pretilachlor
      j. Propachlor
      k. Propisochlor
      l. Thenylchlor
   2. Acetamides
      a. Diphenamid
      b. Napropamide
      c. Naproanilide
   3. Oxyacetamides
      a. Flufenacet
      b. Mefenacet
   4. Tetrazolinones
      a. Fentrazamide
   5. Others
      a. Anilofos
      b. Cafenstrole
      c. Indanofan
      d. Piperophos
P. Inhibition of cell wall (cellulose) synthesis
   1. Nitriles (WSSA Group 20)
      a. Dichlobenil
      b. Chlorthiamid
   2. Benzamides (isoxaben (WSSA Group 21))
      a. Isoxaben
   3. Triazolocarboxamides (flupoxam)
      a. Flupoxam
Q. Uncoupling (membrane disruption): (WSSA Group 24)
   1. Dinitrophenols
      a. DNOC
      b. Dinoseb
      c. Dinoterb
R. Inhibition of Lipid Synthesis by other than ACC inhibition
   1. Thiocarbamates (WSSA Group 8)
      a. Butylate
      b. Cycloate
      c. Dimepiperate
      d. EPTC
      e. Esprocarb
      f. Molinate
      g. Orbencarb
      h. Pebulate
      i. Prosulfocarb
      j. Benthiocarb

TABLE 1-continued k. Tiocarbazil
l. Triallate
m. Vernolate
2. Phosphorodithioates
    a. Bensulide
3. Benzofurans
    a. Benfuresate
    b. Ethofumesate
4. Halogenated alkanoic acids (WSSA Group 26)
    a. TCA
    b. Dalapon
    c. Flupropanate
S. Synthetic auxins (IAA-like) (WSSA Group 4)
    1. Phenoxycarboxylic acids
        a. Clomeprop
        b. 2,4-D
        c. Mecoprop
    2. Benzoic acids
        a. Dicamba
        b. Chloramben
        c. TBA
    3. Pyridine carboxylic acids
        a. Clopyralid
        b. Fluroxypyr
        c. Picloram
        d. Tricyclopyr
    4. Quinoline carboxylic acids
        a. Quinclorac
        b. Quinmerac
    5. Others (benazolin-ethyl)
        a. Benazolin-ethyl
T. Inhibition of Auxin Transport
    1. Phthalamates; semicarbazones (WSSA Group 19)
        a. Naptalam
        b. Diflufenzopyr-Na
U. Other Mechanism of Action
    1. Arylaminopropionic acids
        a. Flamprop-M-methyl/-isopropyl
    2. Pyrazolium
        a. Difenzoquat
    3. Organoarsenicals
        a. DSMA
        b. MSMA
    4. Others
        a. Bromobutide
        b. Cinmethylin
        c. Cumyluron
        d. Dazomet
        e. Daimuron-methyl
        f. Dimuron
        g. Etobenzanid
        h. Fosamine
        i. Metam
        j. Oxaziclomefone
        k. Oleic acid
        l. Pelargonic acid
        m. Pyributicarb In still further methods, an HPPD inhibitor can be applied alone or in combination with another herbicide of interest and can be applied to the plants having the HPPD sequence as disclosed herein or their area of cultivation.

Additional herbicide treatment that can be applied over the plant or seeds having the HPPD polypeptides or active variants and fragments thereof include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)oxy]phenyl](3-fluorobenzoyl)-amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate) (See, WO2007/024782, herein incorporated by reference), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, pyrasulfotole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate.

Additional herbicides include those that are applied over plants having homogentisate solanesyltransferase (HST) polypeptide such as those described in International Publication No. WO 2010/029311(A2), herein incorporated by reference it its entirety.

Other suitable herbicides and agricultural chemicals are known in the art, such as, for example, those described in International Publication No. WO 2005/041654. Other herbicides also include bioherbicides such as those produced by *Streptomyces hygroscopicus, Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Combinations of various herbicides can result in a greater-than-additive (i.e., synergistic) effect on weeds and/or a less-than-additive effect (i.e. safening) on crops or other desirable plants. In certain instances, combinations of HPPD herbicides with other herbicides having a similar spectrum of control but a different mode of action will be particularly advantageous for preventing the development of resistant weeds.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area.

Ranges of the effective amounts of herbicides can be found, for example, in various publications from University Extension services. See, for example, Bernards et al. (2006) *Guide for Weed Management in Nebraska* (www.ianrpubs.url.edu/sendlt/ec130); Regher et al. (2005) *Chemical Weed Control for Fields Crops, Pastures, Rangeland, and Non-cropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

Many plant species can be controlled (i.e., killed or damaged) by the herbicides described herein. Accordingly, the methods of the disclosure are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp *Sesbania* (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass, and a non-selective herbicide resistant ryegrass.

In some embodiments, a plant having the HPPD sequence disclosed herein or active variants and fragments thereof is not significantly damaged by treatment with an HPPD inhibitor applied to that plant, whereas an appropriate control plant is significantly damaged by the same treatment.

Generally, an HPPD inhibitor is applied to a particular field (and any plants growing in it) no more than 1, 2, 3, 4, 5, 6, 7, or 8 times a year, or no more than 1, 2, 3, 4, or 5 times per growing season.

Thus, methods of the disclosure encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein). In other embodiments, the seeds can be coated with at least one fungicide and/or at least one insecticide and/or at least one herbicide or any combination thereof.

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the disclosure and/or on areas in which transgenic plants of the disclosure are to be planted. "Preplant incorporation" involves the incorporation of compounds into the soil prior to planting.

Thus, improved methods of growing a crop and/or controlling weeds such as, for example, "pre-planting burn down," are provided wherein an area is treated with herbicides prior to planting the crop of interest in order to better control weeds. The disclosure also provides methods of growing a crop and/or controlling weeds which are "no-till" or "low-till" (also referred to as "reduced tillage"). In such methods, the soil is not cultivated or is cultivated less frequently during the growing cycle in comparison to traditional methods; these methods can save costs that would otherwise be incurred due to additional cultivation, including labor and fuel costs.

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the disclosure can involve the use of herbicides in combination with herbicide safeners such as benoxacor, BCS (1-bromo-4-[(chloromethyl) sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this disclosure, or applied as seed treatments. Therefore an aspect of the present disclosure relates to the use of a mixture comprising an HPPD inhibitor, at least one other herbicide, and an antidotally effective amount of a herbicide safener.

Seed treatment is useful for selective weed control, because it physically restricts antidoting to the crop plants. Therefore in one embodiment, a method for selectively controlling the growth of weeds in a field comprising treating the seed from which the crop is grown with an antidotally effective amount of safener and treating the field with an effective amount of herbicide to control weeds.

An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

In addition, methods of the disclosure can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multicomponent mixture giving an even broader spectrum of agricultural protection. Examples of such agricultural protectants which can be used in methods of the disclosure include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyraflu-prole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/ nicobifen, bromuconazole, bupirimate, buthiobate, carboxin, carpropamid, captafol, captan, carbendazim, chloroneb, chlorothanlonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

The methods of controlling weeds can further include the application of a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultapsodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC375839), myclobutanil, neo-asozin (ferric methane-arsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai, Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV. Methods of the disclosure may also comprise the use of plants genetically transformed to express proteins (such as *Bacillus thuringiensis* delta-endotoxins) toxic to invertebrate pests. In such embodiments, the effect of exogenously applied invertebrate pest control compounds may be synergistic with the expressed toxin proteins. General references for these agricultural protectants include *The Pesticide Manual*, 13*th Edition*, C. D. S. Tomlin, Ed., British Crop Protection Council, Farnham, Surrey, U.K., 2003 and *The BioPesticide Manual*, 2$^{nd}$ *Edition*, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present disclosure can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this disclosure can also provide a broader spectrum of plant protection and be advantageous for resistance management.

Thus, methods of controlling weeds can employ a herbicide or herbicide combination and may further comprise the use of insecticides and/or fungicides, and/or other agricultural chemicals such as fertilizers. The use of such combined treatments of the disclosure can broaden the spectrum of activity against additional weed species and suppress the proliferation of any resistant biotypes.

Methods can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

C. Method of Detections

Methods for detecting an HPPD polypeptide or an active variant or fragment thereof are provided. Such methods comprise analyzing plant tissues to detect such polypeptides or the polynucleotides encoding the same. The detection methods can directly assay for the presence of the HPPD polypeptide or polynucleotide or the detection methods can indirectly assay for the sequences by assaying the phenotype of the cell plant, plant cell or plant explant expressing the sequence.

In one embodiment, the HPPD polypeptide is detected in the plant tissue using an immunoassay comprising an antibody or antibodies that specifically recognizes an HPPD polypeptide or active variant or fragment thereof. In specific embodiments, the antibody or antibodies which are used are raised to an HPPD polypeptide or active variant or fragment thereof as disclosed herein.

By "specifically or selectively binds" is intended that the binding agent has a binding affinity for a given HPPD polypeptide or fragment or variant disclosed herein, which is greater than 10%, 9%, 8%, 7%, 6%, 5%, 4%, 3%, 2% or 1% of the binding affinity for a known HPPD sequence. One of skill will be aware of the proper controls that are needed to carry out such a determination By "antibodies that specifically bind" is intended that the antibodies will not substantially cross react with another polypeptide. By "not substantially cross react" is intended that the antibody or fragment thereof has a binding affinity for the other polypeptide which is less than 10%, less than 5%, or less than 1%, of the binding affinity for the HPPD polypeptide or active fragment or variant thereof.

In an aspect, the HPPD polypeptide can be detected in plant tissue extracts by subjecting the extract to trypsin digestion, followed by LC-MS. For example, tryptic fragments can be partially separated from each other by reverse-phase liquid chromatography and the column effluent directed into a mass spectrometer. A specific peptide unique to the transgenically expressed HPPD is detected by adjusting the instrument setting so as to record and quantify the peptide according to the exact mass of the signature peptide. Such an exemplary method is described in Example 1 herein.

In still other embodiments, the HPPD polypeptide or active variant or fragment thereof can be inferred in a plant tissue by detecting the presence of a polynucleotide encoding any of the various HPPD polypeptides or active variants and fragments thereof. In one embodiment, the detection method comprises assaying plant tissue using PCR amplification.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the disclosure refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence and specifically detect and/or identify a polynucleotide encoding an HPPD polypeptide or active variant or fragment thereof as describe elsewhere herein. It is recognized that the hybridization conditions or reaction conditions can be determined by the operator to achieve this result. This length may be of any length that is of sufficient length to be useful in a detection method of choice. Such probes and primers can hybridize specifically to a target sequence under high stringency hybridization conditions. Probes and primers according to embodiments of the present disclosure may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide.

Methods for preparing and using probes and primers are described, for example, in *Molecular Cloning: A Laboratory Manual*, 2.sup.nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 10 (Invitrogen); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

D. Method of Identifying HPPD Variants.

Various methods can be employed to identify further HPPD variants. The polynucleotides of the disclosure are optionally used as substrates for a variety of diversity generating procedures, e.g., mutation, recombination and recursive recombination reactions, in addition to their use in standard cloning methods as set forth in, e.g., Ausubel, Berger and Sambrook, i.e., to produce additional HPPD polynucleotides and polypeptides with desired properties. A variety of diversity generating protocols can be used. The procedures can be used separately, and/or in combination to produce one or more variants of a polynucleotide or set of polynucleotides, as well variants of encoded proteins. Individually and collectively, these procedures provide robust, widely applicable ways of generating diversified polynucleotides and sets of polynucleotides (including, e.g., polynucleotide libraries) useful, e.g., for the engineering or rapid evolution of polynucleotides, proteins, pathways, cells and/or organisms with new and/or improved characteristics. The process of altering the sequence can result in, for example, single nucleotide substitutions, multiple nucleotide substitutions, and insertion or deletion of regions of the nucleic acid sequence.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more polynucleotides, which can be selected or screened for polynucleotides that encode proteins with or which confer desirable properties. Following diversification by one or more of the methods herein, or otherwise available to one of skill, any polynucleotides that are produced can be selected for a desired activity or property, e.g. altered Km, use of alternative cofactors, increased kcat, etc. This can include identifying any activity that can be detected, for example, in an automated or automatable format, by any of the assays in the art. For example, modified HPPD polypeptides can be detected by assaying for an increased insensitivity to HPPD inhibitor. Assays to measure such activity are described elsewhere herein. A variety of related (or even unrelated) properties can be evaluated, in serial or in parallel, at the discretion of the practitioner.

Descriptions of a variety of diversity generating procedures, including family shuffling and methods for generating modified nucleic acid sequences encoding multiple enzymatic domains, are found in the following publications and the references cited therein: Soong N. et al. (2000) *Nat Genet* 25(4):436-39; Stemmer et al. (1999) *Tumor Targeting* 4:1-4; Ness et al. (1999) *Nature Biotechnology* 17:893-896; Chang et al. (1999) Nature *Biotechnology* 17:793-797; Minshull and Stemmer (1999) *Current Opinion in Chemical Biology* 3:284-290; Christians et al. (1999) *Nature Biotechnology* 17:259-264; Crameri et al. (1998) *Nature* 391:288-291; Crameri et al. (1997) *Nature Biotechnology* 15:436-438; Zhang et al. (1997) *Proc. Natl. Acad. Sci. USA* 94:4504-4509; Patten et al. (1997) *Current Opinion in Biotechnology* 8:724-733; Crameri et al. (1996) *Nature Medicine* 2:100-103; Crameri et al. (1996) *Nature Biotechnology* 14:315-319; Gates et al. (1996) *Journal of Molecular Biology* 255:373-386; Stemmer (1996) "Sexual PCR and Assembly PCR" In: The Encyclopedia of Molecular Biology. VCH Publishers, New York. pp. 447-457; Crameri and Stemmer (1995) *BioTechniques* 18:194-195; Stemmer et al. (1995) *Gene:* 164:49-53; Stemmer (1995) *Science* 270: 1510; Stemmer (1995) *Bio/Technology* 13:549-553; Stemmer (1994) *Nature* 370:389-391; and Stemmer (1994) *Proc. Natl. Acad. Sci. USA* 91:10747-10751. See also WO2008/073877 and US 20070204369, both of which are herein incorporated by reference in their entirety.

Mutational methods of generating diversity include, for example, site-directed mutagenesis (Ling et al. (1997) *Anal Biochem.* 254(2): 157-178; Dale et al. (1996) *Methods Mol. Biol.* 57:369-374; Smith (1985) *Ann. Rev. Genet.* 19:423-462; Botstein & Shortle (1985) *Science* 229:1193-1201; Carter (1986) *Biochem. J* 237:1-7; and Kunkel (1987) Nucleic Acids & Molecular Biology (Eckstein, F. and Lilley, D. M. J. eds., Springer Verlag, Berlin)); mutagenesis using uracil containing templates (Kunkel (1985) *Proc. Natl. Acad. Sci. USA* 82:488-492; Kunkel et al. (1987) *Methods in Enzymol.* 154, 367-382; and Bass et al. (1988) *Science* 242:240-245); oligonucleotide-directed mutagenesis (*Methods in Enzymol.* 100: 468-500 (1983); *Methods in Enzymol.* 154: 329-350 (1987); Zoller & Smith (1982) *Nucleic Acids Res.* 10:6487-6500; Zoller & Smith (1983) *Methods in Enzymol.* 100:468-500; and Zoller & Smith (1987) *Methods in Enzymol.* 154:329-350); phosphorothioate-modified DNA mutagenesis (Taylor et al. (1985) *Nucl. Acids Res.* 13: 8749-8764; Taylor et al. (1985) *Nucl. Acids Res.* 13: 8765-8787 (1985); Nakamaye & Eckstein (1986) *Nucl. Acids Res.* 14: 9679-9698; Sayers et al. (1988) *Nucl. Acids Res.* 16:791-802; and Sayers et al. (1988) *Nucl. Acids Res.* 16: 803-814); mutagenesis using gapped duplex DNA (Kramer et al. (1984) *Nucl. Acids Res.* 12: 9441-9456; Kramer & Fritz (1987) *Methods in Enzymol.* 154:350-367; Kramer et al. (1988) *Nucl. Acids Res.* 16: 7207; and Fritz et al. (1988) *Nucl. Acids Res.* 16: 6987-6999).

Additional suitable methods include, but are not limited to, point mismatch repair (Kramer et al. (1984) *Cell* 38:879-887), mutagenesis using repair-deficient host strains (Carter et al. (1985) *Nucl. Acids Res.* 13: 4431-4443; and Carter (1987) *Methods in Enzymol.* 154: 382-403), deletion mutagenesis (Eghtedarzadeh & Henikoff (1986) *Nucl. Acids Res.* 14: 5115), restriction-selection and restriction-purification (Wells et al. (1986) *Phil. Trans. R. Soc. Lond. A* 317: 415-423), mutagenesis by total gene synthesis (Nambiar et al. (1984) *Science* 223: 1299-1301; Sakamar and Khorana (1988) *Nucl. Acids Res.* 14: 6361-6372; Wells et al. (1985) *Gene* 34:315-323; and Grundström et al. (1985) *Nucl. Acids Res.* 13: 3305-3316), and double-strand break repair (Mandecki (1986); Arnold (1993) *Current Opinion in Biotechnology* 4:450-455 and *Proc. Natl. Acad. Sci. USA,* 83:7177-7181). Additional details on many of the above methods can be found in *Methods in Enzymology* Volume 154, which also describes useful controls for trouble-shooting problems with various mutagenesis methods.

Additional details regarding various diversity generating methods can be found in the following U.S. patents, PCT publications, and EPO publications: U.S. Pat. Nos. 5,605,793, 5,811,238, 5,830,721, 5,834,252, 5,837,458, WO 95/22625, WO 96/33207, WO 97/20078, WO 97/35966, WO 99/41402, WO 99/41383, WO 99/41369, WO 99/41368, EP 752008, EP 0932670, WO 99/23107, WO 99/21979, WO 98/31837, WO 98/27230, WO 98/13487, WO 00/00632, WO 00/09679, WO 98/42832, WO 99/29902, WO 98/41653, WO 98/41622, WO 98/42727, WO 00/18906, WO 00/04190, WO 00/42561, WO 00/42559, WO 00/42560, WO 01/23401, and, PCT/US01/06775. See, also WO20074303, herein incorporated by reference.

In brief, several different general classes of sequence modification methods, such as mutation, recombination, etc. are applicable to the present disclosure and set forth, e.g., in the references above. That is, alterations to the component nucleic acid sequences to produced modified gene fusion constructs can be performed by any number of the protocols described, either before cojoining of the sequences, or after the cojoining step. The following exemplify some of the different types of preferred formats for diversity generation in the context of the present disclosure, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants are described in several of the references above, e.g., in Stemmer (1994) *Proc. Natl. Acad. Sci. USA* 91:10747-10751.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above.

Whole genome recombination methods can also be used in which whole genomes of cells or other organisms are recombined, optionally including spiking of the genomic recombination mixtures with desired library components (e.g., genes corresponding to the pathways of the present disclosure). These methods have many applications, including those in which the identity of a target gene is not known. Details on such methods are found, e.g., in WO 98/31837 and in PCT/US99/15972. Thus, any of these processes and techniques for recombination, recursive recombination, and whole genome recombination, alone or in combination, can be used to generate the modified nucleic acid sequences and/or modified gene fusion constructs of the present disclosure.

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561, WO 01/23401, WO 00/42560, and, WO 00/42559.

In silico methods of recombination can be affected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in WO 00/42560 and WO 00/42559.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in PCT/US01/06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408 and the references above), and can be applied to the present disclosure. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) *Nature Biotech* 17:1205. This approach can be used to generate an initial a library of variants which can optionally serve as a substrate for one or more in vitro or in vivo recombination methods. See, also, Ostermeier et al. (1999) *Proc. Natl. Acad. Sci. USA*, 96: 3562-67; Ostermeier et al. (1999), *Biological and Medicinal Chemistry* 7: 2139-44.

Mutational methods which result in the alteration of individual nucleotides or groups of contiguous or non-contiguous nucleotides can be favorably employed to introduce nucleotide diversity into the nucleic acid sequences and/or gene fusion constructs of the present disclosure. Many mutagenesis methods are found in the above-cited references; additional details regarding mutagenesis methods can be found in following, which can also be applied to the present disclosure.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11-15 and Caldwell et al. (1992) *PCR Methods Applic.* 2:28-33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science* 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811-7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548-1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., U.S. Pat. Nos. 5,783,431 and 5,824,485) and their use to identify protein activities of interest has been proposed (In addition to the references noted above, see, U.S. Pat. No. 5,958,672. Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) *Gene* 215: 471) prior to diversifying according to any of the methods described herein.

Libraries can be biased towards nucleic acids which encode proteins with desirable enzyme activities. For example, after identifying a variant from a library which exhibits a specified activity, the variant can be mutagenized using any known method for introducing DNA alterations. A library comprising the mutagenized homologues is then screened for a desired activity, which can be the same as or different from the initially specified activity. An example of such a procedure is proposed in U.S. Pat. No. 5,939,250. Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived there from. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are found in WO 00/46344. These methods, including proposed non-stochastic polynucleotide reassembly and site-saturation mutagenesis methods be applied to the present disclosure as well. Random or semi-random mutagenesis using doped or degenerate oligonucleotides is also described in, e.g., Arkin and Youvan (1992) *Biotechnology* 10:297-300; Reidhaar-Olson et al. (1991) *Methods Enzymol.* 208:564-86; Lim and Sauer (1991) *J. Mol. Biol.* 219:359-76; Breyer and Sauer (1989) *J. Biol. Chem.* 264: 13355-60); and U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods. Any of the above described methods can be practiced recursively or in combination to alter nucleic acids, e.g., HPPD encoding polynucleotides.

The above references provide many mutational formats, including recombination, recursive recombination, recursive mutation and combinations or recombination with other forms of mutagenesis, as well as many modifications of these formats. Regardless of the diversity generation format that is used, the nucleic acids of the present disclosure can be recombined (with each other, or with related (or even unrelated) sequences) to produce a diverse set of recombinant nucleic acids for use in the gene fusion constructs and modified gene fusion constructs of the present disclosure, including, e.g., sets of homologous nucleic acids, as well as corresponding polypeptides.

Many of the above-described methodologies for generating modified polynucleotides generate a large number of diverse variants of a parental sequence or sequences. In some embodiments, the modification technique (e.g., some form of shuffling) is used to generate a library of variants that is then screened for a modified polynucleotide or pool of modified polynucleotides encoding some desired functional attribute, e.g., improved HPPD inhibitor insensitivity and/or maintained or improved HPPD activity.

One example of selection for a desired enzymatic activity entails growing host cells under conditions that inhibit the growth and/or survival of cells that do not sufficiently express an enzymatic activity of interest, e.g. the HPPD activity. Using such a selection process can eliminate from consideration all modified polynucleotides except those encoding a desired enzymatic activity. For example, in some embodiments of the disclosed host cells are maintained under conditions that inhibit cell growth or survival in the absence of sufficient levels of HPPD, e.g., a concentration of an HPPD inhibitor that is lethal or inhibits the growth of a wild-type plant of the same variety that lacks or does not express the HPPD polynucleotide or active variant or fragment thereof. Under these conditions, only a host cell harboring a modified nucleic acid that encodes enzymatic activity or activities able to catalyze production of sufficient levels of the product will survive and grow. Some embodiments of the disclosure employ multiples rounds of screening at increasing concentrations of an HPPD inhibitor.

For convenience and high throughput it will often be desirable to screen/select for desired modified nucleic acids in a microorganism, e.g., a bacteria such as *E. coli*. On the other hand, screening in plant cells or plants can in some cases be preferable where the ultimate aim is to generate a modified nucleic acid for expression in a plant system.

In some preferred embodiments of the disclosure throughput is increased by screening pools of host cells expressing different modified nucleic acids, either alone or as part of a gene fusion construct. Any pools showing significant activity can be deconvoluted to identify single variants expressing the desirable activity.

In high throughput assays, it is possible to screen up to several thousand different variants in a single day. For example, each well of a microtiter plate can be used to run a separate assay, or, if concentration or incubation time effects are to be observed, every 5-10 wells can test a single variant.

In addition to fluidic approaches, it is possible, as mentioned above, simply to grow cells on media plates that select for the desired enzymatic or metabolic function. This approach offers a simple and high-throughput screening method.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for application to the present disclosure. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols for the various high throughput devices. Thus, for example, Zymark Corp. provides technical bulletins describing screening systems for detecting the modulation of gene transcription, ligand binding, and the like. Microfluidic approaches to reagent manipulation have also been developed, e.g., by Caliper Technologies (Mountain View, Calif.). Non-limiting embodiments include:

1. A recombinant polypeptide having 4-hydroxyphenylpyruvate dioxygenase (HPPD) activity; wherein the polypeptide having 4-hydroxyphenylpyruvate dioxygenase activity comprises:

```
                                                    (SEQ ID NO: 80)
                    5                   10                  15
Met Gly Pro Thr Pro Thr Ala Thr Ala Ala Gly Ala Ala Val Ala 20                  25                  30
Ala Ala Ser Ala Ala Glu Gln Ala Ala Phe Arg Leu Val Gly His 35                  40                  45
Arg Asn Phe Val Arg Phe Asn Pro Arg Ser Asp Arg Phe Gln Thr 50                  55                  60
Leu Ala Phe His His Val Xaa Xaa Xaa Xaa Xaa Asp Xaa Ala Ser 65                  70                  75
Ala Ala Gly Arg Phe Ser Phe Ala Leu Gly Val Pro Leu Ala Ala 80                  85                  90
Arg Ser Asp Leu Ser Thr Gly Asn Ser Ala His Ala Ser Leu Leu 95                  100                 105
Leu Arg Ser Gly Ser Leu Ser Leu Leu Phe Thr Ala Pro Tyr Ala 110                 115                 120
His Gly Ala Asp Ala Ala Thr Ala Ala Leu Pro Ser Phe Ser Ala 125                 130                 135
Ala Ala Ala Arg Xaa Phe Ala Ala Asp His Gly Leu Ala Val Arg 140                 145                 150
Ala Val Ala Leu Arg Val Ala Asp Ala Glu Asp Xaa Xaa Xaa Ala 155                 160                 165
Ser Xaa Xaa Xaa Gly Ala Xaa Xaa Xaa Xaa Xaa Xaa Xaa Xaa Xaa 170                 175                 180
Xaa Xaa Gly Xaa Xaa Xaa Xaa Xaa Xaa Xaa Xaa Tyr Gly Asp Val 185                 190                 195
Xaa Xaa Arg Tyr Val Ser Xaa Xaa Xaa Xaa Xaa Xaa Xaa Xaa Xaa 200                 205                 210
Xaa Leu Pro Gly Xaa Glu Xaa Val Xaa Xaa Xaa Xaa Xaa Xaa Xaa 215                 220                 225
Xaa Xaa Xaa Xaa Xaa Phe Xaa His Ile Xaa Xaa Xaa Val Pro Glu 230                 235                 240
Leu Xaa Pro Xaa Xaa Xaa Tyr Xaa Xaa Gly Phe Thr Xaa Phe Xaa 245                 250                 255
Xaa Xaa Ala Glu Phe Thr Thr Glu Asp Val Gly Thr Thr Glu Ser 260                 265                 270
Gly Leu Asn Ser Met Ala Leu Ala Asn Asn Ser Glu Asn Val Leu 275                 280                 285
Leu Pro Xaa Asn Glu Pro Val His Gly Thr Lys Arg Arg Ser Gln 290                 295                 300
```

```
                              -continued
Ile Gln Thr Phe Leu Asp Xaa His Gly Gly Pro Gly Val Gln His
                305                 310                 315
Ile Ala Leu Ala Ser Asp Asp Val Leu Arg Thr Leu Arg Glu Met
                320                 325                 330
Arg Ala Arg Ser Ala Met Gly Gly Phe Glu Phe Leu Pro Pro Pro
                335                 340                 345
Xaa Xaa Asp Tyr Tyr Asp Gly Val Xaa Xaa Cys Xaa Xaa Asp Xaa
                350                 355                 360
Leu Xaa Xaa Xaa Gln Xaa Xaa Xaa Cys Gln Xaa Xaa Xaa Val Xaa
                365                 370                 375
Val Asp Arg Xaa Xaa Gly Xaa Xaa Leu Gln Xaa Xaa Thr Xaa
                380                 385                 390
Xaa Xaa Gly Xaa Arg Xaa Xaa Xaa Xaa Xaa Xaa Xaa Xaa Xaa
                395                 400                 405
Xaa Xaa Cys Xaa Xaa Xaa Xaa Xaa Xaa Xaa Glu Tyr Gln Lys
                410                 415                 420
Xaa Xaa Xaa Gly Gly Xaa Gly Xaa Gly Xaa Xaa Xaa Xaa Leu Phe
                425                 430                 435
Lys Xaa Xaa Xaa Xaa Xaa Xaa Xaa Xaa Xaa Xaa Xaa Xaa Xaa Ala
                440
Ala Xaa Xaa Xaa Thr Ala Gln Gly Ser;
``` wherein
- Xaa at position 52 is Glu, Asp, Gly, His, Arg, Ser or Thr;
- Xaa at position 53 is Leu, Phe, Ile or Met;
- Xaa at position 54 is Trp, Cys, Leu or Gln;
- Xaa at position 55 is Cys, Ala, Gly, Thr or Val;
- Xaa at position 56 is Ala, His, Leu, Asn, Gln, Ser or Thr;
- Xaa at position 58 is Ala, Gly or Thr;
- Xaa at position 125 is Arg or Leu;
- Xaa at position 147 is Ala or Ser;
- Xaa at position 148 is Phe, Trp or Tyr;
- Xaa at position 149 is Arg, Ala, Ile, Lys, Met, Pro, Ser, Thr, Val or Trp;
- Xaa at position 152 is Val or Glu;
- Xaa at position 153 is Ala, Phe, Ile, Lys, Leu, Gln, Arg, Thr or Val;
- Xaa at position 154 is Ala, Cys, Gly, Asn, Arg or Thr;
- Xaa at position 157 is Arg, His, Asn, Thr or Val;
- Xaa at position 158 is Pro, Ala, Glu, Gly or Lys;
- Xaa at position 159 is Ala, Cys, Met, Ser, Thr or Val;
- Xaa at position 160 is Phe, Leu, Met or Tyr;
- Xaa at position 161 is Gly, Ala, Glu, Leu, Met, Asn, Pro, Gln, Arg, Ser, Thr, Trp or Tyr;
- Xaa at position 162 is Pro or Thr;
- Xaa at position 163 is Val, Ala, Cys, Met or Thr;
- Xaa at position 164 is Asp, Ala, Glu, His, Ser or Thr;
- Xaa at position 165 is Leu, Cys, Met or Val;
- Xaa at position 166 is Gly, Ala or Pro;
- Xaa at position 167 is Arg or Val;
- Xaa at position 169 is Phe, Ala, His, Trp or Tyr;
- Xaa at position 170 is Arg, Cys, Gly, Ile, Lys, Leu, Met, Pro, Gln, Ser, Thr, Val or Trp;
- Xaa at position 171 is Leu, Phe, Ile, Met or Val;
- Xaa at position 172 is Ala, Pro, Arg or Ser;
- Xaa at position 173 is Glu or Pro;
- Xaa at position 174 is Val, Cys or Ile;
- Xaa at position 175 is Glu, Asp, Val or Trp;
- Xaa at position 176 is Leu, Ala or Met;
- Xaa at position 181 is Val, Phe, Ile, Met or Asn;
- Xaa at position 182 is Leu or Met;
- Xaa at position 187 is Tyr, Cys, Glu, Gly, His, Met or Val;
- Xaa at position 188 is Pro, Asp, Gly or Gln;
- Xaa at position 189 is Asp, Glu, Pro, Ser or Thr;
- Xaa at position 190 is Gly, Ala, Cys, Asp, Glu, Leu, Met, Asn, Pro, Gln, Arg, Ser, Thr, Val or Trp;
- Xaa at position 191 is Ala, Glu, Phe, Gly, His, Ile, Lys, Leu, Met, Asn, Arg, Ser, Thr or Val;
- Xaa at position 192 is Ala or Val;
- Xaa at position 193 is Gly, Ala, His, Ile, Leu, Pro, Gln, Arg, Ser, Thr or Val;
- Xaa at position 194 is Glu, Asp or Leu;
- Xaa at position 195 is Pro, Ala, Cys, Asp, Glu, Gln, Ser, Thr or Val;
- Xaa at position 196 is Phe or Trp;
- Xaa at position 200 is Phe or Cys;
- Xaa at position 202 is Gly, Ala, Glu, Lys, Leu, Thr, Val or Tyr;
- Xaa at position 204 is Ala, Cys, Asp, Glu, Gly, His, Lys, Leu, Met, Asn, Gln, Thr or Val;
- Xaa at position 205 is Ser, Asp, Gly, Leu, Gln, Thr or Val;
- Xaa at position 206 is Pro, Cys, Asp, Lys, Leu, Gln, Ser or Thr;
- Xaa at position 207 is Gly, Gln, Ser or Val;
- Xaa at position 208 is Ala, Gly, His, Gln, Arg or Trp;
- Xaa at position 209 is Ala, Cys, Asp, Glu, Gly, Ile, Lys, Leu, Met, Pro, Gln, Ser, Thr or Trp;
- Xaa at position 210 is Asp, Glu, Gly, Ser or Thr;
- Xaa at position 211 is Tyr, Cys, Phe, Leu, Ser or Trp;
- Xaa at position 212 is Gly or Lys;
- Xaa at position 213 is Leu or Trp;
- Xaa at position 214 is Ser, Lys, Met, Asn, Gln, Arg or Thr;
- Xaa at position 215 is Arg, Ala or Gly;
- Xaa at position 217 is Asp, Gln or Tyr;
- Xaa at position 220 is Val or Thr;

Xaa at position 221 is Gly, Ala, Phe, His, Ile, Leu, Met, Thr or Val;
Xaa at position 222 is Asn, Gly or Val;
Xaa at position 227 is Ala, Asp, Glu, Gly, Ile, Lys, Leu, Met, Asn, Gln, Arg, Ser, Thr or Val;
Xaa at position 229 is Ala or Thr;
Xaa at position 230 is Ala, Arg or Val;
Xaa at position 231 is Ala, Cys, His, Leu, Ser or Thr;
Xaa at position 233 is Met or Val;
Xaa at position 234 is Ala, Cys, Glu, Gly, Lys, Leu, Met, Gln, Ser or Val;
Xaa at position 238 is Gly or Ser;
Xaa at position 240 is His or Arg;
Xaa at position 241 is Glu, Ala, Asp, Gly, Asn, Pro, Arg, Ser or Thr;
Xaa at position 242 is Phe, Ala, Asp or Ser;
Xaa at position 273 is Leu or Val;
Xaa at position 292 is His or Asn;
Xaa at position 331 is Leu, Asp, Gly, Asn or Arg;
Xaa at position 332 is Ser or Ala;
Xaa at position 339 is Arg or Lys;
Xaa at position 340 is Arg, Glu, Lys or Asn;
Xaa at position 342 is Ala, Cys, Leu, Met, Asn, Arg or Val;
Xaa at position 343 is Gly or Arg;
Xaa at position 345 is Val or Ile;
Xaa at position 347 is Thr or Ser;
Xaa at position 348 is Glu or Tyr;
Xaa at position 349 is Ala, Glu, Gln, Arg or Ser;
Xaa at position 351 is Ile, Cys or Val;
Xaa at position 352 is Asn, Glu, Lys, Leu, Gln or Arg;
Xaa at position 353 is Glu, Leu, Met, Ser or Thr;
Xaa at position 356 is Glu, Lys or Arg;
Xaa at position 357 is Leu or Tyr;
Xaa at position 358 is Gly, Glu or Arg;
Xaa at position 360 is Met, Leu or Thr;
Xaa at position 364 is Asp, Gly, Ser or Val;
Xaa at position 365 is Asp or Ala;
Xaa at position 366 is Gln or Glu;
Xaa at position 368 is Val or Leu;
Xaa at position 369 is Leu, Met or Val;
Xaa at position 372 is Ile, Ala, Lys, Gln, Ser or Thr;
Xaa at position 373 is Phe, Gly, Leu, Arg or Val;
Xaa at position 375 is Lys, Leu or Arg;
Xaa at position 376 is Pro, Cys, Gly, Ser, Val or Trp;
Xaa at position 377 is Val, Glu, Gly or Leu;
Xaa at position 379 is Asp or Lys;
Xaa at position 381 is Pro or Asn;
Xaa at position 382 is Thr, Ala, Phe or Ser;
Xaa at position 383 is Phe, Leu or Met;
Xaa at position 384 is Phe, Trp or Tyr;
Xaa at position 385 is Leu, Ile or Val;
Xaa at position 386 is Glu, Cys, Ile or Val;
Xaa at position 387 is Ile, Gly or Leu;
Xaa at position 388 is Ile, Leu, Ser or Val;
Xaa at position 389 is Gln, Gly, Lys or Thr;
Xaa at position 390 is Arg or Asn;
Xaa at position 391 is Ile, Leu or Val;
Xaa at position 392 is Gly, Arg or Val;
Xaa at position 394 is Met, Ile, Lys, Leu, Gln, Val or Tyr;
Xaa at position 395 is Glu, Lys, Gln, Ser or Val;
Xaa at position 396 is Lys, Ala, Leu, Met, Gln, Arg, Thr or Val;
Xaa at position 397 is Asp, Gly or Ser;
Xaa at position 398 is Glu, Ala, Asp, Gly, Pro or Ser;
Xaa at position 399 is Lys, Ala, Asp, Gly, His, Ile, Met, Asn, Gln, Arg, Ser, Thr, Val or Tyr;
Xaa at position 400 is Gly, Glu, Lys or Ser;
Xaa at position 401 is Gln, Ala, Glu, Ser or Val;
Xaa at position 406 is Gly or Cys;
Xaa at position 407 is Gly, Ala, Lys, Leu, Arg, Ser or Thr;
Xaa at position 408 is Cys, Gly, Arg, Thr, Val or Trp;
Xaa at position 411 is Phe, Ala or Leu;
Xaa at position 413 is Lys, Ala, Pro, Arg or Ser;
Xaa at position 415 is Asn or Ala;
Xaa at position 416 is Phe, Arg or Val;
Xaa at position 417 is Gly, Gln or Ser;
Xaa at position 418 is Gln, Ala, Cys, Glu, Gly, Leu or Thr;
Xaa at position 422 is Ser or Met;
Xaa at position 423 is Ile, Val or Trp;
Xaa at position 424 is Glu or Gln;
Xaa at position 425 is Asp, Ala, Glu, Gly, Met, Ser or Thr;
Xaa at position 426 is Tyr, Leu or Trp;
Xaa at position 427 is Glu, Ala, Leu or Met;
Xaa at position 428 is Lys, Arg or Val;
Xaa at position 429 is Ser, Cys, Asp, Gly or Thr;
Xaa at position 430 is Leu, Met or Val;
Xaa at position 431 is Glu, Ala, Phe, Gly, Leu or Asn;
Xaa at position 432 is Ala, Asp, Gly, Lys, Leu, Arg, Ser or Val;
Xaa at position 433 is Lys, Glu, His, Leu, Pro, Arg, Ser or Val;
Xaa at position 434 is Gln, Ala, Cys, Asp, Phe, Gly, His, Lys, Leu or Arg;
Xaa at position 437 is Ala, Phe, Lys or Val;
Xaa at position 438 is Ala, Gly or Arg;
Xaa at position 439 is Ala or Arg;
wherein one or more amino acid(s) designated by Xaa in SEQ ID NO:80 is an amino acid different from the corresponding amino acid of SEQ ID NO:1; and wherein the polypeptide having 4-hydroxyphenylpyruvate dioxygenase activity has improved insensitivity to an HPPD inhibitor compared to the polypeptide of SEQ ID NO:1.

2. A recombinant polypeptide having 4-hydroxyphenylpyruvate dioxygenase (HPPD) activity; wherein the polypeptide having 4-hydroxyphenylpyruvate dioxygenase activity comprises:

```
                                                    (SEQ ID NO: 81)
                5                   10                  15
Met Gly Pro Thr Pro Thr Ala Thr Ala Ala Gly Ala Ala Val Ala 20                  25                  30
Ala Ala Ser Ala Ala Glu Gln Ala Ala Phe Arg Leu Val Gly His 35                  40                  45
Arg Asn Phe Val Arg Phe Asn Pro Arg Ser Asp Arg Phe Gln Thr
```

-continued

```
                50                  55                  60
Leu Ala Phe His His Val Glu Xaa Trp Cys Xaa Asp Ala Ala Ser 65                  70                  75
Ala Ala Gly Arg Phe Ser Phe Ala Leu Gly Val Pro Leu Ala Ala 80                  85                  90
Arg Ser Asp Leu Ser Thr Gly Asn Ser Ala His Ala Ser Leu Leu 95                 100                 105
Leu Arg Ser Gly Ser Leu Ser Leu Leu Phe Thr Ala Pro Tyr Ala 110                 115                 120
His Gly Ala Asp Ala Ala Thr Ala Ala Leu Pro Ser Phe Ser Ala 125                 130                 135
Ala Ala Ala Arg Xaa Phe Ala Ala Asp His Gly Leu Ala Val Arg 140                 145                 150
Ala Val Ala Leu Arg Val Ala Asp Ala Glu Asp Ala Phe Arg Ala 155                 160                 165
Ser Val Ala Ala Gly Ala Arg Xaa Xaa Phe Xaa Pro Val Asp Leu 170                 175                 180
Xaa Arg Gly Xaa Arg Xaa Ala Glu Val Glu Leu Tyr Gly Asp Val 185                 190                 195
Val Xaa Arg Tyr Val Ser Tyr Pro Xaa Xaa Xaa Ala Xaa Glu Pro 200                 205                 210
Phe Leu Pro Gly Phe Glu Gly Val Ala Ser Xaa Gly Ala Ala Asp 215                 220                 225
Xaa Gly Leu Xaa Xaa Phe Xaa His Ile Val Xaa Asn Val Pro Glu 230                 235                 240
Leu Xaa Pro Ala Ala Ala Tyr Met Ala Gly Phe Thr Gly Phe His 245                 250                 255
Glu Phe Ala Glu Phe Thr Thr Glu Asp Val Gly Thr Thr Glu Ser 260                 265                 270
Gly Leu Asn Ser Met Ala Leu Ala Asn Asn Ser Glu Asn Val Leu 275                 280                 285
Leu Pro Leu Asn Glu Pro Val His Gly Thr Lys Arg Arg Ser Gln 290                 295                 300
Ile Gln Thr Phe Leu Asp His His Gly Gly Pro Gly Val Gln His 305                 310                 315
Ile Ala Leu Ala Ser Asp Asp Val Leu Arg Thr Leu Arg Glu Met 320                 325                 330
Arg Ala Arg Ser Ala Met Gly Gly Phe Glu Phe Leu Pro Pro Pro 335                 340                 345
Xaa Xaa Asp Tyr Tyr Asp Gly Val Arg Xaa Cys Xaa Gly Asp Val 350                 355                 360
Leu Thr Glu Xaa Gln Ile Xaa Glu Cys Gln Xaa Leu Xaa Val Xaa 365                 370                 375
Val Asp Arg Asp Asp Xaa Gly Val Leu Leu Gln Ile Xaa Thr Xaa 380                 385                 390
Xaa Val Gly Asp Arg Xaa Xaa Xaa Phe Xaa Glu Xaa Ile Gln Xaa 395                 400                 405
Ile Gly Cys Met Glu Xaa Asp Xaa Xaa Gly Gln Glu Tyr Gln Lys 410                 415                 420
Gly Gly Cys Gly Gly Phe Gly Xaa Gly Asn Phe Xaa Xaa Leu Phe 425                 430                 435
Lys Ser Xaa Glu Asp Tyr Glu Lys Xaa Leu Xaa Xaa Lys Xaa Ala

440
Ala Xaa Xaa Xaa Thr Ala Gln Gly Ser;
``` wherein
  Xaa at position 53 is Leu or Phe;
  Xaa at position 56 is Ala or Ser;
  Xaa at position 125 is Arg or Leu;
  Xaa at position 158 is Pro or Lys;
  Xaa at position 159 is Ala or Cys;
  Xaa at position 161 is Gly, Glu, Gln, Ser, Tyr, Asn or Leu;
  Xaa at position 166 is Gly, Pro or Ala;
  Xaa at position 169 is Phe or His;
  Xaa at position 171 is Leu or Phe;
  Xaa at position 182 is Leu or Met;
  Xaa at position 189 is Asp or Pro;
  Xaa at position 190 is Gly or Thr;
  Xaa at position 191 is Ala, Ser, Leu or Gly;
  Xaa at position 193 is Gly or Gln;
  Xaa at position 206 is Pro, Gln, Ser, Lys or Leu;
  Xaa at position 211 is Tyr, Leu or Ser;
  Xaa at position 214 is Ser, Asn, Thr, Arg or Met;
  Xaa at position 215 is Arg or Gly;
  Xaa at position 217 is Asp or Tyr;
  Xaa at position 221 is Gly, Val or Ala;
  Xaa at position 227 is Ala or Gly;
  Xaa at position 331 is Leu, Asn, Arg, Gly or Asp;
  Xaa at position 332 is Ser or Ala;
  Xaa at position 340 is Arg or Lys;
  Xaa at position 342 is Ala, Val, Met or Cys;
  Xaa at position 349 is Ala, Gln or Glu;
  Xaa at position 352 is Asn or Arg;
  Xaa at position 356 is Glu, Lys or Arg;
  Xaa at position 358 is Gly or Glu;
  Xaa at position 360 is Met or Leu;
  Xaa at position 366 is Gln or Glu;
  Xaa at position 373 is Phe or Val;
  Xaa at position 375 is Lys, Leu or Arg;
  Xaa at position 376 is Pro or Trp;
  Xaa at position 381 is Pro or Asn;
  Xaa at position 382 is Thr or Ser;
  Xaa at position 383 is Phe, Met or Leu;
  Xaa at position 385 is Leu, Val or Ile;
  Xaa at position 387 is Ile or Leu;
  Xaa at position 390 is Arg or Asn;
  Xaa at position 396 is Lys, Thr, Met or Leu;
  Xaa at position 398 is Glu, Asp or Ala;
  Xaa at position 399 is Lys, Asn, Arg, Gln or Ser;
  Xaa at position 413 is Lys or Ala;
  Xaa at position 417 is Gly, Ser or Gln;
  Xaa at position 418 is Gln or Glu;
  Xaa at position 423 is Ile or Trp;
  Xaa at position 429 is Ser, Gly or Thr;
  Xaa at position 431 is Glu or Phe;
  Xaa at position 432 is Ala, Arg, Lys or Ser;
  Xaa at position 434 is Gln, Arg, His, Leu or Lys;
  Xaa at position 437 is Ala, Lys or Phe;
  Xaa at position 438 is Ala, Gly or Arg;
  Xaa at position 439 is Ala or Arg;
  wherein one or more amino acid(s) designated by Xaa in SEQ ID NO:81 is an amino acid different from the corresponding amino acid of SEQ ID NO:1; and wherein the polypeptide having 4-hydroxyphenylpyruvate dioxygenase activity has improved insensitivity to an HPPD inhibitor compared to the polypeptide of SEQ ID NO:1.

3. A recombinant polypeptide having 4-hydroxyphenylpyruvate dioxygenase (HPPD) activity; wherein the polypeptide having 4-hydroxyphenylpyruvate dioxygenase activity comprises:

```
                                                      (SEQ ID NO: 82)
                         5                   10                  15
Met Gly Pro Thr Pro Thr Ala Thr Ala Ala Gly Ala Ala Val Ala 20                  25                  30
Ala Ala Ser Ala Ala Glu Gln Ala Ala Phe Arg Leu Val Gly His 35                  40                  45
Arg Asn Phe Val Arg Phe Asn Pro Arg Ser Asp Arg Phe Gln Thr 50                  55                  60
Leu Ala Phe His His Val Glu Leu Trp Cys Ala Asp Ala Ala Ser 65                  70                  75
Ala Ala Gly Arg Phe Ser Phe Ala Leu Gly Val Pro Leu Ala Ala 80                  85                  90
Arg Ser Asp Leu Ser Thr Gly Asn Ser Ala His Ala Ser Leu Leu 95                  100                 105
Leu Arg Ser Gly Ser Leu Ser Leu Leu Phe Thr Ala Pro Tyr Ala 110                 115                 120
His Gly Ala Asp Ala Ala Thr Ala Ala Leu Pro Ser Phe Ser Ala 125                 130                 135
Ala Ala Ala Arg Arg Phe Ala Ala Asp His Gly Leu Ala Val Arg 140                 145                 150
Ala Val Ala Leu Arg Val Ala Asp Ala Glu Asp Ala Phe Arg Ala 155                 160                 165
Ser Val Ala Ala Gly Ala Arg Xaa Ala Phe Gly Pro Val Asp Leu 170                 175                 180
Gly Arg Gly Phe Arg Leu Ala Glu Val Glu Leu Tyr Gly Asp Val 185                 190                 195
```

```
Val Xaa Arg Tyr Val Ser Tyr Pro Xaa Gly Xaa Ala Gly Glu Pro
                200                 205                 210
Phe Leu Pro Gly Phe Glu Gly Val Ala Xaa Xaa Gly Ala Ala Asp
                215                 220                 225
Xaa Gly Leu Xaa Arg Phe Asp His Ile Val Gly Asn Val Pro Glu
                230                 235                 240
Leu Xaa Pro Ala Ala Ala Tyr Met Ala Gly Phe Thr Gly Phe His
                245                 250                 255
Glu Phe Ala Glu Phe Thr Thr Glu Asp Val Gly Thr Thr Glu Ser
                260                 265                 270
Gly Leu Asn Ser Met Ala Leu Ala Asn Asn Ser Glu Asn Val Leu
                275                 280                 285
Leu Pro Leu Asn Glu Pro Val His Gly Thr Lys Arg Arg Ser Gln
                290                 295                 300
Ile Gln Thr Phe Leu Asp His His Gly Gly Pro Gly Val Gln His
                305                 310                 315
Ile Ala Leu Ala Ser Asp Asp Val Leu Arg Thr Leu Arg Glu Met
                320                 325                 330
Arg Ala Arg Ser Ala Met Gly Gly Phe Glu Phe Leu Pro Pro Pro
                335                 340                 345
Leu Ser Asp Tyr Tyr Asp Gly Val Arg Xaa Cys Xaa Gly Asp Val
                350                 355                 360
Leu Thr Glu Ala Gln Ile Asn Glu Cys Gln Xaa Leu Gly Val Xaa
                365                 370                 375
Val Asp Arg Asp Xaa Gly Val Leu Leu Gln Ile Phe Thr Lys
                380                 385                 390
Xaa Val Gly Asp Arg Pro Thr Phe Phe Xaa Glu Xaa Ile Gln Xaa
                395                 400                 405
Ile Gly Cys Met Glu Lys Asp Glu Lys Gly Gln Glu Tyr Gln Lys
                410                 415                 420
Gly Gly Cys Gly Gly Phe Gly Lys Gly Asn Phe Xaa Gln Leu Phe
                425                 430                 435
Lys Ser Ile Glu Asp Tyr Glu Lys Ser Leu Xaa Xaa Lys Xaa Ala
                440
Ala Ala Ala Ala Thr Ala Gln Gly Ser;
``` wherein
Xaa at position 158 is Pro or Lys;
Xaa at position 182 is Leu or Met;
Xaa at position 189 is Asp or Pro;
Xaa at position 191 is Ala, Gly or Leu;
Xaa at position 205 is Ser or Thr;
Xaa at position 206 is Pro, Gln or Ser;
Xaa at position 211 is Tyr or Leu;
Xaa at position 214 is Ser, Asn or Thr;
Xaa at position 227 is Ala or Gly;
Xaa at position 340 is Arg or Lys;
Xaa at position 342 is Ala or Val;
Xaa at position 356 is Glu, Lys or Arg;
Xaa at position 360 is Met or Leu;
Xaa at position 366 is Gln or Glu;
Xaa at position 376 is Pro or Trp;
Xaa at position 385 is Leu, Ile or Val;
Xaa at position 387 is Ile or Leu;
Xaa at position 390 is Arg or Asn;
Xaa at position 417 is Gly, Gln or Ser;
Xaa at position 431 is Glu or Phe;
Xaa at position 432 is Ala, Arg or Lys;
Xaa at position 434 is Gln, His or Arg;

wherein one or more amino acid(s) designated by Xaa in SEQ ID NO:82 is an amino acid different from the corresponding amino acid of SEQ ID NO:1; and wherein the polypeptide having 4-hydroxyphenylpyruvate dioxygenase activity has improved insensitivity to an HPPD inhibitor compared to the polypeptide of SEQ ID NO:1.

4. A recombinant polypeptide having 4-hydroxyphenylpyruvate dioxygenase (HPPD) activity; wherein the polypeptide having 4-hydroxyphenylpyruvate dioxygenase activity comprises:

(SEQ ID NO: 83)

```
          5                   10                  15
Met Gly Pro Thr Pro Thr Ala Thr Ala Ala Gly Ala Ala Val Ala
                  20                  25                  30
Ala Ala Ser Ala Ala Glu Gln Ala Ala Phe Arg Leu Val Gly His
                  35                  40                  45
Arg Asn Phe Val Arg Phe Asn Pro Arg Ser Asp Arg Phe Gln Thr
                  50                  55                  60
Leu Ala Phe His His Val Glu Leu Trp Cys Ala Asp Ala Ala Ser
                  65                  70                  75
Ala Ala Gly Arg Phe Ser Phe Ala Leu Gly Val Pro Leu Ala Ala
                  80                  85                  90
Arg Ser Asp Leu Ser Thr Gly Asn Ser Ala His Ala Ser Leu Leu
                  95                  100                 105
Leu Arg Ser Gly Ser Leu Ser Leu Leu Phe Thr Ala Pro Tyr Ala
                  110                 115                 120
His Gly Ala Asp Ala Ala Thr Ala Ala Leu Pro Ser Phe Ser Ala
                  125                 130                 135
Ala Ala Ala Arg Arg Phe Ala Ala Asp His Gly Leu Ala Val Arg
                  140                 145                 150
Ala Val Ala Leu Arg Val Ala Asp Ala Glu Asp Ala Phe Arg Ala
                  155                 160                 165
Ser Val Ala Ala Gly Ala Arg Xaa Ala Phe Gly Pro Val Asp Leu
                  170                 175                 180
Gly Arg Gly Phe Arg Leu Ala Glu Val Glu Leu Tyr Gly Asp Val
                  185                 190                 195
Val Xaa Arg Tyr Val Ser Tyr Pro Asp Gly Xaa Ala Gly Glu Pro
                  200                 205                 210
Phe Leu Pro Gly Phe Glu Gly Val Ala Ser Xaa Gly Ala Ala Asp
                  215                 220                 225
Xaa Gly Leu Xaa Arg Phe Asp His Ile Val Gly Asn Val Pro Glu
                  230                 235                 240
Leu Ala Pro Ala Ala Ala Tyr Xaa Ala Gly Phe Thr Gly Phe His
                  245                 250                 255
Glu Phe Ala Glu Phe Thr Thr Glu Asp Val Gly Thr Thr Glu Ser
                  260                 265                 270
Gly Leu Asn Ser Met Ala Leu Ala Asn Asn Ser Glu Asn Val Leu
                  275                 280                 285
Leu Pro Leu Asn Glu Pro Val His Gly Thr Lys Arg Arg Ser Gln
                  290                 295                 300
Ile Gln Thr Phe Leu Asp His His Gly Gly Pro Gly Val Gln His
                  305                 310                 315
Ile Ala Leu Ala Ser Asp Asp Val Leu Arg Thr Leu Arg Glu Met
                  320                 325                 330
Arg Ala Arg Ser Ala Met Gly Gly Phe Glu Phe Leu Pro Pro Pro
                  335                 340                 345
Leu Ser Asp Tyr Tyr Asp Gly Val Arg Xaa Cys Ala Gly Asp Val
                  350                 355                 360
Leu Thr Glu Ala Gln Ile Asn Glu Cys Gln Xaa Leu Gly Val Met
                  365                 370                 375
Val Asp Arg Asp Xaa Gly Val Leu Leu Gln Ile Phe Thr Lys
                  380                 385                 390
Pro Val Gly Asp Arg Pro Thr Phe Phe Xaa Glu Xaa Ile Gln Arg
                  395                 400                 405
Ile Gly Cys Xaa Glu Lys Asp Glu Lys Gly Gln Glu Tyr Gln Lys
```

-continued

```
            410                 415                 420
Gly Gly Cys Gly Gly Phe Gly Lys Gly Asn Phe Xaa Gln Leu Phe 425                 430                 435
Lys Ser Ile Glu Asp Tyr Glu Xaa Ser Leu Glu Xaa Lys Xaa Ala

440
Ala Ala Ala Ala Thr Ala Gln Gly Ser;
``` wherein
 Xaa at position 158 is Pro or Lys;
 Xaa at position 182 is Leu or Met;
 Xaa at position 191 is Ala or Gly;
 Xaa at position 206 is Pro, Ser or Gln;
 Xaa at position 211 is Tyr or Leu;
 Xaa at position 214 is Ser or Asn;
 Xaa at position 233 is Met or Val;
 Xaa at position 340 is Arg or Lys;
 Xaa at position 356 is Glu, Lys or Arg;
 Xaa at position 366 is Gln or Glu;
 Xaa at position 385 is Leu, Ile or Val;
 Xaa at position 387 is Ile or Leu;
 Xaa at position 394 is Met, Val or Lys;
 Xaa at position 417 is Gly, Ser or Gln;
 Xaa at position 428 is Lys or Arg;
 Xaa at position 432 is Ala, Lys or Arg;
 Xaa at position 434 is Gln, Arg or His;
 wherein one or more amino acid(s) designated by Xaa in SEQ ID NO:83 is an amino acid different from the corresponding amino acid of SEQ ID NO:1; and wherein the polypeptide having 4-hydroxyphenylpyruvate dioxygenase activity has improved insensitivity to an HPPD inhibitor compared to the polypeptide of SEQ ID NO:1.

5. The polypeptide of embodiments 1-4, wherein the polypeptide further comprises substitution of one or more conservative amino acids, insertion of one or more amino acids, deletion of one or more amino acids, and combinations thereof.

6. The polypeptide of any of embodiments 1-5, wherein the polypeptide has an ON rate ratio of at least about 0.5; wherein the ON rate ratio is the ratio of the reaction rate with herbicidal inhibitor to the reaction rate without herbicidal inhibitor; and wherein the reaction rates are determined in an in vitro assay.

7. The polypeptide of embodiment 6, wherein the herbicidal inhibitor is mesotrione or tembrione.

8. The polypeptide of embodiment 6 or 7, wherein in vitro assay is carried out in the presence of 60 or 120 nM of the 4-hydroxyphenylpyruvate dioxygenase protein.

9. The polypeptide of any of embodiments 6-8, wherein in vitro assay is carried out in the presence of 100 μM 4-hydroxyphenylpyruvate.

10. The polypeptide of any of embodiments 6-9, wherein the polypeptide has an OFF rate ratio of at least about 0.3; wherein the OFF rate ratio is the ratio of the steady state rate in the presence of inhibitor to the initial reaction rate in the absence of inhibitor; and wherein the reaction rates are determined in an in vitro assay.

11. The polypeptide of embodiment 10, wherein the herbicidal inhibitor is mesotrione or tembrione.

12. The polypeptide of embodiment 10 or 11, wherein the in vitro assay is carried out in the presence of 60 or 120 nM of the 4-hydroxyphenylpyruvate dioxygenase protein.

13. The polypeptide of any of embodiments 10-12, wherein the in vitro assay is carried out in the presence of 100 μM 4-hydroxyphenylpyruvate.

14. The polypeptide of any of embodiments 1-13, wherein the polypeptide has a fitness parameter of about 2 to about 200 $min^{-1}$ $μM^{-1}$; and wherein $$\text{Fitness Parameter} = \frac{k_{cat}}{K_m} \times (\text{ON rate ratio} \times \text{OFF rate ratio}).$$

15. A nucleic acid construct comprising a polynucleotide sequence encoding a polypeptide having 4-hydroxyphenylpyruvate dioxygenase (HPPD) activity; wherein the polypeptide encoded is the polypeptide of any of embodiments 1-14.

16. The nucleic acid construct of embodiment 15, further comprising a promoter operably linked to the polynucleotide sequence.

17. A plant cell comprising a nucleic acid construct comprising a polynucleotide sequence encoding a polypeptide having 4-hydroxyphenylpyruvate dioxygenase (HPPD) activity; wherein the polypeptide encoded is the polypeptide of any of embodiments 1-14.

18. The plant cell of embodiment 17, wherein the nucleic acid construct further comprises a promoter operably linked to the polynucleotide sequence.

19. The plant cell of embodiments 17 or 18, wherein the plant cell exhibits has an improved insensitivity to an HPPD inhibitor compared to a wild type plant cell of the same species, strain or cultivar.

20. The plant cell of any of embodiments 17-19, wherein the polypeptide having 4-hydroxyphenylpyruvate dioxygenase activity is present in an amount from about 1000 ppm to about 5000 ppm.

21. The plant cell of any of embodiments 17-19, wherein the polypeptide having 4-hydroxyphenylpyruvate dioxygenase activity is present in an amount from about 200 ppm to about 4000 ppm.

22. The plant cell of any of embodiments 17-21, wherein the nucleic acid construct is stably incorporated into the genome of the plant cell.

23. The plant cell of any of embodiments 17-22, wherein the plant cell is from a monocot.

24. The plant cell of embodiment 23, wherein the monocot is maize, wheat, rice, barley, sugarcane, sorghum, or rye.

25. The plant cell of any of embodiments 17-22, wherein the plant cell is from a dicot.

26. The plant cell of embodiment 24, wherein the dicot is soybean, *Brassica*, sunflower, cotton, or alfalfa.

27. The plant cell of any of embodiments 17-26, wherein the plant cell further comprises at least one additional polypeptide imparting tolerance to an additional herbicide.

28. The plant cell of embodiment 27, wherein the at least one polypeptide imparting tolerance to an additional herbicide comprises: (a) a sulfonylurea-tolerant acetolactate synthase; (b) an imidazolinone-tolerant acetolactate synthase; (c) a glyphosate-tolerant 5-enolpyruvylshikimate-3-phosphate synthase; (d) a glyphosate-tolerant glyphosate oxidoreductase; (e) a glyphosate-N-acetyltransferase; (f) a phosphinothricin acetyl transferase; (g) a protoporphyrinogen oxidase. (h) an auxin enzyme; (i) a P450 polypeptide; or, (j) an acetyl coenzyme A carboxylase (ACCase).

29. The plant cell of embodiment 27, wherein the at least one polypeptide imparting tolerance to an additional herbicide comprises a high resistance allele of acetolactate synthase (HRA) and/or a glyphosate-N-acetyltransferase polypeptide.

30. The plant cell of embodiment 27, wherein the plant cell further comprises at least one additional polypeptide imparting tolerance to an HPPD herbicide.

31. The plant cell of embodiment 30, wherein the at least one additional polypeptide imparting tolerance to an HPPD herbicide comprises a P450 polypeptide or NSF1.

32. A plant comprising the plant cell of any of embodiments 17-31.

33. An explant comprising the plant cell of any of embodiments 17-31.

34. A transgenic seed produced by the plant of embodiment 32.

35. A method of producing a 4-hydroxyphenylpyruvate dioxygenase (HPPD) herbicide tolerant plant cell comprising transforming a plant cell with a polynucleotide encoding the polypeptide of any of embodiments 1-14 or the nucleic acid construct of embodiments 15-16.

36. The method of embodiment 35, further comprising selecting a plant cell which is resistant to an HPPD herbicide by growing plant cells in the presence of a concentration of an HPPD herbicide that bleaches the plant cell which does not comprise a polynucleotide encoding the polypeptide of any of embodiments 1-14 or the nucleic acid construct of embodiments 15-16.

37. The method of embodiment 36, wherein the method comprises
    (a) culturing the plant cell in the presence of a sufficient concentration of an HPPD herbicide such that the plant cells display bleaching;
    (b) transforming into the plant cells of step (a) a polynucleotide encoding the polypeptide of any of embodiments 1-14 or the nucleic acid construct of embodiments 15-16; and
    (c) growing the plant cells of (b), wherein transformed plants cells no longer display bleaching.

38. The method of embodiment 35, wherein the method further comprises regenerating a transgenic plant from the plant cell.

39. The method of embodiment 35, wherein the transforming the plant cell results in the sTable 2ntegration of the polynucleotide into the genome of the plant cell.

40. The method of embodiment 35, wherein the transforming the plant cell results in the sTable 2ntegration of the polynucleotide into the genome of a chloroplast in the plant cell.

41. A method for controlling weeds in a field containing a crop comprising:
    (a) planting the field with the transgenic seeds of embodiment 34; and,
    (b) applying to any crop and weeds in the field a sufficient amount of an HPPD herbicide to control weeds without significantly affecting the crop.

42. The method of embodiment 41, wherein the HPPD herbicide comprises at least one of triketones, isoxazoles, pyrazoles, or benzobicyclon or active derivatives thereof or an agriculturally acceptable salt thereof.

43. The method of embodiment 42, wherein the HPPD herbicide comprises at least one of mesotrione, sulcotrione, topremezone, and tembotrione, pyrasulfotole, isoxaflutole, benzofenap, pyrazoxyfen, or pyrazolynate or active derivative thereof or an agriculturally acceptable salt thereof.

44. The method of embodiment 41, further comprising applying to the crop and weeds in the field a sufficient amount of at least one additional herbicide comprising glyphosate, bialaphos, phosphinothricin, azafenidin, butafenacil, sulfosate, glufosinate, an ALS inhibitor, or a protox inhibitor.

45. A method for detecting an HPPD polypeptide comprising analyzing plant tissues using an immunoassay comprising at least one antibody that recognizes the polypeptide of any of embodiments 1-14.

46. A method for detecting the presence of a polynucleotide encoding the polypeptide of any of embodiments 1-14 comprising assaying plant tissue using PCR amplification and detecting the polynucleotide.

REFERENCES

Altschul S F, et al. (1990) Basic local alignment search tool. J Mol Biol 215: 403-10.

Amaya A A, et al. (2004) Kinetic analysis of human homogentisate 1,2-dioxygenase. Arch Biochem Biophys 421: 135-42.

An G, et al. (1989) Functional analysis of the 3' control region of the potato wound-inducible proteinase inhibitor II gene. Plant Cell 11: 115-22.

APHIS Petition (09-328-01p) for Determination of Non-Regulated Status of Event FG72 Soybean (2009) Bayer CropScience LP and MS Technologies LLC.

APHIS Revised Petition (12-215-01p) for Determination of Non-Regulated Status for Herbicide-Tolerant Event SYHT0H2 Soybean (2012) Syngenta Seeds Inc and Bayer CropScience AG.

Bagge P, Larsson C (1986) Biosynthesis of aromatic amino acids by highly purified spinach chloroplasts—compartmentation and regulation of the reactions. Physiol Plant 68: 641-47.

Bedbrook J R, et al. Feb. 25, 1997. Nucleic acid fragment encoding herbicide resistant plant acetolactate synthase. U.S. Pat. No. 5,605,011.

Blum T, Briesemeister S, Kohlbacher O (2009) MultiLoc2: integrating phylogeny and gene ontology terms improves subcellular protein localization prediction. BMC Bioinf 10: 274.

Bowen B A, Bruce W B, Lu G, Sims L E, Tagliani L A. Jun. 6, 2000. Synthetic promoters. U.S. Pat. No. 6,072,050.

Brownlee J, Johnson-Winters K, Harrison D H T, Moran, G R (2004) Structure of the ferrous form of (4-hydroxyphenyl)pyruvate dioxygenase from *Streptomyces avermitilis* in complex with the therapeutic herbicide, NTBC. Biochemistry 43: 6370-6377.

Bruce B D (2001) The paradox of plastid transit peptides: conservation of function despite divergence in primary structure. Biochim Biophys Acta 1541: 2-21.

Cahoon R E, Coughlan S J. Jun. 5, 2007. Plant vitamin E biosynthetic enzymes. U.S. Pat. No. 7,226,745.

Cahoon R E, Coughlan S J. Jun. 5, 2007. Plant vitamin E biosynthetic enzymes. U.S. Pat. No. 7,226,745.

Callis J, et al. (1995) Structure and evolution of genes encoding polyubiquitin and ubiquitin-like proteins in *Arabidopsis thaliana* ecotype Columbia. Genetics 139: 921-39.

Comai L, et al. (1988) Chloroplast transport of a ribulose bisphosphate carboxylase small subunit-5-enolpyruvyl 3-phophoshikimate synthase chimeric protein requires part of the mature small subunit in addition to the transit peptide. J Biol Chem 263:15104-15109.

Crameri A, Raillard S A, Bermudez E, Stemmer W P C (1998) DNA shuffling of a family of genes from diverse species accelerates directed evolution. Nature 391: 288-91.

Dey N, Maiti I B (1999) Structure and promoter/leader deletion analysis of mirabilis mosaic virus (MMV) full-length transcript promoter in transgenic plants. Plant Mol Biol 40:771-82.

Duke S O (2012) Why have no new herbicide modes of action appeared in recent years? Pest Manage Sci 68: 505-12.

Emanuelsson O, et al. (2000) Predicting subcellular localization of proteins based on their N-terminal amino acid sequence. J Mol Biol 300: 1005-1016.

Falco S C, Li Z. Jun. 22, 2010. S-adenosyl-L-methionine synthetase promoter and its use in expression of transgenic genes in plants. U.S. Pat. No. 7,741,537.

Fiedler E, Soll J, Schultz G (1982) The formation of homogentisate in the biosynthesis of tocopherol and plastoquinone in spinach chloroplasts. Planta 155: 511-15.

Fritze I M, et al. (2004) The crystal structures of *Zea mays* and *Arabidopsis* 4-hydroxyphenylpyruvate dioxygenase. Plant Physiol 134: 1388-400.

Garcia I, et al. (1997) Subcellular localization and purification of a p-hyroxyphenylpyruvate dioxygenase from cultured carrot cells and characterization of the corresponding cDNA. Biochem J 325: 761-69.

Garcia I, et al. (1999) Characterization and subcellular compartmentation of recombinant 4-hydroxyphenylpyruvate dioxygenase from *Arabidopsis* in transgenic tobacco. Plant Physiol 119: 1507-516.

Green J M, Castle L A (2010) Transitioning from single to multiple herbicide-resistant crops. In V K Nandula ed, Glyphosate Resistance in Crops and Weeds: History, Development, and Management. Wiley, Hoboken, N.J., pp 67-91.

Hawkes T R, et al. (2001) Mesotrione: mechanism of herbicidal activity and selectivity in corn. In Proc. of The BCPC Conference—Weeds 2001, UK British Crop Protection Council, Brighton, UK, pp 563-68.

Hawkes T R, et al. Aug. 5, 2010. Mutant hydroxypphenylpyruvate dioxygenase polypeptides and methods of use. US Patent Application No. 2010/0197503.

Hawkins J, Bodén M (2006) Detecting and sorting targeting peptides with neural networks and support vector machines. J Bioinf Comput Biol 4: 1-18.

Heap I (2014) The International Survey of Herbicide Resistant Weeds. weedscience.org Hoglund A, et al. (2006) MultiLoc: prediction of protein subcellular localization using N-terminal targeting sequences, sequence motifs and amino acid composition. Bioinformatics 22: 1158-165.

Homeyer U, Schultz G (1988) Transport of phenylalanine into vacuoles isolated from barley mesophyll protoplasts. Planta 176: 378-82.

Horton P, et al. (2007) WoLF PSORT: protein localization predictor. Nucleic Acids Res 35: W585-587

Hu R, Fan C, Li H, Zhang Q, Fu Y F (2009) Evaluation of putative reference genes for gene expression normalization in soybean by quantitative real-time RT-PCR. BMC Mol Biol. 10: 93. doi: 10.1186/1471-2199-10-93 PMCID: PMC2761916.

Hu X T, Owens M A (2011) Multiplexed protein quantification in maize leaves by liquid chromatography coupled with tandem mass spectrometry: An alternative tool to immunoassays for target protein analysis in genetically engineered crops. J Agr Food Chem 59: 3551-3558.

Jarvis, P (2008) Targeting of nucleus-encoded proteins to chloroplasts in plants. New Phytol 179: 257-85.

Kapila J, De Rycke R, Van Montagu M, Angenon G (1997) An *Agrobacterium*-mediated transient gene expression system for intact leaves. Plant Sci 122: 101-08.

Klein T M, Wolf E D, Wu R, Sanford J C (1987) High-velocity microprojectiles for delivering nucleic acids into living cells. Nature 327: 70-73.

Lassner M, Wilkinson J Q. Mar. 18, 2008. Plastid transit peptides. U.S. Pat. No. 7,345,143.

Lee D W, Lee S, Lee G, Lee K H, Kim S, Cheong G W, Hwang I (2006) Functional characterization of sequence motifs in the transit peptide of *Arabidopsis* small subunit of rubisco. Plant Physiol 140: 466-483.

Liu Z, Taub C C, McClung C R (1996) Identification of an *Arabidopsis thaliana* ribulose-1,5-bisphosphate carboxylase/oxygenase activase (RCA) minimal promoter regulated by light and the circadian clock. Plant Physiol 112: 43-51.

Loffelhardt W, Kindl H (1979) Conversion of 4-hydroxyphenylpyruvic acid into homogentisatisic acid at the thylakoid membrane of *Lemna gibba*. FEBS Lett 104: 332-34

Matringe M, et al. (2005) p-Hydroxyphenylpyruvate dioxygenase inhibitor-resistant plants. Pest Manage Sci 61: 269-76.

Moran G R (2014) 4-Hydroxyphenylpyruvate dioxygenase and hydroxymandelate synthase: Exemplars of the alpha-keto acid dependent oxygenases. Arch Biochem Biophys 544: 58-68.

Moshiri F, et al. Nov. 20, 2007. Genes encoding 4-hydroxyphenylpyruvate dioxygenase (HPPD) enzymes for plant metabolic engineering. U.S. Pat. No. 7,297,541.

Neidig M L, et al. (2005) Spectroscopic and computational studies of NTBC bound to the non-heme iron enzyme (4-hydroxyphenyl)pyruvate dioxygenase: Active site contributions to drug inhibition Biochem Biophys Res Commun 338: 206-214

Ness J E, Kim S, Gottman A, Pak R, Kreber A, Borchert T, Govindarajan S, Mundorff E C, Minshull J (2002) Synthetic shuffling expands functional protein diversity by allowing amino acids to recombine independently. Nature Biotech 20: 1251-255.

Norris S R, Meyer S E, Callis J (1993) The intron of *Arabidopsis thaliana* polyubiquitin genes is conserved in location and is a quantitative determinant of chimeric gene expression. Plant Mol Biol 21: 895-906.

Norsworthy J K, et al. (2012) Reducing the risks of herbicide resistance: Best management practices and recommendations. Weed Sci 60 supl 1: 31-62.

Odell J T, Nagy F, Chua N H (1985) Identification of DNA sequences required for activity of the cauliflower mosaic virus 35S promoter. Nature 313.6005: 810-12.

Ow D W, Jacobs J D, Howell S H (1987) Functional regions of the cauliflower mosaic virus 35S RNA promoter determined by use of the firefly luciferase gene as a reporter of promoter activity. Proc Natl Acad Sci USA 84:4870-4.

Raspail C, et al. (2011) 4-Hydroxyphenylpyruvate dioxygenase catalysis: identification of catalytic residues and production of a hydroxylated intermediate shared with a structurally unrelated enzyme. J Biol Chem 286:26061-70.

Ruiz-Sola M A, Rodriguez-Conception M (2012) Carotenoid biosynthesis in Arabidopsis: A colorful pathway. In The Arabidopsis Book, Number 10, The American Society of Plant Biologists, ttp://dx/doi.org/10.1199/tab.0158.

Saul H, et al. (2009) The upstream open reading frame of the Arabidopsis AtMHX gene has a strong impact on transcript accumulation through the nonsense-mediated mRNA decay pathway. Plant J 60: 1031-042.

Schein A I, Kissinger J C, and Ungar L H (2001) Chloroplast transit peptide prediction: A peek inside the black box. Nucleic Acids Res 29.16:E82.

Schmutz J, et al. (2010) Genome sequence of the palaeopolyploid soybean. Nature 465: 178-183.

Secor J (1994) Inhibition of barnyardgrass 4-hydroxyphenylpyruvate dioxygenase by sulcotrione. Plant Physiol. 106: 1429-1433.

Siehl, D L (1999) The biosynthesis of tryptophan, tyrosine, and phenylalanine from chorismate. In B Singh ed, Plant Amino Acids: Biochemistry and Biotechnology. Marcel Dekker, New York, pp 171-204.

Siehl D L, et al. (2007) The molecular basis of glyphosate resistance by an optimized microbial acetyltransferase. J Biol Chem 282:11446-55.

Simmons C R, Navarro, and Acevedo P A. Jun. 3, 2010. Gene promoter regulatory element analysis computational methods and their use in transgenic applications. US Patent Application No. 20100138952.

Smale S T, Kadonaga J T (2003) The RNA polymerase II core promoter. Ann Rev Biochem 72: 449-79.

Small I, et al. (1998) Two birds with one stone: Genes that encode products targeted to two or more compartments. Plant Mol Biol 38: 265-77.

Thatcher L F, et al. (2007) Differential gene expression and subcellular targeting of Arabidopsis glutathione S-transferase F8 is achieved through alternative transcription start sites. J Biol Chem 282:28915-28928.

Tzin V, Galili G (2010) New insights into the shikimate and aromatic amino acids biosynthesis pathways in plants. Mol Plant 3: 956-72.

Wen-Jun S, Forde B G (1989) Efficient transformation of spp. by high voltage electroporation. Nucleic Acids Res 17: 8385.

Yang C, et al. (2004) Structural basis for herbicidal inhibitor selectivity revealed by comparison of crystal structures of plant and mammalian 4-hydroxyphenylpyruvate dioxygenases. Biochemistry 43: 10414-0423.

Zannoni V G, Lomtevas N, and Goldfinger S (1969) Oxidation of homogentisic acid to ochronotic pigment in connective tissue. Biochim Biophys Acta 177: 94-105.

Zhang J H, Dawes G, and Stemmer WPC (1997) Directed evolution of a fucosidase from a galactosidase by DNA shuffling and screening. Proc Natl Acad Sci 94: 4504-509.

EXAMPLES

Example 1. Experimental Methods

Immuno-Localization Electron Microscopy

Briefly, native or heterologously expressed HPPD was tagged with affinity purified rabbit anti-HPPD antibodies, which were labeled with goat anti-rabbit F(ab') conjugated with µltrasmall gold particles (Aurion, The Netherlands). Gold labeling was followed by silver enhancement (Aurion). Sections were counterstained with 4% uranyl acetate (aqueous) followed by Reynold's lead citrate and examined by electron microscopy.

Genomic and Transcript Analysis

A synthetic maize wild-type HPPD cDNA (NCBI Reference Sequence: NM_001112312.1) was assembled from commercially synthesized oligonucleotides. During the synthesis of the gene, an NcoI restriction site was engineered into the start of the sequence to facilitate cloning. The change of codons (C)ATG CCC to (C)ATG GGT resulted in the substitution of glycine for proline at position 2. An EST (sgc5c.pk001.j9) coding for soybean HPPD was identified from a DuPont-Pioneer proprietary G. max EST database using conventional bioinformatic tools including BLAST of the HPPD sequence described in Cahoon and Coughlan (2007). The soybean HPPD coding region sequence was cloned from the EST cDNA into a T7-based bacterial expression vector. Expression, purification and characterization of the G. max HPPD protein proved that the encoded protein was a functional HPPD, able to catalyze the reaction from 4-hydroxyphenylpyruvate to homogentisate. Using this soybean HPPD coding sequence as query, Pioneer Unigene PSO409914 was identified. Search of the genome assembly database with the unigene as query resulted in identification of approximately 2 kb genomic sequence upstream of the EST. To validate the genomic sequence, polymerase chain reaction (PCR) primers (forward primer: GCAAGTATTTCAATACAATAGC (SEQ ID NO:84) and reverse primer: GTTATCTGATATGATGTTGC (SEQ ID NO:85)) were designed and used to amplify the HPPD locus from genomic DNA isolated from an elite soybean variety and the common Jack variety, following protocols for isolation of plant genomic DNA (Qiagen, Germantown, Md.). PCR reaction parameters were: Cycle 1: 94° C., 2 min; Cycle 2 to 30: 94° C., 30 s; 65° C., 1 min; 72° C., 5 min; Cycle 31: 72° C., 10 min. A proof-reading DNA polymerase, pfu Turbo (Stratagene, La Jolla, Calif.) was used for PCR amplification. A 4306 bp fragment and a 4310 bp fragment were obtained from elite and Jack, respectively. These fragments were cloned into Zero blunt TOPO PCR cloning vectors (Invitrogen, Carlsbad, Calif.) and fully sequenced. Each locus comprises 3' sequences, HPPD coding region, and upstream genomic sequence. The loci are highly conserved, with an overall 99% sequence identity at the nucleotide level. A 462 bp intron and a 459 bp intron in the HPPD coding region were identified in elite and Jack, respectively.

RNA ligation mediated 5' rapid cloning of cDNA ends (5' RACE) was used to validate transcription start sites for the native HPPD promoter using total RNA extracted from young soybean leaves and First Choice RLM-RACE kit (Ambion) per manufacturer's protocol. Total RNA was isolated with the Qiagen RNeasy mini kit. Linked transcription-translation was performed in wheat germ extracts using 3' truncated G. max HPPD transcription vectors. Tissue specific patterns of expression for G. max HPPD, EPSPS, ALS, and ACT2/7 genes were compiled from expression data in SoyBase (soybase.org) using the Soybean Breeder's Toolbox search.

Expression Vectors for Localization Microscopy

Vectors for transient expression in monocot species were constructed in which N-terminal fragments of monocot HPPD proteins or the soybean HPPD protein and the synthetic monocot consensus peptide were fused to the gene coding for Discosoma sp. red fluorescence protein 2 (DsRed2; Clonetech, Mountain View Calif.) and inserted into a binary expression vector under control of the maize rubisco activase promoter (Liu et al., 1996) or *Arabidopsis* Ubiquitin 10 promoter (Norris, et al., 1993) and terminated with the *Solanum tuberosum* proteinase inhibitor II (pinII) terminator region (An et al., 1989) with a hygromycin selection cassette. The vector also contained an untargeted Zs Green cassette to provide cytoplasmic contrast and a kanamycin selection cassette. All three genes were between left and right border sequences of *Agrobacterium* T-DNA. A positive control vector was identical except that the insert was DsRed2 fused to the chloroplast targeting peptide of *Arabidopsis* rubisco activase, while a negative control was DsRed2 with no targeting sequence.

A second set of florescent vectors was made with N-terminal fragments encoding either the maize or soybean N-terminal HPPD protein fragments fused to a gene encoding *Aequorea coerulescens* green fluorescent protein 1 (AcGFP1) and inserted into a binary expression vector under control of the *Arabidopsis* Ubiquitin 10 promoter (Norris et al., 1993) and terminated with the *G. max* Kunitz trypsin inhibitor 3 terminator region (NCBI accession S45092). Such vectors were used for either stable or transient gene expression in plant cells. Fusions for testing the soybean CTP function contained the sequence encoding amino acid residues 1-42 or 1-86 of the long *G. max* HPPD protein. Another contained the sequence encoding residues 1-44 of the short HPPD protein (corresponding to residues 42-86 of the long protein). A positive control vector was identical except that the AcGFP1 coding region was fused to the 6H1 synthetic chloroplast targeting peptide (Lassner and Wilkinson, 2008), while a negative control was AcGFP1 with no targeting sequence.

Promoter Constructs

Cassettes for testing transient expression of promoters were similar to the DsRed N-terminal test vectors except that *G. max* HPPD promoter-derived fragments replaced the rubisco and UBQ10 promoters. A 2061 bp fragment comprising the native HPPD promoter of elite *G. max* was created from the upstream genomic sequence. The PCR reaction used (forward primer hp0234: GTTTT CCGCGGGTGTTGATCC (SEQ ID NO:86) and reverse primer hp2296: TCATT GGTACCTGGTGTGGTGTGATGCTGC (SEQ ID NO:87)) introduced SacII and KpnI restriction sites. This fragment was isolated by gel-purification, digested with restriction enzymes SacII and KpnI, and ligated to a DsRed2 marker gene to form the native *G. max* HPPD promoter expression cassette. Introduction of the KpnI site between the promoter fragments and DsRed2 resulted in the introduction of a two amino acid linker (GGTACC gly-thr) in the fusion proteins containing the long protein CTP region.

The 1225 bp genomic sequence at the 3' end of the promoter fragment was subjected to in silico promoter analysis using Promoter REAPer and Promoter Delineator (Simmons and Navarro Acevedo, 2007). Genomic sequence from other species including *Arabidopsis thaliana*, *Medicago truncatula*, *Populus trichocarpa*, *Brassica rapa*, *Vitis vinifera*, and the monocot *Sorghum bicolor* were included for comparison in this analysis. With the program Promoter REAPer, regions were identified in the soybean HPPD promoter that are predicted to be important for its activity based on the sequence conservation of a set of DNA motifs across the seven plant species. To evaluate the predicted TATA boxes in promoter activity, a deletion series was created with the 2061 bp template using PCR with forward primer hp0234: GTTTTCCGCGGGTGTTGATCC (SEQ ID NO: 86) and the reverse primers as follows: SHP103C, hp2154: AGCATGGTACCTTGCGTCTGGGTTGAG (SEQ ID NO:88); SHP110C, hp2048: ATCTGGTACCTGATGTT-GATGCGGC (SEQ ID NO:89); SHP000C, hp1962: AGGAGGTACCGTCAAATCCACCTAG (SEQ ID NO:90); SHP102C, hp1791: AGCCTGGTACCTTGTGTGTAAAAAAGATAAGAC (SEQ ID NO:91); and SHP101C, hp1663: TCCTTGGTACCTGATGCACTATATAACG (SEQ ID NO:92). Single or triple mutations in the putative TATA boxes (see Table 4) were created using site-directed mutagenesis (Quick Change, Stratagene). Resultant deletion and mutated promoter fragments were fused with DsRed2 to create cassettes for analysis of expression activity in agro-infiltrated leaf tissues.

SHP101C and SHP102C lack promoter activity due to deletion of active TATA binding sites. To create synthetic promoters using these non-promoter DNA fragments, synthetic element I or II, each flanked by restriction sites XhoI and KpnI, were synthesized and ligated with the 3' ends of the HPPD promoter-derived DNA fragments to create SHP101 and 201 and SHP102 and 202, respectively. Synthetic element I comprises the SynII core (Bowen et al., 2000; sequence 1) sequence followed by the 45 bp putative 5'UTR sequence including the predicted transcription start site from the soybean native HPPD gene (ACAACCAC-CAAGCTCAATCTCAAGCAGCAGCATCACAC-CACACCA (SEQ ID NO:93), nucleotides between TATA3 and ATG). Synthetic element II contains the Rsyn7 region (Bowen et al., 2000, sequence 2) immediately upstream of synthetic element I. In a similar manner, promoters SHP103, 104, 105, 106, 107, 108, and 109 were created with element I and SHP203, 204, 205, 206, 207, 208, and 209 were created with synthetic element II. In SHP110, a partial SynII core sequence is inserted in place of TATA5. In SHP210, TATA5 through transcription start site at −237 is deleted and replaced with Rsyn7 plus the partial SynII core sequence. SHP110e is the same as SHP110 with the addition of a CaMV enhancer (Ow et al., 1987) at the 5' end of the promoter fragment. In SHP111, the sequence encompassing TATA3 through transcription start site at +1 is deleted and replaced with the partial SynII core sequence. In SHP120C an A to T mutation eliminates the start codon of the upORF element.

*Agrobacterium*-Infiltration and Florescence Measurements

All seedling plants were grown in growth chambers with 16 hr light at 375-450 μm m$^{-2}$ s$^{-1}$, 26° C. day and 22° C. night. Expression plasmids for localization studies were transformed into *Agrobacterium tumefaciens* AGL-1 via electroporation according to Shen and Forde (1989) and agro-infiltration (Kapila et. al., 1997) used to introduce the constructs into plant cells. *Agrobacterium* cultures were grown overnight in LB with 40 mg/L kanamycin and a working suspension normalized to 1.0 OD$_{600}$ in 10 mM MgSO$_4$, 400 μm acetosyringone and 1 mM DTT. Leaves of 3-week old maize or sorghum seedlings were infiltrated with the *Agrobacterium*, and examined by fluorescence microscopy two days later (Nikon Eclipse 80i, DsRed2 filter set). Infiltrated leaf samples were derived from plants of uniform developmental stage grown under the same conditions. Leaves of 4-week old *Nicotiana benthamiana*, 8-day old *Phaseolus vulgaris*, (variety Shade) and 10-day old *Glycine max* seedlings were infiltrated with the *Agrobacterium*, and examined by fluorescence microscopy 4 and 5 days later.

*Agrobacterium* strains expressing plasmids for promoter characterization were infiltrated into bush bean leaf tissues. Visual analysis confirmed that the native *G. max* HPPD promoter DNA fragment was able to drive the expression of DsRed2 in infiltrated leaf tissues compared with fluorescent background from leaf tissues infiltrated with a negative control construct consisting of the dMMV promoter (Dey and Maiti, 1999) driving a beta-glucuronidase reporter. Relative promoter strength was determined by quantitative measurement of the red fluorescence generated from expressed DsRed2 protein in infiltrated leaf tissues. Red fluorescence from 50 μg of protein extracted from infiltrated leaf discs was quantified using a Typhoon Trio+ Variable Mode Imager. Infiltration experiments for each construct were repeated at least three times. The background red fluorescence detected in leaves infiltrated with the negative control vector was subtracted for data normalization. The DsRed2 readouts were used to calculate the level of DsRed2 from each construct relative to the DsRed2 expressed from the full native promoter construct (2061 nucleotides 5' to the ATG of the short protein), which was set to 100%. Up to 30 leaf discs infected with the same culture were pooled for analysis. Each pool of infiltrated leaf samples represented (about 260 mg fresh weight) tissue equally derived from 15 plants of uniform developmental stage.

Qualitative assessment of promoter strength was determined 4-5 days post-infection by visually inspecting treated samples under a stereo fluorescent microscope (Leica Microsystems—Wetzlar, Germany); M165 FC with DsRed2 Filter set; Ser. No. 10/447,412), and acquiring images (Leica Microsystems—Wetzlar, Germany; DFC300 FX R2) of representative examples at fixed exposure time of 7 seconds.

HPPD Expression and Purification

A synthetic maize wild-type HPPD gene (referred to herein as the maize wild-type sequence) was assembled from commercially synthesized oligonucleotides to deliver the amino acid sequence of SEQ ID NO:1. During the synthesis of the gene, an NcoI restriction site was engineered into the start of the sequence to facilitate cloning. The change of codons (C)ATG CCC to (C)ATG GGT resulted in the substitution of *Glycine* for Proline at position 2 in SEQ ID NO:1 compared to the maize wild-type protein of WO 1997049816 SEQ ID NO:11.

Wild type and shuffled variant genes were cloned into pVER7062, a modified version of pET24a(+)(Novagen), which places six histidine residues at the N-terminus of the expressed protein. Vectors were electroporated into *E. coli* host strain BL21(DE3). Cells were grown at 30 C in rich medium such as 2×YT containing the selection antibiotic, kanamycin. At a density of about 0.6 OD600, IPTG was added to 0.2 mM, the temperature was reduced to 16 C and growth continued for another 24 hrs. Cells were harvested by centrifugation and stored at −80 C. Cell pellets were lysed in BPER (Pierce) protein extraction reagent containing 0.2 mg/ml lysozyme, 1 mM dithiothreitol, protease inhibitor cocktail (Sigma, bacterial cocktail) and endonuclease. Insoluble cellular debris was removed by centrifugation. HPPD protein was purified from the soluble protein solution by affinity chromatography on the nickel form of nitrilotriacetic acid (Ni-NTA) resin (Qiagen). Protein concentrations were determined by the Bradford method, as supplied by Bio-Rad.

Medium Browning Assay

The homogentisate produced by the HPPD reaction is not further metabolised by *E coli*, but is converted to a brown ochronotic pigment (Zannoni V G et al., Biochimica Et Biophysica Acta 177: 94-105, 1969) Therefore, *E. coli* cells expressing active shuffled maize HPPD enzyme turn the medium brown, which constituted a convenient first tier screen. The screen was made more informative by including an HPPD inhibitor in the medium, requiring that the HPPD variant be desensitized to inhibition as well as active. The intensity of browning was quantified by measuring absorbance at 360 nm. Those wells with absorbance greater that the appropriate standard were advanced to more refined screens involving in vitro enzyme assay.

HPPD Activity Assay

HPPD catalyzes the conversion of 4-hydroxyphenylpyruvate (HPP) to homogentisate (FIG. 17). Substrate and product do not differ in absorbance of light at any useful wavelength. However, the product of the ensuing reaction in tyrosine metabolism, maleylacetoacetate, absorbs strongly at 320 nm. Furthermore, the enzyme catalyzing that reaction is also a dioxygenase having similar mechanism and buffer requirements as HPPD, making homogentisate dioxygenase (HGD) an ideal partner in a coupled assay, as shown.

The HDG gene from *Pseudomonas aeruginosa* (Amaya (2004) *Arch Biochem Biophys* 421, 135-142) was cloned into pVER7062 and electroporated into *E. coli* strain BL21 (DE3). The enzyme was produced by methods similar to those described for HPPD. The purified enzyme has a $K_M$ for homogentisate of 23 μM and a $k_{cat}$ of 100/sec, properties highly suited for instantly converting the homogentisate produced by HPPD to maleylacetoacetate.

HPPD activity was measured by placing an aliquot (e.g., 6 μl) of the substrate HPP at 50-fold the desired final concentration into the wells of a low UV-absorbing assay plate. Reactions were started by adding a mixture (e.g., 294 μl) containing 25 mM Hepes, pH 7, 2 mM ascorbate, 10 μM FeSO4, 1 to 100 μM HPP, 50 nM HGD and 5 to 240 nM HPPD. Absorbance at 320 nm was monitored continuously in a plate-reading spectrophotometer (Spectramax, Molecular Devices).

HPPD Kinetic Parameters

The catalytic performance of wild-type HPPD and variants generated by shuffling was assessed by determining the substrate saturation kinetic parameters. The Michaelis-Menten kinetics protocol of the Spectramax software was customized for HPP concentrations ranging from 3.33 μM to 100 μM. Reaction rates were measured as described above for each concentration of HPP. The software returns values of $K_M$ and Vmax using the Lineweaver-Burke transformation of the Michaelis-Menten equation.

HPPD Inhibitor Sensitivity Parameters

The major HPPD inhibitors used in agriculture today are mesotrione, isoxaflutole, tembotrione, and topramezone. As seen in FIG. 1, the structures share an aromatic ring and a pair of keto oxygens in common with the substrate 4-hydroxyphenylpyruvate, for which they are competitive inhibitors (Secor, 1994). The elements in which the inhibitors differ from the substrates (e.g., cyclohexane ring, substituents on the aromatic ring) present the opportunity to use gene shuffling to enable the enzyme to discriminate between the desired and undesired ligands. All herbicidal inhibitors of HPPD form a tight complex with the enzyme by the dual mechanisms of coordination to the active site iron atom through a pair of keto oxygens and a pi stack of the aromatic ring of the inhibitor between a pair of active site phenylalanines (Neidig et al., 2005). As a result, conventional $I_{50}$ determinations are not able to distinguish differences in binding affinity among various forms of HPPD and the inhibitor. All values will similarly approximate 50% of the enzyme concentration.

To devise a parameter for detecting changes in inhibitor binding affinity, $K_D$, one can utilize the relationship between $K_D$ and the rates of binding and release of inhibitor to and from the enzyme.

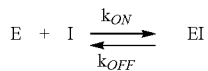

$$E + I \underset{k_{OFF}}{\overset{k_{ON}}{\rightleftarrows}} EI$$

At equilibrium, rates of binding and release are equal. Thus, $$k_{ON}[E][I]=k_{OFF}[EI]$$

Written as a dissociation (products over reactants), the equation can be re-arranged to:

$$\frac{[E][I]}{[EI]} = \frac{k_{OFF}}{k_{ON}} = K_D$$

Figure 13A:
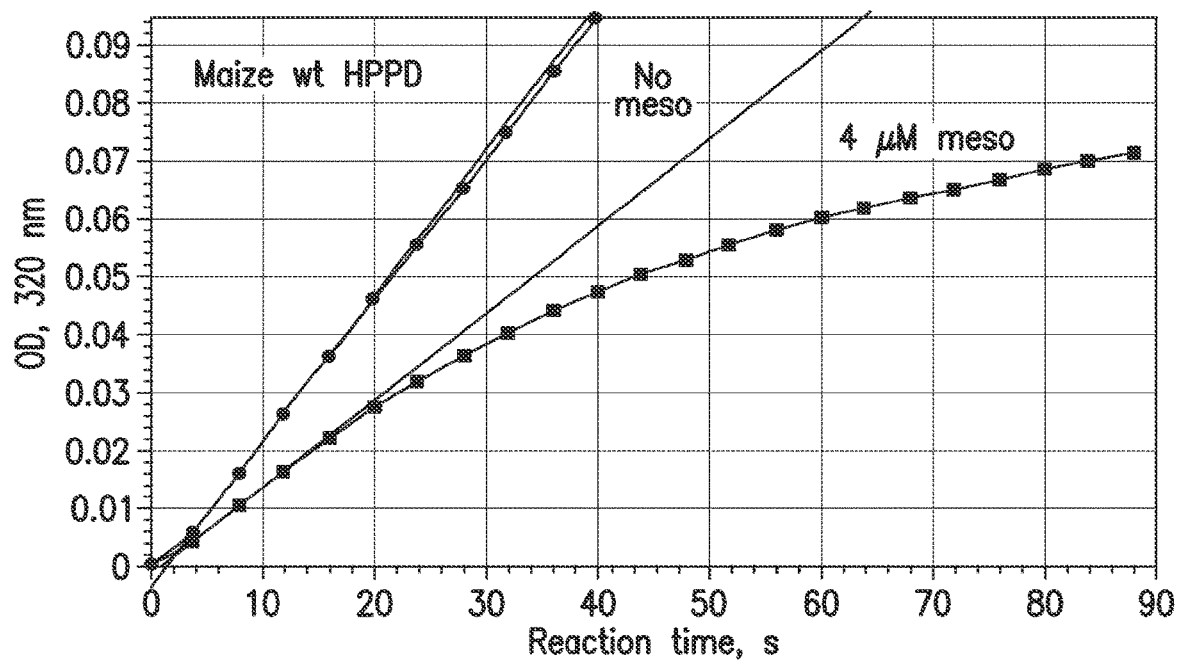
FIGS. 13A-13D. Indirect measurement of rates of association and dissociation of inhibitors and HPPD. Rates of association ($k_{ON}$) are represented by inactivation during catalytic turnover. At time 0, reactions are started with the simultaneous addition of HPP and inhibitor to an aliquot of enzyme. Reaction rates in the 70 to 90 sec interval are recorded and expressed as the ratio of the rate with inhibitor to that with no inhibitor.
Figure 13B:
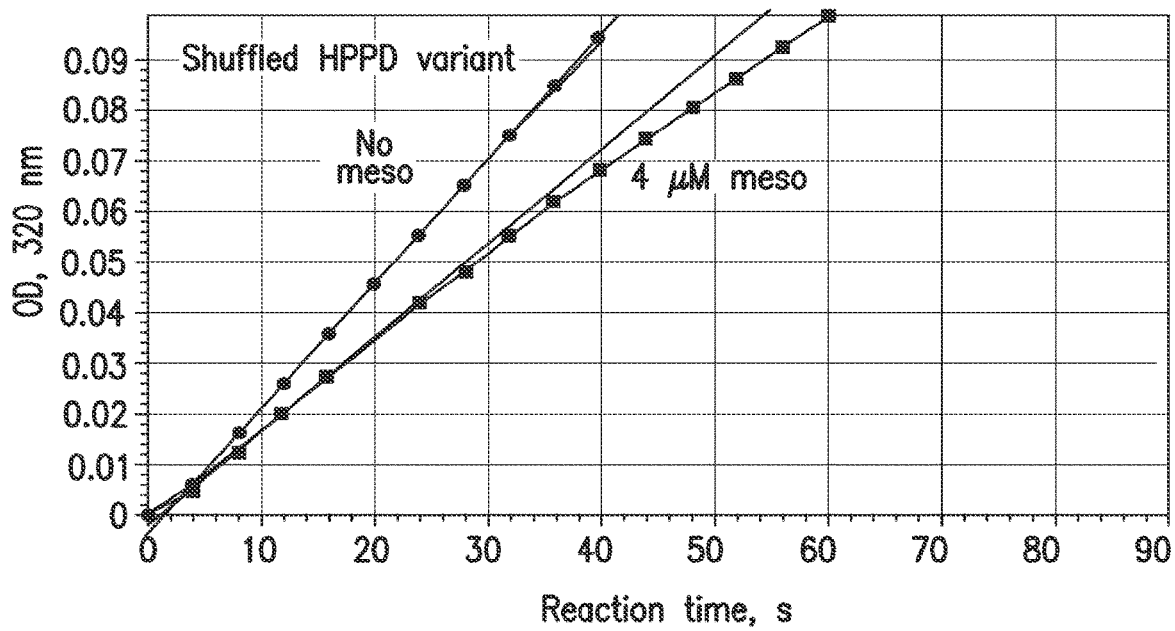

Higher $K_D$ (reduced affinity or increased insensitivity) can be attained with a numerically smaller ON rate, a larger OFF rate or both. To detect and quantify changes in $k_{ON}$ and $k_{OFF}$, observations of the time course of an HPPD reaction as inhibitor binds to and inactivates the enzyme ($k_{ON}$), or is released from a pre-formed enzyme-inhibitor complex ($k_{OFF}$) were used, as shown in FIGS. 13A and 13B. In practice, a quantitative indicator of $k_{ON}$ was obtained by monitoring the time courses of HPPD reactions containing 60 or 120 nM HPPD and 100 µM HPP in the presence and absence of 4 µM inhibitor (e.g., mesotrione or tembotrione). The ratio of the reaction rate with inhibitor to that without inhibitor during the 70 to 90 second interval of the reaction was termed the "ON rate ratio". The smaller the actual $k_{ON}$, the more slowly the HPPD reaction decelerates and the higher the value is for the ON rate ratio. FIGS. 13A and 13B illustrate the contrasting reaction velocity in the 70-90 sec interval for maize wild-type HPPD (FIG. 13A) versus an improved variant (SEQ ID NO:78) (FIG. 13B).

A quantitative indicator of $k_{OFF}$ can be obtained by observing the time course of an HPPD reaction as inhibitor is released from a pre-formed enzyme-inhibitor complex. HPPD and inhibitor were incubated together at concentrations of 7.2 and 8 µM, respectively. Incubations with the same concentrations of enzyme but no inhibitor were done in parallel. After 1 hr at room temperature, 5 to 10 µl of the enzyme-inhibitor complex was dispensed into the wells of the assay plate. Reactions were started with the addition of 290 to 295 µl of 25 mM Hepes, pH 7, 2 mM ascorbate, 10 µM FeSO$_4$, 100 µM HPP and 50 nM HGD. The reactions were monitored at 320 nm for 12 min. Reaction velocity accelerates as inhibitor is released from the enzyme until a steady state is reached, during which the reaction velocity is constant. The ratio of the steady state rate in mixtures containing herbicidal inhibitor to the initial velocity of mixtures lacking inhibitor is termed the "OFF rate ratio".

Figure 13C:
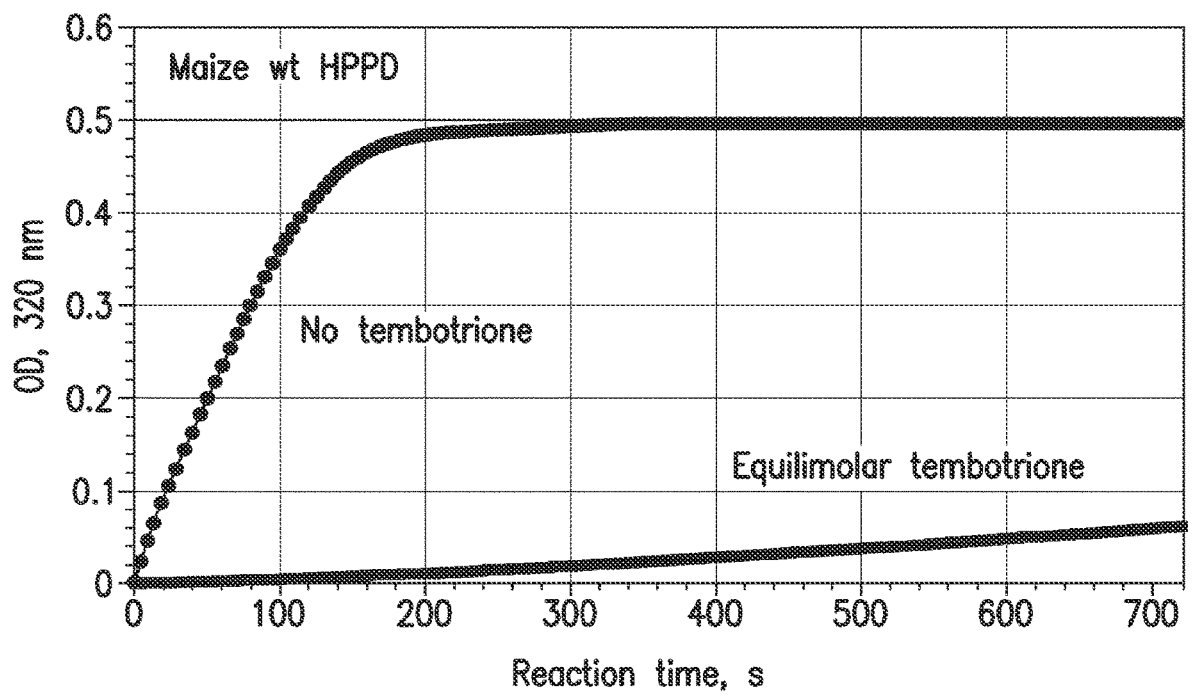
Figure 13D:
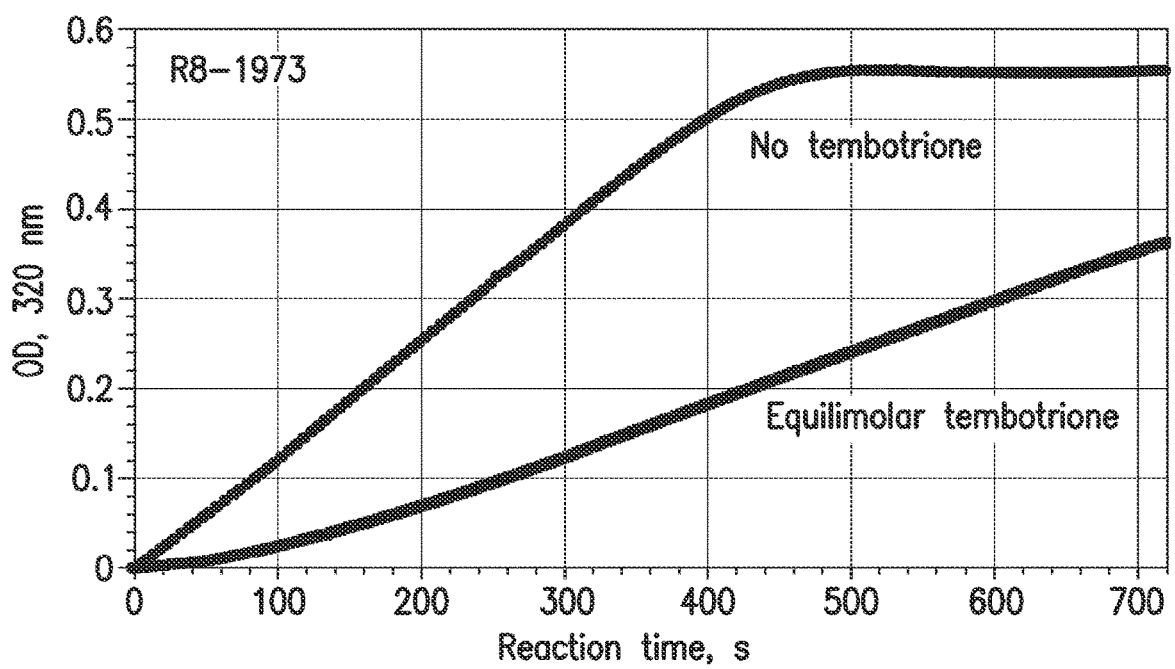

Another parameter to record is the time span required for the reactions with inhibitor to reach the steady state. FIGS. 13C and 13D illustrate the contrasting time span in which maize wild-type HPPD (FIG. 13C) and an improved variant (SEQ ID NO:78) (FIG. 13D) dissociated from mesotrione, as indicated by the accelerating reaction rates. The plateau of absorbance is due to exhaustion of the substrate. With the improved variant, not only was the steady state attained in a shorter time span (80 sec for the variant versus 280 sec for wild type), the velocity attained was twice as high as with wild type, though the enzymes were present at the same concentration (240 nM). This is because a larger fraction of the variant enzyme is free of inhibitor compared to the wild-type enzyme, and the $k_{cat}$ for both is nearly the same, about 220 min$^{-1}$.

It is not certain that the steady state attained in the OFF rate reactions actually represents an equilibrium where OFF rates are now equal to ON rates. Because substrate and inhibitors bind in the same site, the high concentration of substrate present may competitively trap the inhibitor and prevent it from binding again. To be sure that improvement in ON rates is being taken into account, the ON and OFF rate ratios were multiplied, creating an "insensitivity parameter" that is a surrogate for $K_D$. $K_D$ is expressed as $k_{OFF}/k_{ON}$, but because the ON rate ratio is an inverse parameter (the higher the value of ON rate ratio, the lower the value of the represented phenomenon, $k_{ON}$), it is appropriate to multiply ON and OFF rate ratios rather then divide OFF rate ratio by ON rate ratio. Another parameter, which quantifies the combined catalytic and insensitivity properties of the enzyme is $k_{cat}/K_M \times$ ON rate ratio $\times$ OFF rate ratio, and is termed "trait fitness". This parameter is intended to have a meaning similar to the commonly used expression $k_{cat}/K_M \times K_i$.

The diketonitrile form of isoxaflutole was synthesized by DuPont chemists. All other inhibitors were obtained from Sigma-Aldrich. The compounds shown in FIG. 16 can be synthesized by previously described methods known to one skilled in the art.

HPPD Protein Detection in Planta

HPPD protein concentration in young soybean leaves was measured using LC-MS/MS (liquid chromatography coupled with tandem mass spectrometry) according Hu and Owens (2011) with some modifications. 600 µL of PBST buffer were added to extract 10 leaf punches after being lyophilized and ground with Spex Certiprep 2000 GenoGrinder. The total extracted proteins (TEP) were measured with Bradford assay and all the samples were normalized to 0.8 µg/µL TEP. 50 µL normalized transgenic extracts were used for analysis and different amount of protein standards were spiked into 50 µL of negative tissue extracts to prepare standard curves. All samples were then heated for 15 min at 95° C. oven and 80 µL digestion buffer ABCT (100 mM ammonium bicarbonate with 0.05% Tween-20) was added. The samples were reduced with 6 µL of 0.25 M dithiothreitol at 50° C. for 30 min and then were alkylated with 6 µL of 0.3 M iodoacetamide at room temperature in the dark for 30 min. 1 µg of trypsin (in 10 µL) was added to each sample and digestion lasted about 18 hours before 10 µL 10% (v/v) formic acid and 10 µL internal standard (peptide SIEDYEK where K was labeled with sTable 2sotopes $^{13}$C and $^{15}$N) were added. HPPD protein was quantified by its signature tryptic peptide SIEDYEK using Waters UPLC coupled with AB SCIEX QTRAP 4000 or 5500. Autosampler temperature was kept at 5° C. during analysis. 10 µL were injected onto an Aquasil 100×2.1 mm 3µ C18 column (ThermoFisher) kept at 60° C. Mobile phases consisted of 0.1% formic acid (MPA) and 0.1% formic acid in acetonitrile (MPB), and LC was performed at a flow rate of 0.6 mL/min with linear gradient of 5-16% MPB in 2.5 min. The MRM transitions of 442.3/683.3 and 446.3/691.3 were monitored for peptide SIEDYEK and its internal standard peptide, respectively. Chromatogram peak area ratios to the corresponding IS were plotted against protein concentrations. The limit of quantifiable detection of HPPD by mass spec analysis is about 0.003% of total extractable protein (30 ppm, Hu and Owens, 2011)

Stable Soybean Transformation

Soybean plants expressing HPPD variant transgenes were produced using the method of particle gun bombardment (Klein et al., 1987) using a DuPont Biolistic PDS1000/He instrument. A selectable marker used to facilitate soybean transformation was a chimeric gene composed of the S-adenosylmethionine synthase (SAMS) promoter (Falco and Li, 2010) from soybean, a highly resistant allele of soybean acetolactate synthase (Bedbrook et al., 1997), and the native soybean acetolactate synthase terminator region. The selection agent used during the transformation process was chlorsulfuron. HPPD genes were expressed with a synthetic constitutive promoter (Bowen et al., 2000) or the *G. max* HPPD derived promoters, an insensitive HPPD variant, and an *Arabidopsis* ubiquitin3 gene terminator (Callis et al., 1995). Bombardments were carried out with linear DNA fragments purified away from any bacterial vector DNA. The selectable marker gene cassette was in the same DNA fragment as the HPPD cassette. In some cases the characterized CTP sequences 6H1 (Wilkinson and Lassner, 2008) and the *Arabidopsis* rubisco large subunit CTP (Lee et al., 2006) were fused to a truncated maize HPPD variant. Bombarded soybean embryogenic suspension tissue was cultured for one week in the absence of selection agent, then placed in liquid selection medium for 6 weeks. Putative transgenic suspension tissue was sampled for PCR analysis to determine the presence of the HPPD gene. Putative transgenic suspension culture tissue was maintained in selection medium for 3 weeks to obtain enough tissue for plant regeneration. Suspension tissue was matured for 4 weeks using standard procedures; matured somatic embryos were desiccated for 4-7 days and then placed on germination induction medium for 2-4 weeks. Germinated plantlets were transferred to soil in cell pack trays for 3 weeks for acclimatization. Plantlets were potted to 10-inch pots in the greenhouse for evaluation of herbicide resistance.

Herbicide Tolerance Testing

T0 plants with HPPD transgenes were grown to the V2 to V8 growth stage and then sprayed with commercial mesotrione formulation at rate 210 g ai/ha (two times the labeled rate for corn in the field). All mesotrione treatments were applied with 0.25% nonionic surfactant and 1% ammonium sulfate in a spray volume of 374 L/ha. Individual plants were compared to untreated plants of similar genetic background, evaluated for herbicide response at eight days after treatment and assigned a visual response rating from 0 (no effect) to 100 (dead plant). Sibling plants were similarly evaluated with tembotrione at 93 g ai/ha. Protein expression level was determined by mass spectrometry (Hu and Owens, 2011). In the T0 generation, plants that had improved tolerance compared to controls based upon low injury scores (≤30%) were advanced to the T1 generation for more extensive herbicide testing. When sibling clones of the events were available, the same process was carried out on T0 plants using tembotrione.

T1 plants were evaluated for zygosity. Homozygous single-locus transgenic plants and their corresponding null segregants were identified and T2 true breeding seed was obtained from each. Plants were grown to the V1 to V2 growth stage and then sprayed with the commercial formulation of mesotrione at 420 g ai/ha. All treatments were applied with nonionic surfactant and ammonium sulfate in a spray volume of 374 L/ha. Ratings of response to the herbicide were made eight days after treatment, as described for T0 plants.

Homozygous T3 generation seeds were planted in short rows in Johnston, Iowa at a DuPont Pioneer regulated field location. Herbicides were applied at the V4 stage with a backpack sprayer in a spray volume of 140 L/ha at two or four times the labeled rates for corn in the field, which are: mesotrione, 118 g ai/ha; tembotrione, 90 g ai/ha; isoxaflutole, 67 g ai/ha. All treatments included 0.25% v/v nonionic surfactant and 8 lb/100 gal ammonium sulfate. As negative controls, rows of non-transformed plants of the same variety were sprayed at the same rates. Positive control rows received no spray. Visual injury was rated at 3, 7, and 14 days after treatment (DAT).

Example 2. Bioinformatic and Functional Localization Analysis of *Z. mays* (Maize) HPPD A single HPPD gene was identified in *Z. mays* via genomic and EST database searches (NCBI Reference Sequence: NM_001112312.1) giving rise to a 444 amino acid encoded protein (FIG. 3A). ProtComp 6.1 (linux1.softberry.com/berry.phtml) indicated a cytosolic location of maize HPPD (cytoplasmic score=14470; chloroplastic score=1.4). Similarly, WoLF PSORT (Horton et al., 2007) and TargetP (Emanuelsson et al., 2000) predict a cytosolic location of the HPPD protein. PCLR (Schein et al., 2001) predicts non-chloroplast localization with either the N-terminal 55 residues or the whole protein (0.25 with 0.42 threshold), Protein Prowler (Hawkins and Boden, 2006) predicts either a mitochondrial (0.34) or chloroplast (0.39) location and Multiloc (Hoglund et. al., 2006) predicts an extracellular (0.74) localization with the first 50 amino acids of maize HPPD, but a strong chloroplast localization (0.97) for the full maize HPPD sequence.

Figure 10A:
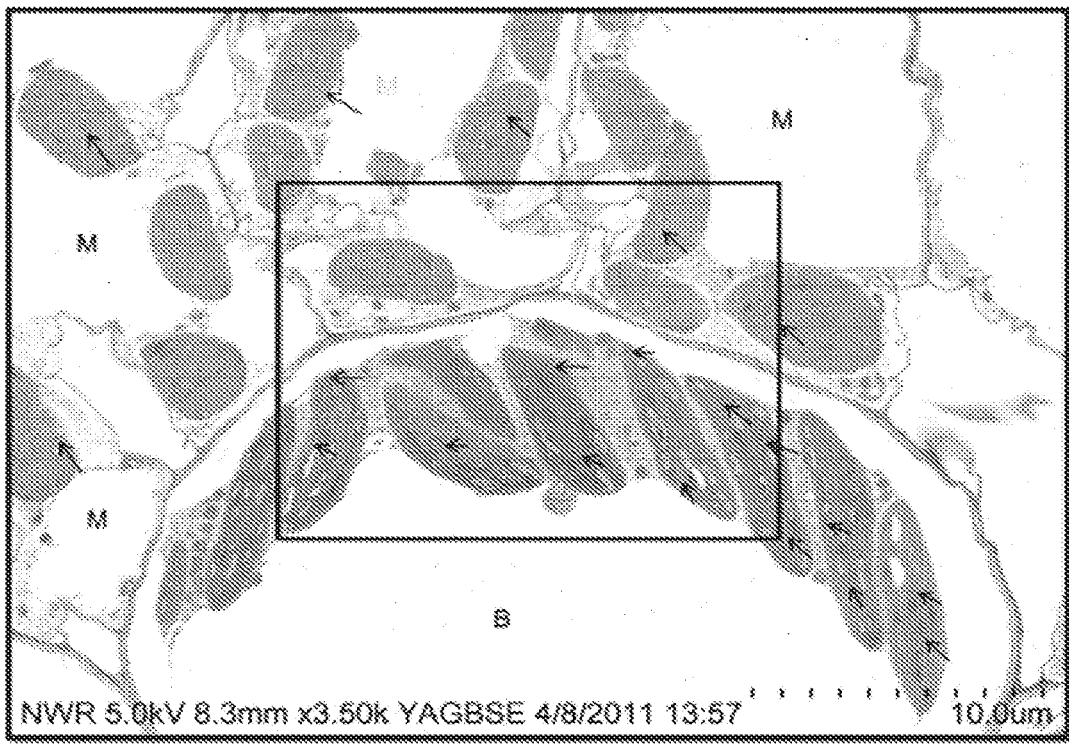
FIGS. 10A and 10B.
Figure 10B:
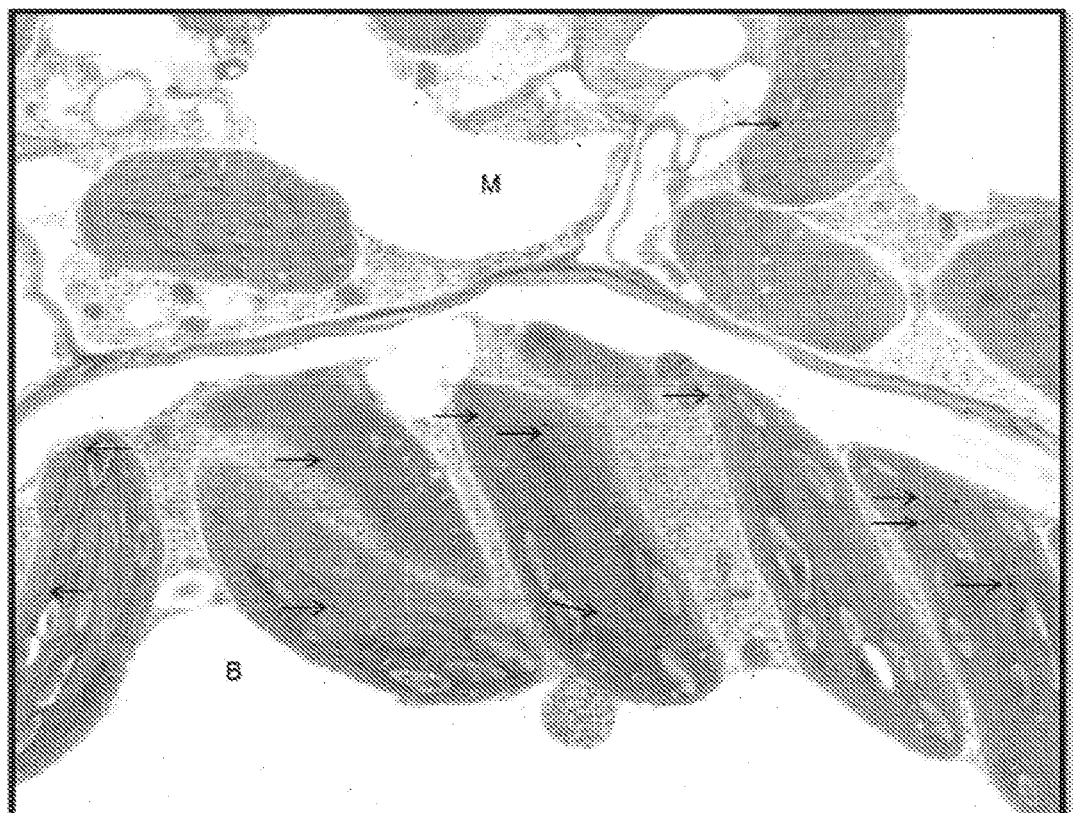
Figure 11A:
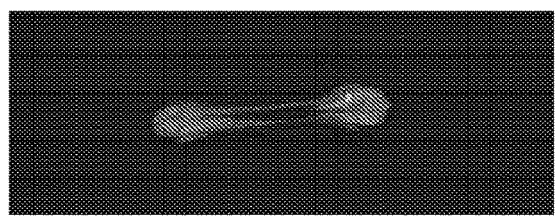
FIGS. 11A-11J. The N-terminal 50 amino acids of maize HPPD directs fluorescent protein to the chloroplasts of maize leaf guard cells.
Figure 11B:
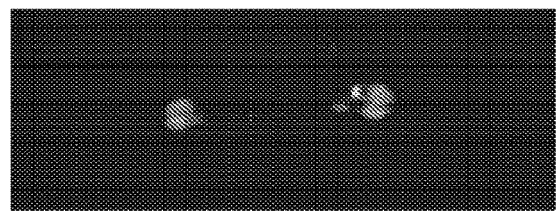
Figure 11E:
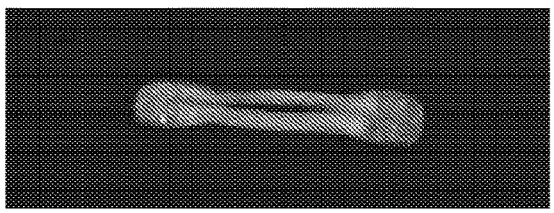
Figure 11F:
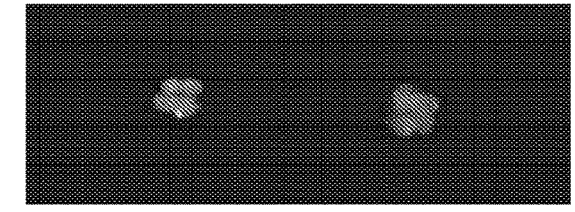
Figure 11G:
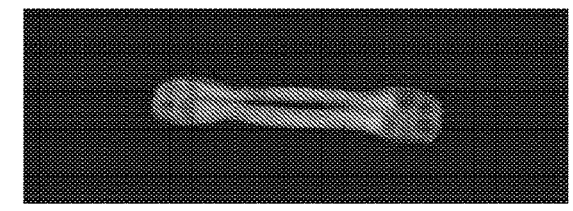
Figure 11C:
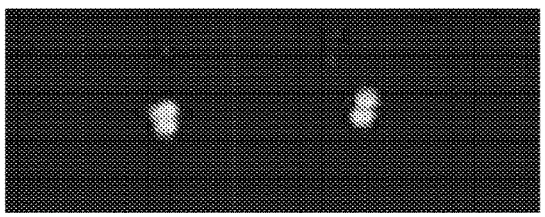
Figure 11D:
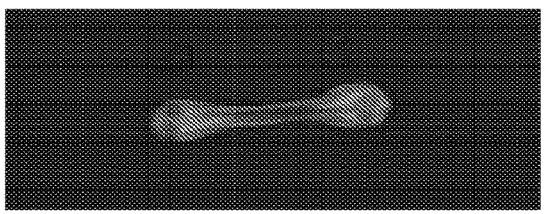
Figure 11H:
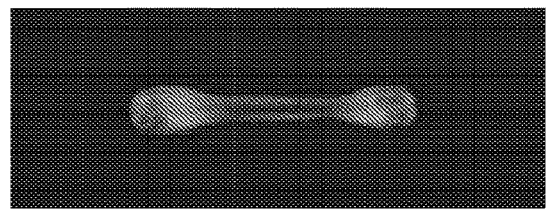
Figure 11I:
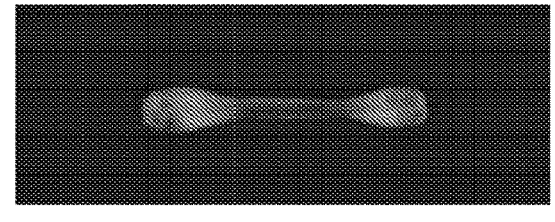
Figure 11J:
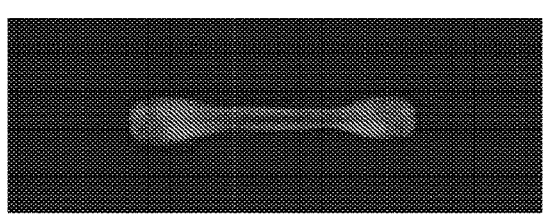

Immuno-localization electron microscopy of maize tissue sections was carried out to detect native HPPD localization. Gold labeling was observed mainly in bundle sheath chloroplasts (range; 5-28 particles per chloroplast, 50 chloroplasts observed (FIG. 10). Particles were also found in mesophyll chloroplasts, but in no other structures. Observations with direct detection of HPPD in maize tissues by labeling, protein purification using antibody pull-down, and mass-spectrometric protein detection all indicated that HPPD accumulation in maize leaves is very low.

To functionally corroborate the localization of maize HPPD, a binary plant transformation vector was constructed in which the portion of the maize HPPD gene coding for the N-terminal 50 amino acids was fused to the gene coding for DsRed2 all under control of the maize rubisco activase promoter. A positive control vector was identical except that the DsRed2 insert was fused to the chloroplast targeting peptide (CTP) of maize rubisco activase, while a negative control was DsRed2 with no targeting sequence. The plasmids were transformed into *Agrobacterium tumefaciens* AGL-1 and *Agrobacterium*-infiltration was used to introduce the constructs into plant cells for transient expression. *Agrobacterium*-infiltration is a well described method (Kapila et. al., 1997) of introducing an *Agrobacterium* cell suspension to plant cells of intact tissues so that reproducible infection and subsequent plant derived transgene expression may be measured or studied. Leaves of 3-week old maize seedlings were infiltrated with the *Agrobacterium*, and examined by fluorescence microscopy of hand sections two days later. With the vector where DsRed2 was fused to rubisco activase CTP, red fluorescence was seen in discrete packets in a pattern resembling peri-nuclear chloroplasts, as expected (FIG. 3B). A similar pattern was seen when DsRed2 was fused to the N-terminal 50 amino acids of maize HPPD (FIG. 3C). Without targeting, fluorescence was diffuse with some concentration in the nucleus (FIG. 3D). In another experiment confirming these results, maize leaf tissue was co-bombarded with DNA from both the DsRed2-containing test plasmids and a plasmid encoding untargeted cycle 3 green fluorescence protein (C3GFP). Transformation of guard cells with vectors encoding either rubisco activase CTP-DsRed2 or the N-terminal 50 amino acids of maize HPPD fused to DsRed2 clearly resulted in plastid targeting of the DsRed2 reporter, whereas untargeted C3CFP showed no overlap with the DsRed2 signal (FIG. 11).

Figure 3F:
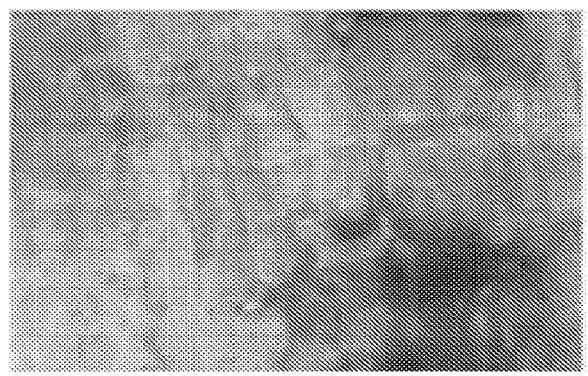
Figure 3G:
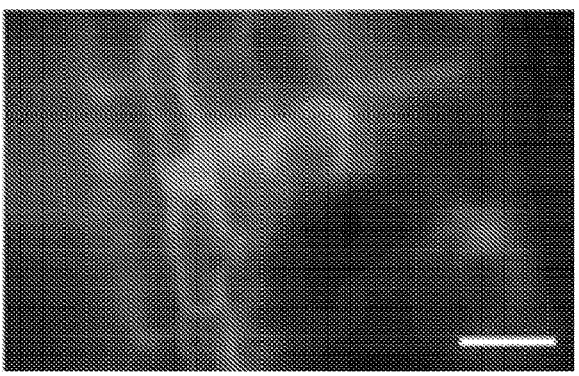

To determine the length of the functional CTP for maize HPPD, vectors were constructed in which the portion of the maize HPPD gene coding for the N-terminal 0, 10, 20, 30, 40 or 50 amino acids was fused to the gene coding for DsRed2 and evaluated with transient expression following agro-infiltration of maize leaves. Microscopy revealed that 50 amino acids of the maize HPPD N-terminus effectively targeted DsRed2 to plastids (FIG. 3G), but 40 amino acids or fewer failed to do so, with DsRed2 fluorescence visible only in the cytoplasm (FIGS. 3E and 3F). This result indicates that more than 40 amino acids of the N-terminus are required for chloroplast localization and that 50 amino acids is sufficient for targeting.

Figure 3H:
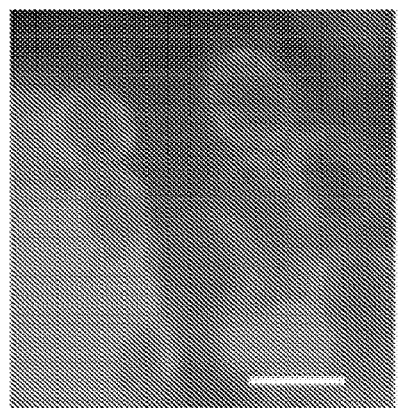
Figure 3I:
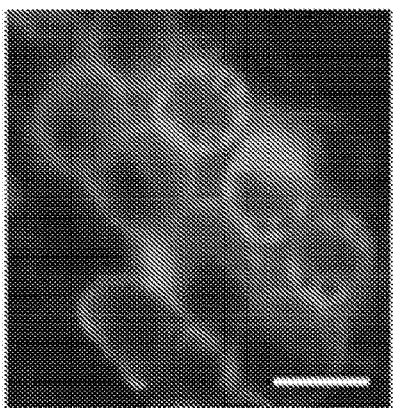
Figure 3J:
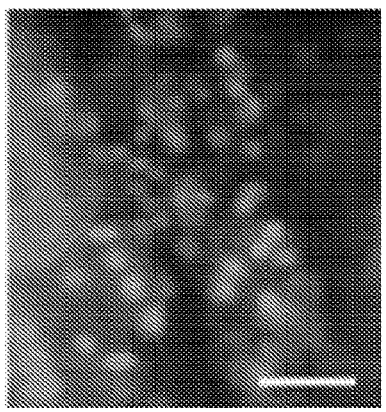
Figure 3K:
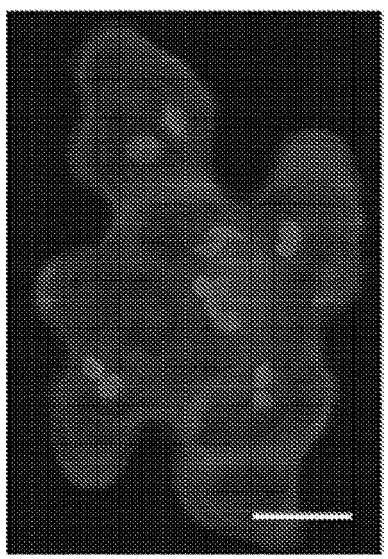
Figure 3L:
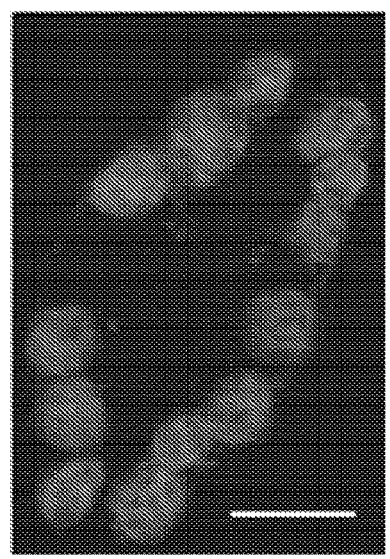
Figure 3M:
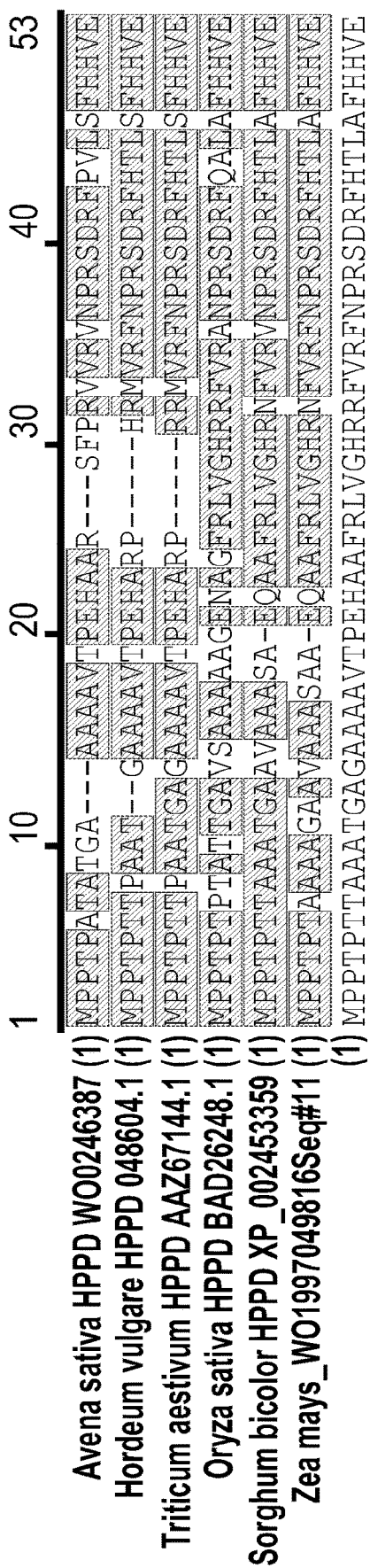

To investigate if the maize HPPD protein is unique, several monocot sequences were compared. FIG. 3J provides an N-terminal alignment of monocot HPPD proteins having identities of 59-85%. A vector constructed in which the Oryza sativa HPPD N-terminal sequence was fused to the gene coding for DsRed2 was assayed in maize leaves as described. Microscopy revealed that the 53 amino acid rice N-terminal sequence effectively targeted DsRed2 to maize plastids. In view of the conservation among the sequence of the monocot HPPD proteins, a consensus monocot HPPD chloroplast targeting peptide sequences was determined. The consensus sequence, MPPTPTTAAATGAGAAAAVT-PEHAAFRLVGHRRFVRFNPRSDRFHTLAFHHVE (SEQ ID NO:94), targeted the DsRed2 protein to the maize chloroplasts. To further confirm the monocot functional similarity, the vectors targeting DsRed2 with 0, 10, 20, 30, 40, and 50 amino acids of the maize HPPD N-terminus were tested by agro-infiltration in sorghum (Sorghum bicolor) leaves. The results matched those obtained in maize. The data indicate that the monocot HPPD proteins share a homologous chloroplast targeting motif and function.

The function of the monocot HPPD sequence in dicots was explored by transient expression in bush bean (Phaseolus vulgaris), tobacco (Nicotiana benthamiana), and soybean cells. The sequence encoding amino acids 1-50 of the maize HPPD protein was fused to a gene encoding AcGFP1 and inserted into a binary expression vector under control of the Arabidopsis Ubiquitin 10 promoter. A positive control vector was identical except that the AcGFP1 coding region was fused to the 6H1 synthetic chloroplast targeting peptide (Lassner and Wilkinson, 2008), while a negative control was AcGFP1 with no targeting sequence. The first 50 amino acids of maize HPPD were sufficient to drive chloroplast import of AcGFP1 in epidermal cells of P. vulgaris, although some green fluorescence remained in the cytoplasm. In N. benthamiana the AcGFP1 remained in the cytoplasm with none apparent in the chloroplasts. Results by bombardment in soybean showed AcGFP1 in both plastids and cytoplasm (FIG. 3H). This shows that the maize HPPD CTP is recognized in dicot plant cells, but may be inefficiently processed. Stably transformed soybean plants expressing the 50 amino acid N-terminal CTP fused to AcGFP1 showed strong fluorescence in the chloroplasts (FIG. 3I), indicating that the inefficient translocation can be due to the high template concentration that occurs in transient expression conditions.

Example 3. Bioinformatic and Functional Localization Analysis of G. max (Soybean) HPPD G. max is a polyploid derived from 2 evolutionary genome duplications (Schmutz et al, 2010) and as such appears to have multiple paralogous HPPD genes. As some of the annotated genes appear incomplete or have rare ESTs, glyma14g03410.1 on chromosome 14 was studied. This soybean HPPD protein has been previously annotated as a 449 amino acid protein with N-terminal sequence MPIPMC-NEIQ (Cahoon and Coughlin, 2007; sequence 36) and as a 443 amino acid protein with N-terminal sequence MCNEIQAQAQ (Genbank ABQ96868). Analysis of genomic and EST data revealed that an in-frame N-terminal extension of the previously annotated coding region exists, adding 41 amino acids to produce a 490 amino acid full-length HPPD protein as shown in FIG. 4A. Furthermore, EST data reveal two major mRNAs, one of which is able to support translation of the 490 amino acid protein and a smaller EST that is able to support translation of the 449 amino acid protein.

5' cap-dependent rapid cloning of cDNA ends (5' RACE) revealed two major transcripts for the native soybean HPPD gene. Cloning and sequencing of these PCR products revealed a shorter transcript that was designated as starting at position +1. The longer transcript began at position −237 relative to the shorter transcription start site (FIG. 4A). Sequence of multiple clones for each 5' RACE product indicated an approximately 4 nucleotide variation between individual transcripts for both sites. Linked in vitro transcription and translation indicated that both mRNAs are translated and make the predicted size protein (truncated for convenience, FIG. 4B). The +1 transcript is translated to produce a single protein, designated the "short" protein. The −237 transcript yields two proteins, with the lower molecular weight band at the same MW as the single protein produced from the +1 transcript, indicating that translation can initiate at both positions on the long transcript. The higher MW protein produced from the −237 transcript is designated the "long" protein.

Bioinformatic evaluation of the shorter soybean HPPD sequence did not predict a chloroplast or other targeting sequence. However, a chloroplast targeting function was predicted for the N-terminally extended form by ProtComp 9.0 (linux1.softberry.com), WoLF PSORT (Horton et al., 2007) and PCLR (Schein et al., 2001). TargetP (Emanuelsson et al., 2000) indicates chloroplast localization, but gave a higher score to 'other' while MultiLoc2 (Blum et al., 2009) predicted a cytoplasmic localization for both the first 42 and the first 86 amino acids of the long protein. Functional analysis was required to clarify the predictions.

Figure 4C:
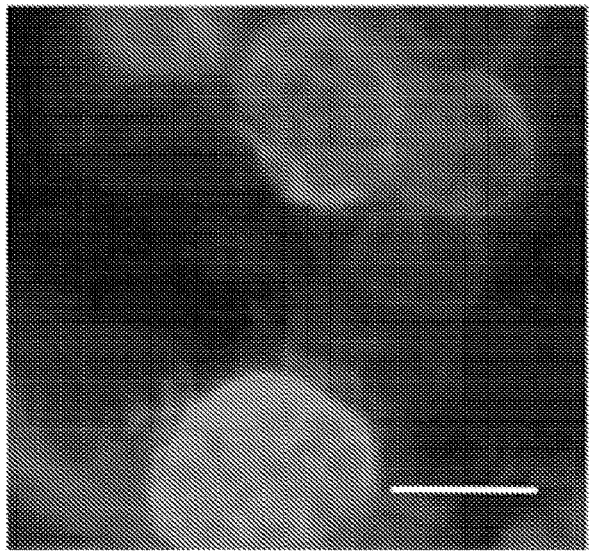
Figure 4D:
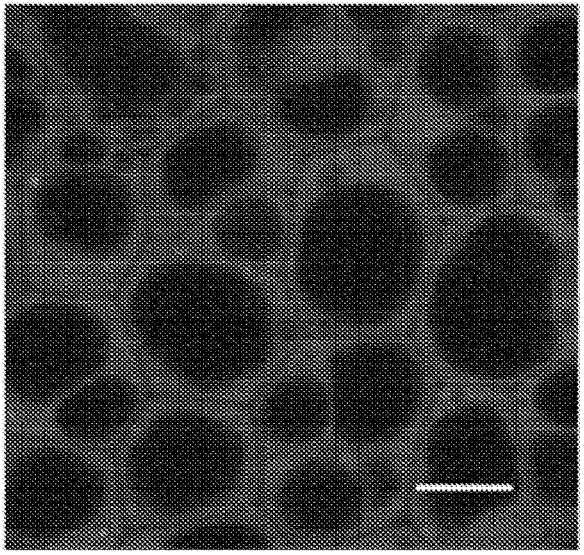
Figure 4E:
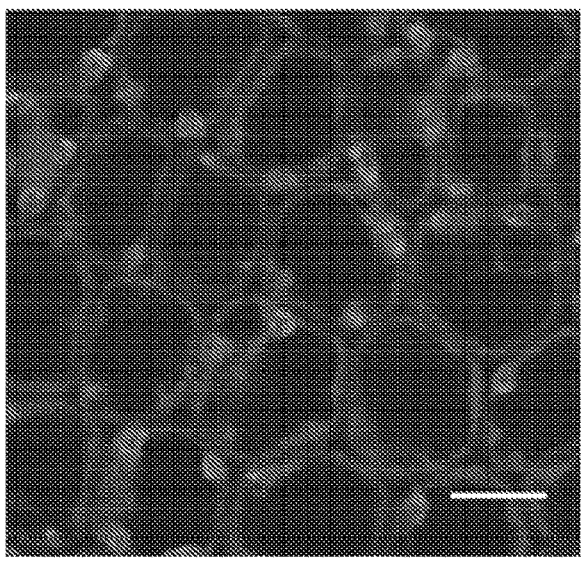
Figure 12A:
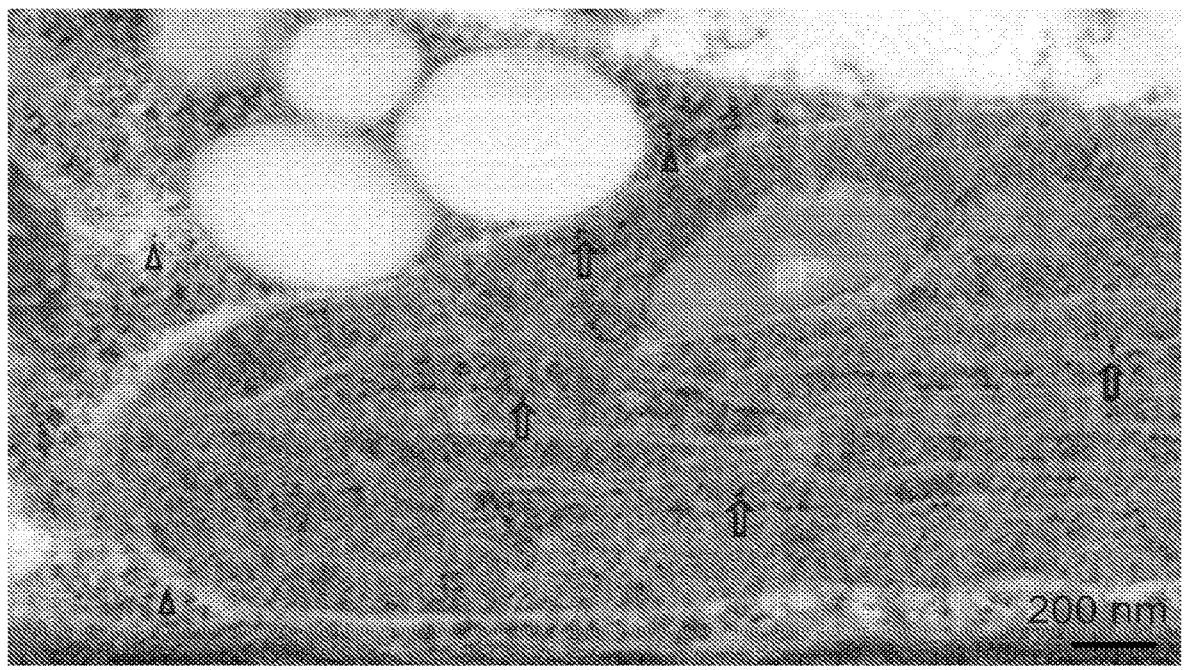
FIGS. 12A and 12B. Each of FIGS. 12A and 12B show immuno-localization electron microscopy of HPPD in soybean cotyledons shows label in chloroplasts and cytoplasm. Affinity purified rabbit anti-soy HPPD antibody was obtained as described for FIGS. 10A and 10B. Pieces of green soybean cotyledon (6 days after planting) were cut under fixative (4% paraformaldehyde, 0.1% glutaraldehyde, 0.1 M sucrose in 0.1M Na Phosphate Buffer, pH 7.2) and held in fixative for 20 min under vacuum at room temperature, then overnight at 4° C. Sectioning, labeling, counterstaining and microscopy were as in FIG. 1S with 10 nm gold. Gold particles were observed exclusively in chloroplasts and cytosol. Most of the fields captured show a greater portion of the label in chloroplasts.
Figure 12B:
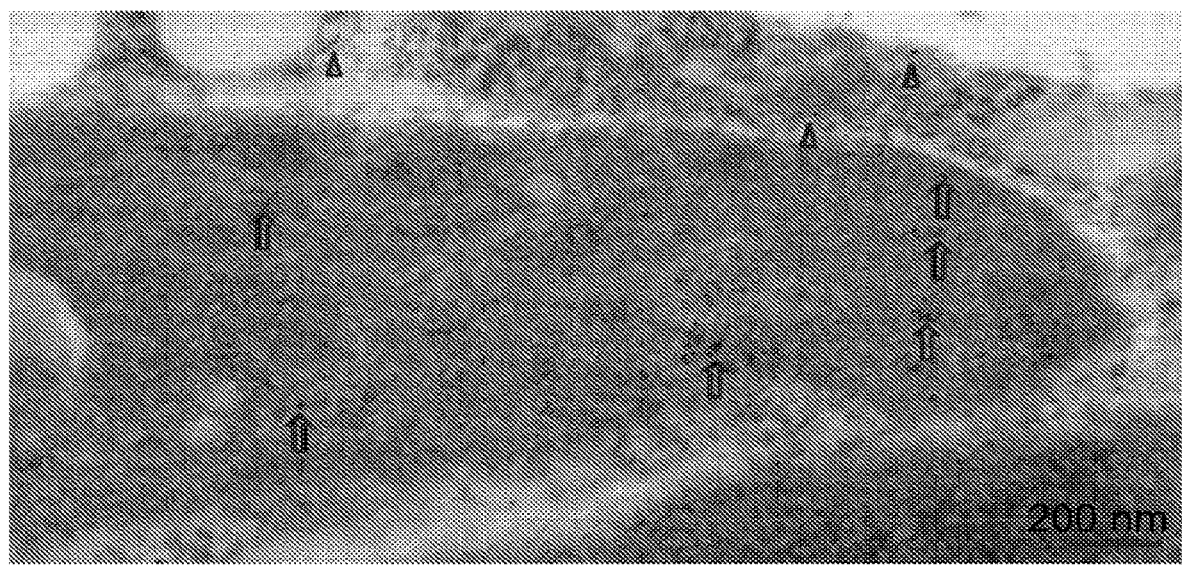

Transient expression experiments indicated that the long HPPD protein is imported to chloroplasts, while the short protein remains in the cytosol. Plant expression cassettes were constructed fusing portions of the N-terminus of the soybean HPPD to either DsRed2 or AcGFP1. The first fusion contained amino acid residues 1-42 of the long protein while the second fusion contained residues 1-44 of the short HPPD protein (corresponding to residues 42-86 of the long protein). The third fusion contained the full 1-86 amino acids of the long HPPD protein. These cassettes, under control of the Arabidopsis Ubiquitin 10 promoter, were used to infect soybean seedling leaves. As shown in FIG. 4C-E, fluorescence is clearly visible in the chloroplasts of infected cells only when the marker gene is fused to amino acid residues 1-86. When the fusion is made with the shorter sequences of both proteins, fluorescence is visible only in the cytoplasm. The pattern of dual localization seen with the reporter constructs was confirmed by immunolocalization electron microscopy (FIGS. 12A and 12B).

Thus, the N-terminal 42 amino acids of the long protein is predicted to be a CTP, but to be functional, a longer sequence is required.

Although the N-terminal sequences of maize and soybean HPPD differ considerably (FIG. 4F), they are both able to target proteins in the heterologous species. Leaves of 4-week old maize seedlings were infiltrated with the *Agrobacterium* carrying the soybean constructs and examined by fluorescence microscopy. Transient expression indicated that the long HPPD protein N-terminus did target the marker protein to maize cell chloroplasts, while the protein variant with the shorter N-terminus delivered the protein to the cytosol. Thus, the dicot chloroplast targeting region of soybean HPPD is able to function in monocot cells.

Because the reported HPPD sequences were mis-annotated for soybean, available sequence data for *Arabidopsis* and another legume, *Medicago trunculata* (alfalfa), were examined to determine if other related dicot species showed the same N-terminal extension. The *Arabidopsis* chromosome 1 HPPD gene NC_003070.9 (Genbank) encodes a 418 amino acid open reading frame with no upstream open reading frames extending the HPPD protein. The lack of N-terminal extension is punctuated by two in-frame stop codons 15 nucleotides upstream of the ATG start. On the other hand, a search of the *M. trunculata* genome returned a predicted HPPD gene located on chromosome 5 (NC_016411.1; Genbank). The annotated predicted protein of 437 amino acids is preceded by a long open reading frame that could initiate at methionines adding 74 or 115 amino acids. The 74 N-terminal extension showed a very strong chloroplast localization score with PCLR (Schein et al., 2001) while the 115 amino acid extension did not.

Example 4. Directed Evolution of the Maize HPPD Protein for Increased Insensitivity to Herbicide Inhibitors Directed evolution is an iterative process whereby beneficial diversity is discovered and iteratively recombined to evolve variants that achieve a desired protein engineering goal. A goal was to create an HPPD enzyme that retained kinetic activity yet was insensitive to most or all HPPD-inhibiting herbicides. Characterization of the maize and soybean HPPD proteins showed that the former was 40-fold less sensitive to mesotrione than the latter (see Table 2 below, which shows kinetic parameters of *E. coli* purified proteins of wild-type HPPD enzymes from maize and soybean). Inhibition measurements are for the herbicidal compound mesotrione. The maize enzyme was, therefore, chosen for use in soybean plants. Final evaluation of shuffled HPPD enzymes was carried out with multiple HPPD herbicides to select the most robust variant.

TABLE 2

| HPPD Variant | SEQ ID NO. | Kinetic parameters | | | Insensitivity parameters | | | Fitness | | |
|---|---|---|---|---|---|---|---|---|---|---|
| | | $k_{cat}$, min$^{-1}$ | $K_M$, μM | $k_{cat}/K_M$ | ON rate ratio | OFF rate ratio | ON × OFF | Fold vs wt | ON × OFF × $k_{cat}/K_M$ | Fold vs Zm wt |
| Z. mays wt | 1 | 219 | 6.4 | 34.2 | 0.20 | 0.31 | 0.06 | | 2.10 | 1 |
| G. max wt | — | 100 | 3.0 | 33.3 | 0.20 | 0.007 | 0.0014 | 0.023 | 0.047 | 0.02 |
| R1 Exemplar | — | 86 | 4.0 | 21.6 | 0.44 | 0.12 | 0.05 | 0.9 | 1.2 | 0.6 |
| R2 Exemplar | — | 50 | 2.7 | 18.9 | 0.70 | 0.18 | 0.13 | 2.1 | 2.4 | 1.1 |
| R3 Exemplar | — | 95.6 | 2.6 | 36.8 | 0.58 | 0.13 | 0.08 | 1.3 | 2.9 | 1.4 |
| R4 Exemplar | — | 117 | 4.3 | 27.5 | 0.61 | 0.16 | 0.10 | 1.6 | 2.7 | 1.3 |
| R5-9043 | — | 146 | 5.9 | 24.7 | 0.60 | 0.63 | 0.38 | 6.2 | 9.3 | 4.4 |
| R6-9075 | 79 | 114 | 4.0 | 28.9 | 0.68 | 0.68 | 0.46 | 7.6 | 13.4 | 6.4 |
| R7-9070 | 2 | 88.9 | 2.9 | 30.7 | 0.67 | 0.83 | 0.56 | 9.11 | 16.6 | 7.9 |
| R8-1973 | 8 | 70.8 | 2.0 | 35.2 | 0.73 | 1.00 | 0.73 | 11.9 | 25.5 | 12.2 |

In the first 6 rounds, shuffled gene variant libraries were made based on the maize HPPD protein template using techniques including family shuffling, single-gene shuffling, back-crossing, semi-synthetic and synthetic shuffling (Zhang J-H et al., 1997; Crameri et al., 1998; Ness et al., 2002). The amino acid diversity for those libraries originated from phylogenetic sequence diversity, random mutagenesis, site-directed mutagenesis, and structural features based on crystal structures of proteins in Protein Data Bank (PDB; pdb.org/pdb/home/home.do). Typically, four to five thousand variants per library were screened for kinetic and insensitivity parameters. Genes coding for shuffled variants of HPPD were expressed in *E. coli*. The library was plated out on rich agar medium, and individual colonies were picked and grown in rich medium. Colonies with active HPPD enzyme cause the medium to turn brown due to the conversion of homogentisate to a brown ochronotic pigment (Zannoni V G et al., 1969). Proteins with the ability to turn the medium brown in the presence of 100 μM mesotrione in rounds 1 to 6 or tembotrione in rounds 7 and 8 were subjected to detailed analysis. Kinetic characteristics of $k_{ON}$, $k_{OFF}$, $k_{cat}$ and $K_m$ were determined (Table 2).

Figure 5:
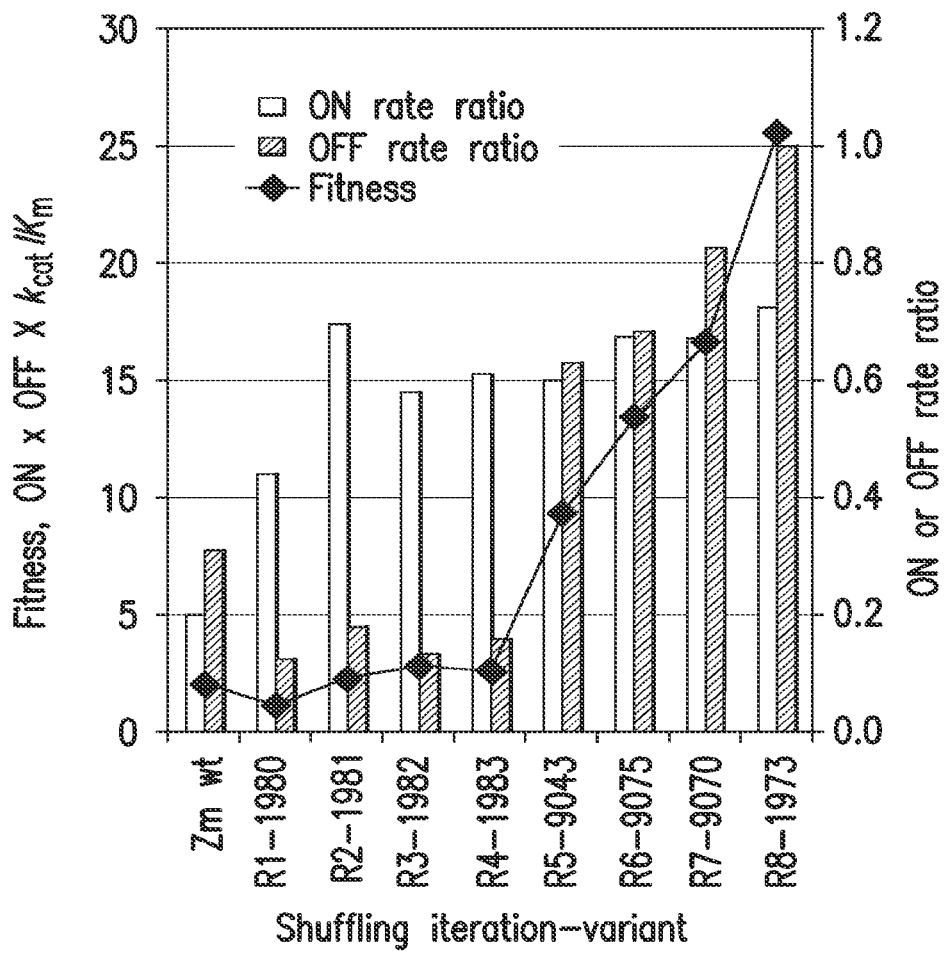
FIG. 5. Progression of enzyme fitness with rounds of shuffling. Bars indicate ON and OFF rate ratios, the insensitivity parameters that are functions of the rate constants for association and dissociation of enzyme and inhibitor, respectively. "Fitness" is the product of $k_{cat}/K_m$ and insensitivity parameters (ON rate ratio and OFF rate ratio, see text for details), and approximates $k_{cat}/K_m \times K_i$.
Figure 6:
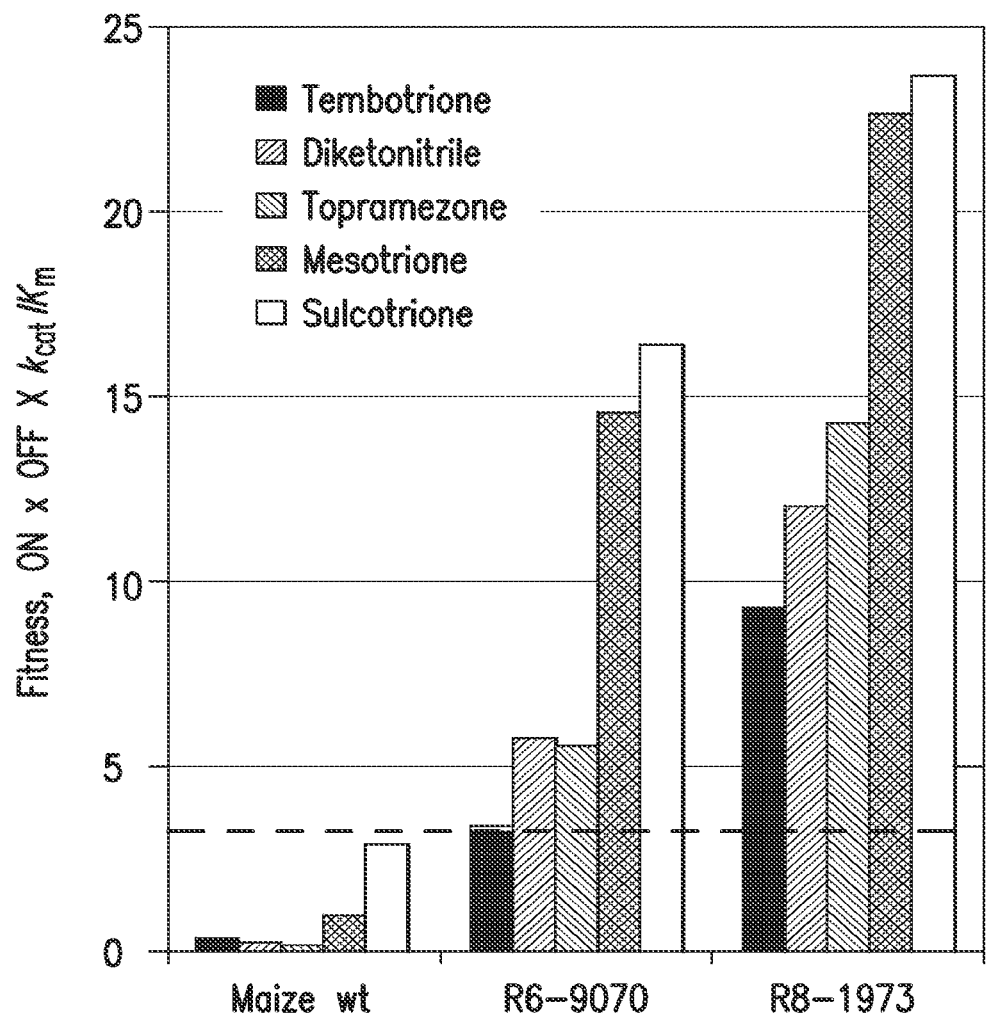
FIG. 6. Selection for insensitivity to mesotrione or tembotrione resulted in cross-insensitivity to other herbicidal inhibitors. "Fitness" is the product of $k_{cat}/K_m$ and insensitivity parameters, and approximates $k_{cat}/K_m \times K_i$. The dotted line is drawn at the fitness level that provided tolerance in soybean to twice the labeled field rate (for maize) of tembotrione in 2013 field trials.

The diversity of substitutions identified through phylogenetic sequence diversity, random mutagenesis, site-directed mutagenesis, and structural features based on crystal structures of proteins in Protein Data Bank (PDB; pdb.org/pdb/home/home.do in the improved HPPD enzymes of this study is listed in Table 3 and 3b. Diversity not accessible through these methods but identified by saturation mutagenesis are shown in Example 7. Table 3 shows exemplary diversity contributing to improvement of insensitive maize HPPD. Indicated amino acids are neutral or beneficial to HPPD fitness. Table 3b shows diversity identified by saturation mutagenesis of Round 7, variant 9070 (SEQ ID NO:2) and fitness (ON rate ratio×OFF rate ratio×kcat/Km) relative to Round 7, variant 9070 (SEQ ID NO:2) for the inhibitors indicated therein. Native maize wild-type sequence is shown for comparison. In many cases a single substitution was identified, while at other positions, many neutral or beneficial substitutions were identified. The additional increment of enzyme fitness seen in round 8 (Table 2; FIGS. 5 and 6) was attained through mutations not present in the natural diversity, but accessed only through saturation mutagenesis. The variant with the highest fitness parameter, Round 8, variant 1973 (SEQ ID NO:8), had 26 amino acid substitutions relative to native maize HPPD.

TABLE 3

| | Position | | | | | | | | |
|---|---|---|---|---|---|---|---|---|---|
| | 32 | 40 | 42 | 44 | 46 | 47 | 68 | 71 | 98 | 114 |
| Maize WT | N | S | R | H | L | A | G | A | F | A |
| Diversity | R | A | H | VG QSC LI | V | S | A | V | L | S |

| | Position | | | | | | | | |
|---|---|---|---|---|---|---|---|---|---|
| | 120 | 122 | 125 | 137 | 144 | 146 | 150 | 161 | 167 | 175 |
| Maize WT | A | A | R | V | A | D | A | G | R | E |
| Diversity | P | T | S | I | V | V | S | S | G | G |

| | Position | | | | | | | | |
|---|---|---|---|---|---|---|---|---|---|
| | 184 | 187 | 193 | 202 | 207 | 209 | 211 | 219 | 221 | 225 |
| Maize WT | Y | Y | G | G | G | A | Y | I | G | E |
| Diversity | F | H | D | R | D | V | C | VLM | VASC | D |

| | Position | | | | | | | | |
|---|---|---|---|---|---|---|---|---|---|
| | 226 | 233 | 241 | 253 | 260 | 261 | 262 | 268 | 278 | 282 |
| Maize WT | L | F | E | A | M | V | L | N | H | R |
| Diversity | M | VCL MI | G | T | VLI | A | WI | G | R | K |

| | Position | | | | | | | | |
|---|---|---|---|---|---|---|---|---|---|
| | 289 | 291 | 301 | 303 | 316 | 320 | 327 | 328 | 330 | 331 |
| Maize WT | F | D | M | L | Q | A | M | A | P | T |
| Diversity | Y | E | I | V | RK | S | L | P | R | GQPLH |

| | Position | | | | | | | | |
|---|---|---|---|---|---|---|---|---|---|
| | 341 | 347 | 352 | 360 | 377 | 382 | 383 | 387 | 395 | 405 |
| Maize WT | R | T | K | L | V | T | L | I | E | K |
| Diversity | DEA CI | S | DEN | M | LI | A | F | M | G | E |

| | Position | | | | | | | | |
|---|---|---|---|---|---|---|---|---|---|
| | 414 | 417 | 418 | 425 | 437 | 438 | 440 | 442 | 443 | 444 |
| Maize WT | G | S | Q | D | A | A | A | Q | G | S |
| Diversity | DTFV QASR MHYK | G | E | E | P | E | TVK | A | Q | G |

TABLE 3b

| | ON × OFF × kcat/km fold vs Round 7, variant 9070 | | | | |
|---|---|---|---|---|---|
| Mutation* | tembo | meso | DKN | Topra | Sulco |
| Q366E | 1.8 | 1.8 | 1.7 | 1.9 | 1.4 |
| G417S | 1.6 | 1.3 | 0.9 | 1.2 | 1.1 |
| A432R | 1.6 | 1.5 | 2.1 | 1.4 | 1.3 |
| G417Q | 1.5 | 1.5 | 1.0 | 1.4 | 1.2 |
| L385V | 1.4 | 1.0 | 1.1 | 1.3 | 1.0 |
| P206Q | 1.4 | 1.1 | 1.2 | 1.1 | 1.0 |
| A432K | 1.4 | 1.6 | 1.6 | 1.5 | 1.5 |
| S214N | 1.3 | 1.1 | 1.4 | 1.2 | 1.1 |
| L385I | 1.3 | 1.1 | 1.2 | 1.2 | 1.1 |
| P158K | 1.3 | 1.0 | 1.0 | 1.1 | 0.9 |
| E356R | 1.2 | 1.1 | 1.1 | 1.1 | 1.1 |
| E356K | 1.2 | 1.2 | 1.1 | 0.9 | 1.1 |
| R340K | 1.2 | 1.3 | 2.2 | 1.1 | 1.3 |
| I387L | 1.1 | 1.3 | 1.6 | 1.0 | 1.3 |
| Y211L | 1.1 | 0.9 | 1.1 | 1.1 | 0.9 |
| Q434R | 1.1 | 1.1 | 1.1 | 1.1 | 1.1 |
| P206S | 1.1 | 0.9 | 1.1 | 1.0 | 0.8 |
| Q434H | 1.1 | 1.3 | 1.4 | 1.1 | 1.3 |
| A191G | 1.0 | 1.1 | 1.1 | 1.1 | 1.1 |
| L182M | 1.0 | 0.8 | 0.9 | 0.9 | 0.9 |

*Mutation shown relative to Round 7, variant 9070 (SEQ ID NO: 2)

FIG. 5 illustrates the progression of desensitization to mesotrione from wild type to the best variant that emerged from the round 8 library. Improved (slower) rates of association of enzyme and mesotrione, manifested in the assay as a higher value for ON rate ratio, were readily attained. Values ranged from that of the wild type, 0.2, to the theoretical maximum value of 1.0, meaning that the reaction with inhibitor did not measurably slow compared to the reaction with no inhibitor during the first 90 seconds.

Improved (faster) rates of dissociation were less common, being attained in the early rounds either not at all or at the expense of reduced catalytic efficiency. In the examples shown in FIG. 5, catalytic efficiency was retained, but in the first 4 rounds of shuffling, OFF rate ratio actually decreased. However, variants with OFF rate ratios up to 0.7 were observed in rounds 5 to 8. Variants sufficiently improved in ON rate, OFF rate or both so as to result in improved insensitivity parameter (ON rate ratio×OFF rate ratio) included many with values in the range of 0.27 to 0.7, representing more than a 14-fold improved insensitivity compared to maize wild-type HPPD (FIG. 5 and Table 2). No attempt was made to improve $k_{cat}$, but rather to find a sequence context in which improved insensitivity could be attained with little or no loss of enzyme turnover rate ($k_{cat}$) or catalytic efficiency ($k_{cat}/K_M$). The number of mutations required was such that enzyme fitness (ON×OFF×$k_{cat}/K_M$) improved only 2-fold until round 5, but improved another 7- to 15-fold, depending on the inhibitor, in rounds 6 through 8, for overall improvements of 20- and 35-fold for mesotrione and tembotrione, respectively (Table 2, FIG. 6).

Because there are diverse chemotypes among the registered herbicidal inhibitors of HPPD, a commercially valuable trait should confer tolerance to most or all of these registered chemistries. To ensure that directed evolution met that criterion, parents for each successive library were tested for insensitivity to the other inhibitors shown in FIG. 1, using the same procedures as for mesotrione. The result was that improved insensitivity, and hence enzyme fitness, obtained by selection with mesotrione or tembotrione was accompanied by improved insensitivity to all other inhibitors (FIG. 6).

Example 5. HPPD Expression Analysis in Soybean Plants

Figure 7:
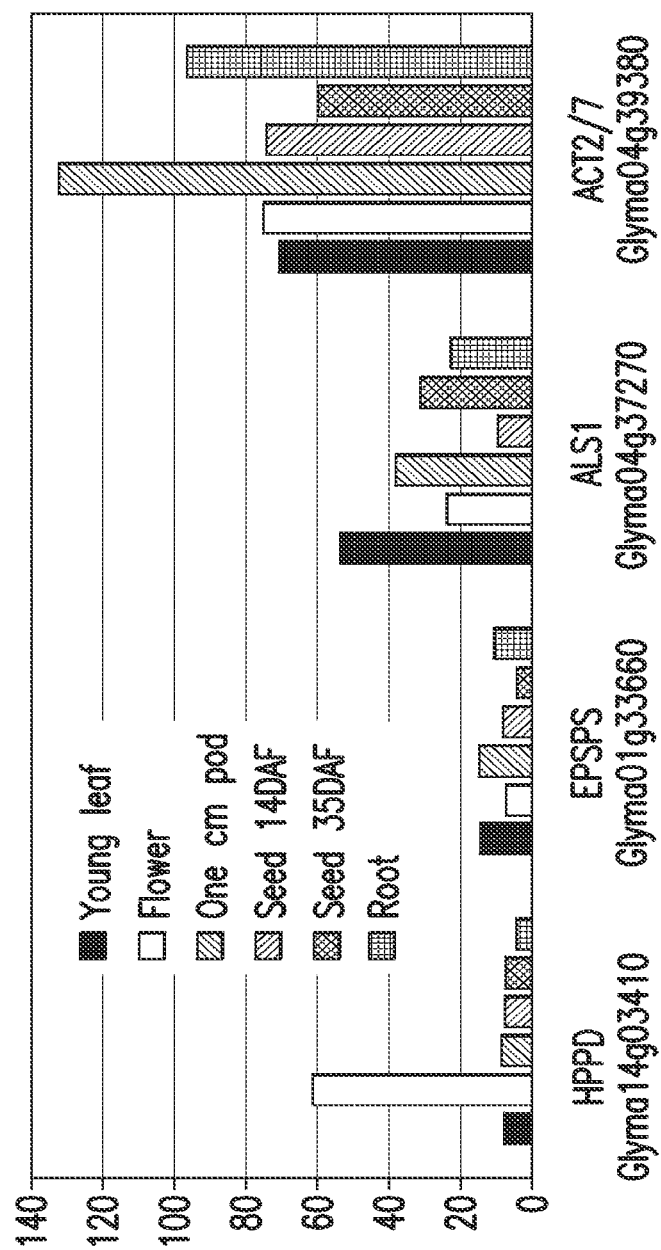
FIG. 7. Expression of soybean HPPD ESTs in specific tissues compared to EPSPS and ALS with ACT2/7 as a moderately expressing control gene. Units of expression are reads/kilobase/million, normalized from raw data (SoyBase.org).

To mimic the pattern of expression with regard to growth stage, tissue and subcellular location, and uncharacterized signaling cues, the transgene promoters were based on the native soybean HPPD promoter. Attempts to directly isolate or measure native HPPD protein accumulation indicated low abundance in leaves. This was confirmed by EST analysis. Profiles of transcript abundance in multiple tissues from soybean (SoyBase.org) were compared to other well-known herbicide target genes, EPSPS (glyphosate target) and ALS (ALS-inhibitor target) (FIG. 7). HPPD and EPSPS appear to be expressed at a low level in all tissues other than flowers compared to the well-characterized ACT2/7 gene (Hu et al., 2009). Preserving the native expression pattern for HPPD while substituting the improved insensitive maize HPPD variant genes can confer robust herbicide tolerance with only moderate overexpression of the transgene.

Example 6. Isolation and Characterization of the Soybean HPPD Promoter

Figure 8B:
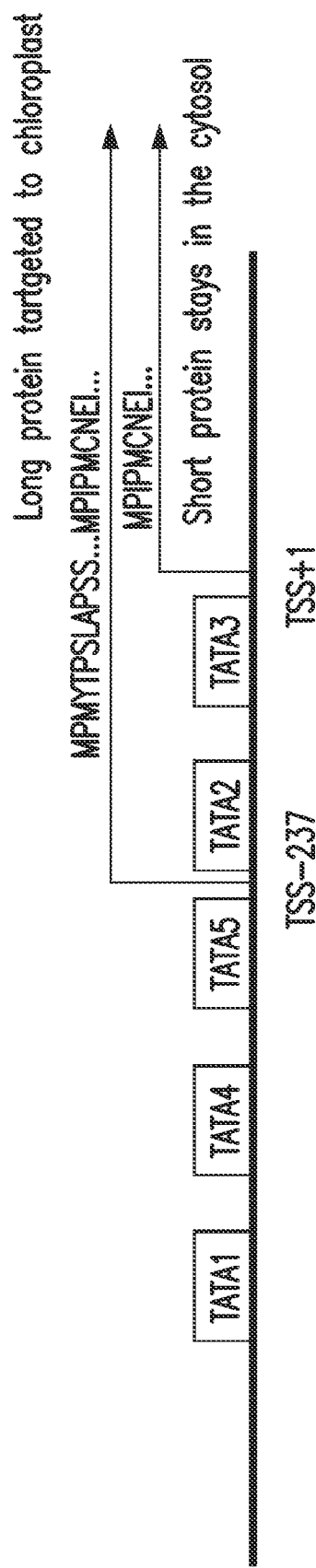

A 1225 bp genomic sequence at the 5' end of the G. max HPPD gene was isolated, sequenced and subjected to promoter analysis using Promoter REAPer and Promoter Delineator (Simmons and Navarro Acevaedo, 2010). Five putative TATA boxes, GTATAAATAA (SEQ ID NO:95; TATA1), CCAATATATG (SEQ ID NO:96; TATA2), CCTTATATATC (SEQ ID NO:97; TATA3), TATATAATAA (SEQ ID NO:98; TATA4), and GAATATAAG (SEQ ID NO:99; TATA5) were identified as shown in FIG. 8A. The open reading frame starting from the first ATG after TATA3 encodes the 449 amino acid short protein. TATA2 is within the long protein transcript and TATA3 is embedded in the coding region for the long protein. Based on the known transcripts, TATA5 and TATA3 appear to be best situated for the long and short transcripts, respectively. Each is situated approximately 35 nucleotides from the transcription initiation as expected for eukaryotic promoters (Smale and Kadonaga, 2003). Open reading frame (ORF) analysis of the long transcript indicates a short ORF encoding 7 AAs starting at position −195. Downstream of this, the long ORF begins at position −99 and continues in frame comprising the short protein, which starts at +25. A schematic of the G. max HPPD promoter, transcripts, and translation products is shown in FIG. 8B.

To evaluate the predicted TATA boxes for activity, 3' deletions and various mutations of the promoter region were constructed and the fragments fused with DsRed2 for expression analysis using transient expression in bushbean leaf tissue (Table 4). Table 4 shows representative HPPD promoter activity data. DsRed2 measurements are relative to full G. max HPPD promoter in extracts of bush bean leaves 3 days after agro-infiltration with described promoter:DsRed2 fusion constructs. The full promoter:DsRed2 construct with both transcripts intact should produce both a 41 residue N-terminal HPPD:DsRed2 fusion protein and the DsRed2 protein alone. The fluorescence value of the fusion protein was not measured in comparison to the DsRed2 protein. It was previously shown that the 41 amino acids fused to DsRed2 did produce red fluorescence without conferring chloroplast localization (FIG. 4C). Deletion of a 613 bp DNA fragment upstream of the short protein transcription start site, including all 5 putative TATA boxes, resulted in a DNA fragment that was not able to drive DsRed2 expression to a level above the background. When TATA3 and the short transcript region were deleted with the DsRed2 initiating at the same position as the long protein, 90% of the full promoter region accumulation of DsRed2 was measured, showing the contribution of the upstream transcript. To eliminate translation of the fusion protein and leave only the contribution of the short protein, a stop codon was introduced upstream of the DsRed2 start Only the short transcript DsRed2 would be translated in this construct. The same amount of DsRed2 accumulated as when both the fusion and the downstream DsRed2 could be translated. Thus, it appears that both transcripts are capable of supporting translation activity but this activity is not additive. Total HPPD product from the native promoter could be regulated via competition for transcription and/or translation. Deletions of TATA2 and 3, TATA2, 3, and 5, or TATA2, 3, 4, and 5 abolished promoter activity. It was unexpected that deletion of TATA2 and 3 did not default to TATA5 and the upstream (−237) transcription initiation for DsRed2 expression (see FIG. 8 and Table 4).

TABLE 4

| Promoter Description | Promoter Variant | Average Relative Promoter Strength (%) |
| --- | --- | --- |
| Native G. max HPPD promoter region Deletions series | Gm HPPD | 100 |
| Deletion of TATA2, TATA3, and TATA5 | SHP000C | 2 |
| Deletion of all 5 TATA | SHP101C | 0 |
| Deletion of TATA 2, 3, 4, and 5 | SHP102C | 0 |
| Deletion of TATA3 | SHP103C | 90 |
| Deletion of TATA2 and TATA3 | SHP110C | 3 |

TABLE 4-continued

| Promoter Description | Promoter Variant | Average Relative Promoter Strength (%) |
|---|---|---|
| Mutations in TATA3 | | |
| A to C mutation in TATA3 | SHP104C | 23 |
| T to C in TATA1 and A to C in TATA3 | SHP105C | 30 |
| T to C in TATA1, T to G in TATA2, and A to C in TATA3 | SHP106C | 21 |
| TAT to GCA mutation in TATA3 | SHP107C | 15 |
| ATA to CCG in TATA1 and TAT to GCA in TATA3 | SHP108C | 19 |
| TAT to CAG in TATA5, TAT to GCA in TATA3 | SHP114C | 11 |
| Mutations in other TATA boxes | | |
| TAT to CAG mutation in TATA2 | SHP111C | 93 |
| TAT to CAG mutation in TATA4 | SHP112C | 97 |
| TAT to CAG mutation in TATA5 | SHP113C | 89 |
| Point mutation to eliminate upORF start codon | SHP120C | 105 |
| Point mutation to insert stop codon just upstream of +1 transcription start site | SHP121C | 92 |
| Synthetic promoters | | |
| Deletion of all 5 TATA + element I[a] | SHP101 | 3 |
| Deletion of TATA 2, 3, 4, and 5 + element I | SHP102 | 4 |
| Deletion of TATA3 + element I | SHP103 | 310 |
| T to C in TATA1, T to G in TATA2, and A to C in TATA3 + element I | SHP106 | 377 |
| TAT to GCA mutation in TATA3 + element I | SHP107 | 129 |
| Deletion of all 5 TATA + element II[b] | SHP201 | 23 |
| Deletion of TATA3 + element II | SHP203 | 272 |
| T to C in TATA1, T to G in TATA2, and A to C in TATA3 + element II | SHP206 | 195 |

[a] Element I is a synthetic core promoter sequence derived from Sequence 1 in Bowen et al., 2000
[b] Element II consists of Element 1 plus a transcription enhancer region called Rsyn7 derived from Sequence 2 in Bowen et al., 2000.

A second method to characterize the role of the predicted TATA sequences was mutagenesis of the specific sequences, changing either 1 or 3 nucleotides. In all cases, if TATA3 was mutated, no matter what other mutations were present, promoter activity was reduced by 70-90%. A triplet nucleotide change reduced the activity more than a single nucleotide change. Triplet nucleotide mutations in either TATA2, TATA4, or TATA5 showed little or no effect on accumulation when DsRed2 replaced the short protein open reading frame. Upstream ORFs have been shown to reduce both transcription and translation in plant genes (Saul et al., 2009). A mutation to eliminate the ATG start codon of the HPPD upORF did not have any affect as DsRed2 was within 5% of that measured with the unaltered promoter construct. Both deletion and mutation analysis provide evidence that TATA3 is important in maintaining full activity of the soy HPPD promoter but, because deletion of the TATA3 sequence altogether still leaves 90% promoter activity, other elements are also functional.

Example 7. Derivations of Soybean HPPD Promoter for Transgene Expression

To create transgene expression cassettes for HPPD inhibitor herbicide tolerance in soybean, cassettes were constructed with the intention of maintaining the HPPD regulatory information while modestly increasing the expression level. In one case, the inactive fragment with deletion of TATA3, 2 and 5 was fused with a synthetic core promoter sequence (Element I in Table 4, Bowen et al., 2000; sequence 1) followed by the 45 bp 5'UTR sequence including the predicted transcription start site from the soybean native HPPD gene comprising the nucleotides between TATA3 and ATG. In other cases either TATA3 or TATA5 were replaced with the synthetic core promoter to drive the short or long transcripts at an increased level. DsRed2 fusion constructs with these promoters showed that inclusion of the synthetic TATA region resulted in two- to three-fold increased DsRed2 accumulation (Table 4). The 35S enhancer region (Ow et al., 1987) at the 5' end of the altered promoter fragments or an enhancing region called Rsyn7 containing OCS transcription factor motif sequences (Element II in Table 4, Bowen et al., 2000; sequence 2) near the core TATA box were added to increase expression. Plant transformation constructs were designed either with full-length insensitive maize HPPD in combination with promoters giving rise to only one transcript or with the N-terminal 86 amino acids of the long chloroplast targeting sequence of G. max followed by the conserved mature maize HPPD protein starting at amino acid 50 (FIG. 4F). The latter was designed to provide dual targeting of a highly insensitive HPPD enzyme. Final functional validation of the promoter/CTP/variant HPPD cassettes was by herbicide tolerance efficacy testing of transgenic soybean plants.

Example 8. Generating and Identifying Beneficial Novel Amino Acid Diversity

Saturation Mutagenesis of Maize HPPD

The backbone gene for saturation mutagenesis was Round 7, variant 9070 (SEQ ID NO:2), which had the highest fitness parameter with inhibitors such as mesotrione and tembotrione among the variants generated previously (US20120042413(A1). Libraries were created for each position in the Round 7, variant 9070 (SEQ ID NO:2) using NNK (where N represents a 25% mix each of adenine, thymine, guanine, and cytosine nucleotides; and K represents a 50% mix each of thymine and guanine nucleotides) as the degenerate codon for the position to be mutagenized. PCR reaction mixtures contained a mutagenic forward primer (NNK codon flanked by 28 nucleotides matching with template at each side of the NNK) and a reverse primer that was the complement of the sequence preceding the forward primer, 28 nucleotides in length. To eliminate the mis-matched bubble, a second PCR reaction was performed with a forward, resolution primer that matched the 28 nucleotides of the template upstream of the NNK site, and the same reverse primer as in the first reaction. The template for the second PCR reaction was the product of the first, diluted 10-fold. To make circular double stranded DNA plasmids from the blunt ended PCR products, the products were digested with T4 polynucleotide kinase, T4 DNA ligase, and DpnI (to disrupt the parental DNA template). After desalting by µltrafiltration, the ligation products were ready for transformation and downstream applications.

The transformation mixture for each position mutagenized was plated on LB agar containing kanamycin. 47-94 colonies from each plate were picked into LB liquid, in 96-well format. The cells were sub-cultured into 2×YT medium unmodified, or containing 50 µM tembotrione or 100 µM mesotrione and evaluated by their ability to turn the medium brown, as described in Example 1. Wells in which the medium turned as brown as or browner than the Round 7, variant 9070 (SEQ ID NO:2) controls were selected as hits. The amino acid substitutions in Round 7, variant 9070 (SEQ ID NO:2) of the 554 variants selected as hits are listed in Megatable 1. Sequencing of entire plates selected at random indicated that on average, 17 amino acid substitutions were accessed per position.

The variants selected in the medium browning screen were expressed in E. coli and purified as described in Example 1, then evaluated for affinity for tembotrione by obtaining the ON and OFF rate ratios described in Example 1. The results for insensitivity evaluation (ON and OFF rate ratio) of 119 single substitutions (relative to Round 7, variant 9070 (SEQ ID NO:2)) selected from medium browning in the presence of 100 µM tembotrione are shown in Table 5.

TABLE 5

| Substitution | $k_{cat}$ min$^{-1}$ | ON ratio | OFF ratio | ON × OFF | ON × OFF, fold vs wt | ON × OFF × kcat Value | Fold vs wt |
|---|---|---|---|---|---|---|---|
| 331N | 40.4 | 0.75 | 0.43 | 0.32 | 63.0 | 12.99 | 12.14 |
| 438G | 33.8 | 0.74 | 0.42 | 0.31 | 60.3 | 10.41 | 9.73 |
| 331R | 30.3 | 0.73 | 0.38 | 0.28 | 54.6 | 8.44 | 7.89 |
| 437K | 35.7 | 0.76 | 0.36 | 0.27 | 52.9 | 9.63 | 9.00 |
| 438R | 29.2 | 0.75 | 0.33 | 0.25 | 48.5 | 7.23 | 6.76 |
| 385V | 21.4 | 0.75 | 0.33 | 0.25 | 48.2 | 5.26 | 4.92 |
| 376W | 23.1 | 0.68 | 0.34 | 0.23 | 46.0 | 5.42 | 5.07 |
| 417S | 18.5 | 0.82 | 0.28 | 0.23 | 45.2 | 4.26 | 3.98 |
| 161E | 17.2 | 0.78 | 0.29 | 0.23 | 44.8 | 3.92 | 3.67 |
| 161Q | 27.7 | 0.77 | 0.30 | 0.23 | 44.8 | 6.33 | 5.91 |
| 439R | 24.7 | 0.73 | 0.30 | 0.22 | 43.3 | 5.45 | 5.09 |
| 161S | 24.5 | 0.76 | 0.29 | 0.22 | 43.2 | 5.41 | 5.06 |
| 182M | 26.0 | 0.79 | 0.28 | 0.22 | 42.5 | 5.63 | 5.26 |
| 171F | 16.6 | 0.75 | 0.28 | 0.21 | 41.8 | 3.54 | 3.31 |
| 215G | 24.4 | 0.79 | 0.27 | 0.21 | 41.8 | 5.19 | 4.85 |
| 191S | 12.4 | 0.75 | 0.28 | 0.21 | 40.8 | 2.59 | 2.42 |
| 158K | 50.4 | 0.77 | 0.27 | 0.21 | 40.6 | 10.44 | 9.76 |
| 332A | 41.5 | 0.75 | 0.28 | 0.21 | 40.5 | 8.58 | 8.02 |
| 161Y | 21.6 | 0.78 | 0.26 | 0.20 | 40.0 | 4.40 | 4.11 |
| 385I | 27.5 | 0.75 | 0.27 | 0.20 | 39.5 | 5.55 | 5.18 |
| 331G | 29.0 | 0.73 | 0.27 | 0.20 | 39.1 | 5.78 | 5.40 |
| 161N | 23.5 | 0.78 | 0.25 | 0.20 | 38.6 | 4.63 | 4.33 |
| 417Q | 20.6 | 0.74 | 0.27 | 0.20 | 38.4 | 4.04 | 3.77 |
| 161L | 14.0 | 0.77 | 0.25 | 0.19 | 37.8 | 2.71 | 2.53 |
| 159C | 21.0 | 0.79 | 0.24 | 0.19 | 37.6 | 4.03 | 3.77 |
| 166P | 11.4 | 0.77 | 0.25 | 0.19 | 37.2 | 2.17 | 2.03 |
| 166A | 23.1 | 0.77 | 0.24 | 0.19 | 36.4 | 4.29 | 4.01 |
| 331D | 32.4 | 0.75 | 0.25 | 0.18 | 36.2 | 5.98 | 5.59 |
| 169H | 13.8 | 0.75 | 0.25 | 0.18 | 36.0 | 2.54 | 2.38 |
| 366E | 20.1 | 0.75 | 0.24 | 0.18 | 34.9 | 3.58 | 3.35 |
| 382S | 29.6 | 0.71 | 0.24 | 0.17 | 33.0 | 4.97 | 4.65 |
| 360L | 26.5 | 0.77 | 0.22 | 0.17 | 32.6 | 4.41 | 4.12 |
| 390N | 30.3 | 0.75 | 0.22 | 0.17 | 32.4 | 5.00 | 4.67 |
| 189P | 26.2 | 0.76 | 0.22 | 0.16 | 32.3 | 4.31 | 4.02 |
| 358E | 15.5 | 0.69 | 0.23 | 0.16 | 31.5 | 2.49 | 2.33 |
| 356K | 38.8 | 0.75 | 0.21 | 0.16 | 31.2 | 6.18 | 5.78 |
| 206Q | 35.4 | 0.74 | 0.21 | 0.16 | 30.8 | 5.57 | 5.20 |
| 191L | 21.5 | 0.77 | 0.20 | 0.16 | 30.5 | 3.35 | 3.13 |
| 432R | 30.6 | 0.78 | 0.20 | 0.16 | 30.4 | 4.75 | 4.44 |
| 356R | 39.1 | 0.75 | 0.21 | 0.15 | 30.0 | 5.97 | 5.58 |
| 205T | 25.1 | 0.74 | 0.20 | 0.15 | 29.0 | 3.72 | 3.48 |
| 340K | 44.7 | 0.75 | 0.20 | 0.15 | 28.7 | 6.56 | 6.13 |
| 376V | 31.0 | 0.71 | 0.21 | 0.15 | 28.7 | 4.53 | 4.23 |
| 206S | 35.5 | 0.75 | 0.20 | 0.15 | 28.5 | 5.15 | 4.82 |
| 437F | 12.7 | 0.76 | 0.19 | 0.14 | 28.1 | 1.82 | 1.70 |
| 214N | 35.4 | 0.76 | 0.19 | 0.14 | 27.9 | 5.04 | 4.71 |
| 399Y | 27.8 | 0.71 | 0.20 | 0.14 | 27.9 | 3.95 | 3.70 |
| 357Y | 28.7 | 0.72 | 0.20 | 0.14 | 27.5 | 4.03 | 3.76 |
| 399H | 28.8 | 0.72 | 0.19 | 0.14 | 27.4 | 4.02 | 3.75 |
| 387L | 33.3 | 0.75 | 0.19 | 0.14 | 27.0 | 4.58 | 4.28 |
| 352K | 32.2 | 0.70 | 0.19 | 0.13 | 26.2 | 4.30 | 4.02 |
| 221V | 9.8 | 0.75 | 0.18 | 0.13 | 26.1 | 1.30 | 1.21 |
| 437V | 19.9 | 0.67 | 0.20 | 0.13 | 26.0 | 2.63 | 2.46 |
| 432K | 31.5 | 0.76 | 0.17 | 0.13 | 25.7 | 4.13 | 3.86 |
| 399N | 37.4 | 0.75 | 0.17 | 0.13 | 25.2 | 4.81 | 4.50 |
| 396V | 29.0 | 0.72 | 0.18 | 0.13 | 25.2 | 3.73 | 3.49 |
| 211L | 36.9 | 0.77 | 0.17 | 0.13 | 25.0 | 4.72 | 4.41 |
| 217Y | 20.7 | 0.76 | 0.17 | 0.13 | 24.9 | 2.63 | 2.45 |
| 431F | 28.9 | 0.80 | 0.16 | 0.13 | 24.5 | 3.61 | 3.37 |
| 195E | 16.6 | 0.69 | 0.18 | 0.12 | 24.4 | 2.07 | 1.93 |
| 231S | 20.9 | 0.68 | 0.18 | 0.12 | 23.8 | 2.54 | 2.37 |
| 399R | 34.8 | 0.74 | 0.17 | 0.12 | 23.6 | 4.18 | 3.91 |
| 200C | 21.4 | 0.73 | 0.16 | 0.12 | 23.6 | 2.57 | 2.40 |
| 396T | 37.7 | 0.71 | 0.17 | 0.12 | 23.5 | 4.51 | 4.22 |
| 187M | 23.5 | 0.70 | 0.17 | 0.12 | 23.2 | 2.78 | 2.60 |
| 227G | 34.6 | 0.79 | 0.15 | 0.12 | 23.2 | 4.09 | 3.83 |
| 432V | N.A. | 0.67 | 0.17 | 0.12 | 23.1 | 0.00 | 0.00 |
| 190M | 17.7 | 0.71 | 0.16 | 0.12 | 22.9 | 2.07 | 1.93 |
| 375L | 36.1 | 0.71 | 0.16 | 0.12 | 22.8 | 4.20 | 3.92 |
| 352R | 39.4 | 0.75 | 0.15 | 0.11 | 21.9 | 4.40 | 4.11 |
| 202T | 13.1 | 0.70 | 0.16 | 0.11 | 21.9 | 1.46 | 1.36 |
| 399Q | 36.1 | 0.72 | 0.15 | 0.11 | 21.5 | 3.96 | 3.70 |
| 202A | 12.0 | 0.69 | 0.16 | 0.11 | 21.5 | 1.32 | 1.23 |
| 396M | 35.4 | 0.73 | 0.15 | 0.11 | 21.4 | 3.86 | 3.61 |
| 399S | 35.8 | 0.70 | 0.15 | 0.11 | 21.3 | 3.90 | 3.64 |
| 434R | 52.1 | 0.73 | 0.15 | 0.11 | 21.2 | 5.63 | 5.26 |
| 221A | 42.2 | 0.62 | 0.17 | 0.10 | 20.3 | 4.37 | 4.09 |
| 195V | 20.1 | 0.73 | 0.14 | 0.10 | 20.2 | 2.07 | 1.93 |
| 214T | 39.2 | 0.74 | 0.14 | 0.10 | 20.2 | 4.03 | 3.76 |
| 191G | 42.6 | 0.77 | 0.13 | 0.10 | 20.1 | 4.36 | 4.08 |
| 206K | 21.9 | 0.74 | 0.14 | 0.10 | 19.9 | 2.23 | 2.08 |
| 342V | 40.6 | 0.78 | 0.13 | 0.10 | 19.7 | 4.08 | 3.82 |
| 398D | 38.7 | 0.72 | 0.14 | 0.10 | 19.6 | 3.87 | 3.62 |
| 434H | 51.9 | 0.78 | 0.13 | 0.10 | 19.5 | 5.16 | 4.82 |
| 193Q | 23.9 | 0.77 | 0.13 | 0.10 | 19.3 | 2.35 | 2.20 |
| 189E | 21.6 | 0.72 | 0.14 | 0.10 | 19.2 | 2.11 | 1.98 |
| 211S | 18.9 | 0.79 | 0.12 | 0.10 | 19.1 | 1.83 | 1.71 |
| 190E | 27.2 | 0.72 | 0.13 | 0.10 | 18.7 | 2.59 | 2.42 |
| 190T | 28.0 | 0.75 | 0.13 | 0.10 | 18.6 | 2.66 | 2.48 |
| 396L | 40.5 | 0.57 | 0.17 | 0.09 | 18.6 | 3.85 | 3.60 |
| 432S | 34.6 | 0.72 | 0.13 | 0.09 | 18.6 | 3.28 | 3.06 |
| 056S | 41.9 | 0.78 | 0.12 | 0.09 | 18.5 | 3.97 | 3.71 |
| 423W | 36.7 | 0.48 | 0.19 | 0.09 | 18.0 | 3.37 | 3.15 |
| 383M | 45.9 | 0.70 | 0.13 | 0.09 | 17.5 | 4.11 | 3.84 |
| 206L | 18.3 | 0.76 | 0.12 | 0.09 | 17.3 | 1.62 | 1.51 |
| 383L | 47.2 | 0.66 | 0.13 | 0.08 | 16.3 | 3.92 | 3.67 |
| 192V | 17.6 | 0.73 | 0.11 | 0.08 | 16.2 | 1.45 | 1.36 |
| 342M | 52.3 | 0.73 | 0.11 | 0.08 | 16.0 | 4.28 | 4.00 |
| 125L | 37.3 | 0.76 | 0.11 | 0.08 | 16.0 | 3.04 | 2.84 |
| 432L | 30.7 | 0.67 | 0.12 | 0.08 | 15.7 | 2.47 | 2.30 |
| 413A | 39.0 | 0.59 | 0.13 | 0.08 | 15.5 | 3.09 | 2.88 |
| 214R | 25.4 | 0.75 | 0.10 | 0.08 | 14.9 | 1.94 | 1.81 |
| 434L | 55.5 | 0.71 | 0.11 | 0.08 | 14.8 | 4.20 | 3.93 |
| 053F | 47.0 | 0.75 | 0.10 | 0.08 | 14.8 | 3.54 | 3.31 |
| 349Q | 42.6 | 0.76 | 0.10 | 0.07 | 14.7 | 3.19 | 2.98 |
| 434K | 58.5 | 0.70 | 0.11 | 0.07 | 14.5 | 4.33 | 4.05 |
| 398A | 42.8 | 0.72 | 0.10 | 0.07 | 14.4 | 3.14 | 2.93 |
| 342C | 71.5 | 0.71 | 0.10 | 0.07 | 14.0 | 5.09 | 4.76 |
| 381N | 55.8 | 0.74 | 0.10 | 0.07 | 13.7 | 3.91 | 3.66 |
| 227E | 27.5 | 0.72 | 0.10 | 0.07 | 13.7 | 1.93 | 1.80 |
| 375R | 71.8 | 0.60 | 0.10 | 0.06 | 12.1 | 4.43 | 4.14 |
| 373V | 49.2 | 0.76 | 0.08 | 0.06 | 12.0 | 3.01 | 2.81 |
| 349E | 47.9 | 0.76 | 0.08 | 0.06 | 11.6 | 2.84 | 2.65 |
| 429G | 50.2 | 0.74 | 0.08 | 0.06 | 11.6 | 2.97 | 2.78 |
| 234K | 33.8 | 0.65 | 0.09 | 0.06 | 11.6 | 2.00 | 1.87 |
| 429T | 53.7 | 0.72 | 0.08 | 0.06 | 11.5 | 3.16 | 2.95 |
| 202K | 9.2 | 0.61 | 0.09 | 0.06 | 11.3 | 0.53 | 0.50 |
| 214M | 22.6 | 0.74 | 0.07 | 0.06 | 10.9 | 1.25 | 1.17 |
| 418E | 83.8 | 0.69 | 0.05 | 0.04 | 7.1 | 3.03 | 2.83 |
| Zm wt | 210 | 0.17 | 0.03 | 0.0051 | 1.00 | 1.07 | 1.00 |
| 9070 | 34.2 | 0.74 | 0.21 | 0.15 | 30.0 | 5.25 | 4.90 |

Thirty nine variants were desensitized to tembotrione compared with the backbone enzyme, Round 7, variant 9070 (SEQ ID NO:2) and all were desensitized compared with maize wild type HPPD (SEQ ID NO:1). Because the assay for ON rate ratio includes an initial rate measurement at saturating hydroxyphenylpyruvate without inhibitor and with known enzyme concentration, an estimate of $k_{cat}$ was available. Taking into account $k_{cat}$ and insensitivity parameters, 30 variants were selected for measurement of substrate saturation kinetic parameters and re-evaluation of insensitivity to tembotrione. The kinetic and insensitivity parameters were determined as described in Example 1, and were multiplied to generate the "trait fitness" parameter. The complete list of variants, i.e., of selected single substitutions in SEQ ID NO:2, analyzed with multiple inhibitors and the results obtained are shown in Table 6. The same set of 30 variants were evaluated for insensitivity to mesotrione, sulcotrione, isoxaflutole (its active diketonitrile form, abbreviated DKN in Table 6) and topramezone.

All variants desensitized to tembotrione were desensitized to all other inhibitors, but not to the same magnitude or proportion. Fold improvement with tembotrione and diketonitrile (Trait fitness for the mutant/Trait fitness for maize wild type) was generally greater than with mesotrione or sulcotrione because the native maize HPPD was already less sensitive to inhibition by the latter two inhibitors. Further, each variant was not proportionately desensitized to all inhibitors. When trait fitness for tembotrione is plotted versus trait fitness for the other inhibitors, the correlation coefficients ($R^2$ value) obtained are 0.74 with mesotrione, 0.64 with sulcotrione, 0.86 with diketonitrile and 0.94 with topramezone (data not shown). These results show that although beneficial substitutions identified by selection with one inhibitor accrues benefits with other inhibitors, though selection with inhibitors outside of those used here may result in a different set of preferred substitutions.

TABLE 6

| | Kinetic parameters | | | Insensitivity parameter, ON × OFF | | | | |
|---|---|---|---|---|---|---|---|---|
| Substitution | $k_{cat}$, min$^{-1}$ | $K_M$ (uM) | $k_{cat}/K_M$ | Tembotrione | Mesotrione | Sulcotrione | DKN | Topramezon |
| 366E | 38.8 | 1.61 | 24.1 | 0.33 | 0.78 | 0.74 | 0.44 | 0.48 |
| 417Q | 33.5 | 1.56 | 21.5 | 0.33 | 0.73 | 0.74 | 0.39 | 0.39 |
| 432R | 56.7 | 1.97 | 28.8 | 0.23 | 0.53 | 0.59 | 0.27 | 0.31 |
| 432K | 67.5 | 2.08 | 32.4 | 0.21 | 0.52 | 0.59 | 0.26 | 0.29 |
| 417S | 26.7 | 1.41 | 18.9 | 0.33 | 0.67 | 0.77 | 0.41 | 0.41 |
| 214N | 84.6 | 3.62 | 23.4 | 0.25 | 0.48 | 0.59 | 0.33 | 0.32 |
| 385I | 46.1 | 2.29 | 20.1 | 0.28 | 0.56 | 0.70 | 0.41 | 0.38 |
| 158K | 47.1 | 2.49 | 18.9 | 0.29 | 0.54 | 0.63 | 0.38 | 0.37 |
| 385V | 30.3 | 1.91 | 15.9 | 0.34 | 0.65 | 0.78 | 0.33 | 0.49 |
| 191G | 71.7 | 2.46 | 29.1 | 0.19 | 0.40 | 0.51 | 0.25 | 0.24 |
| 211L | 77.6 | 3.2 | 24.2 | 0.22 | 0.37 | 0.47 | 0.25 | 0.27 |
| 340K | 73.5 | 2.41 | 30.5 | 0.16 | 0.44 | 0.54 | 0.23 | 0.22 |
| 206Q | 66.6 | 2.63 | 25.3 | 0.19 | 0.46 | 0.53 | 0.26 | 0.27 |
| 214T | 84.2 | 2.94 | 28.6 | 0.17 | 0.41 | 0.50 | 0.21 | 0.23 |
| 360L | 32.6 | 1.71 | 19.0 | 0.25 | 0.51 | 0.63 | 0.34 | 0.32 |
| 434H | 84.5 | 2.77 | 30.5 | 0.15 | 0.46 | 0.55 | 0.21 | 0.22 |
| 387L | 74.3 | 2.46 | 30.2 | 0.15 | 0.46 | 0.56 | 0.26 | 0.21 |
| 356K | 65.8 | 2.6 | 25.3 | 0.18 | 0.48 | 0.55 | 0.25 | 0.23 |
| 356R | 79.0 | 2.89 | 27.3 | 0.16 | 0.44 | 0.53 | 0.21 | 0.24 |
| 182M | 56.1 | 2.88 | 19.5 | 0.23 | 0.44 | 0.60 | 0.30 | 0.29 |
| 434R | 80.9 | 2.74 | 29.5 | 0.15 | 0.39 | 0.47 | 0.18 | 0.22 |
| 206S | 67.9 | 3.36 | 20.2 | 0.20 | 0.46 | 0.53 | 0.29 | 0.29 |
| 191L | 32.9 | 2.74 | 12.0 | 0.33 | 0.45 | 0.56 | 0.38 | 0.37 |
| 227G | 45.3 | 2.61 | 17.4 | 0.22 | 0.52 | 0.63 | 0.26 | 0.28 |
| 390N | 50.2 | 2.86 | 17.5 | 0.20 | 0.45 | 0.58 | 0.29 | 0.27 |
| 342V | 54.2 | 2.59 | 20.9 | 0.17 | 0.42 | 0.51 | 0.22 | 0.23 |
| 431F | 30.8 | 1.77 | 17.4 | 0.19 | 0.53 | 0.59 | 0.26 | 0.27 |
| 189P | 41.8 | 3.35 | 12.5 | 0.25 | 0.51 | 0.62 | 0.32 | 0.31 |
| 205T | 34.4 | 2.72 | 12.6 | 0.22 | 0.47 | 0.60 | 0.30 | 0.29 |
| 376W | 36.1 | 5.51 | 6.5 | 0.31 | 0.39 | 0.16 | 0.37 | 0.32 |
| 907O | 55.1 | 2.35 | 23.4 | 0.19 | 0.45 | 0.56 | 0.24 | 0.26 |
| Zm wt | 219 | 6.4 | 34.2 | 0.0051 | 0.0437 | 0.0872 | 0.0096 | 0.0154 |

| | Trait fitness, ON × OFF × $k_{cat}/K_M$ | | | | |
|---|---|---|---|---|---|
| Substitution | Tembotrione | Mesotrione | Sulcotrione | DKN | Topramezon |
| 366E | 8.0 | 18.7 | 17.8 | 10.6 | 11.6 |
| 417Q | 7.0 | 15.8 | 15.8 | 8.4 | 8.4 |
| 432R | 6.7 | 15.2 | 17.0 | 7.8 | 8.8 |
| 432K | 6.7 | 17.0 | 19.2 | 8.5 | 9.4 |
| 417S | 6.2 | 12.6 | 14.5 | 7.7 | 7.8 |
| 214N | 5.8 | 11.2 | 13.8 | 7.6 | 7.5 |
| 385I | 5.6 | 11.4 | 14.2 | 8.2 | 7.6 |
| 158K | 5.5 | 10.3 | 12.0 | 7.1 | 7.1 |
| 385V | 5.4 | 10.3 | 12.4 | 5.2 | 7.8 |
| 191G | 5.4 | 11.7 | 14.9 | 7.2 | 6.9 |
| 211L | 5.4 | 9.1 | 11.5 | 6.1 | 6.5 |
| 340K | 5.0 | 13.3 | 16.4 | 7.0 | 6.7 |
| 206Q | 4.9 | 11.6 | 13.4 | 6.7 | 6.7 |
| 214T | 4.8 | 11.7 | 14.3 | 6.1 | 6.5 |
| 360L | 4.8 | 9.7 | 12.0 | 6.5 | 6.0 |
| 434H | 4.7 | 14.1 | 16.7 | 6.5 | 6.7 |
| 387L | 4.7 | 14.0 | 17.0 | 7.8 | 6.5 |
| 356K | 4.5 | 12.2 | 13.9 | 6.3 | 5.8 |
| 356R | 4.5 | 11.9 | 14.4 | 5.7 | 6.5 |

TABLE 6-continued

| | | | | | |
|---|---|---|---|---|---|
| 182M | 4.5 | 8.7 | 11.7 | 5.9 | 5.7 |
| 434R | 4.3 | 11.4 | 13.9 | 5.4 | 6.5 |
| 206S | 4.1 | 9.4 | 10.7 | 5.9 | 6.0 |
| 191L | 3.9 | 5.4 | 6.7 | 4.5 | 4.4 |
| 227G | 3.7 | 9.0 | 10.9 | 4.5 | 4.9 |
| 390N | 3.5 | 7.9 | 10.1 | 5.2 | 4.7 |
| 342V | 3.5 | 8.7 | 10.6 | 4.6 | 4.7 |
| 431F | 3.4 | 9.2 | 10.3 | 4.6 | 4.7 |
| 189P | 3.1 | 6.3 | 7.7 | 4.0 | 3.9 |
| 205T | 2.8 | 6.0 | 7.6 | 3.8 | 3.7 |
| 376W | 2.1 | 2.5 | 1.1 | 2.4 | 2.1 |
| 9070 | 4.4 | 10.5 | 13.0 | 5.6 | 6.2 |
| Zm wt | 0.174 | 1.494 | 2.981 | 0.328 | 0.525 |

Example 9. Combining Beneficial Diversity to Optimize Fitness

To extend the benefits of the single substitutions identified in Example 2, twenty of the most preferred substitutions distributed among 14 positions in were selected for construction of a combinatorial library. The best of these, Q366E, was selected as the backbone for a library in which the remaining 19 substitutions were allowed to combine randomly. To construct the libraries, the technique of semi-synthetic shuffling was used, as described earlier (Ness J E et al., Nature Biotech 20, 1251-1255, 2002). Two libraries were made in which the frequency of mutations averaged 2.7 or 4.1 per gene and screened for insensitivity to tembotrione, as described in Example 2. Insensitivity parameters for tembotrione and $k_{cat}$ of 77 variants obtained from saturation mutagenesis followed by combinatorial shuffling and selected from the medium browning screen are shown in Table 7.

TABLE 7

| Seq ID NO. | Variant name | ON rate ratio | OFF rate ratio | ON × OFF | kcat | ON × OFF × kcat |
|---|---|---|---|---|---|---|
| 1 | Mz wt | 0.213 | 0.033 | 0.007 | 97.4 | 0.68 |
| 2 | 9070 | 0.744 | 0.116 | 0.086 | 40.0 | 3.45 |
| 3 | 9070Q366E | 0.760 | 0.273 | 0.208 | 20.1 | 4.18 |
| 4 | P056028-A-01 | 0.697 | 0.249 | 0.173 | 39.1 | 6.78 |
| 5 | P056028-A-02 | 0.680 | 0.387 | 0.263 | 38.6 | 10.15 |
| 6 | P056028-F-05 | 0.700 | 0.395 | 0.276 | 27.4 | 7.57 |
| 7 | P056028-G-01 | 0.742 | 0.320 | 0.238 | 32.2 | 7.65 |
| 8 | P056028-G-01R | 0.719 | 0.280 | 0.201 | 70.8 | 14.24 |
| 9 | P056028-B-02 | 0.800 | 0.469 | 0.375 | 28.2 | 10.58 |
| 10 | P056028-F-01 | 0.718 | 0.304 | 0.218 | 31.3 | 6.82 |
| 11 | P056028-D-08 | 0.681 | 0.361 | 0.246 | 27.5 | 6.77 |
| 12 | P056028-E-04 | 0.740 | 0.360 | 0.267 | 19.2 | 5.13 |
| 13 | P056028-A-06 | 0.760 | 0.281 | 0.214 | 27.0 | 5.77 |
| 14 | P056028-F-02 | 0.730 | 0.430 | 0.314 | 28.2 | 8.84 |
| 15 | P056028-C-01 | 0.742 | 0.310 | 0.230 | 25.9 | 5.95 |
| 16 | P056028-E-02 | 0.761 | 0.326 | 0.248 | 23.6 | 5.86 |
| 17 | P056028-C-07 | 0.714 | 0.382 | 0.273 | 21.2 | 5.80 |
| 18 | P056028-A-03 | 0.748 | 0.243 | 0.181 | 24.0 | 4.36 |
| 19 | P056028-C-05 | 0.715 | 0.375 | 0.268 | 21.7 | 5.80 |
| 20 | P056028-A-08 | 0.669 | 0.324 | 0.217 | 26.2 | 5.68 |
| 21 | P056028-D-03 | 0.770 | 0.453 | 0.349 | 19.6 | 6.83 |
| 22 | P056028-B-09 | 0.648 | 0.187 | 0.121 | 34.5 | 4.19 |
| 23 | P056028-A-10 | 0.707 | 0.367 | 0.260 | 16.8 | 4.35 |
| 24 | P056028-A-11 | 0.706 | 0.366 | 0.258 | 8.6 | 2.21 |
| 25 | P056028-A-04 | 0.724 | 0.133 | 0.096 | 11.1 | 1.06 |
| 26 | P056028-A-05 | 0.707 | 0.280 | 0.198 | 17.7 | 3.50 |
| 27 | P056028-A-07 | 0.726 | 0.329 | 0.239 | 19.5 | 4.65 |
| 28 | P056028-A-09 | 0.692 | 0.339 | 0.235 | 13.9 | 3.26 |
| 29 | P056028-B-01 | 0.745 | 0.309 | 0.230 | 18.6 | 4.28 |
| 30 | P056028-B-10 | 0.703 | 0.327 | 0.230 | 17.9 | 4.12 |
| 31 | P056028-B-03 | 0.732 | 0.353 | 0.259 | 17.9 | 4.63 |
| 32 | P056028-B-04 | 0.718 | 0.273 | 0.196 | 16.5 | 3.24 |
| 33 | P056028-B-05 | 0.734 | 0.287 | 0.211 | 18.3 | 3.85 |

TABLE 7-continued

| Seq ID NO. | Variant name | ON rate ratio | OFF rate ratio | ON × OFF | kcat | ON × OFF × kcat |
|---|---|---|---|---|---|---|
| 34 | P056028-B-06 | 0.713 | 0.353 | 0.252 | 20.0 | 5.03 |
| 35 | P056028-B-07 | 0.788 | 0.389 | 0.307 | 9.2 | 2.83 |
| 36 | P056028-B-08 | 0.681 | 0.325 | 0.221 | 15.5 | 3.44 |
| 37 | P056028-C-10 | 0.699 | 0.356 | 0.249 | 14.6 | 3.63 |
| 38 | P056028-C-11 | 0.731 | 0.293 | 0.214 | 12.3 | 2.64 |
| 39 | P056028-C-02 | 0.717 | 0.379 | 0.272 | 18.8 | 5.11 |
| 40 | P056028-C-03 | 0.739 | 0.356 | 0.263 | 13.7 | 3.62 |
| 41 | P056028-C-04 | 0.727 | 0.322 | 0.234 | 22.7 | 5.32 |
| 42 | P056028-C-06 | 0.742 | 0.351 | 0.261 | 10.6 | 2.77 |
| 43 | P056028-C-08 | 0.712 | 0.381 | 0.271 | 13.5 | 3.65 |
| 44 | P056028-C-09 | 0.706 | 0.314 | 0.222 | 17.0 | 3.76 |
| 45 | P056028-D-01 | 0.728 | 0.348 | 0.254 | 21.3 | 5.39 |
| 46 | P056028-D-10 | 0.670 | 0.253 | 0.170 | 18.1 | 3.07 |
| 47 | P056028-D-11 | 0.719 | 0.261 | 0.188 | 17.1 | 3.21 |
| 48 | P056028-D-02 | 0.730 | 0.299 | 0.218 | 24.3 | 5.31 |
| 49 | P056028-D-04 | 0.696 | 0.197 | 0.137 | 12.4 | 1.71 |
| 50 | P056028-D-05 | 0.730 | 0.508 | 0.371 | 12.6 | 4.66 |
| 51 | P056028-D-06 | 0.731 | 0.424 | 0.310 | 9.9 | 3.07 |
| 52 | P056028-D-07 | 0.775 | 0.370 | 0.286 | 9.1 | 2.60 |
| 53 | P056028-D-09 | 0.652 | 0.371 | 0.242 | 13.0 | 3.16 |
| 54 | P056028-E-10 | 0.702 | 0.339 | 0.238 | 11.5 | 2.73 |
| 55 | P056028-E-11 | 0.721 | 0.304 | 0.219 | 16.9 | 3.70 |
| 56 | P056028-E-03 | 0.735 | 0.412 | 0.303 | 16.9 | 5.10 |
| 57 | P056028-E-05 | 0.704 | 0.325 | 0.229 | 15.2 | 3.48 |
| 58 | P056028-E-06 | 0.346 | 0.186 | 0.064 | 28.2 | 1.76 |
| 59 | P056028-E-07 | 0.585 | 0.262 | 0.153 | 20.6 | 3.08 |
| 60 | P056028-E-08 | 0.685 | 0.410 | 0.281 | 12.6 | 3.55 |
| 61 | P056028-E-09 | 0.676 | 0.308 | 0.208 | 14.9 | 3.10 |
| 62 | P056028-F-10 | 0.726 | 0.291 | 0.211 | 13.7 | 2.89 |
| 63 | P056028-F-11 | 0.706 | 0.322 | 0.228 | 22.1 | 5.04 |
| 64 | P056028-F-03 | 0.738 | 0.491 | 0.363 | 13.0 | 4.73 |
| 65 | P056028-F-04 | 0.660 | 0.245 | 0.161 | 16.7 | 2.70 |
| 66 | P056028-F-06 | 0.739 | 0.305 | 0.225 | 14.5 | 3.25 |
| 67 | P056028-F-07 | 0.735 | 0.322 | 0.236 | 21.4 | 5.04 |
| 68 | P056028-F-08 | 0.705 | 0.377 | 0.266 | 12.1 | 3.23 |
| 69 | P056028-F-09 | 0.700 | 0.360 | 0.252 | 17.1 | 4.30 |
| 70 | P056028-G-10 | 0.607 | 0.259 | 0.157 | 29.3 | 4.61 |
| 71 | P056028-G-02 | 0.761 | 0.304 | 0.231 | 23.0 | 5.30 |
| 72 | P056028-G-04 | 0.752 | 0.248 | 0.186 | 13.6 | 2.54 |
| 73 | P056028-G-05 | 0.739 | 0.361 | 0.267 | 16.7 | 4.47 |
| 74 | P056028-G-06 | 0.725 | 0.382 | 0.277 | 12.0 | 3.30 |
| 75 | P056028-G-07 | 0.702 | 0.304 | 0.213 | 15.3 | 3.23 |
| 76 | P056028-G-08 | 0.737 | 0.379 | 0.279 | 11.8 | 3.29 |
| 77 | P056028-G-09 | 0.716 | 0.385 | 0.275 | 15.8 | 4.37 |

Combinatorial variants exhibiting insensitivity and $k_{cat}$ near those of the backbone sequence were further analyzed for kinetic parameters ($k_{cat}$ and $K_M$ obtained by substrate saturation kinetic analysis) and insensitivity parameters for mesotrione, sulcotrione, topramezone and the diketonitrile form of isoxaflutole. Trait fitness of combinatorial variants of HPPD were compared with wild type and Round 7, variant 9070 (SEQ ID NO:2; see Table 8). The data show that when variants composed of random combinations of single substitutions were selected based on fitness with tembotrione, fitness for the other inhibitors was also improved.

verify single copy inserts and for protein analysis to measure HPPD accumulation in young leaves. Events with high injury routinely occurred due to the variability inherent in

TABLE 8

| SEQ ID NO | Variant Name | Kinetic parameters | | | Insensitivity, tembotrione | | | | Insensitivity, mesotrione | | | |
|---|---|---|---|---|---|---|---|---|---|---|---|---|
| | | | | | Rate ratio | | | Trait | Rate ratio | | | Trait |
| | | $k_{cat}$ | $K_M$ | $k_{cat}/K_M$ | ON | OFF | ON × OFF | fitness | ON | OFF | ON × OFF | Fitness |
| 22 | P056028-B-09 | 93.2 | 3.00 | 31.6 | 0.75 | 0.35 | 0.26 | 8.28 | 0.67 | 1.00 | 0.67 | 21.2 |
| 4 | P056028-A-01 | 72.4 | 2.49 | 29.1 | 0.84 | 0.43 | 0.36 | 10.43 | 0.67 | 1.00 | 0.67 | 19.6 |
| 18 | P056028-A-03 | 62.8 | 2.98 | 21.0 | 0.80 | 0.40 | 0.32 | 6.81 | 0.70 | 1.00 | 0.70 | 14.8 |
| 21 | P056028-D-03 | 44.2 | 2.08 | 21.3 | 0.77 | 0.45 | 0.35 | 7.44 | 0.68 | 1.00 | 0.68 | 14.5 |
| 9 | P056028-B-02 | 58.7 | 3.00 | 19.6 | 0.80 | 0.47 | 0.37 | 7.35 | 0.63 | 1.00 | 0.63 | 12.3 |
| 7 | P056028-G-01 | 41.4 | 2.06 | 20.4 | 0.77 | 0.47 | 0.36 | 7.32 | 0.71 | 1.00 | 0.71 | 14.6 |
| 8 | P056028-G-01R | 70.8 | 2.02 | 35.3 | 0.72 | 0.28 | 0.20 | 7.09 | 0.73 | 1.00 | 0.73 | 25.6 |
| 12 | P056028-E-04 | 29.0 | 2.11 | 13.8 | 0.74 | 0.36 | 0.27 | 3.68 | 0.67 | 1.00 | 0.67 | 9.2 |
| 14 | P056028-F-02 | 45.5 | 2.22 | 20.5 | 0.73 | 0.43 | 0.31 | 6.43 | 0.67 | 1.00 | 0.67 | 13.7 |
| 5 | P056028-A-02 | 31.4 | 1.76 | 17.8 | 0.68 | 0.39 | 0.26 | 4.69 | 0.59 | 1.00 | 0.59 | 10.5 |
| 13 | P056028-A-06 | 74.6 | 4.05 | 18.4 | 0.76 | 0.28 | 0.21 | 3.94 | 0.63 | 0.74 | 0.47 | 8.6 |
| 6 | P056028-F-05 | 32.3 | 2.39 | 13.5 | 0.70 | 0.39 | 0.28 | 3.74 | 0.64 | 1.00 | 0.64 | 8.7 |
| 2 | 9070 | 88.9 | 2.91 | 30.7 | 0.80 | 0.22 | 0.17 | 5.36 | 0.66 | 0.89 | 0.59 | 18.1 |
| 3 | 9070Q366E | 30.8 | 1.57 | 19.5 | 0.82 | 0.33 | 0.27 | 5.25 | 0.72 | 1.00 | 0.72 | 14.0 |
| 1 | Zm wt | 219 | 6.41 | 34.2 | 0.20 | 0.04 | 0.007 | 0.26 | 0.20 | 0.31 | 0.062 | 2.1 |

| SEQ ID NO | Variant Name | Insensitivity, sulcotrione | | | | Insensitivity, isoxaflutole (DKN) | | | | Insensitivity, topramezone | | | |
|---|---|---|---|---|---|---|---|---|---|---|---|---|---|
| | | Rate ratio | | | Trait | Rate ratio | | | Trait | Rate ratio | | | Trait |
| | | ON | OFF | ON × OFF | fitness | ON | OFF | ON × OFF | fitness | ON | OFF | ON × OFF | Fitness |
| 22 | P056028-B-09 | 0.78 | 0.88 | 0.68 | 21.6 | 0.77 | 0.33 | 0.25 | 7.93 | 0.80 | 0.48 | 0.38 | 12.12 |
| 4 | P056028-A-01 | 0.80 | 1.22 | 0.97 | 28.4 | 0.82 | 0.44 | 0.36 | 10.45 | 0.85 | 0.60 | 0.51 | 14.86 |
| 18 | P056028-A-03 | 0.80 | 0.93 | 0.75 | 15.7 | 0.81 | 0.43 | 0.34 | 7.25 | 0.81 | 0.47 | 0.38 | 7.97 |
| 21 | P056028-D-03 | 0.76 | 1.11 | 0.84 | 17.9 | 0.76 | 0.40 | 0.31 | 6.51 | 0.80 | 0.58 | 0.46 | 9.88 |
| 9 | P056028-B-02 | 0.81 | 1.00 | 0.81 | 15.8 | 0.80 | 0.43 | 0.35 | 6.78 | 0.79 | 0.53 | 0.42 | 8.17 |
| 7 | P056028-G-01 | 0.78 | 1.14 | 0.89 | 18.2 | 0.77 | 0.42 | 0.32 | 6.55 | 0.80 | 0.57 | 0.46 | 9.31 |
| 12 | P056028-G-01R | 0.75 | 1.11 | 0.83 | 11.5 | 0.77 | 0.38 | 0.29 | 3.98 | 0.81 | 0.53 | 0.43 | 5.91 |
| 14 | P056028-E-04 | 0.72 | 1.09 | 0.79 | 16.1 | 0.75 | 0.42 | 0.31 | 6.44 | 0.80 | 0.60 | 0.48 | 9.85 |
| 5 | P056028-F-02 | 0.69 | 1.28 | 0.88 | 15.8 | 0.70 | 0.43 | 0.30 | 5.35 | 0.69 | 0.64 | 0.44 | 7.87 |
| 13 | P056028-A-02 | 0.77 | 0.76 | 0.58 | 10.8 | 0.77 | 0.28 | 0.22 | 3.97 | 0.76 | 0.32 | 0.24 | 4.52 |
| 6 | P056028-A-06 | 0.73 | 1.13 | 0.82 | 11.1 | 0.73 | 0.42 | 0.31 | 4.16 | 0.76 | 0.57 | 0.44 | 5.91 |
| 2 | 9070 | 0.81 | 0.71 | 0.38 | 11.8 | 0.82 | 0.20 | 0.11 | 3.30 | 0.79 | 0.25 | 0.13 | 3.99 |
| 3 | 9070Q366E | 0.80 | 1.13 | 0.50 | 9.69 | 0.83 | 0.39 | 0.17 | 3.40 | 0.81 | 0.57 | 0.26 | 5.04 |
| 1 | Zm wt | 0.30 | 0.28 | 0.042 | 1.45 | 0.08 | 0.01 | 0.0005 | 0.015 | 0.100 | 0.045 | 0.002 | 0.077 |

Example 10. Tolerance to Multiple HPPD-Inhibiting Herbicides in Transformed Soybean A 1228 bp genomic sequence at the 3' end of the *G. max* HPPD gene was isolated, sequenced and analyzed for promoter elements as described earlier (US20120042414(A1). Elements were modified so as to decrease or increase expression and various transformation cassettes, designed to direct a range of expression of shuffled maize HPPD, were constructed (see US Patent Publication US2012/0042414 (A1). Transgenic soybean events were created using particle bombardment of embryogenic callus cultures and selection with either hygromycin or chlorsulfuron. T0 regenerated plants were acclimated to greenhouse conditions in soil for two weeks and sprayed with two times labeled use rate of mesotrione. When sibling regenerants from the same event were available, the second plant was sprayed with 2× tembotrione. For each construct approximately 30 events were created with one or two copies of the HPPD insert at a single locus. To assess the expression cassettes, the number of events from each construct that showed 30% or less injury to 2× mesotrione and 2× tembotrione (on sibling plants) were counted. T0 plants were sampled for DNA analysis to verify single copy inserts and for protein analysis to measure HPPD accumulation in young leaves. Events with high injury routinely occurred due to the variability inherent in random genomic insertion methods. Plants with less than 30% visible injury were grown to maturity and the T1 seeds that were harvested were sown in the greenhouse or the field. The T1 plants were treated with 472 g/ha (4× field rate) mesotrione and screened by PCR to identify homozygotes. Tolerant, homozygous lines were grown and harvested for field trials.

A field trial performed in 2013 was designed to test: 1) various promoters known to drive a range of expression levels, described in US20120042414(A1), and 2) two N-terminal variations of the HPPD protein 9075 (SEQ ID NO:79), which is polypeptide sequence corresponding to Round 7, variant 9070 (SEQ ID NO:2) with R316 changed to Q. In one case, the N-terminus is that of the full-length enzyme. In the other case, the first 44 amino acids of SEQ ID NO:79 were replaced with the first 86 amino acids of the long form of soy HPPD (see US Patent Publication US2012/0042412(A1)). Both N-termini were previously shown to direct transgenically expressed HPPD to both chloroplasts and cytosol (see US Patent Publication US2012/0042412 (A1)). Transformation events from several of the constructs were highly tolerant to mesotrione, tembotrione, and isoxaflutole at two to four times labeled field application rates.

For positive control comparisons, the strong synthetic viral-based promoters SUP and SCP1 (Bowen et al., 2000) were used to drive various HPPD variants. Repeated occurrences of wrinkled leaf and chlorotic leaf phenotypes along with occasional sterility in the SUP and SCP1 events indicated that these promoters were not suitable for commercial event production. Measurements of HPPD protein accumulation in young leaves of T0 plants as shown in Table 9 revealed that the strong synthetic promoters accumulated HPPD protein near 1% of total soluble protein (10,000 ppm). The soybean derived HPPD promoters led to accumulation of HPPD protein in tolerant events at levels in the range of 0.02-0.1% total soluble protein (200-1000 ppm). In general, promoters with added synthetic core elements and enhancers produced more tolerant events and more protein than promoters with mutations and deletions. The lower expressing HPPD constructs provided higher recovery of phenotypically normal plants.

To look more closely at the role of the dual targeting of heterologous HPPD in soybean, constructs with N-terminal truncations (no targeting), truncated maize HPPD protein fused to known CTP elements (single transcript), and soybean N-terminal 1-86 fused to truncated maize HPPD for dual targeting were compared. All localization scenarios resulted in production of herbicide tolerant events, of varying efficacy (Table 9). Table 9 shows greenhouse characterization of T0 transgenic soybean plants expressing HPPD cassettes with varied promoters and an insensitive HPPD gene. Visual injury rating, 0 (no injury)-100 (dead) scale, average of 3 plots. DAT, days after treatment; All treatments were sprayed after two weeks acclimation from transformation (V2-V8) and included 0.25% v/v NIS and 8 lb/100 gal $(NH_4)_2SO_4$. Neither protein accumulation nor construct properties alone explain the spectrum of variability in green house T0 efficacy results. In all cases, however, tolerance to mesotrione at the maize field rate was more easily achieved than tolerance to tembotrione.

Because T0 plants are heterozygous for the HPPD insert and because field conditions can be more stringent than greenhouse conditions, field testing of homozygous lines is essential to fully evaluate the efficacy of the transgene traits. Field tests in 2013 with a round 6 desensitized HPPD variant showed that several events created were highly tolerant to mesotrione, tembotrione, and isoxaflutole at 2× or 4× treatment levels. Some transient injury was apparent, but by 14 days after treatment, the plants were almost completely recovered as shown in FIG. 9. Tabulated results for 2 different events are shown in Table 10, which shows data obtained from transgenic soybean plants expressing insensitive HPPD variant constructs showing tolerance to three different HPPD-inhibitor herbicides in the field.

Seed were homozygous for single copy inserts in elite genetics. Visual injury rating, 0 (no injury)-100 (dead) scale, average of 3 plots. In the table, the following abbreviations are used: DAT, days after treatment; 2× and 4×, treatment levels. All treatments were sprayed at the V4 stage and included 0.25% v/v NIS and 8 lb/100 gal $(NH_4)_2SO_4$.

TABLE 10

| Event Cassette | DAT | Isoxaflutole 2X | Isoxaflutole 4X | Mesotrione 2X | Mesotrione 4X | Tembotrione 2X |
|---|---|---|---|---|---|---|
| PRO206:FL9075 | 3 | 1 | 3 | 10 | 20 | 8 |
| PRO206:FL9075 | 7 | 0.7 | 1.0 | 1.7 | 8.3 | 4.3 |
| PRO206:FL9075 | 14 | 0.0 | 0.0 | 0.0 | 3.3 | 1.0 |
| PRO110e:Soy N-term | 3 | 0 | 2 | 13 | 20 | 13 |
| PRO110e:Soy N-term | 7 | 0.0 | 0.0 | 3.7 | 11.7 | 19.0 |

TABLE 9

| Promoter | N-terminus fusion | HPPD 9075 start | # Events meso screen | % Events ≤30% injury meso[d] | # Events tembo screen | % Events ≤30% injury tembo[e] | HPPD protein, ppm ave ≤30% injury[f] |
|---|---|---|---|---|---|---|---|
| SHP210[a] | GM-HPPD N1-86 | 50 | 15 | 100 | 12 | 100 | 326 |
| SUP | none | 24 | 29 | 79 | 8 | 50 | 12779 |
| SHP110[b] | GM-HPPD N1-86 | 50 | 13 | 100 | 11 | 27 | 266 |
| SHP103C | none | 1 | 26 | 80 | 26 | 42 | 594 |
| SHP106 | 6H1 CTP | 24 | 6 | 100 | 5 | 0 | 69 |
| SHP206[c] | none | 1 | 22 | 86 | na | na | 679 |
| SHP110e[c] | GM-HPPD N1-86 | 50 | 43 | 81 | na | na | 876 |
| SHP111 | GM-HPPD N1-86 | 50 | 37 | 70 | 13 | 7.7 | 318 |
| SHP120C | GM-HPPD N1-86 | 50 | 57 | 61 | 31 | 3.2 | 165 |
| SHP110 | GM-HPPD N1-86 | 50 | 13 | 38 | 1 | 0 | 382 |
| SHP103C | AT-RBCS CTP | 24 | 28 | 17 | 25 | 0 | 397 |

[a]Promoter SHP210 has deletion of TATA5, 2 and 3 with insertion of Element II at the 3' end of the promoter.
[b]Promoter SHP110 has deletion of TATA5, 2 and 3 with insertion of Element I at the 3" end of the promoter.
[c]Construct events tested in 2013 field tests.
[d]210 g ai/ha mesotrione, evaluated at 8 days after treatment
[e]93 g ai/ha tembotrione, evaluated at 8 days after treatment
[f]Parts per million of total soluble protein.

TABLE 10-continued

| Event Cassette | DAT | Isoxaflutole 2X | Isoxaflutole 4X | Mesotrione 2X | Mesotrione 4X | Tembotrione 2X |
|---|---|---|---|---|---|---|
| PRO110e:Soy N-term | 14 | 0.0 | 0.0 | 0.0 | 0.7 | 4.0 |

PRO206: Promoter 206 described in US20120042414(A1)
PRO110e: Promoter SHP110, described in US20120042414(A1) with the addition of a CaMV enhancer
FL9075: Full-length shuffled maize variant 9075 (SEQ ID NO: 79)
Soy N-term: 9075 (SEQ ID NO: 79) in which the first 44 amino acids were replaced with the first 86 amino acids of the long form of soy HPPD (US20120042412(A1))
Mesotrione 1x = 0.105 lb ai/a = 118 g ai/ha
Tembotrione 1x = 0.08 lb ai/a = 90 g ai/ha
Isoxaflutole 1x = 0.06 lb ai/a = 67 g ai/ha
All treatments were at the V4 stage and included 0.25% v/v NIS and 8 lb/100 gal NH42SO4.

Figure 14:
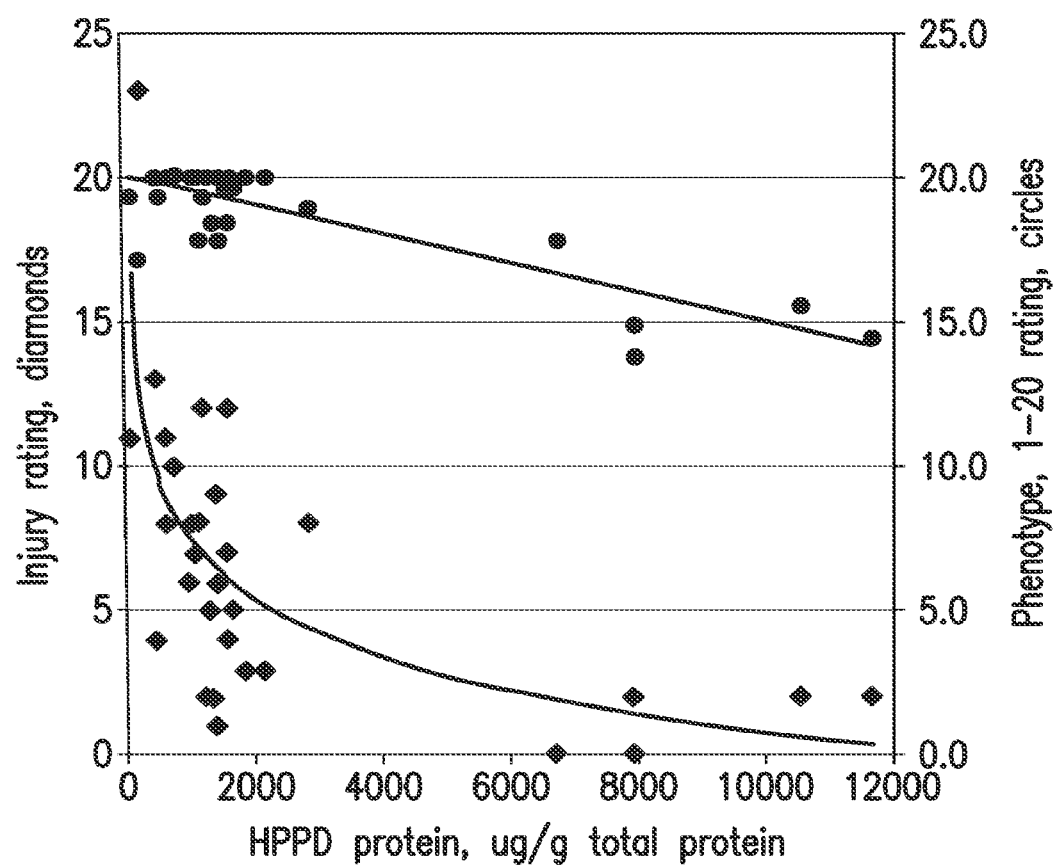
FIG. 14. The figure shows data indicating the influence of transgene expression level on trait efficacy and plant phenotype of soybean plants treated with tembotrione in the field. Tembotrione was applied at 180 g/ha (twice the labeled rate for maize) at the V4 stage. Phenotype was rated on mature plants in late summer. Filled diamonds: Injury rating, 0, no injury, 100, dead plant; 14 days after treatment. Open circles: Phenotype rating; 20, no symptoms; 1, leaf crinkling, empty seed pods. Correlation (R2), log plot, for injury versus protein=0.48. Correlation (R2), linear regression, for phenotype versus protein=0.70.

The data set from the field trial also illustrates the importance of attaining an expression level that is neither too low nor too high. FIG. 14 plots the efficacy of the transgenic trait, expressed as the visual rating of injury on a 100 scale as a function of the expression level, µg HPPD/g total protein. Excellent tolerance was obtained at a level of ~500-1000 µg/g, while lower expression results in more injury. However, perhaps because the HPPD reaction is practically irreversible and not inhibited by product, excessive catalytic capacity was associated with abnormal phenotypes such as chlorosis and leaf wrinkling (FIG. 14). The data show that symptoms are associated with high expression level.

The velocity of an enzyme catalyzed reaction is a function of $k_{cat}/K_M$, [E] and [S], where E is enzyme and S is substrate. The substrate concentration in soybean tissues is unknown but presumed to be constant, while enzyme concentration is determined by the expression level. In the presence of inhibitor, the fraction of the enzyme that is free to react with substrate is proportional to the $K_i$ of the inhibitor. A common parameter used to quantify performance of an enzyme in the presence of an inhibitor is $k_{cat}/K_M \times K_i$, which takes into account catalytic efficiency and inhibitor affinity. An approximation of that expression is the "trait fitness" parameter, $k_{cat}/K_M \times (ON \times OFF)$. Fitness times [E], or expression level, quantifies the expected performance in vivo, depending on substrate and inhibitor concentrations. Those are not known, but from the data presented, an empirical estimate of the range of values for the quantity "fitness parameter"×"expression level" is the following:

Fitness range, 2 to 200 $min^{-1}uM^{-1}$
Expression range, 200 to 2000 µg/g
Fitness×expression range, 400 to 400,000 $min^{-1}uM^{-1}$

Example 11. Identification of Shuffled Variants of Maize HPPD for Tolerance to as Vet Non-Commercialized Herbicidal Inhibitors The value of the substitutions identified as beneficial for desensitizing the enzyme to tembotrione is not limited to tembotrione, but extends to mesotrione, sulcotrione, topramezone and isoxaflutole diketonitrile. To discover a variant that confers tolerance to a new HPPD-inhibiting herbicide, the 554 single substitutions are screened by the same tiered screen as in Examples 2 and 3. It is anticipated that different sets of preferred substitutions will emerge depending on the structure of the inhibitor. The substitutions identified are then combined randomly and the resulting library screened as described, and novel recombinant variants selected for fitness to the novel compound are identified. Thus, any of the 554 substitutions identified, either singly or in combination, can be useful in developing a tolerance trait for future inhibitor classes.

Figure 16:
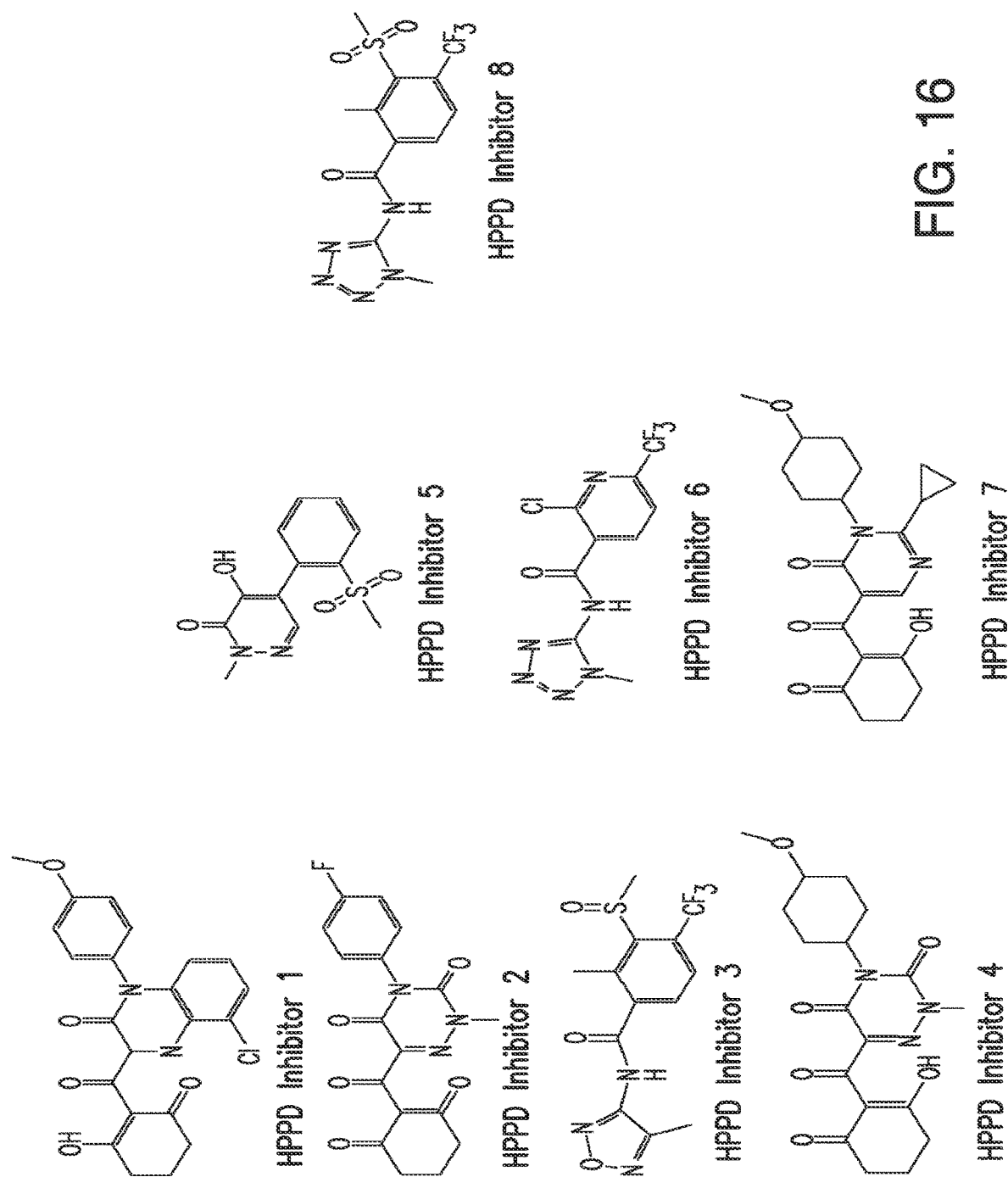
FIG. 16. The figure shows the chemical structures for various HPPD inhibitors.

For example, Round 6, variant 9070 (SEQ ID NO:2) and Round 8, variant 1973 (SEQ ID NO:8) can be compared with maize wild type HPPD (SEQ ID NO:1) for their ability to catalyze the HPPD reaction in the presence of additional HPPD inhibiting compounds, e.g., compounds such as those depicted in FIGS. 1 and 16. Compounds such as those depicted in FIGS. 1 and 16, can be purchased or synthesized following published synthesis methods. Enzymes are purified and kinetic and insensitivity parameters are determined as described in herein above. It is anticipated that the catalytic efficiency as indicated by $k_{cat}/K_M$ can be retained through multiple rounds of shuffling, while insensitivity to additional HPPD inhibitors can be increased, e.g., increased insensitivity to HPPD inhibitors depicted in FIGS. 1 and 16. Example 10 above describes a field trial in which a Round 6 HPPD variant expressed in soybean plants provided a high degree of tolerance to mesotrione, tembotrione and isoxaflutole. The most stringent condition for tolerance was a spray rate of two times the labeled rate of tembotrione. Therefore, fitness of the Round 6 variant to tembotrione can be used as the minimal level needed for efficacy when expressed in a suitable expression construct, to which can be compared additional variants of HPPD obtained through additional rounds of shuffling. In addition, the insensitivity to the novel HPPD inhibitors can be determined and shuffled variants selected wherein the insensitivity to novel HPPD inhibitors is increased.

Megatable Legends
Megatable 1.

The definitions of the column headings are as follows: "MUT ID," a unique identifier for each substitutions; "Position," amino acid position according to the numbering convention of SEQ ID NO:1, "Ref. A.A.," the standard single letter code for the amino acid present in the SEQ ID NO:1 sequence at the indicated position; and "Substitution," the standard single letter code for the amino acid present in the mutant sequence at the indicated position.

Megatable 2.

The definitions of the column headings are as follows: "MUT ID," a unique identifier for each substitutions; "Position," amino acid position according to the numbering convention of SEQ ID NO:1, "Ref. A.A.," the standard single letter code for the amino acid present in the SEQ ID NO:1 sequence at the indicated position; and "Substitution," the standard single letter code for the amino acid present in the mutant sequence at the indicated position. The remaining column headings refer to the kinetic parameters described herein above, i.e. "kcat" indicates the parameter $k_{cat}$; "ON rat." Refers to the ON ratio parameter; "OFF rat." refers to the OFF ratio parameter; "ON×OFF" refers to the calculated value that is the product of the ON ratio and OFF ratio parameters; "Fold vs. wt" is the calculated increase in "ON×OFF" value versus the wild-type sequence, SEQ ID NO:1; "ON×OFF×kcat" refers to the calculated value that is the product of the ON ratio, OFF ratio, and $k_{cat}$; and the last column with "Fold vs. wt" refers to the fold-increase in calculated value that is the product of the ON ratio, OFF ratio, and $k_{cat}$ of the indicated mutant versus the wild-type sequence, SEQ ID NO:1.

Megatable 3.

The definitions of the column headings are as follows: "SEQ ID" is the SEQ ID NO for the sequences herein above; and "Variant name" is a trivial but unique name for the indicated sequence. The remaining column headings refer to the kinetic parameters described herein above, i.e. "ON ratio" Refers to the ON ratio parameter; "OFF ratio" refers to the OFF ratio parameter; "ON×OFF" refers to the calculated value that is the product of the ON ratio and OFF ratio parameters; "kcat" indicates the parameter $k_{cat}$; and "ON×OFF×kcat" refers to the calculated value that is the product of the ON ratio, OFF ratio, and $k_{cat}$.

| MUT ID | Position | Ref A.A. | Substitution | Activity 1st tier |
|---|---|---|---|---|
| 1 | 52 | E | D | + |
| 2 | 52 | E | G | + |
| 3 | 52 | E | H | + |
| 4 | 52 | E | R | + |
| 5 | 52 | E | S | + |
| 6 | 52 | E | T | + |
| 7 | 53 | L | F | + |
| 8 | 53 | L | I | + |
| 9 | 53 | L | M | + |
| 10 | 54 | W | C | + |
| 11 | 54 | W | L | + |
| 12 | 54 | W | Q | + |
| 13 | 55 | C | A | + |
| 14 | 55 | C | G | + |
| 15 | 55 | C | T | + |
| 16 | 55 | C | V | + |
| 17 | 56 | A | H | + |
| 18 | 56 | A | L | + |
| 19 | 56 | A | N | + |
| 20 | 56 | A | Q | + |
| 21 | 56 | A | S | + |
| 22 | 56 | A | T | + |
| 23 | 58 | A | G | + |
| 24 | 58 | A | T | + |
| 25 | 125 | R | L | + |
| 26 | 147 | A | S | + |
| 27 | 148 | F | W | + |
| 28 | 148 | F | Y | + |
| 29 | 149 | R | A | + |
| 30 | 149 | R | I | + |
| 31 | 149 | R | K | + |
| 32 | 149 | R | M | + |
| 33 | 149 | R | P | + |
| 34 | 149 | R | S | + |
| 35 | 149 | R | T | + |
| 36 | 149 | R | V | + |
| 37 | 149 | R | W | + |
| 38 | 152 | V | E | + |
| 39 | 153 | A | F | + |
| 40 | 153 | A | I | + |
| 41 | 153 | A | K | + |
| 42 | 153 | A | L | + |
| 43 | 153 | A | Q | + |
| 44 | 153 | A | R | + |
| 45 | 153 | A | T | + |
| 46 | 153 | A | V | + |
| 47 | 154 | A | C | + |
| 48 | 154 | A | G | + |
| 49 | 154 | A | N | + |
| 50 | 154 | A | R | + |
| 51 | 154 | A | T | + |
| 52 | 157 | R | H | + |
| 53 | 157 | R | N | + |
| 54 | 157 | R | T | + |
| 55 | 157 | R | V | + |
| 56 | 158 | P | A | + |
| 57 | 158 | P | E | + |
| 58 | 158 | P | G | + |
| 59 | 158 | P | K | + |
| 60 | 159 | A | C | + |
| 61 | 159 | A | M | + |
| 62 | 159 | A | S | + |
| 63 | 159 | A | T | + |
| 64 | 159 | A | V | + |
| 65 | 160 | F | L | + |
| 66 | 160 | F | M | + |
| 67 | 160 | F | Y | + |
| 68 | 161 | G | A | + |
| 69 | 161 | G | E | + |
| 70 | 161 | G | L | + |
| 71 | 161 | G | M | + |
| 72 | 161 | G | N | + |
| 73 | 161 | G | P | + |
| 74 | 161 | G | Q | + |
| 75 | 161 | G | R | + |
| 76 | 161 | G | S | + |
| 77 | 161 | G | T | + |
| 78 | 161 | G | W | + |
| 79 | 161 | G | Y | + |
| 80 | 162 | P | T | + |
| 81 | 163 | V | A | + |
| 82 | 163 | V | C | + |
| 83 | 163 | V | M | + |
| 84 | 163 | V | T | + |
| 85 | 164 | D | A | + |
| 86 | 164 | D | E | + |
| 87 | 164 | D | H | + |
| 88 | 164 | D | S | + |
| 89 | 164 | D | T | + |
| 90 | 165 | L | C | + |
| 91 | 165 | L | M | + |
| 92 | 165 | L | V | + |
| 93 | 166 | G | A | + |
| 94 | 166 | G | P | + |
| 95 | 167 | R | + | + |
| 96 | 167 | R | V | + |
| 97 | 169 | F | A | + |
| 98 | 169 | F | H | + |
| 99 | 169 | F | W | + |
| 100 | 169 | F | Y | + |
| 101 | 170 | R | C | + |
| 102 | 170 | R | G | + |
| 103 | 170 | R | I | + |
| 104 | 170 | R | K | + |
| 105 | 170 | R | L | + |
| 106 | 170 | R | M | + |
| 107 | 170 | R | P | + |
| 108 | 170 | R | Q | + |
| 109 | 170 | R | S | + |
| 110 | 170 | R | T | + |
| 111 | 170 | R | V | + |
| 112 | 170 | R | W | + |
| 113 | 171 | L | F | + |
| 114 | 171 | L | I | + |
| 115 | 171 | L | M | + |
| 116 | 171 | L | V | + |
| 117 | 172 | A | P | + |
| 118 | 172 | A | R | + |
| 119 | 172 | A | S | + |
| 120 | 173 | E | P | + |
| 121 | 174 | V | C | + |
| 122 | 174 | V | I | + |
| 123 | 175 | E | D | + |
| 124 | 175 | E | V | + |
| 125 | 175 | E | W | + |
| 126 | 175 | E | + | + |
| 127 | 176 | L | A | + |
| 128 | 176 | L | M | + |
| 129 | 181 | V | F | + |
| 130 | 181 | V | I | + |
| 131 | 181 | V | M | + |
| 132 | 181 | V | N | + |
| 133 | 182 | L | M | + |
| 134 | 187 | Y | C | + |
| 135 | 187 | Y | E | + |
| 136 | 187 | Y | G | + |
| 137 | 187 | Y | H | + |
| 138 | 187 | Y | M | + |
| 139 | 187 | Y | V | + |
| 140 | 188 | P | D | + |

-continued

Megatable 1

| MUT ID | Position | Ref A.A. | Substitution | Activity 1st tier |
|---|---|---|---|---|
| 141 | 188 | P | G | + |
| 142 | 188 | P | Q | + |
| 143 | 189 | D | E | + |
| 144 | 189 | D | P | + |
| 145 | 189 | D | S | + |
| 146 | 189 | D | T | + |
| 147 | 190 | G | A | + |
| 148 | 190 | G | C | + |
| 149 | 190 | G | D | + |
| 150 | 190 | G | E | + |
| 151 | 190 | G | L | + |
| 152 | 190 | G | M | + |
| 153 | 190 | G | N | + |
| 154 | 190 | G | P | + |
| 155 | 190 | G | Q | + |
| 156 | 190 | G | R | + |
| 157 | 190 | G | S | + |
| 158 | 190 | G | T | + |
| 159 | 190 | G | V | + |
| 160 | 190 | G | W | + |
| 161 | 191 | A | E | + |
| 162 | 191 | A | F | + |
| 163 | 191 | A | G | + |
| 164 | 191 | A | H | + |
| 165 | 191 | A | I | + |
| 166 | 191 | A | K | + |
| 167 | 191 | A | L | + |
| 168 | 191 | A | M | + |
| 169 | 191 | A | N | + |
| 170 | 191 | A | R | + |
| 171 | 191 | A | S | + |
| 172 | 191 | A | T | + |
| 173 | 191 | A | V | + |
| 174 | 192 | A | V | + |
| 175 | 193 | G | A | + |
| 176 | 193 | G | H | + |
| 177 | 193 | G | I | + |
| 178 | 193 | G | L | + |
| 179 | 193 | G | P | + |
| 180 | 193 | G | Q | + |
| 181 | 193 | G | R | + |
| 182 | 193 | G | S | + |
| 183 | 193 | G | T | + |
| 184 | 193 | G | V | + |
| 185 | 194 | E | D | + |
| 186 | 194 | E | L | + |
| 187 | 195 | P | A | + |
| 188 | 195 | P | C | + |
| 189 | 195 | P | D | + |
| 190 | 195 | P | E | + |
| 191 | 195 | P | Q | + |
| 192 | 195 | P | S | + |
| 193 | 195 | P | T | + |
| 194 | 195 | P | V | + |
| 195 | 196 | F | W | + |
| 196 | 200 | F | C | + |
| 197 | 202 | G | A | + |
| 198 | 202 | G | E | + |
| 199 | 202 | G | K | + |
| 200 | 202 | G | L | + |
| 201 | 202 | G | T | + |
| 202 | 202 | G | V | + |
| 203 | 202 | G | Y | + |
| 204 | 204 | A | C | + |
| 205 | 204 | A | D | + |
| 206 | 204 | A | E | + |
| 207 | 204 | A | G | + |
| 208 | 204 | A | H | + |
| 209 | 204 | A | K | + |
| 210 | 204 | A | L | + |
| 211 | 204 | A | M | + |
| 212 | 204 | A | N | + |
| 213 | 204 | A | Q | + |
| 214 | 204 | A | T | + |
| 215 | 204 | A | V | + |
| 216 | 205 | S | D | + |
| 217 | 205 | S | G | + |
| 218 | 205 | S | L | + |
| 219 | 205 | S | Q | + |
| 220 | 205 | S | T | + |
| 221 | 205 | S | V | + |
| 222 | 206 | P | C | + |
| 223 | 206 | P | D | + |
| 224 | 206 | P | K | + |
| 225 | 206 | P | L | + |
| 226 | 206 | P | Q | + |
| 227 | 206 | P | S | + |
| 228 | 206 | P | T | + |
| 229 | 207 | G | Q | + |
| 230 | 207 | G | S | + |
| 231 | 207 | G | V | + |
| 232 | 208 | A | G | + |
| 233 | 208 | A | H | + |
| 234 | 208 | A | Q | + |
| 235 | 208 | A | R | + |
| 236 | 208 | A | W | + |
| 237 | 209 | A | C | + |
| 238 | 209 | A | D | + |
| 239 | 209 | A | E | + |
| 240 | 209 | A | G | + |
| 241 | 209 | A | I | + |
| 242 | 209 | A | K | + |
| 243 | 209 | A | L | + |
| 244 | 209 | A | M | + |
| 245 | 209 | A | P | + |
| 246 | 209 | A | Q | + |
| 247 | 209 | A | S | + |
| 248 | 209 | A | T | + |
| 249 | 209 | A | W | + |
| 250 | 210 | D | E | + |
| 251 | 210 | D | G | + |
| 252 | 210 | D | S | + |
| 253 | 210 | D | T | + |
| 254 | 211 | Y | C | + |
| 255 | 211 | Y | F | + |
| 256 | 211 | Y | L | + |
| 257 | 211 | Y | S | + |
| 258 | 211 | Y | W | + |
| 259 | 212 | G | K | + |
| 260 | 213 | L | W | + |
| 261 | 214 | S | K | + |
| 262 | 214 | S | M | + |
| 263 | 214 | S | N | + |
| 264 | 214 | S | Q | + |
| 265 | 214 | S | R | + |
| 266 | 214 | S | T | + |
| 267 | 215 | R | A | + |
| 268 | 215 | R | G | + |
| 269 | 217 | D | Q | + |
| 270 | 217 | D | Y | + |
| 271 | 220 | V | T | + |
| 272 | 221 | G | A | + |
| 273 | 221 | G | F | + |
| 274 | 221 | G | H | + |
| 275 | 221 | G | I | + |
| 276 | 221 | G | L | + |
| 277 | 221 | G | M | + |
| 278 | 221 | G | T | + |
| 279 | 221 | G | V | + |
| 280 | 222 | N | G | + |
| 281 | 222 | N | V | + |
| 282 | 227 | A | D | + |
| 283 | 227 | A | E | + |
| 284 | 227 | A | G | + |
| 285 | 227 | A | I | + |
| 286 | 227 | A | K | + |
| 287 | 227 | A | L | + |
| 288 | 227 | A | M | + |

Megatable 1

| MUT ID | Position | Ref A.A. | Substitution | Activity 1st tier |
|---|---|---|---|---|
| 289 | 227 | A | N | + |
| 290 | 227 | A | Q | + |
| 291 | 227 | A | R | + |
| 292 | 227 | A | S | + |
| 293 | 227 | A | T | + |
| 294 | 227 | A | V | + |
| 295 | 229 | A | T | + |
| 296 | 230 | A | R | + |
| 297 | 230 | A | V | + |
| 298 | 231 | A | C | + |
| 299 | 231 | A | H | + |
| 300 | 231 | A | L | + |
| 301 | 231 | A | S | + |
| 302 | 231 | A | T | + |
| 303 | 233 | M | V | + |
| 304 | 234 | A | C | + |
| 305 | 234 | A | E | + |
| 306 | 234 | A | G | + |
| 307 | 234 | A | K | + |
| 308 | 234 | A | L | + |
| 309 | 234 | A | M | + |
| 310 | 234 | A | Q | + |
| 311 | 234 | A | S | + |
| 312 | 234 | A | V | + |
| 313 | 238 | G | S | + |
| 314 | 240 | H | R | + |
| 315 | 241 | E | A | + |
| 316 | 241 | E | D | + |
| 317 | 241 | E | G | + |
| 318 | 241 | E | N | + |
| 319 | 241 | E | P | + |
| 320 | 241 | E | R | + |
| 321 | 241 | E | S | + |
| 322 | 241 | E | T | + |
| 323 | 242 | F | A | + |
| 324 | 242 | F | D | + |
| 325 | 242 | F | S | + |
| 326 | 273 | L | V | + |
| 327 | 292 | H | N | + |
| 328 | 331 | L | D | + |
| 329 | 331 | L | G | + |
| 330 | 331 | L | N | + |
| 331 | 331 | L | R | + |
| 332 | 332 | S | A | + |
| 333 | 339 | R | K | + |
| 334 | 340 | R | E | + |
| 335 | 340 | R | K | + |
| 336 | 340 | R | N | + |
| 337 | 342 | A | C | + |
| 338 | 342 | A | L | + |
| 339 | 342 | A | M | + |
| 340 | 342 | A | N | + |
| 341 | 342 | A | R | + |
| 342 | 342 | A | V | + |
| 343 | 343 | G | R | + |
| 344 | 345 | V | I | + |
| 345 | 347 | T | S | + |
| 346 | 348 | E | Y | + |
| 347 | 349 | A | E | + |
| 348 | 349 | A | Q | + |
| 349 | 349 | A | R | + |
| 350 | 349 | A | S | + |
| 351 | 351 | I | C | + |
| 352 | 351 | I | V | + |
| 353 | 352 | N | E | + |
| 354 | 352 | N | K | + |
| 355 | 352 | N | L | + |
| 356 | 352 | N | Q | + |
| 357 | 352 | N | R | + |
| 358 | 353 | E | L | + |
| 359 | 353 | E | M | + |
| 360 | 353 | E | S | + |
| 361 | 353 | E | T | + |
| 362 | 356 | E | K | + |
| 363 | 356 | E | R | + |
| 364 | 357 | L | Y | + |
| 365 | 358 | G | E | + |
| 366 | 358 | G | R | + |
| 367 | 360 | M | L | + |
| 368 | 360 | M | T | + |
| 369 | 364 | D | G | + |
| 370 | 364 | D | S | + |
| 371 | 364 | D | V | + |
| 372 | 365 | D | A | + |
| 373 | 366 | Q | E | + |
| 374 | 368 | V | L | + |
| 375 | 369 | L | M | + |
| 376 | 369 | L | V | + |
| 377 | 372 | I | A | + |
| 378 | 372 | I | K | + |
| 379 | 372 | I | Q | + |
| 380 | 372 | I | S | + |
| 381 | 372 | I | T | + |
| 382 | 373 | F | G | + |
| 383 | 373 | F | L | + |
| 384 | 373 | F | R | + |
| 385 | 373 | F | V | + |
| 386 | 375 | K | L | + |
| 387 | 375 | K | R | + |
| 388 | 376 | P | C | + |
| 389 | 376 | P | G | + |
| 390 | 376 | P | S | + |
| 391 | 376 | P | V | + |
| 392 | 376 | P | W | + |
| 393 | 377 | V | E | + |
| 394 | 377 | V | G | + |
| 395 | 377 | V | L | + |
| 396 | 379 | D | K | + |
| 397 | 381 | P | N | + |
| 398 | 382 | T | A | + |
| 399 | 382 | T | F | + |
| 400 | 382 | T | S | + |
| 401 | 383 | F | L | + |
| 402 | 383 | F | M | + |
| 403 | 384 | F | W | + |
| 404 | 384 | F | Y | + |
| 405 | 385 | L | I | + |
| 406 | 385 | L | V | + |
| 407 | 386 | E | C | + |
| 408 | 386 | E | I | + |
| 409 | 386 | E | V | + |
| 410 | 387 | I | G | + |
| 411 | 387 | I | L | + |
| 412 | 388 | I | L | + |
| 413 | 388 | I | S | + |
| 414 | 388 | I | V | + |
| 415 | 389 | Q | G | + |
| 416 | 389 | Q | K | + |
| 417 | 389 | Q | T | + |
| 418 | 390 | R | N | + |
| 419 | 391 | I | L | + |
| 420 | 391 | I | V | + |
| 421 | 392 | G | R | + |
| 422 | 392 | G | V | + |
| 423 | 394 | M | I | + |
| 424 | 394 | M | K | + |
| 425 | 394 | M | L | + |
| 426 | 394 | M | Q | + |
| 427 | 394 | M | V | + |
| 428 | 394 | M | Y | + |
| 429 | 395 | E | K | + |
| 430 | 395 | E | Q | + |
| 431 | 395 | E | S | + |
| 432 | 395 | E | V | + |
| 433 | 396 | K | A | + |
| 434 | 396 | K | L | + |
| 435 | 396 | K | M | + |
| 436 | 396 | K | Q | + |

Megatable 1

| MUT ID | Position | Ref A.A. | Substitution | Activity 1st tier |
|---|---|---|---|---|
| 437 | 396 | K | R | + |
| 438 | 396 | K | T | + |
| 439 | 396 | K | V | + |
| 440 | 397 | D | G | + |
| 441 | 397 | D | S | + |
| 442 | 398 | E | A | + |
| 443 | 398 | E | D | + |
| 444 | 398 | E | G | + |
| 445 | 398 | E | P | + |
| 446 | 398 | E | S | + |
| 447 | 399 | K | A | + |
| 448 | 399 | K | D | + |
| 449 | 399 | K | G | + |
| 450 | 399 | K | H | + |
| 451 | 399 | K | I | + |
| 452 | 399 | K | M | + |
| 453 | 399 | K | N | + |
| 454 | 399 | K | Q | + |
| 455 | 399 | K | R | + |
| 456 | 399 | K | S | + |
| 457 | 399 | K | T | + |
| 458 | 399 | K | V | + |
| 459 | 399 | K | Y | + |
| 460 | 400 | G | E | + |
| 461 | 400 | G | K | + |
| 462 | 400 | G | S | + |
| 463 | 401 | Q | A | + |
| 464 | 401 | Q | E | + |
| 465 | 401 | Q | S | + |
| 466 | 401 | Q | V | + |
| 467 | 406 | G | C | + |
| 468 | 407 | G | A | + |
| 469 | 407 | G | K | + |
| 470 | 407 | G | L | + |
| 471 | 407 | G | R | + |
| 472 | 407 | G | S | + |
| 473 | 407 | G | T | + |
| 474 | 408 | C | G | + |
| 475 | 408 | C | R | + |
| 476 | 408 | C | T | + |
| 477 | 408 | C | V | + |
| 478 | 408 | C | W | + |
| 479 | 411 | F | A | + |
| 480 | 411 | F | L | + |
| 481 | 413 | K | A | + |
| 482 | 413 | K | P | + |
| 483 | 413 | K | R | + |
| 484 | 413 | K | S | + |
| 485 | 415 | N | A | + |
| 486 | 416 | F | R | + |
| 487 | 416 | F | V | + |
| 488 | 417 | G | Q | + |
| 489 | 417 | G | S | + |
| 490 | 418 | Q | A | + |
| 491 | 418 | Q | C | + |
| 492 | 418 | Q | E | + |
| 493 | 418 | Q | G | + |
| 494 | 418 | Q | L | + |
| 495 | 418 | Q | T | + |
| 496 | 422 | S | M | + |
| 497 | 423 | I | V | + |
| 498 | 423 | I | W | + |
| 499 | 424 | E | Q | + |
| 500 | 425 | D | A | + |
| 501 | 425 | D | E | + |
| 502 | 425 | D | G | + |
| 503 | 425 | D | M | + |
| 504 | 425 | D | S | + |
| 505 | 425 | D | T | + |
| 506 | 426 | Y | L | + |
| 507 | 426 | Y | W | + |
| 508 | 427 | E | A | + |
| 509 | 427 | E | L | + |
| 510 | 427 | E | M | + |
| 511 | 428 | K | R | + |
| 512 | 428 | K | R | + |
| 513 | 428 | K | V | + |
| 514 | 429 | S | C | + |
| 515 | 429 | S | D | + |
| 516 | 429 | S | G | + |
| 517 | 429 | S | T | + |
| 518 | 430 | L | M | + |
| 519 | 430 | L | V | + |
| 520 | 431 | E | A | + |
| 521 | 431 | E | F | + |
| 522 | 431 | E | G | + |
| 523 | 431 | E | L | + |
| 524 | 431 | E | N | + |
| 525 | 432 | A | D | + |
| 526 | 432 | A | G | + |
| 527 | 432 | A | K | + |
| 528 | 432 | A | L | + |
| 529 | 432 | A | R | + |
| 530 | 432 | A | S | + |
| 531 | 432 | A | V | + |
| 532 | 433 | K | E | + |
| 533 | 433 | K | H | + |
| 534 | 433 | K | L | + |
| 535 | 433 | K | P | + |
| 536 | 433 | K | R | + |
| 537 | 433 | K | S | + |
| 538 | 433 | K | V | + |
| 539 | 434 | Q | A | + |
| 540 | 434 | Q | C | + |
| 541 | 434 | Q | D | + |
| 542 | 434 | Q | F | + |
| 543 | 434 | Q | G | + |
| 544 | 434 | Q | H | + |
| 545 | 434 | Q | K | + |
| 546 | 434 | Q | L | + |
| 547 | 434 | Q | R | + |
| 548 | 437 | A | F | + |
| 549 | 437 | A | K | + |
| 550 | 437 | A | V | + |
| 551 | 438 | A | G | + |
| 552 | 438 | A | R | + |
| 553 | 439 | A | R | + |

Megatable 2

| MUT. NO. | Pos. | Ref. AA | Sub. | kcat | ON Rat. | OFF Rat. | ON × OFF | Fold vs. wt | ON × OFF kcat | Fold vs. wt |
|---|---|---|---|---|---|---|---|---|---|---|
| SEQ ID NO 1 | | | | 210 | 0.17 | 0.03 | 0.0051 | 1.00 | 1.07 | 1.00 |
| SEQ ID NO 2 | | | | 34.2 | 0.74 | 0.21 | 0.15 | 30.0 | 5.25 | 4.90 |
| 330 | 331 | L | N | 40.4 | 0.75 | 0.43 | 0.32 | 63.0 | 12.99 | 12.14 |
| 551 | 438 | A | G | 33.8 | 0.74 | 0.42 | 0.31 | 60.3 | 10.41 | 9.73 |
| 331 | 331 | L | R | 30.3 | 0.73 | 0.38 | 0.28 | 54.6 | 8.44 | 7.89 |
| 549 | 437 | A | K | 35.7 | 0.76 | 0.36 | 0.27 | 52.9 | 9.63 | 9.00 |
| 552 | 438 | A | R | 29.2 | 0.75 | 0.33 | 0.25 | 48.5 | 7.23 | 6.76 |

-continued

Megatable 2

| MUT. NO. | Pos. | Ref. AA | Sub. | kcat | ON Rat. | OFF Rat. | ON × OFF | Fold vs. wt | ON × OFF kcat | Fold vs. wt |
|---|---|---|---|---|---|---|---|---|---|---|
| 406 | 385 | L | V | 21.4 | 0.75 | 0.33 | 0.25 | 48.2 | 5.26 | 4.92 |
| 392 | 376 | P | W | 23.1 | 0.68 | 0.34 | 0.23 | 46.0 | 5.42 | 5.07 |
| 489 | 417 | G | S | 18.5 | 0.82 | 0.28 | 0.23 | 45.2 | 4.26 | 3.98 |
| 69 | 161 | G | E | 17.2 | 0.78 | 0.29 | 0.23 | 44.8 | 3.92 | 3.67 |
| 74 | 161 | G | Q | 27.7 | 0.77 | 0.30 | 0.23 | 44.8 | 6.33 | 5.91 |
| 553 | 439 | A | R | 24.7 | 0.73 | 0.30 | 0.22 | 43.3 | 5.45 | 5.09 |
| 76 | 161 | G | S | 24.5 | 0.76 | 0.29 | 0.22 | 43.2 | 5.41 | 5.06 |
| 133 | 182 | L | M | 26.0 | 0.79 | 0.28 | 0.22 | 42.5 | 5.63 | 5.26 |
| 113 | 171 | L | F | 16.6 | 0.75 | 0.28 | 0.21 | 41.8 | 3.54 | 3.31 |
| 268 | 215 | R | G | 24.4 | 0.79 | 0.27 | 0.21 | 41.8 | 5.19 | 4.85 |
| 171 | 191 | A | S | 12.4 | 0.75 | 0.28 | 0.21 | 40.8 | 2.59 | 2.42 |
| 59 | 158 | P | K | 50.4 | 0.77 | 0.27 | 0.21 | 40.6 | 10.44 | 9.76 |
| 332 | 332 | S | A | 41.5 | 0.75 | 0.28 | 0.21 | 40.5 | 8.58 | 8.02 |
| 79 | 161 | G | Y | 21.6 | 0.78 | 0.26 | 0.20 | 40.0 | 4.40 | 4.11 |
| 405 | 385 | L | I | 27.5 | 0.75 | 0.27 | 0.20 | 39.5 | 5.55 | 5.18 |
| 329 | 331 | L | G | 29.0 | 0.73 | 0.27 | 0.20 | 39.1 | 5.78 | 5.40 |
| 72 | 161 | G | N | 23.5 | 0.78 | 0.25 | 0.20 | 38.6 | 4.63 | 4.33 |
| 488 | 417 | G | Q | 20.6 | 0.74 | 0.27 | 0.20 | 38.4 | 4.04 | 3.77 |
| 70 | 161 | G | L | 14.0 | 0.77 | 0.25 | 0.19 | 37.8 | 2.71 | 2.53 |
| 60 | 159 | A | C | 21.0 | 0.79 | 0.24 | 0.19 | 37.6 | 4.03 | 3.77 |
| 94 | 166 | G | P | 11.4 | 0.77 | 0.25 | 0.19 | 37.2 | 2.17 | 2.03 |
| 93 | 166 | G | A | 23.1 | 0.77 | 0.24 | 0.19 | 36.4 | 4.29 | 4.01 |
| 328 | 331 | L | D | 32.4 | 0.75 | 0.25 | 0.18 | 36.2 | 5.98 | 5.59 |
| 98 | 169 | F | H | 13.8 | 0.75 | 0.25 | 0.18 | 36.0 | 2.54 | 2.38 |
| 373 | 366 | Q | E | 20.1 | 0.75 | 0.24 | 0.18 | 34.9 | 3.58 | 3.35 |
| 400 | 382 | T | S | 29.6 | 0.71 | 0.24 | 0.17 | 33.0 | 4.97 | 4.65 |
| 367 | 360 | M | L | 26.5 | 0.77 | 0.22 | 0.17 | 32.6 | 4.41 | 4.12 |
| 418 | 390 | R | N | 30.3 | 0.75 | 0.22 | 0.17 | 32.4 | 5.00 | 4.67 |
| 144 | 189 | D | P | 26.2 | 0.76 | 0.22 | 0.16 | 32.3 | 4.31 | 4.02 |
| 365 | 358 | G | E | 15.5 | 0.69 | 0.23 | 0.16 | 31.5 | 2.49 | 2.33 |
| 362 | 356 | E | K | 38.8 | 0.75 | 0.21 | 0.16 | 31.2 | 6.18 | 5.78 |
| 226 | 206 | P | Q | 35.4 | 0.74 | 0.21 | 0.16 | 30.8 | 5.57 | 5.20 |
| 167 | 191 | A | L | 21.5 | 0.77 | 0.20 | 0.16 | 30.5 | 3.35 | 3.13 |
| 529 | 432 | A | R | 30.6 | 0.78 | 0.20 | 0.16 | 30.4 | 4.75 | 4.44 |
| 363 | 356 | E | R | 39.1 | 0.75 | 0.21 | 0.15 | 30.0 | 5.97 | 5.58 |
| 335 | 340 | R | K | 44.7 | 0.75 | 0.20 | 0.15 | 28.7 | 6.56 | 6.13 |
| 227 | 206 | P | S | 35.5 | 0.75 | 0.20 | 0.15 | 28.5 | 5.15 | 4.82 |
| 548 | 437 | A | F | 12.7 | 0.76 | 0.19 | 0.14 | 28.1 | 1.82 | 1.70 |
| 263 | 214 | S | N | 35.4 | 0.76 | 0.19 | 0.14 | 27.9 | 5.04 | 4.71 |
| 411 | 387 | I | L | 33.3 | 0.75 | 0.19 | 0.14 | 27.0 | 4.58 | 4.28 |
| 279 | 221 | G | V | 9.8 | 0.75 | 0.18 | 0.13 | 26.1 | 1.30 | 1.21 |
| 527 | 432 | A | K | 31.5 | 0.76 | 0.17 | 0.13 | 25.7 | 4.13 | 3.86 |
| 453 | 399 | K | N | 37.4 | 0.75 | 0.17 | 0.13 | 25.2 | 4.81 | 4.50 |
| 256 | 211 | Y | L | 36.9 | 0.77 | 0.17 | 0.13 | 25.0 | 4.72 | 4.41 |
| 270 | 217 | D | Y | 20.7 | 0.76 | 0.17 | 0.13 | 24.9 | 2.63 | 2.45 |
| 521 | 431 | E | F | 28.9 | 0.80 | 0.16 | 0.13 | 24.5 | 3.61 | 3.37 |
| 455 | 399 | K | R | 34.8 | 0.74 | 0.17 | 0.12 | 23.6 | 4.18 | 3.91 |
| 438 | 396 | K | T | 37.7 | 0.71 | 0.17 | 0.12 | 23.5 | 4.51 | 4.22 |
| 284 | 227 | A | G | 34.6 | 0.79 | 0.15 | 0.12 | 23.2 | 4.09 | 3.83 |
| 386 | 375 | K | L | 36.1 | 0.71 | 0.16 | 0.12 | 22.8 | 4.20 | 3.92 |
| 357 | 352 | N | R | 39.4 | 0.75 | 0.15 | 0.11 | 21.9 | 4.40 | 4.11 |
| 454 | 399 | K | Q | 36.1 | 0.72 | 0.15 | 0.11 | 21.5 | 3.96 | 3.70 |
| 435 | 396 | K | M | 35.4 | 0.73 | 0.15 | 0.11 | 21.4 | 3.86 | 3.61 |
| 456 | 399 | K | S | 35.8 | 0.70 | 0.15 | 0.11 | 21.3 | 3.90 | 3.64 |
| 547 | 434 | Q | R | 52.1 | 0.73 | 0.15 | 0.11 | 21.2 | 5.63 | 5.26 |
| 272 | 221 | G | A | 42.2 | 0.62 | 0.17 | 0.10 | 20.3 | 4.37 | 4.09 |
| 266 | 214 | S | T | 39.2 | 0.74 | 0.14 | 0.10 | 20.2 | 4.03 | 3.76 |
| 163 | 191 | A | G | 42.6 | 0.77 | 0.13 | 0.10 | 20.1 | 4.36 | 4.08 |
| 224 | 206 | P | K | 21.9 | 0.74 | 0.14 | 0.10 | 19.9 | 2.23 | 2.08 |
| 342 | 342 | A | V | 40.6 | 0.78 | 0.13 | 0.10 | 19.7 | 4.08 | 3.82 |
| 443 | 398 | E | D | 38.7 | 0.72 | 0.14 | 0.10 | 19.6 | 3.87 | 3.62 |
| 544 | 434 | Q | H | 51.9 | 0.78 | 0.13 | 0.10 | 19.5 | 5.16 | 4.82 |
| 180 | 193 | G | Q | 23.9 | 0.77 | 0.13 | 0.10 | 19.3 | 2.35 | 2.20 |
| 257 | 211 | Y | S | 18.9 | 0.79 | 0.12 | 0.10 | 19.1 | 1.83 | 1.71 |
| 158 | 190 | G | T | 28.0 | 0.75 | 0.13 | 0.10 | 18.6 | 2.66 | 2.48 |
| 434 | 396 | K | L | 40.5 | 0.57 | 0.17 | 0.09 | 18.6 | 3.85 | 3.60 |
| 530 | 432 | A | S | 34.6 | 0.72 | 0.13 | 0.09 | 18.6 | 3.28 | 3.06 |
| 21 | 56 | A | S | 41.9 | 0.78 | 0.12 | 0.09 | 18.5 | 3.97 | 3.71 |
| 498 | 423 | I | W | 36.7 | 0.48 | 0.19 | 0.09 | 18.0 | 3.37 | 3.15 |
| 402 | 383 | F | M | 45.9 | 0.70 | 0.13 | 0.09 | 17.5 | 4.11 | 3.84 |
| 225 | 206 | P | L | 18.3 | 0.76 | 0.12 | 0.09 | 17.3 | 1.62 | 1.51 |
| 401 | 383 | F | L | 47.2 | 0.66 | 0.13 | 0.08 | 16.3 | 3.92 | 3.67 |
| 339 | 342 | A | M | 52.3 | 0.73 | 0.11 | 0.08 | 16.0 | 4.28 | 4.00 |
| 25 | 125 | R | L | 37.3 | 0.76 | 0.11 | 0.08 | 16.0 | 3.04 | 2.84 |

Megatable 2

| MUT. NO. | Pos. | Ref. AA | Sub. | kcat | ON Rat. | OFF Rat. | ON × OFF | Fold vs. wt | ON × OFF kcat | Fold vs. wt |
|---|---|---|---|---|---|---|---|---|---|---|
| 481 | 413 | K | A | 39.0 | 0.59 | 0.13 | 0.08 | 15.5 | 3.09 | 2.88 |
| 265 | 214 | S | R | 25.4 | 0.75 | 0.10 | 0.08 | 14.9 | 1.94 | 1.81 |
| 546 | 434 | Q | L | 55.5 | 0.71 | 0.11 | 0.08 | 14.8 | 4.20 | 3.93 |
| 7 | 53 | L | F | 47.0 | 0.75 | 0.10 | 0.08 | 14.8 | 3.54 | 3.31 |
| 348 | 349 | A | Q | 42.6 | 0.76 | 0.10 | 0.07 | 14.7 | 3.19 | 2.98 |
| 545 | 434 | Q | K | 58.5 | 0.70 | 0.11 | 0.07 | 14.5 | 4.33 | 4.05 |
| 442 | 398 | E | A | 42.8 | 0.72 | 0.10 | 0.07 | 14.4 | 3.14 | 2.93 |
| 337 | 342 | A | C | 71.5 | 0.71 | 0.10 | 0.07 | 14.0 | 5.09 | 4.76 |
| 397 | 381 | P | N | 55.8 | 0.74 | 0.10 | 0.07 | 13.7 | 3.91 | 3.66 |
| 387 | 375 | K | R | 71.8 | 0.60 | 0.10 | 0.06 | 12.1 | 4.43 | 4.14 |
| 385 | 373 | F | V | 49.2 | 0.76 | 0.08 | 0.06 | 12.0 | 3.01 | 2.81 |
| 347 | 349 | A | E | 47.9 | 0.76 | 0.08 | 0.06 | 11.6 | 2.84 | 2.65 |
| 516 | 429 | S | G | 50.2 | 0.74 | 0.08 | 0.06 | 11.6 | 2.97 | 2.78 |
| 517 | 429 | S | T | 53.7 | 0.72 | 0.08 | 0.06 | 11.5 | 3.16 | 2.95 |
| 262 | 214 | S | M | 22.6 | 0.74 | 0.07 | 0.06 | 10.9 | 1.25 | 1.17 |
| 492 | 418 | Q | E | 83.8 | 0.69 | 0.05 | 0.04 | 7.1 | 3.03 | 2.83 |

Megatable 3

| SEQ ID | Variant Name | ON ratio | OFF ratio | ON × OFF | kcat | ON × OFF × kcat |
|---|---|---|---|---|---|---|
| 1 | Mz wt | 0.213 | 0.033 | 0.007 | 97.4 | 0.68 |
| 2 | 9070 | 0.744 | 0.116 | 0.086 | 40.0 | 3.45 |
| 3 | 9070Q366E | 0.760 | 0.273 | 0.208 | 20.1 | 4.18 |
| 4 | P056028-A-01 | 0.697 | 0.249 | 0.173 | 39.1 | 6.78 |
| 5 | P056028-A-02 | 0.680 | 0.387 | 0.263 | 38.6 | 10.15 |
| 6 | P056028-F-05 | 0.700 | 0.395 | 0.276 | 27.4 | 7.57 |
| 7 | P056028-G-01 | 0.742 | 0.320 | 0.238 | 32.2 | 7.65 |
| 8 | P056028-G-01R | 0.719 | 0.280 | 0.201 | 70.8 | 14.24 |
| 9 | P056028-B-02 | 0.800 | 0.469 | 0.375 | 28.2 | 10.58 |
| 10 | P056028-F-01 | 0.718 | 0.304 | 0.218 | 31.3 | 6.82 |
| 11 | P056028-D-08 | 0.681 | 0.361 | 0.246 | 27.5 | 6.77 |
| 12 | P056028-E-04 | 0.740 | 0.360 | 0.267 | 19.2 | 5.13 |
| 13 | P056028-A-06 | 0.760 | 0.281 | 0.214 | 27.0 | 5.77 |
| 14 | P056028-F-02 | 0.730 | 0.430 | 0.314 | 28.2 | 8.84 |
| 15 | P056028-C-01 | 0.742 | 0.310 | 0.230 | 25.9 | 5.95 |
| 16 | P056028-E-02 | 0.761 | 0.326 | 0.248 | 23.6 | 5.86 |
| 17 | P056028-C-07 | 0.714 | 0.382 | 0.273 | 21.2 | 5.80 |
| 18 | P056028-A-03 | 0.748 | 0.243 | 0.181 | 24.0 | 4.36 |
| 19 | P056028-C-05 | 0.715 | 0.375 | 0.268 | 21.7 | 5.80 |
| 20 | P056028-A-08 | 0.669 | 0.324 | 0.217 | 26.2 | 5.68 |
| 21 | P056028-D-03 | 0.770 | 0.453 | 0.349 | 19.6 | 6.83 |
| 22 | P056028-B-09 | 0.648 | 0.187 | 0.121 | 34.5 | 4.19 |
| 23 | P056028-A-10 | 0.707 | 0.367 | 0.260 | 16.8 | 4.35 |
| 24 | P056028-A-11 | 0.706 | 0.366 | 0.258 | 8.6 | 2.21 |
| 25 | P056028-A-04 | 0.724 | 0.133 | 0.096 | 11.1 | 1.06 |
| 26 | P056028-A-05 | 0.707 | 0.280 | 0.198 | 17.7 | 3.50 |
| 27 | P056028-A-07 | 0.726 | 0.329 | 0.239 | 19.5 | 4.65 |
| 28 | P056028-A-09 | 0.692 | 0.339 | 0.235 | 13.9 | 3.26 |
| 29 | P056028-B-01 | 0.745 | 0.309 | 0.230 | 18.6 | 4.28 |
| 30 | P056028-B-10 | 0.703 | 0.327 | 0.230 | 17.9 | 4.12 |
| 31 | P056028-B-03 | 0.732 | 0.353 | 0.259 | 17.9 | 4.63 |
| 32 | P056028-B-04 | 0.718 | 0.273 | 0.196 | 16.5 | 3.24 |
| 33 | P056028-B-05 | 0.734 | 0.287 | 0.211 | 18.3 | 3.85 |
| 34 | P056028-B-06 | 0.713 | 0.353 | 0.252 | 20.0 | 5.03 |
| 35 | P056028-B-07 | 0.788 | 0.389 | 0.307 | 9.2 | 2.83 |
| 36 | P056028-B-08 | 0.681 | 0.325 | 0.221 | 15.5 | 3.44 |
| 37 | P056028-C-10 | 0.699 | 0.356 | 0.249 | 14.6 | 3.63 |
| 38 | P056028-C-11 | 0.731 | 0.293 | 0.214 | 12.3 | 2.64 |
| 39 | P056028-C-02 | 0.717 | 0.379 | 0.272 | 18.8 | 5.11 |
| 40 | P056028-C-03 | 0.739 | 0.356 | 0.263 | 13.7 | 3.62 |
| 41 | P056028-C-04 | 0.727 | 0.322 | 0.234 | 22.7 | 5.32 |
| 42 | P056028-C-06 | 0.742 | 0.351 | 0.261 | 10.6 | 2.77 |
| 43 | P056028-C-08 | 0.712 | 0.381 | 0.271 | 13.5 | 3.65 |
| 44 | P056028-C-09 | 0.706 | 0.314 | 0.222 | 17.0 | 3.76 |
| 45 | P056028-D-01 | 0.728 | 0.348 | 0.254 | 21.3 | 5.39 |
| 46 | P056028-D-10 | 0.670 | 0.253 | 0.170 | 18.1 | 3.07 |
| 47 | P056028-D-11 | 0.719 | 0.261 | 0.188 | 17.1 | 3.21 |
| 48 | P056028-D-02 | 0.730 | 0.299 | 0.218 | 24.3 | 5.31 |
| 49 | P056028-D-04 | 0.696 | 0.197 | 0.137 | 12.4 | 1.71 |
| 50 | P056028-D-05 | 0.730 | 0.508 | 0.371 | 12.6 | 4.66 |
| 51 | P056028-D-06 | 0.731 | 0.424 | 0.310 | 9.9 | 3.07 |
| 52 | P056028-D-07 | 0.775 | 0.370 | 0.286 | 9.1 | 2.60 |
| 53 | P056028-D-09 | 0.652 | 0.371 | 0.242 | 13.0 | 3.16 |
| 54 | P056028-E-10 | 0.702 | 0.339 | 0.238 | 11.5 | 2.73 |
| 55 | P056028-E-11 | 0.721 | 0.304 | 0.219 | 16.9 | 3.70 |
| 56 | P056028-E-03 | 0.735 | 0.412 | 0.303 | 16.9 | 5.10 |
| 57 | P056028-E-05 | 0.704 | 0.325 | 0.229 | 15.2 | 3.48 |
| 58 | P056028-E-06 | 0.346 | 0.186 | 0.064 | 28.2 | 1.76 |
| 59 | P056028-E-07 | 0.585 | 0.262 | 0.153 | 20.6 | 3.08 |
| 60 | P056028-E-08 | 0.685 | 0.410 | 0.281 | 12.6 | 3.55 |
| 61 | P056028-E-09 | 0.676 | 0.308 | 0.208 | 14.9 | 3.10 |
| 62 | P056028-F-10 | 0.726 | 0.291 | 0.211 | 13.7 | 2.89 |
| 63 | P056028-F-11 | 0.706 | 0.322 | 0.228 | 22.1 | 5.04 |
| 64 | P056028-F-03 | 0.738 | 0.491 | 0.363 | 13.0 | 4.73 |
| 65 | P056028-F-04 | 0.660 | 0.245 | 0.161 | 16.7 | 2.70 |
| 66 | P056028-F-06 | 0.739 | 0.305 | 0.225 | 14.5 | 3.25 |
| 67 | P056028-F-07 | 0.735 | 0.322 | 0.236 | 21.4 | 5.04 |
| 68 | P056028-F-08 | 0.705 | 0.377 | 0.266 | 12.1 | 3.23 |
| 69 | P056028-F-09 | 0.700 | 0.360 | 0.252 | 17.1 | 4.30 |
| 70 | P056028-G-10 | 0.607 | 0.259 | 0.157 | 29.3 | 4.61 |
| 71 | P056028-G-02 | 0.761 | 0.304 | 0.231 | 23.0 | 5.30 |
| 72 | P056028-G-04 | 0.752 | 0.248 | 0.186 | 13.6 | 2.54 |
| 73 | P056028-G-05 | 0.739 | 0.361 | 0.267 | 16.7 | 4.47 |
| 74 | P056028-G-06 | 0.725 | 0.382 | 0.277 | 12.0 | 3.30 |
| 75 | P056028-G-07 | 0.702 | 0.304 | 0.213 | 15.3 | 3.23 |
| 76 | P056028-G-08 | 0.737 | 0.379 | 0.279 | 11.8 | 3.29 |
| 77 | P056028-G-09 | 0.716 | 0.385 | 0.275 | 15.8 | 4.37 |

That which is claimed:

1. A recombinant polypeptide having 4-hydroxyphenylpyruvate dioxygenase (HPPD) activity and comprising an amino acid sequence that is at least 90% identical to SEQ ID NO: 2, wherein the polypeptide has a mutation at one or more amino acid residues corresponding to Q366, A432, S214, P158, A191, R340, P206, Q434, E356, or L182 of SEQ ID NO: 2 and has improved insensitivity to an HPPD inhibitor compared to the polypeptide of SEQ ID NO:1.

2. The polypeptide of claim 1, wherein the mutation is selected from the group consisting of Q366E, A432R, A432K, S213N, S214T, P158K, A191G, A191L, R340K, P206Q, P206S, Q434R, Q434H, E356K, E356R, and L182M.

3. The polypeptide of claim 1, wherein the polypeptide has an ON rate ratio of at least 0.5; wherein the ON rate ratio is the ratio of the reaction rate with herbicidal inhibitor to the reaction rate without herbicidal inhibitor; and wherein the reaction rates are determined in an in vitro assay.

4. The polypeptide of claim 3, wherein the herbicidal inhibitor is mesotrione or tembrione.

5. The polypeptide of claim 4, wherein in vitro assay is carried out in the presence of 60 or 120 nM of the 4-hydroxyphenylpyruvate dioxygenase protein; and 100 µM 4-hydroxyphenylpyruvate.

6. The polypeptide of claim 3, wherein the polypeptide has an OFF rate ratio of at least 0.3; wherein the OFF rate ratio is the ratio of the steady state rate in the presence of inhibitor to the initial reaction rate in the absence of inhibitor; and wherein the reaction rates are determined in an in vitro assay.

7. A nucleic acid construct comprising a polynucleotide sequence encoding the polypeptide of claim 1.

8. The nucleic acid construct of claim 7, further comprising a promoter operably linked to the polynucleotide sequence.

9. A plant cell comprising a nucleic acid construct comprising a polynucleotide sequence encoding a polypeptide having 4-hydroxyphenylpyruvate dioxygenase (HPPD) activity and comprising an amino acid sequence that is at least 90% identical to SEQ ID NO: 2, wherein the polypeptide has a mutation at one or more amino acid residues corresponding to Q366, A432, S214, P158, A191, R340, P206, Q434, E356, or L182 of SEQ ID NO: 2 and has improved insensitivity to an HPPD inhibitor compared to the polypeptide of SEQ ID NO:1.

10. The plant cell of claim 9, wherein the nucleic acid construct further comprises a promoter operably linked to the polynucleotide sequence.

11. The plant cell of claim 9, wherein the plant cell exhibits has an improved insensitivity to an HPPD inhibitor compared to a wild type plant cell of the same species, strain or cultivar.

12. The plant cell of claim 9, wherein the plant cell further comprises at least one additional polypeptide imparting tolerance to an additional herbicide.

13. The plant cell of claim 12, wherein the at least one polypeptide imparting tolerance to an additional herbicide comprises: (a) a sulfonylurea-tolerant acetolactate synthase; (b) an imidazolinone-tolerant acetolactate synthase; (c) a glyphosate-tolerant 5-enolpyruvylshikimate-3-phosphate synthase; (d) a glyphosate-tolerant glyphosate oxido-reductase; (e) a glyphosate-N-acetyltransferase; (f) a phosphinothricin acetyl transferase; (g) a protoporphyrinogen oxidase; (h) AAD1 or AAD12; (i) a P450 polypeptide NSF1; or, (j) an acetyl coenzyme A carboxylase (ACCase).

14. The plant cell of claim 12, wherein the at least one polypeptide imparting tolerance to an additional herbicide comprises an HRA high resistance allele of acetolactate synthase and/or a glyphosate-N-acetyltransferase polypeptide.

15. The plant cell of claim 12, wherein the plant cell further comprises at least one additional polypeptide imparting tolerance to an HPPD herbicide.

16. A plant comprising the plant cell of claim 9.

17. A transgenic seed produced by the plant of claim 16 wherein the seed comprises the plant cell.

18. A method for controlling weeds in an area of cultivation, the method comprising:
a. planting an area of cultivation with seeds and/or plants comprising a nucleic acid construct comprising a polynucleotide sequence encoding a polypeptide having 4-hydroxyphenylpyruvate dioxygenase (HPPD) activity and comprising an amino acid sequence that is at least 90% identical to SEQ ID NO: 2, wherein the polypeptide has a mutation at one or more amino acid residues corresponding to Q366, A432, S214, P158, A191, R340, P206, Q434, E356, or L182 of SEQ ID NO: 2 and has improved insensitivity to an HPPD inhibitor compared to the polypeptide of SEQ ID NO:1; and b. applying to the seeds and/or plants and weeds a sufficient amount of an HPPD inhibitor to control the weeds without significantly affecting the seeds and/or plants.

19. The method of claim 18, wherein the HPPD inhibitor is selected from the group consisting of mesotrione, sulcotrione, topremezone, tembotrione, and isoxaflutole.

20. The method of claim 18, wherein two or more HPPD inhibitors are applied.

* * * * *